United States Patent [19]

Smith et al.

[11] Patent Number: 5,658,786
[45] Date of Patent: Aug. 19, 1997

[54] DNA ENCODING RAT TAURINE TRANSPORTER AND USES THEREOF

[75] Inventors: Kelli E. Smith, Wayne, N.J.; Richard L. Weinshank, New York, N.Y.; Laurence A. Borden, Hackensack; Paul R. Hartig, Princeton, both of N.J.

[73] Assignee: Synaptic Pharmaceutical Corporation, Paramus, N.J.

[21] Appl. No.: 295,814

[22] PCT Filed: Mar. 4, 1993

[86] PCT No.: PCT/US93/01959

§ 371 Date: Dec. 19, 1994

§ 102(e) Date: Dec. 19, 1994

[87] PCT Pub. No.: WO93/18143

PCT Pub. Date: Sep. 16, 1993

Related U.S. Application Data

[63] Continuation-in-part of Ser. No. 959,936, Oct. 13, 1992, abandoned, which is a continuation-in-part of Ser. No. 847,742, Mar. 4, 1992, abandoned.

[51] Int. Cl.⁶ .............. C12N 1/19; C12N 1/21; C12N 15/12; C12N 15/79
[52] U.S. Cl. .......... 435/365; 536/23.5; 435/69.1; 435/252.3; 435/255.1; 435/320.1; 435/325
[58] Field of Search .............. 536/23.5, 24.3, 536/24.31, 24.33; 435/6, 69.1, 172.3, 240.2, 255.1, 252.3, 320.1

[56] References Cited

PUBLICATIONS

Mayser, W. et al., *FEBS Letters*, 295 (1,2,3):203–206, Dec. 1991.
R.D. Blakely, et al., *J. Neuroc.* (Mar. 1991) 56(3):860–871.
Q.-R. Liu, et al., *Proc. Natl. Acad. Sci.* (Jul. 1992) 89:6639–6643.
G.R. Uhl, *Trends in Neuros.* (Jul. 1992) 15(7):265–268.
S. Unchida, et al., *Proc. Natl. Acad. Sci.* (Sep. 1, 1992) 89(17):8230–8234.
K.E. Smith, et al., *Soc. for Neuros. Abs.* (Oct. 25–30, 1992) 18(1):473, abs. No. 202.3.
Q.-R. Lui. et al., *Proc. Natl. Acad. Sci.* (Dec. 15, 1992) 89(24) 12145–12149.
M.D. Adams, et al., *Nature* (Feb. 13, 1992) 355:632–634.
D.L. Martin, et al., *J. Biol. Chem.* (Aug. 10, 1979) 254(15):7076–7084.

*Primary Examiner*—Stephen Walsh
*Assistant Examiner*—Claire Kaufman
*Attorney, Agent, or Firm*—John P. White

[57] ABSTRACT

This invention provides isolated nucleic acid molecules encoding two mammalian GABA transporters, a mammalian taurine transporter and two human GABA transporters and methods of isolating these nucleic acid molecules. Further provided are vectors comprising the nucleic acid molecules as well as mammalian cells comprising such vectors, and antibodies directed to the GABA and taurine transporters. Nucleic acid probes useful for detecting nucleic acid molecules encoding GABA and taurine transporters are also provided. Antisense oligonucleotides complementary to any sequences of a nucleic acid molecule which encodes a GABA or taurine transporter are further provided. Pharmaceutical compounds related to GABA and taurine transporters are provided. Nonhuman transgenic animals which express DNA encoding a normal or a mutant GABA or taurine transporter are also provided. Further provided are methods for determining substrate binding, detecting expression, drug screening, and treatments for alleviating abnormalities associated with GABA and taurine transporters.

13 Claims, 37 Drawing Sheets

FIG. 1A-1

```
        -120                  -100                  -80
          .                     .                    .
    GGCAGCGAACACAAGCGCATCCGGTAGAACGGAAAGAACAGGAATTGCAGAGTGACTTCA

-60                   -40                  -20
          .                     .                    .
    AGTCTCCATACGATTTACTACCCGGGTGACGGCAGTGACTCGACAGAGTAGCGGCTGCAG 0                    20                    40
          .                     .                    .
    GTGGGATGGATAACAGGGTCTCGGGAACGACCAGTAATGGAGAGACAAAGCCAGTGTGTC
            M  D  N  R  V  S  G  T  T  S  N  G  E  T  K  P  V  C  P 60                    80                   100
          .                     .                    .
    CAGTCATGGAGAAGGTGGAGGAAGACGGTACCTTGGAACGGGAGCAATGGACCAACAAGA
      V  M  E  K  V  E  E  D  G  T  L  E  R  E  Q  W  T  N  K  M 120                   140                   160
          .                     .                    .
    TGGAGTTCGTACTGTCAGTGGCGGGAGAGATCATTGGCTTAGGCAACGTCTGGAGGTTTC
      E  F  V  L  S  V  A  G  E  I  I  G  L  G  N  V  W  R  F  P 180                   200                   220
          .                     .                    .
    CCTATCTCTGCTACAAGAACGGGGGAGGTGCCTTCTTTATTCCCTACCTCATCTTCCTAT
      Y  L  C  Y  K  N  G  G  A  F  F  I  P  Y  L  I  F  L  F 240                   260                   280
          .                     .                    .
    TTACCTGTGGCATTCCTGTCTTCTTCCTGGAGACAGCGCTTGGCCAGTACACCAACCAGG
      T  C  G  I  P  V  F  F  L  E  T  A  L  G  Q  Y  T  N  Q  G 300                   320                   340
          .                     .                    .
    GAGGCATCACAGCCTGGAGGAAAATCTGTCCCATCTTCGAGGGCATCGGCTATGCCTCAC
      G  I  T  A  W  R  K  I  C  P  I  F  E  G  I  G  Y  A  S  Q 360                   380                   400
          .                     .                    .
    AGATGATCGTCAGCCTTCTCAATGTCTACTACATCGTTGTCCTGGCCTGGGCCCTCTTCT
      M  I  V  S  L  L  N  V  Y  Y  I  V  V  L  A  W  A  L  F  Y 420                   440                   460
          .                     .                    .
    ACCTCTTCAGCAGCTTCACCACTGACCTCCCCTGGGGTAGCTGCAGCCACGAGTGGAATA
      L  F  S  S  F  T  T  D  L  P  W  G  S  C  S  H  E  W  N  T
```

FIG. 1A-2

```
          480                 500                  520
            .                   .                    .
CAGAAAACTGTGTGGAGTTCCAGAAAACCAACAATTCCCTGAATGTGACTTCTGAGAATG
  E  N  C  V  E  F  Q  K  T  N  N  S  L  N  V  T  S  E  N  A 540                 560                  580
            .                   .                    .
CCACATCCCCTGTCATCGAGTTCTGGGAGAGGCGAGTCCTGAAGATCTCAGATGGCATCC
  T  S  P  V  I  E  F  W  E  R  R  V  L  K  I  S  D  G  I  Q 600                 620                  640
            .                   .                    .
AGCACCTGGGGTCCCTGCGCTGGGAGCTGGTCCTGTGCCTCCTGCTTGCCTGGATCATCT
   H  L  G  S  L  R  W  E  L  V  L  C  L  L  A  W  I  I  C 660                 680                  700
            .                   .                    .
GCTATTTCTGCATCTGGAAAGGGGTCAAGTCCACAGGCAAGGTGGTGTACTTCACAGCTA
  Y  F  C  I  W  K  G  V  K  S  T  G  K  V  V  Y  F  T  A  T 720                 740                  760
            .                   .                    .
CTTTCCCTTACCTCATGCTGGTGGTCCTGTTGATCCGAGGAGTAACACTGCCTGGAGCAG
  F  P  Y  L  M  L  V  V  L  L  I  R  G  V  T  L  P  G  A  A 780                 800                  820
            .                   .                    .
CCCAGGGAATTCAGTTTTACCTGTACCCCAACATCACACGTCTGTGGGATCCCCAGGTGT
   Q  G  I  Q  F  Y  L  Y  P  N  I  T  R  L  W  D  P  Q  V  W 840                 860                  880
            .                   .                    .
GGATGGATGCGGGCACCCAGATCTTCTTCTCCTTTGCCATCTGCCTGGGGTGCCTCACGG
   M  D  A  G  T  Q  I  F  F  S  F  A  I  C  L  G  C  L  T  A 900                 920                  940
            .                   .                    .
CCCTGGGCAGCTACAACAAGTACCACAACAACTGCTACAGGGACTGCGTCGCCCTTTGCA
  L  G  S  Y  N  K  Y  H  N  N  C  Y  R  D  C  V  A  L  C  I 960                 980                 1000
            .                   .                    .
TTCTCAACAGCAGCACCAGCTTCGTGGCCGGGTTTGCCATCTTCTCCATCCTGGGCTTCA
  L  N  S  S  T  S  F  V  A  G  F  A  I  F  S  I  L  G  F  M 1020                1040                 1060
            .                   .                    .
TGTCTCAGGAGCAGGGCGTACCCATATCTGAGGTTGCTGAATCAGGCCCTGGCCTGGCAT
   S  Q  E  Q  G  V  P  I  S  E  V  A  E  S  G  P  G  L  A  F
```

FIG. 1A-3

```
         1080                1100                1120
           .                   .                   .
TCATCGCCTACCCTCGAGCTGTGGTGATGTTACCTTTCTCGCCTTTGTGGGCCTGCTGTT
  I  A  Y  P  R  A  V  V  M  L  P  F  S  P  L  W  A  C  C  F 1140                1160                1180
           .                   .                   .
TCTTCTTCATGGTGGTTCTCCTGGGACTAGACAGCCAGTTTGTGTGTGTAGAAAGCCTCG
  F  F  M  V  V  L  L  G  L  D  S  Q  F  V  C  V  E  S  L  V 1200                1220                1240
           .                   .                   .
TGACAGCGCTGGTGGACATGTATCCCCGGGTGTTCCGTAAGAAGAACCGGAGGGAGATTC
  T  A  L  V  D  M  Y  P  R  V  F  R  K  K  N  R  R  E  I  L 1260                1280                1300
           .                   .                   .
TCATCCTCATCGTGTCTGTCGTCTCTTTCTTCATCGGGCTCATTATGCTCACAGAGGGCG
  I  L  I  V  S  V  V  S  F  F  I  G  L  I  M  L  T  E  G  G 1320                1340                1360
           .                   .                   .
GCATGTACGTGTTCCAGCTCTTCGACTACTATGCGGCCAGTGGCATGTGTCTTCTCTTTG
  M  Y  V  F  Q  L  F  D  Y  Y  A  A  S  G  M  C  L  L  F  V 1380                1400                1420
           .                   .                   .
TGGCCATCTTTGAGTCCCTCTGTGTGGCTTGGGTTTACGGAGCCAGCCGCTTCTATGACA
  A  I  F  E  S  L  C  V  A  W  V  Y  G  A  S  R  F  Y  D  N 1440                1460                1480
           .                   .                   .
ACATTGAAGATATGATTGGGTACAAGCCGTGGCCTCTTATCAAATACTGTTGGCTCTTTT
  I  E  D  M  I  G  Y  K  P  W  P  L  I  K  Y  C  W  L  F  F 1500                1520                1540
           .                   .                   .
TCACGCCAGCTGTGTGCCTGGCAACCTTCCTGTTCTCCCTGATCAAATACACGCCACTGA
  T  P  A  V  C  L  A  T  F  L  F  S  L  I  K  Y  T  P  L  T 1560                1580                1600
           .                   .                   .
CCTACAACAAGAAGTACACATATCCATGGTGGGGGGATGCCCTGGGGTGGCTCCTAGCTC
  Y  N  K  K  Y  T  Y  P  W  W  G  D  A  L  G  W  L  L  A  L 1620                1640                1660
           .                   .                   .
TGTCCTCCATGGTCTGCATTCCTGCCTGGAGCATCTACAAGCTCAGGACTCTCAAGGGCC
  S  S  M  V  C  I  P  A  W  S  I  Y  K  L  R  T  L  K  G  P
```

FIG. 1A-4

```
              1680                  1700                  1720
               .                     .                     .
        CACTCAGAGAGAGACTTCGCCAGCTCGTGTGCCCGGCTGAAGACCTTCCCCAGAAGAGCC
          L  R  E  R  L  R  Q  L  V  C  P  A  E  D  L  P  Q  K  S  Q 1740                  1760                  1780
               .                     .                     .
        AACCAGAGCTGACTTCTCCAGCGACACCGATGACGTCCCTCCTCAGGCTCACAGAACTGG
           P  E  L  T  S  P  A  T  P  M  T  S  L  L  R  T  E  L  E 1800                  1820                  1840
               .                     .                     .
        AGTCTAACTGCTAGGGACGAGGCCTTTGACACACCTGCGAGTCTGTCTGTGGGGACAGCT
            S  N  C 1860                  1880                  1900
               .                     .                     .
        ACAGACACAGAGGGCAGAACCACCCCTCCGTGCTGGGGCAGAGAGACA
```

FIG. 1B-1

```
          -10                    10                    30
           .                      .                     .
GGCGGCAGGGCGGCCATGACTGCGGAGCAAGCGCTGCCCCTGGGCAACGGGAAGGCGGCC
               M  T  A  E  Q  A  L  P  L  G  N  G  K  A  A 50                    70                    90
           .                      .                     .
GAGGAGGCGCGAGGGTCCGAGGCGCTGGGCGGCGGCGGCGGGGGCGCGGCGGGGACGCGC
 E  E  A  R  G  S  E  A  L  G  G  G  G  G  A  A  G  T  R 110                   130                   150
           .                      .                     .
GAGGCGCGCGACAAGGCGGTCCACGAGCGCGGTCACTGGAACAACAAGGTGGAGTTCGTG
 E  A  R  D  K  A  V  H  E  R  G  H  W  N  N  K  V  E  F  V 170                   190                   210
           .                      .                     .
TTGAGCGTAGCGGGAGAGATCATCGGTCTGGGCAACGTGTGGCGCTTCCCCTACCTGTGC
 L  S  V  A  G  E  I  I  G  L  G  N  V  W  R  F  P  Y  L  C 230                   250                   270
           .                      .                     .
TACAAGAACGGCGGAGGGGCATTCCTGATTCCTTACGTGGTGTTTTTCATCTGCTGTGGA
 Y  K  N  G  G  G  A  F  L  I  P  Y  V  V  F  F  I  C  C  G 290                   310                   330
           .                      .                     .
ATCCCCGTCTTCTTCCTGGAAACGGCTCTGGGGCAGTTCACGAGCGAGGGCGGCATCACG
 I  P  V  F  F  L  E  T  A  L  G  Q  F  T  S  E  G  G  I  T 350                   370                   390
           .                      .                     .
TGCTGGAGGAGAGTCTGTCCTTTATTTGAAGGCATCGGCTATGCAACACAGGTGATCGAG
 C  W  R  R  V  C  P  L  F  E  G  I  G  Y  A  T  Q  V  I  E 410                   430                   450
           .                      .                     .
GCGCATCTCAATGTCTACTACATCATCATCCTGGCGTGGGCCATCTTCTACTTAAGCAAC
 A  H  L  N  V  Y  Y  I  I  I  L  A  W  A  I  F  Y  L  S  N 470                   490                   510
           .                      .                     .
TGCTTCACCACCGAGCTCCCCTGGGCCACCTGTGGGCATGAGTGGAACACAGAGAAATGT
 C  F  T  T  E  L  P  W  A  T  C  G  H  E  W  N  T  E  K  C 530                   550                   570
           .                      .                     .
GTGGAGTTCCAGAAGCTGAACTTCAGCAACTACAGTCATGTGTCCCTGCAGAACGCAACC
 V  E  F  Q  K  L  N  F  S  N  Y  S  H  V  S  L  Q  N  A  T
```

FIG. 1B-2

```
        590                   610                   630
         .                     .                     .
TCCCCGGTCATGGAGTTCTGGGAACGCCGGGTCTTGGCTATATCTGATGGCATTGAACAC
 S  P  V  M  E  F  W  E  R  R  V  L  A  I  S  D  G  I  E  H 650                   670                   690
         .                     .                     .
ATCGGGAACCTCCGATGGGAGCTGGCACTGTGTCTCCTGGCGGCTTGGACCATCTGCTAC
 I  G  N  L  R  W  E  L  A  L  C  L  L  A  A  W  T  I  C  Y 710                   730                   750
         .                     .                     .
TTCTGCATCTGGAAGGGTACGAAGTCAACTGGAAAGGTCGTGTATGTCACTGCAACCTTC
 F  C  I  W  K  G  T  K  S  T  G  K  V  V  Y  V  T  A  T  F 770                   790                   810
         .                     .                     .
CCCTACATCATGCTGCTGATCCTCCTGATCCGAGGGGTCACGTTGCCGGGTGCCTCGGAA
 P  Y  I  M  L  L  I  L  L  I  R  G  V  T  L  P  G  A  S  E 830                   850                   870
         .                     .                     .
GGCATCAAGTTCTACCTGTACCCTGACCTCTCCCGGCTCTCTGATCCACAGGTGTGGGTG
 G  I  K  F  Y  L  Y  P  D  L  S  R  L  S  D  P  Q  V  W  V 890                   910                   930
         .                     .                     .
GATGCTGGGACGCAGATCTTTTTCTCCTATGCCATCTGCCTGGGCTGCCTGACCGCTCTG
 D  A  G  T  Q  I  F  F  S  Y  A  I  C  L  G  C  L  T  A  L 950                   970                   990
         .                     .                     .
GGGAGTTACAACAACTATAACAACAACTGCTACAGGGACTGTATTATGCTCTGCTGTCTG
 G  S  Y  N  N  Y  N  N  N  C  Y  R  D  C  I  M  L  C  C  L 1010                  1030                  1050
         .                     .                     .
AACAGTGGCACCAGCTTCGTGGCTGGGTTTGCTATCTTCTCAGTCCTGGGCTTCATGGCG
 N  S  G  T  S  F  V  A  G  F  A  I  F  S  V  L  G  F  M  A 1070                  1090                  1110
         .                     .                     .
TACGAGCAGGGCGTGCCTATTGCTGAGGTGGCAGAATCAGGTCCTGGACTGGCTTTCATC
 Y  E  Q  G  V  P  I  A  E  V  A  E  S  G  P  G  L  A  F  I 1130                  1150                  1170
         .                     .                     .
GCCTACCCCAAGGCTGTCACTATGATGCCCCTGTCCCCATTGTGGGCCACCCTGTTCTTC
 A  Y  P  K  A  V  T  M  M  P  L  S  P  L  W  A  T  L  F  F
```

FIG. 1B-3

```
              1190                      1210                       1230
               .                         .                          .         .
ATGATGCTCATCTTCCTGGGCCTGGACAGTCAGTTTGTGTGTGTGGAGAGCCTTGTGACA
 M  M  L  I  F  L  G  L  D  S  Q  F  V  C  V  E  S  L  V  T 1250                      1270                       1290
               .                         .                          .         .
GCCGTGGTTGACATGTACCCCAAGGTCTTCCGGCGGGGCTACCGGCGAGAACTGCTCATC
 A  V  V  D  M  Y  P  K  V  F  R  R  G  Y  R  R  E  L  L  I 1310                      1330                       1350
               .                         .                          .         .
CTGGCCCTGTCCATTGTCTCTTATTTCCTAGGCCTGGTGATGCTGACAGAGGGAGGCATG
 L  A  L  S  I  V  S  Y  F  L  G  L  V  M  L  T  E  G  G  M 1370                      1390                       1410
               .                         .                          .         .
TACATTTTCCAGCTTTTTGACTCATACGCCGCCAGTGGCATGTGCTTGCTCTTCGTGGCC
 Y  I  F  Q  L  F  D  S  Y  A  A  S  G  M  C  L  L  F  V  A 1430                      1450                       1470
               .                         .                          .         .
ATCTTTGAGTGTGTCTGCATCGGCTGGGTGTATGGAAGTAACAGGTTCTATGACAATATT
 I  F  E  C  V  C  I  G  W  V  Y  G  S  N  R  F  Y  D  N  I 1490                      1510                       1530
               .                         .                          .         .
GAGGACATGATTGGATACCGGCCACTGTCACTCATCAAGTGGTGCTGGAAAGTTGTGACC
 E  D  M  I  G  Y  R  P  L  S  L  I  K  W  C  W  K  V  V  T 1550                      1570                       1590
               .                         .                          .         .
CCTGGGATCTGTGCGGGCATCTTCATCTTCTTTCTGGTCAAGTACAAGCCGCTCAAGTAC
 P  G  I  C  A  G  I  F  I  F  F  L  V  K  Y  K  P  L  K  Y 1610                      1630                       1650
               .                         .                          .         .
AACAATGTGTACACATATCCTGCTTGGGGCTACGGCATTGGCTGGCTCATGGCTCTGTCC
 N  N  V  Y  T  Y  P  A  W  G  Y  G  I  G  W  L  M  A  L  S 1670                      1690                       1710
               .                         .                          .         .
TCCATGCTGTGCATCCCGCTCTGGATCTTCATCAAGCTGTGGAAGACAGAGGGCACCCTG
 S  M  L  C  I  P  L  W  I  F  I  K  L  W  K  T  E  G  T  L 1730                      1750                       1770
               .                         .                          .         .
CCCGAGAAATTACAGAAGTTGACAGTCCCCAGCGCTGATCTGAAAATGAGGGGCAAGCTT
 P  E  K  L  Q  K  L  T  V  P  S  A  D  L  K  M  R  G  K  L
```

FIG. 1B-4

```
          1790                    1810                    1830
            .                       .                       .
GGGGCCAGCCCACGGATGGTGACCGTTAATGACTGTGAGGCCAAGGTCAAAGGCGACGGT
 G   A   S   P   R   M   V   T   V   N   D   C   E   A   K   V   K   G   D   G 1850                    1870                    1890
            .                       .                       .
ACCATCTCTGCCATCACAGAGAAGGAGACGCACTTCTGATCCCCGCCAGCCACTTGGATG
 T   I   S   A   I   T   E   K   E   T   H   F

1910
            .
TGTCTCCAGCCTTCCTTC
```

FIG. 1C-1

```
        -120               -100                -80
          .                  .                  .
GCCAACGCCGCGATCGCCGCCAATCCCGCCAGCCTCGGGCCGGGCCATCCGCTGTGGGCT

-60                -40                -20
          .                  .                  .
TAGCCACCCAGATGCAGAGCCAGTGCCACAGCCTCTTCAGAGGAGCCTCTCAAGCAAAAC 0                  20                 40
          .                  .                  .
GAGGAGATGGCCACCAAGGAGAAGCTTCAATGTCTGAAAGACTTCCACAAAGACATCCTG
          M  A  T  K  E  K  L  Q  C  L  K  D  F  H  K  D  I  L 60                 80                100
          .                  .                  .
AAGCCTTCTCCAGGGAAGAGCCCAGGCACGCGGCCTGAGGATGAGGCTGATGGGAAGCCC
 K  P  S  P  G  K  S  P  G  T  R  P  E  D  E  A  D  G  K  P 120                140                160
          .                  .                  .
CCTCAGAGGGAGAAGTGGTCCAGCAAGATCGACTTTGTGCTGTCTGTGGCCGGAGGCTTC
 P  Q  R  E  K  W  S  S  K  I  D  F  V  L  S  V  A  G  G  F 180                200                220
          .                  .                  .
GTGGGTTTGGGCAATGTCTGGCGTTTCCCGTACCTCTGCTACAAAAATGGTGGAGGTGCA
 V  G  L  G  N  V  W  R  F  P  Y  L  C  Y  K  N  G  G  A 240                260                280
          .                  .                  .
TTCCTCATACCGTATTTTATTTTCCTGTTTGGGAGCGGCCTGCCTGTGTTTTTCCTGGAG
 F  L  I  P  Y  F  I  F  L  F  G  S  G  L  P  V  F  F  L  E 300                320                340
          .                  .                  .
GTCATCATAGGCCAGTACACCTCAGAAGGGGGCATCACCTGCTGGGAGAAGATCTGCCCC
 V  I  I  G  Q  Y  T  S  E  G  G  I  T  C  W  E  K  I  C  P 360                380                400
          .                  .                  .
TTGTTCTCTGGCATTGGCTACGCGTCCATCGTCATCGTGTCCCTCCTGAATGTGTACTAC
 L  F  S  G  I  G  Y  A  S  I  V  I  V  S  L  L  N  V  Y  Y 420                440                460
          .                  .                  .
ATCGTCATCCTGGCCTGGGCCACATACTACCTATTCCAGTCTTTCCAGAAGGATCTTCCC
 I  V  I  L  A  W  A  T  Y  Y  L  F  Q  S  F  Q  K  D  L  P
```

FIG. 1C-2

```
         480                    500                    520
          .                      .                      .
TGGGCCCACTGCAACCATAGCTGGAACACGCCACAGTGCATGGAGGACACCCTGCGTAGG
 W   A   H   C   N   H   S   W   N   T   P   Q   C   M   E   D   T   L   R   R 540                    560                    580
          .                      .                      .
AACGAGAGTCACTGGGTCTCCCTTAGCGCCGCCAACTTCACTTCGCCTGTGATCGAGTTC
 N   E   S   H   W   V   S   L   S   A   A   N   F   T   S   P   V   I   E   F 600                    620                    640
          .                      .                      .
TGGGAGCGCAACGTGCTCAGCCTGTCCTCCGGAATCGACCACCCAGGCAGTCTGAAATGG
 W   E   R   N   V   L   S   L   S   S   G   I   D   H   P   G   S   L   K   W 660                    680                    700
          .                      .                      .
GACCTCGCGCTCTGCCTCCTCTTAGTCTGGCTCGTCTGTTTTTTCTGCATCTGGAAGGGT
 D   L   A   L   C   L   L   L   V   W   L   V   C   F   F   C   I   W   K   G 720                    740                    760
          .                      .                      .
GTTCGGTCCACAGGCAAGGTTGTCTACTTCACTGCTACTTTCCCGTTTGCCATGCTTCTG
 V   R   S   T   G   K   V   V   Y   F   T   A   T   F   P   F   A   M   L   L 780                    800                    820
          .                      .                      .
GTGCTGCTGGTCCGTGGACTGACCCTGCCAGGTGCTGGTGAAGGCATCAAATTCTACCTG
 V   L   L   V   R   G   L   T   L   P   G   A   G   E   G   I   K   F   Y   L 840                    860                    880
          .                      .                      .
TACCCTAACATCAGCCGCCTTGAGGACCCACAGGTGTGGATCGACGCTGGAACTCAGATA
 Y   P   N   I   S   R   L   E   D   P   Q   V   W   I   D   A   G   T   Q   I 900                    920                    940
          .                      .                      .
TTCTTTTCCTACGCTATCTGCCTGGGGGCCATGACCTCACTGGGAAGCTATAACAAGTAC
 F   F   S   Y   A   I   C   L   G   A   M   T   S   L   G   S   Y   N   K   Y 960                    980                   1000
          .                      .                      .
AAGTATAACTCGTACAGGGACTGTATGCTGCTGGGATGCCTGAACAGTGGTACCAGTTTT
 K   Y   N   S   Y   R   D   C   M   L   L   G   C   L   N   S   G   T   S   F 1020                   1040                   1060
          .                      .                      .
GTGTCTGGCTTCGCAATTTTTTCCATCCTGGGCTTCATGGCACAAGAGCAAGGGGTGGAC
 V   S   G   F   A   I   F   S   I   L   G   F   M   A   Q   E   Q   G   V   D
```

FIG. 1C-3

```
            1080                    1100                    1120
              .                       .                       .
ATTGCTGATGTGGCTGAGTCAGGTCCTGGCTTGGCCTTCATTGCCTACCCAAAAGCTGTG
 I  A  D  V  A  E  S  G  P  G  L  A  F  I  A  Y  P  K  A  V 1140                    1160                    1180
              .                       .                       .
ACCATGATGCCGCTGCCCACCTTTTGGTCCATTCTGTTTTTTATTATGCTCCTCTTGCTT
 T  M  M  P  L  P  T  F  W  S  I  L  F  F  I  M  L  L  L 1200                    1220                    1240
              .                       .                       .
GGACTGGACAGCCAGTTTGTTGAAGTCGAAGGACAGATCACATCCTTGGTTGATCTTTAC
 G  L  D  S  Q  F  V  E  V  E  G  Q  I  T  S  L  V  D  L  Y 1260                    1280                    1300
              .                       .                       .
CCGTCCTTCCTAAGGAAGGGTTATCGTCGGGAAATCTTCATTGCCATCGTGTGCAGCATC
 P  S  F  L  R  K  G  Y  R  R  E  I  F  I  A  I  V  C  S  I 1320                    1340                    1360
              .                       .                       .
AGCTACCTGCTGGGGCTGACGATGGTGACGGAGGGTGGCATGTATGTGTTTCAACTCTTT
 S  Y  L  L  G  L  T  M  V  T  E  G  G  M  Y  V  F  Q  L  F 1380                    1400                    1420
              .                       .                       .
GACTACTATGCAGCTAGTGGTGTATGCCTTTTGTGGGTCGCATTCTTTGAATGTTTTGTT
 D  Y  Y  A  A  S  G  V  C  L  L  W  V  A  F  F  E  C  F  V 1440                    1460                    1480
              .                       .                       .
ATTGCCTGGATATATGGCGGTGATAACTTATATGACGGTATTGAGGACATGATCGGCTAT
 I  A  W  I  Y  G  G  D  N  L  Y  D  G  I  E  D  M  I  G  Y 1500                    1520                    1540
              .                       .                       .
CGGCCTGGACCCTGGATGAAGTACAGCTGGGCTGTCATCACTCCAGCTCTCTGTGTTGGA
 R  P  G  P  W  M  K  Y  S  W  A  V  I  T  P  A  L  C  V  G 1560                    1580                    1600
              .                       .                       .
TGTTTCATCTTCTCTCTCGTCAAGTATGTACCCCTGACCTACAACAAAGTCTACCGGTAC
 C  F  I  F  S  L  V  K  Y  V  P  L  T  Y  N  K  V  Y  R  Y 1620                    1640                    1660
              .                       .                       .
CCTGATTGGGCAATCGGGCTGGGCTGGGGCCTGGCCCTTTCCTCCATGGTGTGTATCCCC
 P  D  W  A  I  G  L  G  W  G  L  A  L  S  S  M  V  C  I  P
```

FIG. 1C-4

```
            1680                1700                1720
             .                   .                   .
TTGGTCATTGTCATCCTCCTCTGCCGGACGGAGGGACCGCTCCGCGTGAGAATCAAATAC
 L  V  I  V  I  L  L  C  R  T  E  G  P  L  R  V  R  I  K  Y 1740                1760                1780
             .                   .                   .
CTGATAACCCCCAGGGAGCCCAACCGCTGGGCTGTGGAGCGTGAAGGGGCTACGCCCTTT
 L  I  T  P  R  E  P  N  R  W  A  V  E  R  E  G  A  T  P  F 1800                1820                1840
             .                   .                   .
CACTCCAGAGCAACCCTCATGAACGGTGCACTCATGAAACCCAGTCACGTCATTGTGGAG
 H  S  R  A  T  L  M  N  G  A  L  M  K  P  S  H  V  I  V  E 1860                1880                1900
             .                   .                   .
ACCATGATGTGAGGTCCGGGCTGTGTGACCGGCGCCGCTTTCCTGCCGTTTACTAACCTT
 T  M  M 1920                1940                1960
             .                   .                   .
AGATTCTCCTAGGACCAGGTTTACAGAGCTTTATATTTGTACTAGGATTTTTT
```

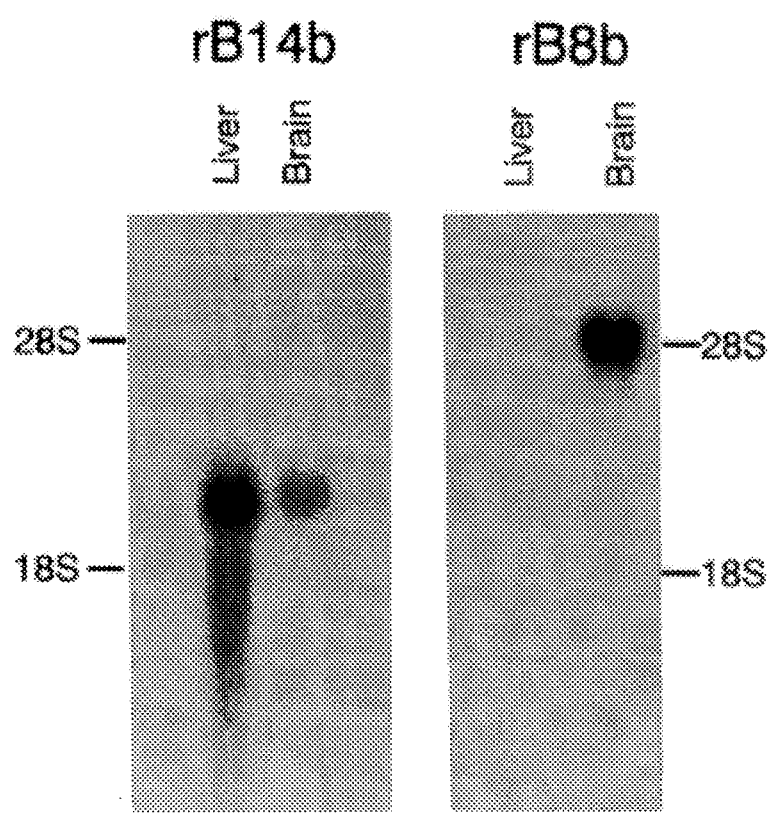

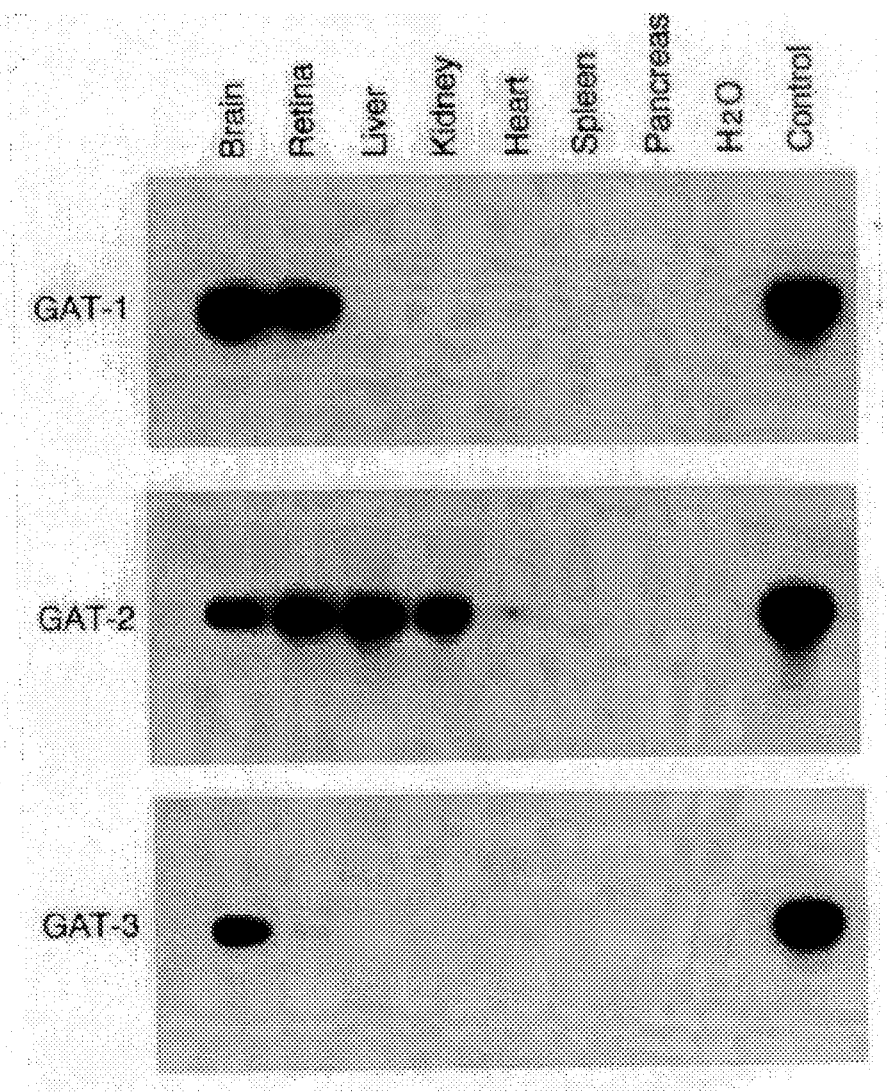

FIG. 6A

| | | |
|---|---|---|
| Taurine | MATKEKLQCLKDFHKDILKPSPGKSPGTRP...EDEADGKPPQREK | 43 |
| GAT-1 | MATDNSKVADGQISTEVSEAPVASDKPKTLVVKVQKKAGDLPDRDT | 46 |
| Betaine | MDRKVAVPEDGPPVVSWLPEEGEKL..DQEGEDQVKDRGQ | 38 |
| Glycine | MAVAHGPVATSSPEQNGAVPSEATKKDQNLTRGN | 34 |

| | | I | | |
|---|---|---|---|---|
| Taurine | WSSKIDFVLSVAGGFVGLGNVWRFPYLCYKNGGGAFLIPYFTFLFGSGLP | 93 |
| GAT-1 | VKGRFDFLMSCVGYAIGLGNVWRFPYLCGKNGGGAFLIPYFLTLFAGVP | 96 |
| Betaine | WTNKWFVLSVAGEIIGLGNVWRFPYLCYKNGGGAFFIPYFFFTCGIP | 88 |
| Glycine | WGNQIEFVLTSVGYAVGLGNVWRFPYLCYRNGGGAFMFPYFIMLVFCGIP | 84 |

| | | | III | |
|---|---|---|---|---|
| Taurine | VFFLEVIIGQYTSEGGITCWEKICPLFSGIGYASIVLVSLLNVYYIVILA | 143 |
| GAT-1 | LFLLECSLGQYTSIGGLGVW.KLAPMFKGVGLAAAVLSFWLNIYYIVIIS | 145 |
| Betaine | VFLEVALGQYTSQGSVTAWRKICPLLQGIGLASVVIESYLNIYYIIJLA | 138 |
| Glycine | LFFMELSFGQFASQGCLGVW.RISAMFKGVGYGMVVSTYIGIYYNVVIC | 133 |

| | | | |
|---|---|---|---|
| Taurine | WATYYLFQSFQKDLPWAHCNHSWNTPQC...MEDTLRRNESHWVSLSAA. | 189 |
| GAT-1 | WALYYLYNSFTTTLPWKQCDNPWNTDRC...F..SNYSLVNTT.. | 183 |
| Betaine | WALFLFSSFTSELPWTTCTNTWNTEHC..MD.FLNHSGARTATSSE. | 182 |
| Glycine | IAFYYFFSSMTHVLPWAYCNNPWNTPDCAGVLDASNLTNGSRPTALSGNL | 183 |

```
                        ┌─VIII─────────────────────────────────────────────────────────────┐
Taurine    PLPTFWSLFFIMLLLLGLDSQFVEVEGQITSLVDLYPSFLRKGYRRE IF   431
GAT-1      PISPLWAILFFSMLLMLGIDSQFCTVEGGFITALVDEYPRLLRN.RRELL   423
Betaine    PLSQLWSCLFFIMLIFLGLDSQFVCVECLVTASMDMFPSQLRKSGRRELL   424
Glycine    PISPLWSLLFFMLILLGLGTQFCLLETLVTAIVDEVGNE.WILQKKTYV   432

┌─IX──────────────────────────────────────────────────────────────┐           ┌─X──
Taurine    IAIVCSISYLLGLTMVTEGGHYVFQLFDYYAASGVCLLWVAFFECFVTAW   481
GAT-1      IAVCIVSYLIGLSNITQGGIYVFKLFDYYSASGMSLLFLVFFECVISW.   473
Betaine    ILAVFCYLAGLFLVTEGGMYIFQLFDYYASSGICLLFLAMFEVICISW    474
Glycine    TLGVAVAGFLLGIPLTSQAGIYWLLLMDNYAAS.FSLVVISCIMCVSEMY   481

┌─XI─────────────
Taurine    LYGGDNLYDGIEDMIGYRPGPWMKYSWAVITPALCVGCFIFSLVKYVPLT   531
GAT-1      FYGVNRFYDNIQEMVGSRPCIWWKLCWSFFTPIIVAGVFLFSAVQMTPLT   523
Betaine    VYGADRFYDNIEDMIGYRPWPLVKISWLFLTPGLOLATFLFSLSQYTPLK   524
Glycine    LYGHRNYFQDIQMMLGFPPPLFFQICWRFVSPTIIFFILIEFTVIQYRPIT  531

─────────────────────────────┐         ┌─XII─────────────────
Taurine    YNKVYYRYPDWAIGLGWGLALSSMVCTPLVIVILLCRTEG.PLRVRIKYLI   580
GAT-1      MGS.YFPKWGQGVGWNLMALSSMVLIPGYMAYMFLTLKG.SLKQRLQVMI   571
Betaine    YNNIYVYPPWGYSIGWFLALSSMICVPLFVIITLKTRG.SFKKRLRQLT   573
Glycine    YNH.TQYPGHAVAIGFLMALSSVICIPLYALFQLCRTDGDTLLQRLKNAT   580

────┐
Taurine    TPREPNRWAVEREGATPFHSRATLMNGALMKPSHVIVETM.......    621
GAT-1      QPSEDIVRPENGPEQPQAGSSASKEAYI.......VGEKETHL....    599
Betaine    TPDPSLPQPKQHLYLDGGTSQDCGPSPTKEGLIVGEKETHL......    614
Glycine    KPSRDWGPALLEHRTGRYAPTTTPSPEDGFEVQPLHPDKAQIPIVGSNGS 630

Taurine    .......     
GAT-1      .......  621
Betaine    .......  599
Glycine    SRLQDSRI 614
                    639
```

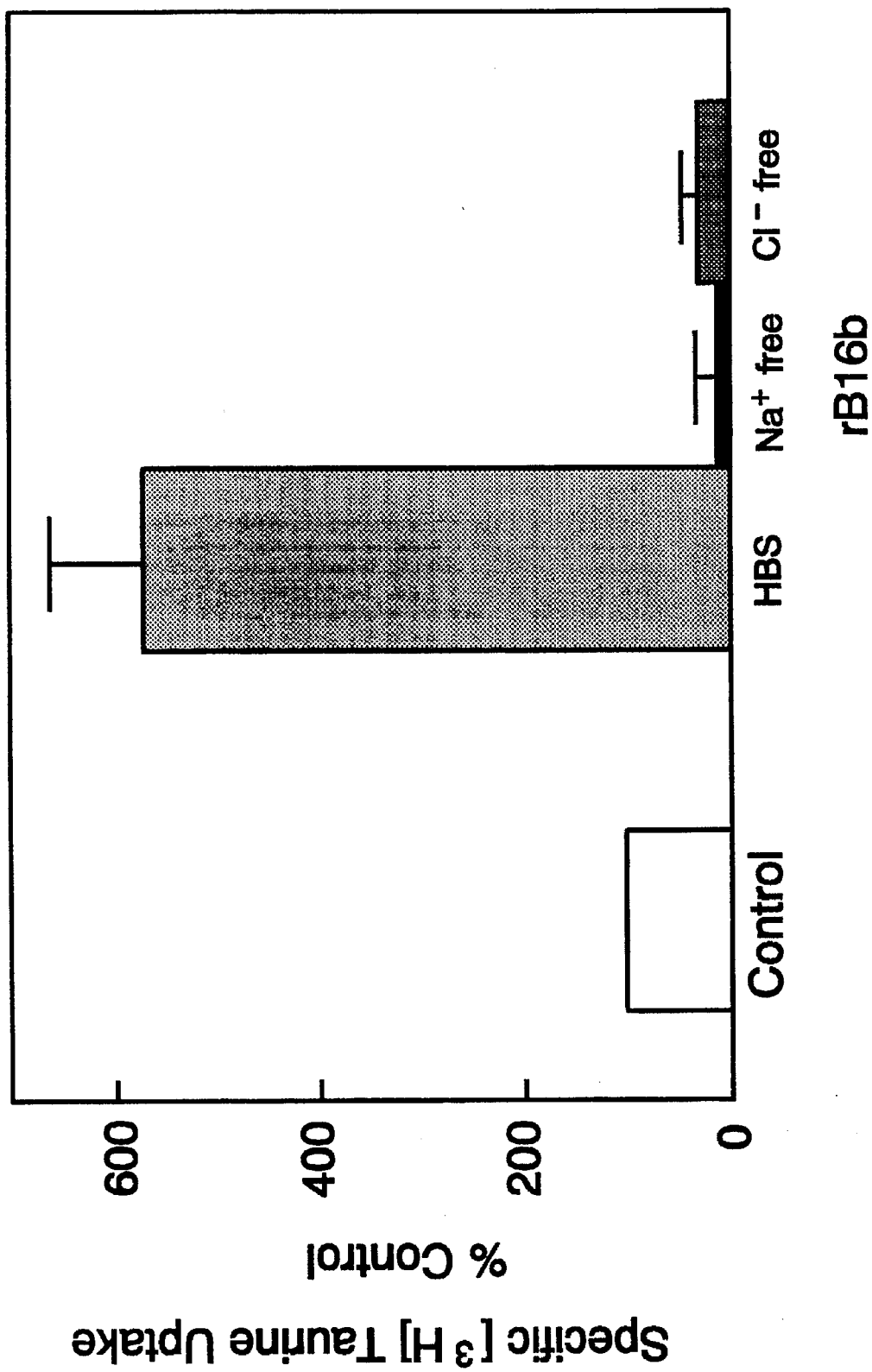

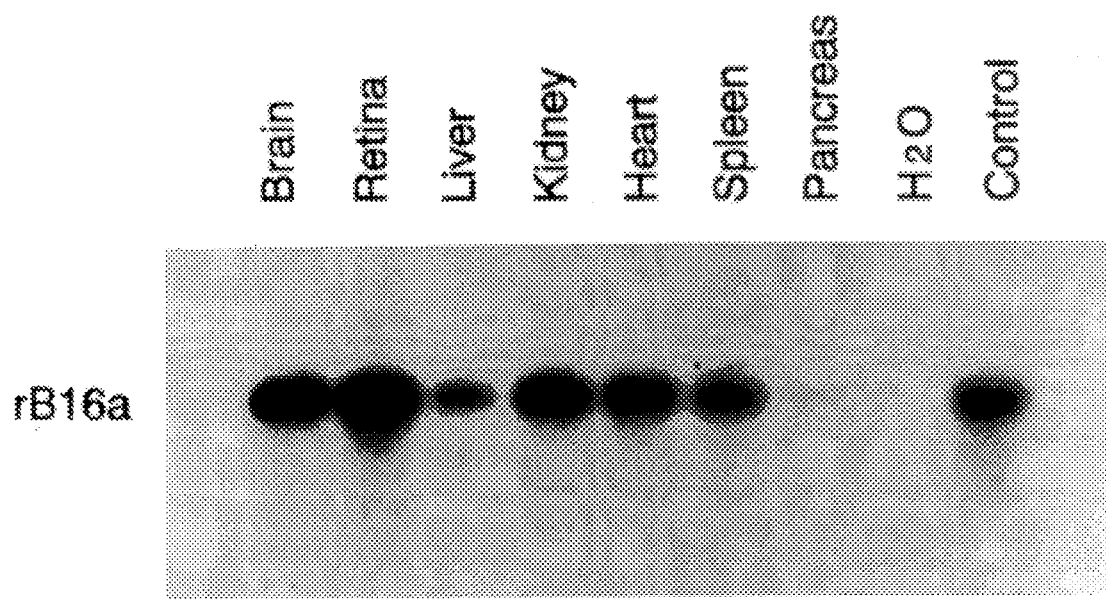

FIG. 10A-1

```
          10                    30                    50
           .                     .                     .
CTGGCTTTCATCGCTTACCCGCGGGCTGTGGTGATGCTGCCCTTCTCTCCTCTCTGGGCC
 L  A  F  I  A  Y  P  R  A  V  V  M  L  P  F  S  P  L  W  A 70                    90                   110
           .                     .                     .
TGCTGTTTCTTCTTCATGGTCGTTCTCCTGGGACTGGATAGCCAGTTTGTGTGTGTAGAA
 C  C  F  F  F  M  V  V  L  L  G  L  D  S  Q  F  V  C  V  E 130                   150                   170
           .                     .                     .
AGCCTGGTGACAGCGCTGGTGGACATGTACCCTCACGTGTTCCGCAAGAAGAACCGGAGG
 S  L  V  T  A  L  V  D  M  Y  P  H  V  F  R  K  K  N  R  R 190                   210                   230
           .                     .                     .
GAAGTCCTCATCCTTGGAGTATCTGTCGTCTCCTTCCTTGTGGGGCTGATCATGCTCACA
 E  V  L  I  L  G  V  S  V  V  S  F  L  V  G  L  I  M  L  T 250                   270                   290
           .                     .                     .
GAGGGCGGAATGTACGTGTTCCAGCTCTTTGACTACTATGCGGCCAGTGGCATGTGCCTC
 E  G  G  M  Y  V  F  Q  L  F  D  Y  Y  A  A  S  G  M  C  L 310                   330                   350
           .                     .                     .
CTGTTCGTGGCCATCTTCGAGTCCCTCTGTGTGGCTTGGGTTTACGGAGCCAAGCGCTTC
 L  F  V  A  I  F  E  S  L  C  V  A  W  V  Y  G  A  K  R  F 370                   390                   410
           .                     .                     .
TACGACAACATCGAAGACATGATTGGGTACAGGCCATGGCCTCTTATCAAATACTGTTGG
 Y  D  N  I  E  D  M  I  G  Y  R  P  W  P  L  I  K  Y  C  W 430                   450                   470
           .                     .                     .
CTCTTCCTCACACCAGCTGTGTGCACAGCCACCTTTCTCTTCTCCCTGATAAAGTACACT
 L  F  L  T  P  A  V  C  T  A  T  F  L  F  S  L  I  K  Y  T 490                   510                   530
           .                     .                     .
CCGCTGACCTACAACAAGAAGTACACGTACCCGTGGTGGGGCGATGCCCTGGGCTGGCTC
 P  L  T  Y  N  K  K  Y  T  Y  P  W  W  G  D  A  L  G  W  L 550                   570                   590
           .                     .                     .
CTGGCTCTGTCCTCCATGGTCTGCATTCCTGCCTGGAGCCTCTACAGACTCGGAACCCTC
 L  A  L  S  S  M  V  C  I  P  A  W  S  L  Y  R  L  G  T  L
```

FIG. 10A-2

```
        610               630                650
         .                 .                  .
AAGGGCCCCTTCAGAGAGAGAATCCGTCAGCTCATGTGCCCAGCCGAGGACCTGCCCCAG
 K  G  P  F  R  E  R  I  R  Q  L  M  C  P  A  E  D  L  P  Q 670               690                710
         .                 .                  .
CGGAACCCAGCAGGACCCTCGGCTCCCGCCACCCCCAGGACCTCACTGCTCAGACTCACA
 R  N  P  A  G  P  S  A  P  A  T  P  R  T  S  L  L  R  L  T 730               750                770
         .                 .                  .
GAGCTAGAGTCTCACTGCTAGGGGCAGGCCCTTGGATGGTGCCTGTGTGCCTGGCCTTG
 E  L  E  S  H  C 790               810                830
         .                 .                  .
GGGATGGCTGTGGAGGGAACGTGGCAGAAGCAGCCCCATGTGCTTCCCTGCCCCCGACCT 850               870                890
         .                 .                  .
GGAGTGGATAAGACAAGAGGGGTATTTTGGAGTCCACCTGCTGAGCTGGAGGCCTCCCAC 910               930                950
         .                 .                  .
TGCAACTTTTCAGCTCAGGGGTTGTTGAACAGATGTGAAAGGCCAGTGCCAAGAGTGTCC 970               990               1010
         .                 .                  .
CTCTGAGACCCTTGGGAAGCTGGGTGGGGCTGGTAGGTGGGGCGAGACTTGCTGGCTTC 1030              1050
         .                 .
GGGCCCTCTCATCCTTCATTCCATTAAATCC
```

FIG. 10B-1

```
         -30                       -10                        10
          .                         .                          .
AGCCGGGCCGGCGCACGAGGCAGCCAGCGCGGCCATGACGGCGGAGAAGGCGCTGCCCCT
                                    M  T  A  E  K  A  L  P  L 30                        50                        70
          .                         .                          .
GGGCAATGGGAAGGCTGCTGAGGAGGCGCGGGAGTCCGAGGCGCCGGGTGGCGGCTGCAG
 G  N  G  K  A  A  E  E  A  R  E  S  E  A  P  G  G  G  C  S 90                       110                       130
          .                         .                          .
CAGCGGGGGCGCGGCGCCCGCGCGCCACCCGCGCGTCAAGCGCGACAAGGCGGTCCACGA
 S  G  G  A  A  P  A  R  H  P  R  V  K  R  D  K  A  V  H  E 150                       170                       190
          .                         .                          .
GCGCGGCCACTGGAACAACAAGGTGGAGTTCGTGCTGAGCGTGGCCGGGGAGATCATTGG
 R  G  H  W  N  N  K  V  E  F  V  L  S  V  A  G  E  I  I  G 210                       230                       250
          .                         .                          .
GCTGGGCAACGTGTGGCGCTTCCCCTACCTGTGCTACAAGAACGGAGGAGGGCATTCCT
 L  G  N  V  W  R  F  P  Y  L  C  Y  K  N  G  G  G  A  F  L 270                       290                       310
          .                         .                          .
GATTCCCTACGTGGTGTTTTTTATTTGCTGTGGAATTCCTGTTTTTTTCCTGGAGACAGC
 I  P  Y  V  V  F  F  I  C  C  G  I  P  V  F  F  L  E  T  A 330                       350                       370
          .                         .                          .
TCTGGGGCAGTTCACAAGTGAAGGTGGCATTACGTGTTGGAGGAAAGTTTGCCCTTTATT
 L  G  Q  F  T  S  E  G  G  I  T  C  W  R  K  V  C  P  L  F 390                       410                       430
          .                         .                          .
TGAAGGCATTGGCTATGCAACACAGGTGATTGAGGCCCATCTGAATGTGTACTACATCAT
 E  G  I  G  Y  A  T  Q  V  I  E  A  H  L  N  V  Y  Y  I  I 450                       470                       490
          .                         .                          .
CATCCTGGCATGGGCCATTTTTTACCTGAGCAACTGCTTCACTACTGAGCTACCCTGGGC
 I  L  A  W  A  I  F  Y  L  S  N  C  F  T  T  E  L  P  W  A 510                       530                       550
          .                         .                          .
TACCTGTGGGCATGAGTGGAACACAGAGAATTGTGTGGAGTTCCAGAAACTGAATGTGAG
 T  C  G  H  E  W  N  T  E  N  C  V  E  F  Q  K  L  N  V  S
```

FIG. 10B-2

```
           570                 590                 610
            .                   .                   .
CAACTACAGCCATGTGTCTCTGCAGAATGCCACCTCCCCTGTCATGGAGTTTTGGGAGCA
 N  Y  S  H  V  S  L  Q  N  A  T  S  P  V  M  E  F  W  E  H 630                 650                 670
            .                   .                   .
CCGGGTCCTGGCCATCTCTGACGGGATCGAGCACATCGGGAACCTTCGCTGGGAGCTGGC
 R  V  L  A  I  S  D  G  I  E  H  I  G  N  L  R  W  E  L  A 690                 710                 730
            .                   .                   .
CTTGTGTCTCTTGGCAGCCTGGACCATCTGTTACTTCTGTATCTGGAAGGGGACCAAGTC
 L  C  L  L  A  A  W  T  I  C  Y  F  C  I  W  K  G  T  K  S 750                 770                 790
            .                   .                   .
TACAGGAAAGGTTGTATACGTGACTGCGACATTCCCCTACATCATGCTGCTGATCCTCCT
 T  G  K  V  V  Y  V  T  A  T  F  P  Y  I  M  L  L  I  L  L 810                 830                 850
            .                   .                   .
GATACGAGGGGTCACGTTGCCCGGGGCCTCAGAGGGCATCAAGTTCTACTTGTACCCTGA
 I  R  G  V  T  L  P  G  A  S  E  G  I  K  F  Y  L  Y  P  D 870                 890                 910
            .                   .                   .
CCTCTCCCGGCTCTCCGACCCCCAGGTCTGGGTAGATGCTGGAACGCAGATCTTTTTCTC
 L  S  R  L  S  D  P  Q  V  W  V  D  A  G  T  Q  I  F  F  S 930                 950                 970
            .                   .                   .
CTATGCCATTTGCCTGGGCTGTCTGACCGCTCTGGGAAGTTATAACAATTATAACAACAA
 Y  A  I  C  L  G  C  L  T  A  L  G  S  Y  N  N  Y  N  N  N 990                1010                1030
            .                   .                   .
CTGCTACAGGGACTGCATCATGCTCTGTTGCCTGAACAGCGGCACCAGCTTCGTGGCTGG
 C  Y  R  D  C  I  M  L  C  C  L  N  S  G  T  S  F  V  A  G 1050                1070                1090
            .                   .                   .
GTTTGCCATCTTCTCAGTCCTGGGTTTTATGGCGTACGAGCAGGGGGTACCCATTGCTGA
 F  A  I  F  S  V  L  G  F  M  A  Y  E  Q  G  V  P  I  A  E 1110                1130                1150
            .                   .                   .
GGTGGCAGAGTCAGGCCCCGGCCTGGCCTTTATTGCGTACCCCAAGGCGGTCACCATGAT
 V  A  E  S  G  P  G  L  A  F  I  A  Y  P  K  A  V  T  M  M
```

FIG. 10B-3

```
     1170                1190                1210
      .                   .                   .
GCCTCTCTCCCCGCTGTGGGCCACCTTGTTCTTCATGATGCTCATCTTCCTGGGCCTGGA
 P  L  S  P  L  W  A  T  L  F  F  M  M  L  I  F  L  G  L  D 1230                1250                1270
      .                   .                   .
CAGCCAGTTTGTGTGTGTGGAAAGCCTGGTGACCGCCGTGGTGGACATGTACCCCAAGGT
 S  Q  F  V  C  V  E  S  L  V  T  A  V  V  D  M  Y  P  K  V 1290                1310                1330
      .                   .                   .
TTTCCGGAGGGGTTACCGGCGGGAGCTGCTCATCCTAGCCTTGTCTGTTATCTCCTATTT
 F  R  R  G  Y  R  R  E  L  L  I  L  A  L  S  V  I  S  Y  F 1350                1370                1390
      .                   .                   .
TCTGGGCCTCGTGATGTTAACAGAGGGTGGCATGTACATCTTCCAGCTCTTTGACTCCTA
 L  G  L  V  M  L  T  E  G  G  M  Y  I  F  Q  L  F  D  S  Y 1410                1430                1450
      .                   .                   .
TGCCGCCAGTGGGATGTGCCTTCTCTTCGTGGCCATCTTTGAGTGCATCTGCATCGGCTG
 A  A  S  G  M  C  L  L  F  V  A  I  F  E  C  I  C  I  G  W 1470                1490                1510
      .                   .                   .
GGTGTATGGAAGCAACCGGTTCTATGATAACATTGAAGACATGATTGGCTACCGGCCACC
 V  Y  G  S  N  R  F  Y  D  N  I  E  D  M  I  G  Y  R  P  P 1530                1550                1570
      .                   .                   .
GTCGCTCATTAAGTGGTGCTGGATGATCATGACCCCTGGGATCTGCGCGGGGATCTTCAT
 S  L  I  K  W  C  W  M  I  M  T  P  G  I  C  A  G  I  F  I 1590                1610                1630
      .                   .                   .
CTTCTTCTTGATCAAGTACAAGCCACTCAAGTACAACAACATCTACACCTACCCAGCCTG
 F  F  L  I  K  Y  K  P  L  K  Y  N  N  I  Y  T  Y  P  A  W 1650                1670                1690
      .                   .                   .
GGGCTATGGCATTGGCTGGCTCATGGCCCTGTCCTCCATGCTCTGCATCCCGCTCTGGAT
 G  Y  G  I  G  W  L  M  A  L  S  S  M  L  C  I  P  L  W  I 1710                1730                1750
      .                   .                   .
CTGCATCACAGTGTGGAAGACGGAGGGGACACTGCCCGAGAAACTCCAGAAGTTGACGAC
 C  I  T  V  W  K  T  E  G  T  L  P  E  K  L  Q  K  L  T  T
```

FIG. 10B-4

```
1770                1790               1810
  .        .         .        .         .        .
CCCCAGCACAGATCTGAAAATGCGGGGCAAGCTTGGGGTGAGCCCACGGATGGTGACAGT
 P  S  T  D  L  K  M  R  G  K  L  G  V  S  P  R  M  V  T  V 1830                1850               1870
  .        .         .        .         .        .
TAATGACTGTGATGCCAAACTCAAGAGTGACGGGACCATCGCAGCCATCACAGAGAAGGA
 N  D  C  D  A  K  L  K  S  D  G  T  I  A  A  I  T  E  K  E 1890                1910               1930
  .        .         .        .         .        .
GACGCACTTCTGAGCGGCCACCAGCCATCTGGGGCTCTTCTTCCTTTCTTCCCCCCGTGT
 T  H  F  *

1950
  .
ATGTAAATGAA
```

DNA ENCODING RAT TAURINE TRANSPORTER AND USES THEREOF

This application is a U.S. national stage application corresponding to PCT International Application PCT/US93/01959, filed Mar. 4, 1993, which is a continuation-in-part in the U.S. of U.S. Ser. No. 07/959,936, filed Oct. 13, 1992, now abandoned, which is a continuation-in-part of U.S. Ser. No. 07/847,742, filed Mar. 4, 1992, now abandoned, the contents of all of which are hereby incorporated by reference into the subject application.

BACKGROUND OF THE INVENTION

Throughout this application various publications are referred to by partial citations within parenthesis. Full citations for these publications may be found at the end of the specification immediately preceding the claims. The disclosures of these publications, in their entireties, are hereby incorporated by reference into this application in order to more fully describe the state of the art to which this invention pertains.

Chemical neurotransmission is a multi-step process which involves release of neurotransmitter from the presynaptic terminal, diffusion across the synaptic cleft, and binding to receptors resulting in an alteration in the electrical properties of the postsynaptic neuron. For most neurotransmitters, transmission is terminated by the rapid uptake of neurotransmitter via specific, high-affinity transporters located in the presynaptic terminal and/or surrounding glial cells (29). Since inhibition of uptake by pharmacologic agents increases the levels of neurotransmitter in the synapse, and thus enhances synaptic transmission, neurotransmitter transporters provide important targets for therapeutic intervention.

The amino acid GABA is the major inhibitory neurotransmitter in the vertebrate central nervous system and is thought to serve as the neurotransmitter at approximately 40% of the synapses in the mammalian brain (13,28). GABAergic transmission is mediated by two classes of GABA receptors. The more prevalent is termed $GABA_A$, which is a multi-subunit protein containing an intrinsic ligand-gated chloride channel in addition to binding sites for a variety of neuroactive drugs including benzodiazepines and barbiturates (35,73). In contrast, $GABA_B$ receptors couple to G-proteins and thereby activate potassium channels (2,35) and possible alter levels of the second messenger cyclic AMP (35). Positive modulation of $GABA_A$ receptors by diazepam and related benzodiazepines has proven extremely useful in the treatment of generalized anxiety (77) and in certain forms of epilepsy (57).

Inhibition of GABA uptake provides a novel therapeutic approach to enhance inhibitory GABAergic transmission in the central nervous system (36,62). Considerable evidence indicates that GABA can be taken up by both neurons and glial cells, and that the transporters on the two cell types are pharmacologically distinct (15,36,62). A GABA transporter with neuronal-type pharmacology designated GAT-1 has previously been purified and cloned (21), but the molecular properties of other GABA transporters including glial transporter(s) have not yet been elucidated. We now report the cloning of two additional GABA transporters (GAT-2 and GAT-3) with distinct pharmacology and localization, revealing previously unsuspected heterogeneity in GABA transporters.

Taurine (2-aminoethane sulfonic acid) is a sulfur-containing amino acid present in high concentrations in mammalian brain as well as various non-neural tissues. Many functions have been ascribed to taurine in both the nervous system and peripheral tissues. The best understood (and phylogenetically oldest) function of taurine is as an osmoregulator (26,75). Osmoregulation is essential to normal brain function and may also play a critical role in various pathophysiological states such as epilepsy, migraine, and ischemia. The primary mechanism by which neurons and glial cells regulate osmolarity is via the selective accumulation and release of taurine. Taurine influx is mediated via specific, high-affinity transporters which may contribute to efflux as well. Since taurine is slowly degraded, transport is an important means of regulating extracellular taurine levels.

Taurine is structurally related to the inhibitory amino acid γ-aminobutyric acid (GABA) and exerts inhibitory effects on the brain, suggesting a role as a neurotransmitter or neuromodulator. Taurine can be released from both neurons and glial cells by receptor-mediated mechanisms as well as in response to cell volume changes (64). Its effects in the CNS may be mediated by $GABA_A$ and $GABA_B$ receptors (34,56) and by specific taurine receptors (78). Additionally, taurine can also regulate calcium homeostasis in excitable tissues such as the brain and heart (26,41), via an intracellular site of action. Together, the inhibitory and osmoregulatory properties of taurine suggest that it acts as a cytoprotective agent in the brain. Depletion of taurine results in retinal degeneration in cats (70), supporting a role in neuronal survival.

Although most animals possess the ability to synthesize taurine, many are unable to generate sufficient quantities and therefore rely on dietary sources. Taurine transport is thus critical to the maintenance of appropriate levels of taurine in the body. High-affinity, sodium-dependent taurine uptake has been observed in brain and various peripheral tissues (27,64), but little is known about the molecular properties of the taurine transporter(s). Cloning of the taurine transporter will not only help elucidate the function of this important neuro-active molecule, but may also provide important insight into novel therapeutic approaches to treat neurological disorders.

cDNA clones (designated rB14b, rB8b, and rB16a) encoding transporters for two novel GABA transporters and a taurine transporter, respectively, have been isolated from rat brain, and their functional properties have been examined in mammalian cells. The transporters encoded by rB14b and rBSb display high-affinity for GABA ($K_m$=4 μM), and exhibit pharmacological properties distinct from the neuronal GABA transporter; the transporter encoded by rB16a displays high-affinity for taurine. All three are dependent on external sodium and chloride for transport activity. The nucleotide sequences of the three clones predict proteins of 602, 627, and 621 amino acids, respectively. Hydropathy analysis reveals stretches of hydrophobic amino acids suggestive of 12 transmembrane domains, similar to that proposed for other cloned neurotransmitter transporters. The cloning of two additional GABA transporters and a taurine transporter from rat brain reveals previously undescribed heterogeneity in inhibitory amino acid transporter genes.

The use of human gene products in the process of drug development offers significant advantages over those of other species, which may not exhibit the same pharmacological profiles. To facilitate this human-target based approach to drug design in the area of inhibitory amino acid transporters, we used the nucleotide sequences of the rat GAT-2 and GAT-3 cDNAs to clone the human homologue of each gene. cDNA clones (designated hHE7a, hS3a, hFB16a and hFB20a encoding the human homologue of the two novel GABA transporters GAT-2 and GAT-3 have been isolated.

SUMMARY OF THE INVENTION

This invention provides an isolated nucleic acid molecule encoding a mammalian GABA transporter. In one embodiment of this invention, the nucleic acid molecule comprises a plasmid designated pEVJB-rB14b (ATCC Accession No. 75203, deposited Feb. 7, 1992). In another embodiment of this invention, the nucleic acid molecule comprises a plasmid designated pEVJB-rB5b (ATCC Accession No. 75201, deposited Feb. 7, 1992).

This invention also provides an isolated nucleic acid molecule encoding a mammalian taurine transporter. In one embodiment of this invention, the nucleic acid molecule comprises a plasmid designated pEVJB-rB16a (ATCC Accession No. 75202, deposited Feb. 7, 1992).

This invention further provides isolated nucleic acid molecules encoding the human homologue of the mammalian GABA transporters. In one embodiment of this invention, the nucleic acid molecule comprises a plasmid designated pcEXV-hGAT-3 (ATCC Accession No. 75324, deposited Oct. 8, 1992). In another embodiment of this invention, the nucleic acid molecule comprises a plasmid designated pBluescript-hHE7a (ATCC Accession No. 75322, deposited Oct. 8, 1992). In another embodiment of this invention, the nucleic acid molecule comprises the plasmid pBluescript-hS3a (ATCC Accession No. 75323, deposited Oct. 8, 1992).

This invention provides a nucleic acid probe comprising a nucleic acid molecule of at least 15 nucleotides capable of specifically hybridizing with a sequence included within the sequence of a nucleic acid molecule encoding a mammalian GABA transporter. This invention also provides a nucleic acid molecule of at least 15 nucleotides capable of specifically hybridizing with a sequence included within the sequence of a nucleic acid molecule encoding a mammalian taurine transporter. This invention also provides a nucleic acid probe comprising a nucleic acid molecule of at least 15 nucleotides capable of specifically hybridizing with a sequence included within the sequence of a nucleic acid molecule encoding a human GABA transporter. This invention also provides a nucleic acid probe comprising a nucleic acid molecule of at least 15 nucleotides capable of specifically hybridizing with a sequence included within the sequence of a nucleic acid molecule encoding a human taurine transporter.

This invention further provides an antisense oligonucleotide having a sequence capable of binding specifically to an mRNA molecule encoding a mammalian GABA transporter so as to prevent translation of the mRNA molecule. This invention also provides an antisense oligonucleotide having a sequence capable of binding specifically to an mRNA molecule encoding a mammalian taurine transporter so as to prevent translation of the mRNA molecule. This invention also provides an antisense oligonucleotide having a sequence capable of binding specifically to an mRNA molecule encoding a human GABA transporter so as to prevent translation of the mRNA molecule. This invention also provides an antisense oligonucleotide having a sequence capable of binding specifically to an mRNA molecule encoding a human taurine transporter so as to prevent translation of the mRNA molecule.

A monoclonal antibody directed to a mammalian GABA transporter is provided by this invention. A monoclonal antibody directed to a mammalian taurine transporter is also provided by this invention. A monoclonal antibody directed to a human GABA transporter is also provided by this invention. A monoclonal antibody directed to a human taurine transporter is also provided by this invention.

This invention provides a pharmaceutical composition comprising an amount of a substance effective to alleviate the abnormalities resulting from overexpression of a mammalian GABA transporter and a pharmaceutically acceptable carrier as well as a pharmaceutical composition comprising an amount of a substance effective to alleviate abnormalities resulting from underexpression of GABA transporter and a pharmaceutically acceptable carrier.

A pharmaceutical composition comprising an amount of a substance effective to alleviate the abnormalities resulting from overexpression of a mammalian taurine transporter and a pharmaceutically acceptable carrier as well as a pharmaceutical composition comprising an amount of a substance effective to alleviate abnormalities resulting from underexpression of a taurine transporter and a pharmaceutically acceptable carrier is also provided by this invention.

A pharmaceutical composition comprising an amount of a substance effective to alleviate the abnormalities resulting from overexpression of a human GABA transporter and a pharmaceutically acceptable carrier as well as a pharmaceutical composition comprising an amount of a substance effective to alleviate abnormalities resulting from underexpression of a human GABA transporter and a pharmaceutically acceptable carrier is also provided by this invention.

A pharmaceutical composition comprising an amount of a substance effective to alleviate the abnormalities resulting from overexpression of a human taurine transporter and a pharmaceutically acceptable carrier as well as a pharmaceutical composition comprising an amount of a substance effective to alleviate abnormalities resulting from underexpression of a human taurine transporter and a pharmaceutically acceptable carrier is also provided by this invention.

This invention also provides a transgenic, nonhuman mammal whose genome comprises DNA encoding a mammalian GABA transporter so positioned within such genome as to be transcribed into antisense mRNA complementary to mRNA encoding the GABA transporter and when hybridized to mRNA encoding the GABA transporter, the complementary mRNA reduces the translation of the mRNA encoding the GABA transporter.

This invention also provides a transgenic, nonhuman mammal whose genome comprises DNA encoding a mammalian taurine transporter so positioned within such genome as to be transcribed into antisense mRNA complementary to mRNA encoding the taurine transporter and when hybridized to mRNA encoding the taurine transporter, the complementary mRNA reduces the translation of the mRNA encoding the taurine transporter.

This invention also provides a transgenic, nonhuman mammal whose genome comprises DNA encoding a human GABA transporter so positioned within such genome as to be transcribed into antisense mRNA which is complementary to mRNA encoding the human GABA transporter and when hybridized to mRNA encoding the human GABA transporter, the antisense mRNA thereby reduces the translation of mRNA encoding the human GABA transporter.

This invention also provides a transgenic, nonhuman mammal whose genome comprises DNA encoding a human taurine transporter so positioned within such genome as to be transcribed into antisense mRNA which is complementary to mRNA encoding the human taurine transporter and when hybridized to mRNA encoding the human taurine transporter, the antisense mRNA thereby reduces the translation of mRNA encoding the human taurine transporter.

This invention also provides a transgenic, nonhuman mammal whose genome comprises DNA encoding a mammalian GABA transporter so positioned within such genome as to be transcribed into antisense mRNA which is complementary to mRNA encoding the transporter and when hybridized to mRNA encoding the transporter, the antisense mRNA thereby prevents the translation of mRNA encoding the transporter.

This invention also provides a transgenic, nonhuman mammal whose genome comprises DNA encoding a mammalian taurine transporter so positioned within such genome as to be transcribed into antisense mRNA which is complementary to mRNA encoding the transporter and when hybridized to mRNA encoding the transporter, the antisense mRNA thereby prevents the translation of mRNA encoding the transporter.

This invention also provides a transgenic, nonhuman mammal whose genome comprises DNA encoding a human GABA transporter so positioned within such genome as to be transcribed into antisense mRNA which is complementary to mRNA encoding the transporter and when hybridized to mRNA encoding the human GABA transporter, the antisense mRNA thereby prevents the translation of mRNA encoding the human GABA transporter.

This invention also provides a transgenic, nonhuman mammal whose genome comprises DNA encoding a human taurine transporter so positioned within such genome as to be transcribed into antisense mRNA which is complementary to mRNA encoding the human taurine transporter and when hybridized to mRNA encoding the human taurine transporter, the antisense mRNA thereby prevents the translation of mRNA encoding the human taurine transporter.

This invention provides a method of screening drugs to identify drugs which specifically interact with, and bind to, a mammalian GABA transporter on the surface of a cell which comprises contacting a mammalian cell comprising an isolated DNA molecule encoding a mammalian GABA transporter, the protein encoded thereby is expressed on the cell surface, with a plurality of drugs, determining those drugs which bind to the mammalian cell, and thereby identifying drugs which specifically interact with, and bind to, a mammalian GABA transporter.

This invention provides a method of screening drugs to identify drugs which specifically interact with, and bind to, a mammalian taurine transporter on the surface of a cell which comprises contacting a mammalian cell comprising an isolated DNA molecule encoding a mammalian taurine transporter, the protein encoded thereby is expressed on the cell surface, with a plurality of drugs, determining those drugs which bind to the mammalian cell, and thereby identifying drugs which specifically interact with, and bind to, a mammalian taurine transporter.

This invention provides a method of screening drugs to identify drugs which specifically interact with, and bind to, a human GABA transporter on the surface of a cell which comprises contacting a mammalian cell comprising an isolated DNA molecule encoding a human GABA transporter, the protein encoded thereby is expressed on the cell surface, with a plurality of drugs, determining those drugs which bind to the mammalian cell, and thereby identifying drugs which specifically interact with, and bind to, a human GABA transporter.

This invention provides a method of screening drugs to identify drugs which specifically interact with, and bind to, a human taurine transporter on the surface of a cell which comprises contacting a mammalian cell comprising an isolated DNA molecule encoding a human taurine transporter, the protein encoded thereby is expressed on the cell surface, with a plurality of drugs, determining those drugs which bind to the mammalian cell, and thereby identifying drugs which specifically interact with, and bind to, a human taurine transporter.

This invention also provides a method of determining the physiological effects of expressing varying levels of mammalian GABA transporters which comprises producing a transgenic nonhuman animal whose levels of mammalian GABA transporter expression are varied by use of an inducible promoter which regulates mammalian GABA transporter expression.

This invention also provides a method of determining the physiological effects of expressing varying levels of mammalian taurine transporters which comprises producing a transgenic nonhuman animal whose levels of mammalian taurine transporter expression are varied by use of an inducible promoter which regulates mammalian taurine transporter expression.

This invention also provides a method of determining the physiological effects of expressing varying levels of human GABA transporters which comprises producing a transgenic nonhuman animal whose levels of human GABA transporter expression are varied by use of an inducible promoter which regulates human GABA transporter expression.

This invention also provides a method of determining the physiological effects of expressing varying levels of human taurine transporters which comprises producing a transgenic nonhuman animal whose levels of human taurine transporter expression are varied by use of an inducible promoter which regulates human taurine transporter expression.

This invention further provides a method of determining the physiological effects of expressing varying levels of mammalian GABA transporters which comprises producing a panel of transgenic nonhuman animals each expressing a different amount of mammalian GABA transporter.

This invention further provides a method of determining the physiological effects of expressing varying levels of mammalian taurine transporters which comprises producing a panel of transgenic nonhuman animals each expressing a different amount of mammalian taurine transporter.

This invention further provides a method of determining the physiological effects of expressing varying levels of human GABA transporters which comprises producing a panel of transgenic nonhuman animals each expressing a different amount of human GABA transporter.

This invention further provides a method of determining the physiological effects of expressing varying levels of human taurine transporters which comprises producing a panel of transgenic nonhuman animals each expressing a different amount of human taurine transporter.

This invention provides a method for diagnosing a predisposition to a disorder associated with the expression of a specific mammalian GABA transporter allele and a method for diagnosing a predisposition to a disorder associated with the expression of a specific mammalian taurine transporter allele which comprises: a.) obtaining DNA of subjects suffering from the disorder; b.) performing a restriction digest of the DNA with a panel of restriction enzymes; c.) electrolphoretically separating the resulting DNA fragments on a sizing gel; d.) contacting the resulting gel with a nucleic acid probe capable of specifically hybridizing to DNA encoding a mammalian GABA or a mammalian taurine transporter and labelled with a detectable marker; e.) detecting labelled bands which have hybridized to the DNA encoding a mammalian GABA or taurine transporter labelled with a detectable marker to create a unique band pattern specific to the DNA of subjects suffering from the disorder; f.) preparing DNA obtained for diagnosis by steps a–e; and g.) comparing the unique band pattern specific to the DNA of subjects suffering from the disorder from step e and the DNA obtained for diagnosis from step f to determine whether the patterns are the same or different and to diagnose thereby predisposition to the disorder if the patterns are the same.

This invention provides a method for diagnosing a predisposition to a disorder associated with the expression of a specific human GABA transporter allele or a specific human taurine transporter allele which comprises: a.) obtaining DNA of subjects suffering from the disorder; b.) performing a restriction digest of the DNA with a panel of restriction enzymes; c.) electrophoretically separating the resulting DNA fragments on a sizing gel; d.) contacting the resulting gel with a nucleic acid probe capable of specifically hybridizing to DNA encoding a human GABA or human taurine transporter and labelled with a detectable marker; e.) detecting labelled bands which have hybridized to the DNA encoding a human GABA or human taurine transporter labelled with a detectable marker to create a unique band pattern specific to the DNA of subjects suffering from the disorder; f.) preparing DNA obtained for diagnosis by steps a–e; and g.) comparing the unique band pattern specific to the DNA of subjects suffering from the disorder from step e and the DNA obtained for diagnosis from step f to determine whether the patterns are the same or different and to diagnose thereby predisposition to the disorder if the patterns are the same.

This invention provides a method for determining whether a substrate not known to be capable of binding to a mammalian transporter can bind to the mammalian GABA transporter which comprises contacting a mammalian cell comprising an isolated DNA molecule encoding the GABA transporter with the substrate under conditions permitting binding of substrates known to bind to a transporter, detecting the presence of any of the substrate bound to the GABA transporter, and thereby determining whether the substrate binds to the GABA transporter.

This invention provides a method for determining whether a substrate not known to be capable of binding to a taurine transporter can bind to a taurine transporter which comprises contacting a mammalian cell comprising an isolated DNA molecule encoding the taurine transporter with the substrate under conditions permitting binding of substrates known to bind to a transporter, detecting the presence of any of the substrate bound to the taurine transporter, and thereby determining whether the substrate binds to the taurine transporter.

This invention provides a method for determining whether a substrate not known to be capable of binding to a human GABA transporter can bind to a human GABA transporter which comprises contacting a mammalian cell comprising an isolated DNA molecule encoding the human GABA transporter with the substrate under conditions permitting binding of substrates known to bind to a transporter, detecting the presence of any of the substrate bound to the human GABA transporter, and thereby determining whether the substrate binds to the human GABA transporter.

This invention provides a method for determining whether a substrate not known to be capable of binding to a human taurine transporter can bind to a human taurine transporter which comprises contacting a mammalian cell comprising an isolated DNA molecule encoding the human taurine transporter with the substrate under conditions permitting binding of substrates known to bind to a transporter, detecting the presence of any of the substrate bound to the human taurine transporter, and thereby determining whether the substrate binds to the human taurine transporter.

BRIEF DESCRIPTION OF THE FIGURES

Figure 2A:
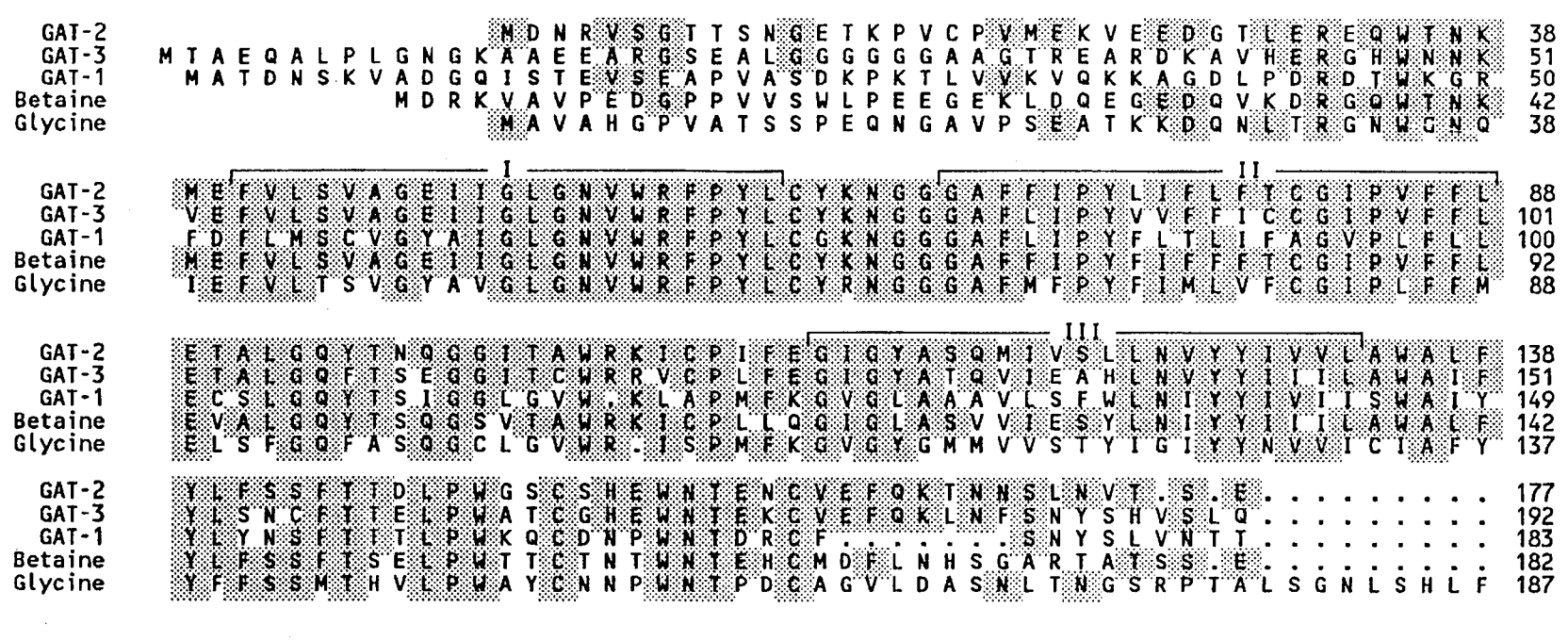
Figure 2B:
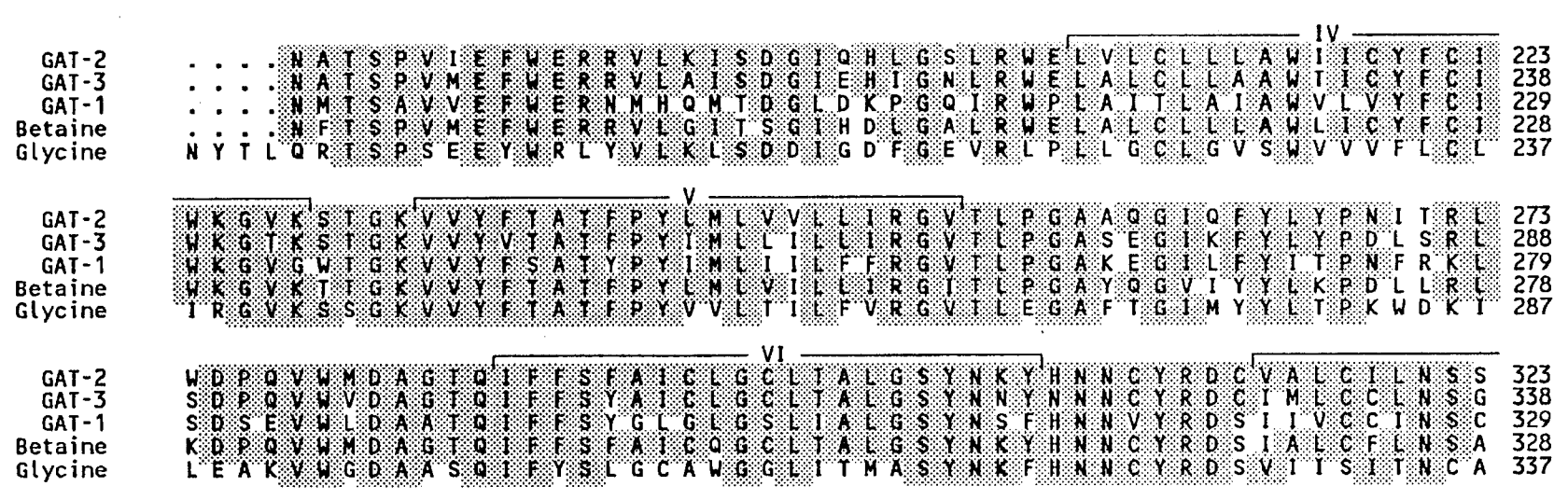
Figure 2C:
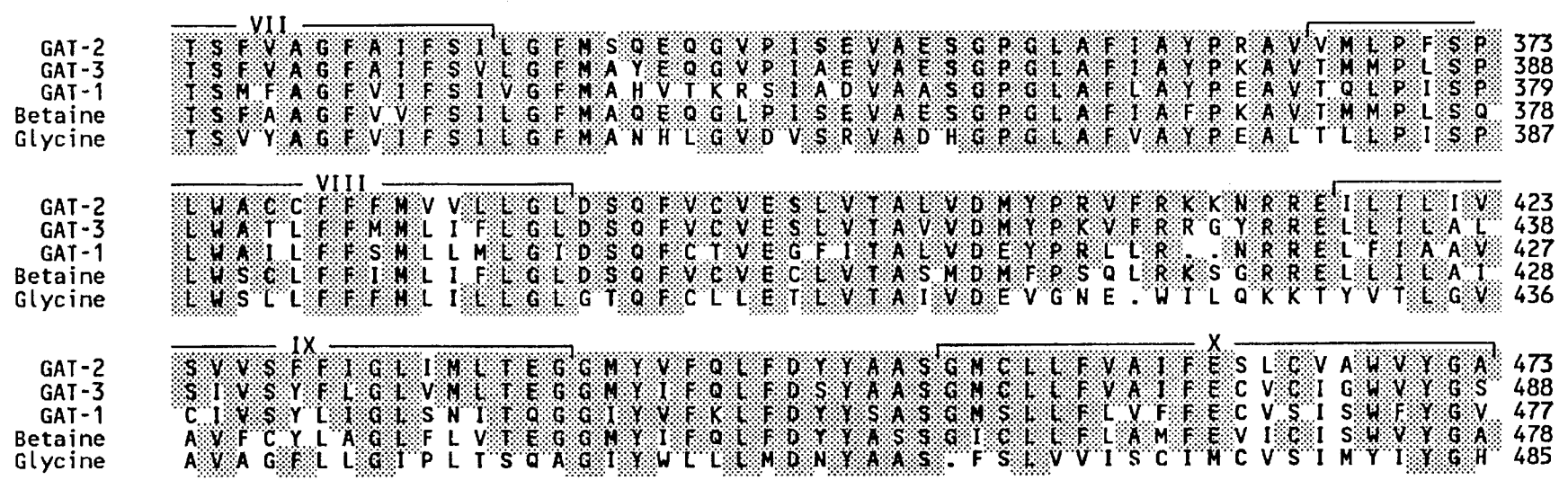
Figure 2D:
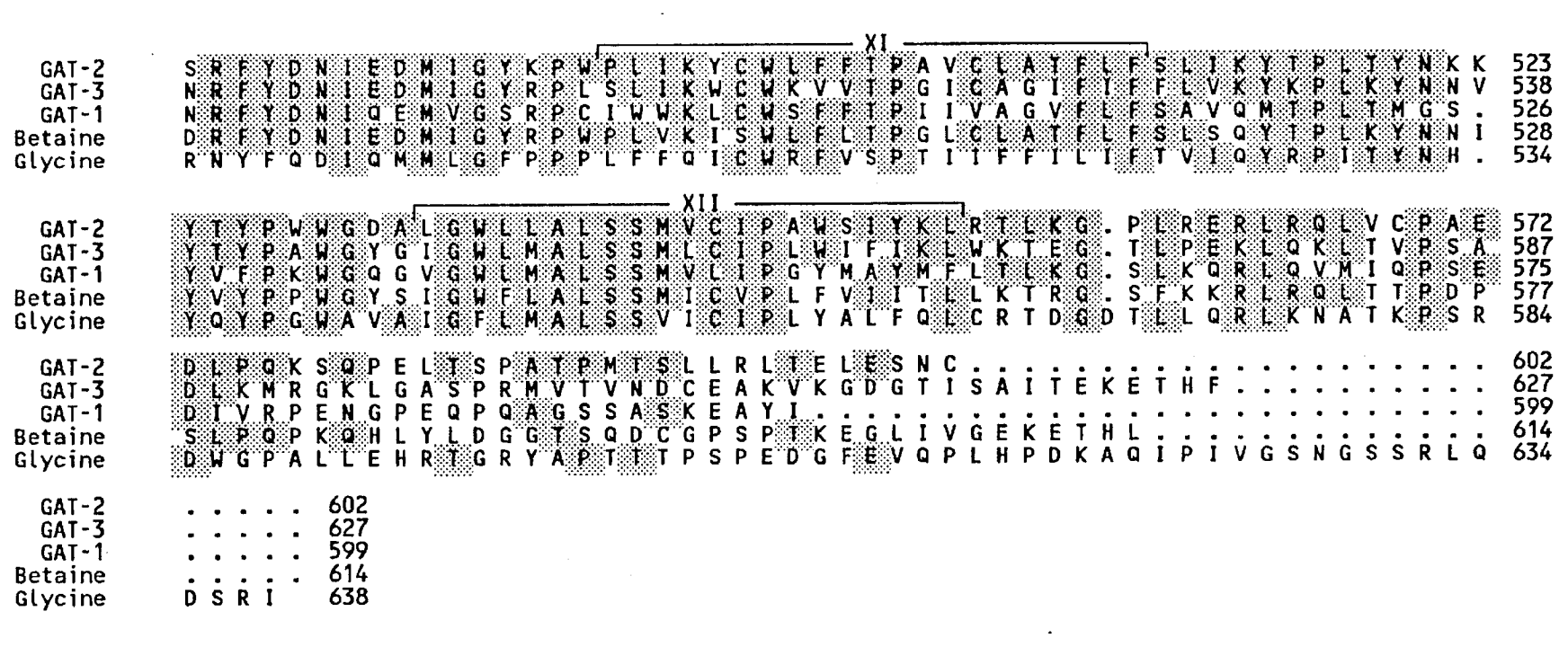

FIGS. 1A-1 to 1E-2 Nucleotide Sequence, Deduced Amino Acid Sequence and Putative Membrane Topology of Two Novel Mammalian GABA Transporters and a Novel Mammalian Taurine Transporter. FIGS. 1A-1 to 1A-4 Mammalian GABA transporter encoded by GAT-2 (rB14b)(Seq. I.D. Nos. 1 and 2). Nucleotides are presented in the 5' to 3' orientation and the coding region is numbered starting from the putative initiating methionine and ending in the termination codon. Deduced amino acid sequence by translation of a long open reading frame is shown. FIGS. 1B-1 to 1B-2 Mammalian GABA transporter encoded by GAT-3 (rBSb) (Seq. I.D. Nos. 3, and 4). Nucleotides are presented in the 5' to 3' orientation and the coding region is numbered starting from the putative initiating methionine and ending in the termination codon. Deduced amino acid sequence by translation of a long open reading frame is shown. FIGS. 1C-1 to 1C-4 Taurine transporter encoded by rB16a (Seq. I.D. Nos. 5 and 6). Nucleotides are presented in the 5' to 3' orientation and the coding region is numbered starting from the putative initiating methionine and ending in the termination codon. Deduced amino acid sequence by translation of a long open reading frame is shown. FIGS. 1D-1 and 1D-2 Deduced amino acid sequence and putative membrane topology of GABA tranporter GAT-2 (rB14b) SEQ ID NO: 2. Deduced amino acid sequence by translation of a long open reading frame in rB14b is shown. Residues which are identical to those of GAT-3 (rBSb) are shaded. Membrane topology is modeled after that proposed for GAT-1 (21). FIGS. 1E-1 and 1E-2 Deduced amino acid sequence and putative membrane topology of taurine transporter (rB16a) SEQ ID NO: 6. Deduced amino acid sequence by translation of a long open reading frame in rB16a is shown. Membrane topology is modeled after that proposed for GAT-1 (21).

FIGS. 2A–2D Alignment of the novel GABA transporters with the rat neuronal GABA transporter, the betaine transporter, and the glycine transporter. The twelve putative α-helical membrane spanning domains (I–XII) are bracketed. Residues identical to those of GAT-2 are shaded. GAT-2 is the GABA transporter encoded by rB14b; GAT-3 is the GABA transporter encoded by rBSb; GAT-1 is the rat neuronal GABA transporter (SEQ ID NO: 11) (21), Betaine is the dog betains transporter (SEQ ID NO: 12) (79), and Glycine is the rat glycine transporter (SEQ ID NO: 13) (68).

were incubated with the indicated concentrations of [$^3$H] GABA for 30 seconds and the accumulated radioactivity was determined. The specific activity of the [$^3$H]GABA was reduced with unlabeled GABA. Data represent specific transport expressed as nmoles per minute per mg protein, and are from a single experiment that was repeated with similar results (see Text).

FIGS. 5A–5B Localization of GABA transporters. FIG. 5A Northern blot analysis of mRNAs encoding GAT-2 (rB14b) and GAT-3 (rBSb). Total RNA (25 µg) from rat brain and liver was separated by formaldehyde/agarose gel electrophoresis, blotted to nylon membranes, and hybridized at high stringency with $^{32}$P-labeled GABA transporter cDNAs (rB14b and rBSb, respectively). The autoradiogram was developed after a four day exposure. The locations of ribosomal RNAs are indicated at the side. The hybridizing transcripts are ≈2.4 kb (GAT-2) and ≈4.7 kb (GAT-3). FIG. 5B Tissue distribution of mRNAs encoding GAT-1, GAT-2, and GAT-3 as determined by PCR. Single-stranded cDNA converted from poly A+ RNA was used for PCR amplification (30 cycles) of GABA transporter cDNA sequences. Amplified products were detected by hybridization with specific oligonucleotide probes; autoradiograms of the Southern blots are shown. GAT-1 is the neuronal GABA transporter (SEQ ID NO: 11). GAT-2 is the transporter encoded by rBSb. GAT-3 is the transporter by rB14b. Equivalent samples of poly A+ RNA (not treated with reverse transcriptase) subjected to identical PCR conditions showed no hybridization with the three probes (not shown). Cyclophilin cDNA was amplified to an equal extent from all tissues examined (not shown). Each experiment was repeated at least once with similar results.

Figure 6B:
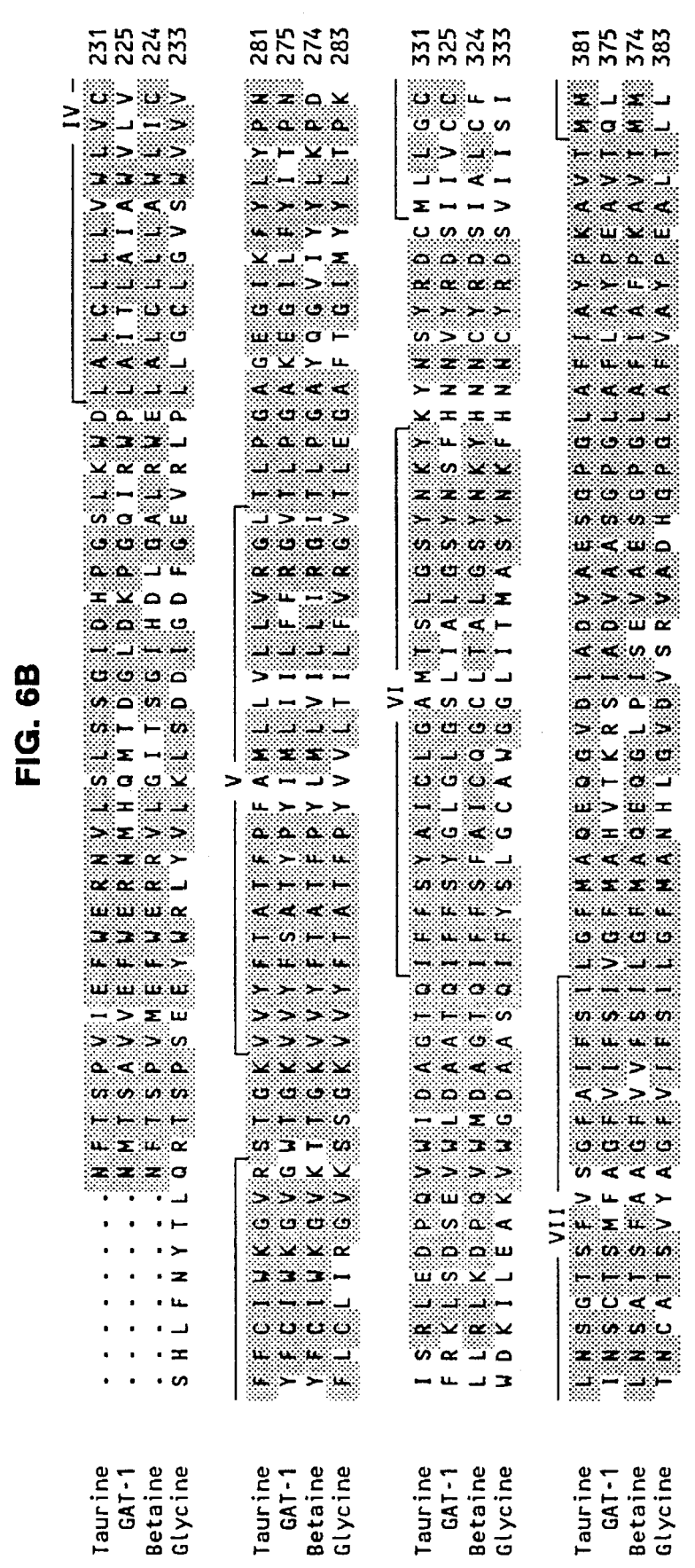

FIGS. 6A–6C Alignment of the taurine transporter with the GABA transporter GAT-1, the betdine transporter, and the glycine transporter. The twelve putative α-helical membrane spanning domains (I–XII) are bracketed. Residues identical to those of the taurine transporter are shaded. Taurine is the taurine transporter encoded by rB16a; GAT-1 is the rat brain GABA transporter (SEQ ID NO: 11) (21); Betaine is the dog betaine transporter (SEQ ID NO: 12) (79); Glycine is the rat glycine transporter (SEQ ID NO: 13) (68).

FIG. 7 Taurine transport by COS cells transfected with clone rB16a. Non-transfected COS cells (control) or COS cells transfected with rB16a were incubated for 10 minutes (37° C.) with 50 nM [$^3$H]taurine in either HBS (150 mM NaCl) or in a similar solution in which Na$^+$ was replaced by equimolar Li$^+$ (Na$^+$-free), or Cl$^-$ was replaced by acetate (Cl$^-$-free). Data show the specific uptake of taurine, expressed as % of control cells. Each bar represents the mean±SEM of 3–7 experiments.

Figure 8:
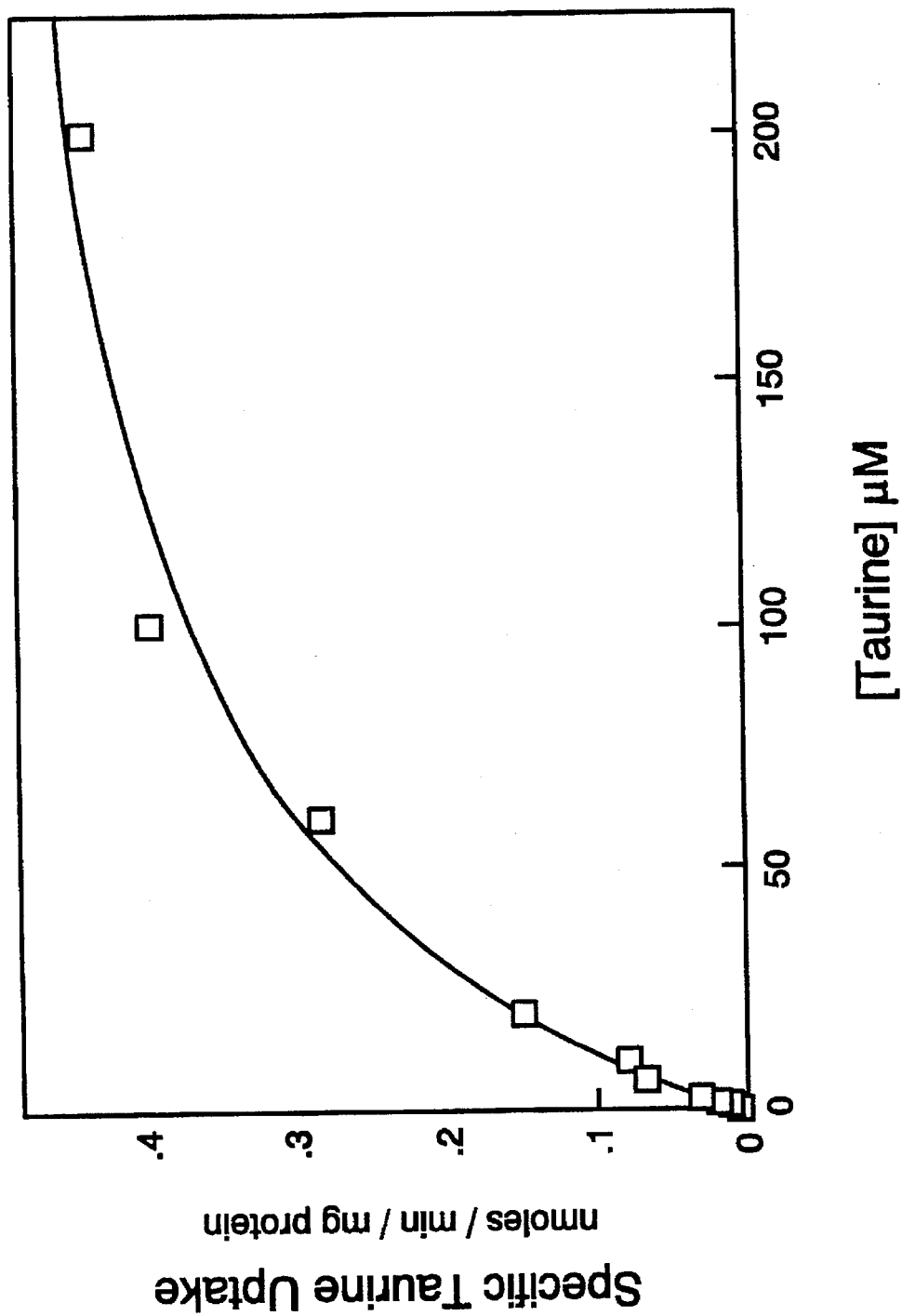

FIG. 8 Concentration dependence of taurine transport. COS cells transfected with rB16a were incubated with the indicated concentrations of [$^3$H]taurine for 30 seconds and the accumulated radioactivity was determined. The specific activity of [$^3$H]taurine was reduced with unlabeled taurine. Data represent specific transport expressed as nmoles per minute per mg protein, and are from a single experiment that was repeated with similar results (see Text).

Figure 9B:
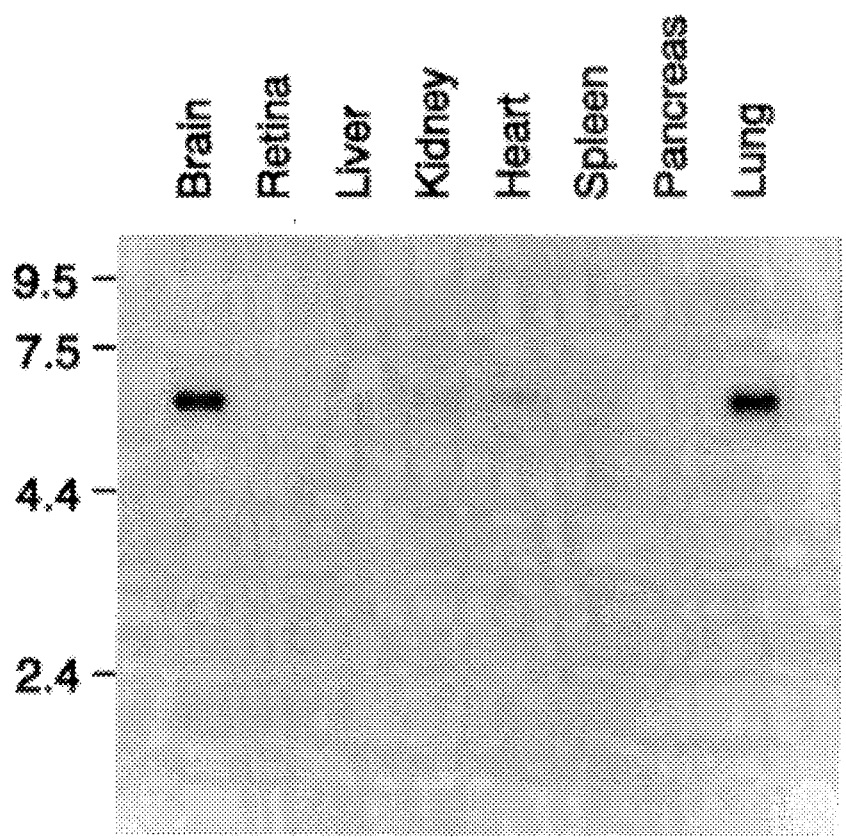

FIGS. 9A–9B Localization of the taurine transporter. FIG. 9A. Tissue distribution of mRNA encoding the taurine transporter as determined by PCR. Single-stranded cDNA converted from poly A+ RNA was used for PCR amplification (30 cycles) of taurine transporter cDNA from a variety of rat tissues. A plasmid containing the cloned taurine transporter was amplified under identical conditions as a control. Amplified products were detected by hybridization with an oligonucleotide probe specific to the taurine transporter; an autoradiogram of the Southern blot is shown. Equivalent samples of poly A+ RNA (not treated with reverse transcriptase) subjected to identical PCR conditions showed no hybridization with the transporter probe (not shown), indicating that the signals obtained with cDNA were not a result of genomic DNA contamination. The experiment was repeated with similar results. FIG. 9B Northern blot analysis of mRNA encoding the taurine transporter. Poly A+ RNA (5 µg) from a variety of rat tissues was separated by formaldehyde/agarose gel electrophoresis, blotted to a nylon membrane, and hybridized at high stringency with $^{32}$P-labeled taurine transporter cDNA (rB16a). The autoradiogram was developed after an overnight exposure. Size standards are indicated at the left in kilobases. The hybridizing transcript is ~6.2 kb.

Figures 1, 1D:
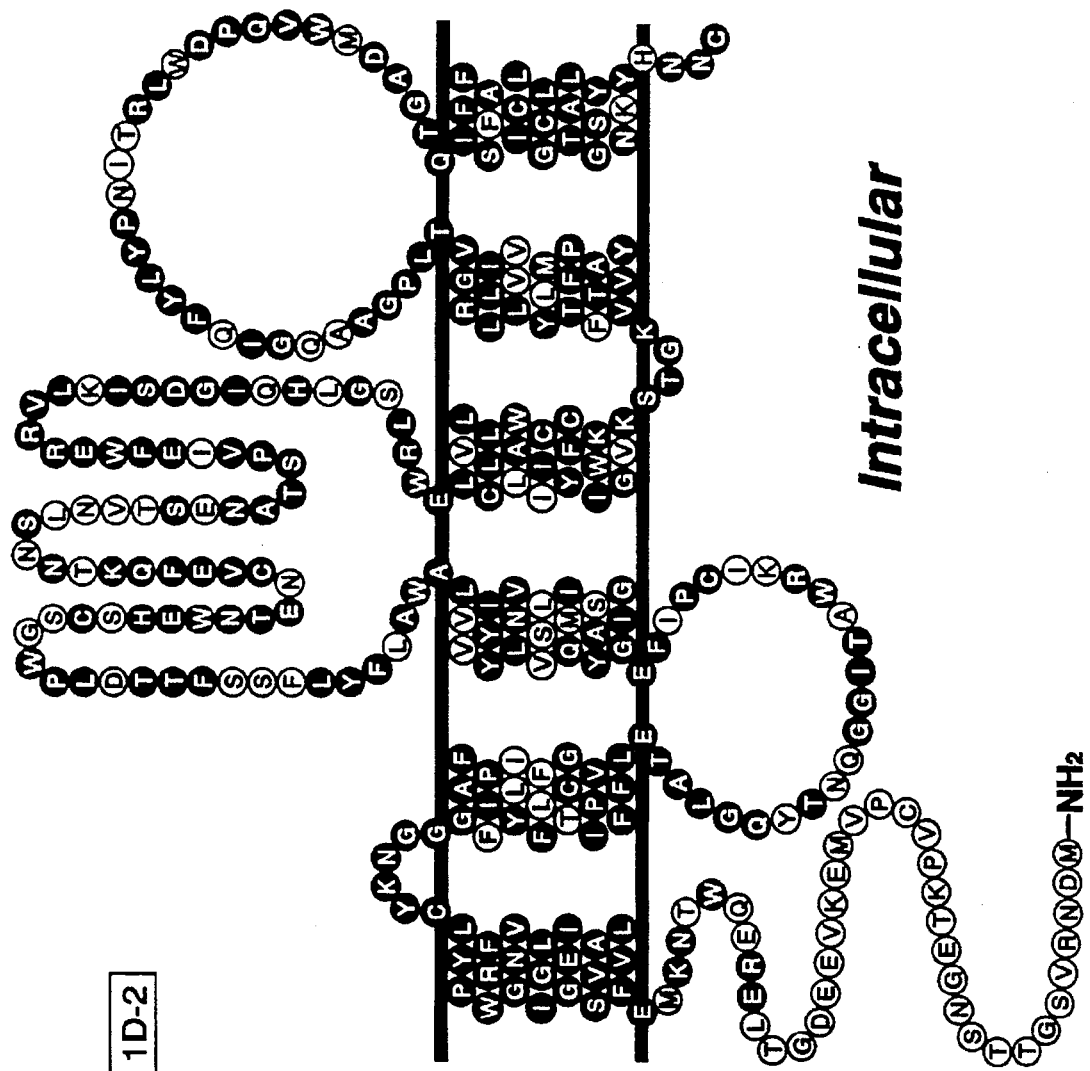
Figures 1, 1D, 2:
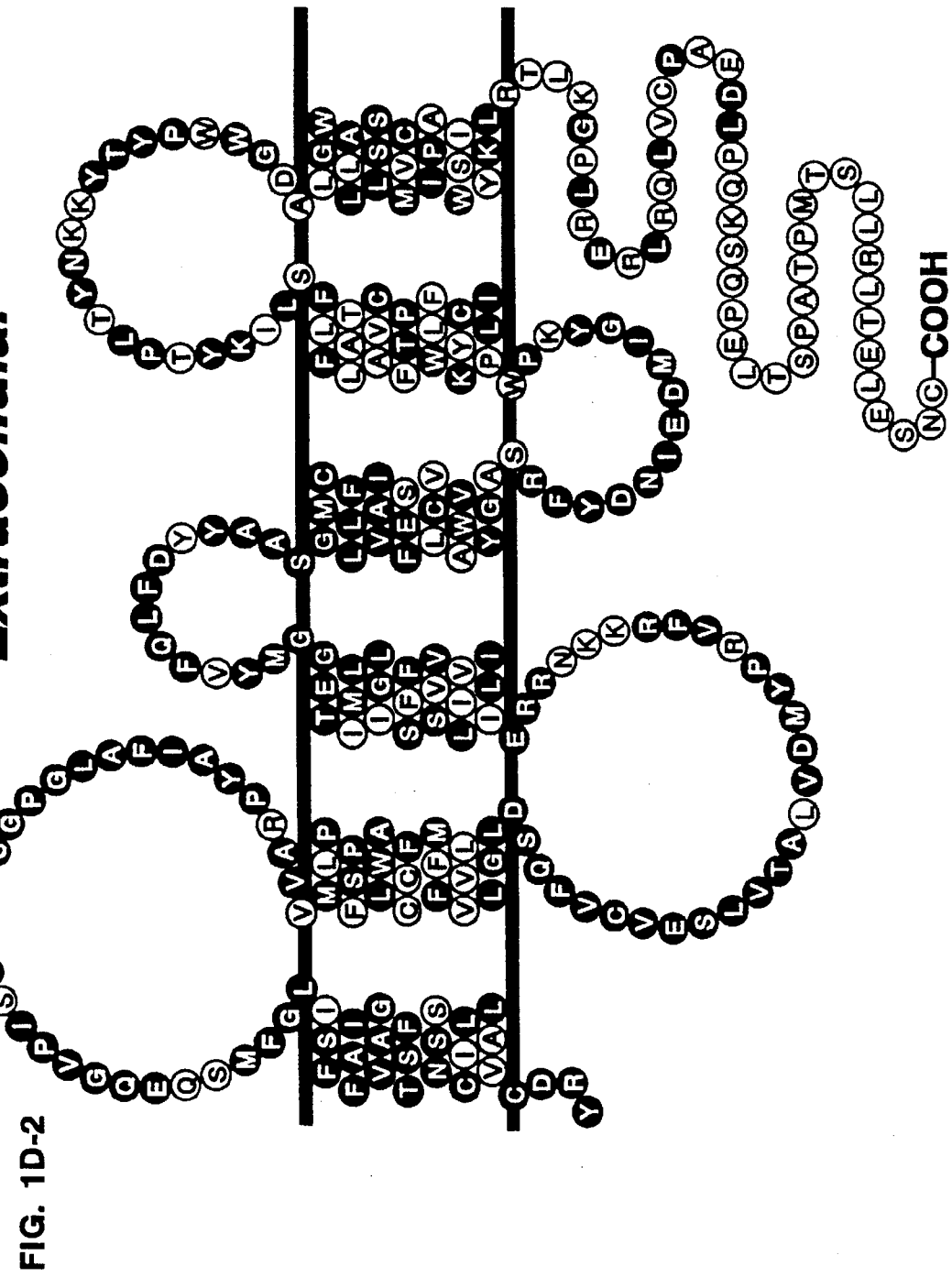
Figure 4A:
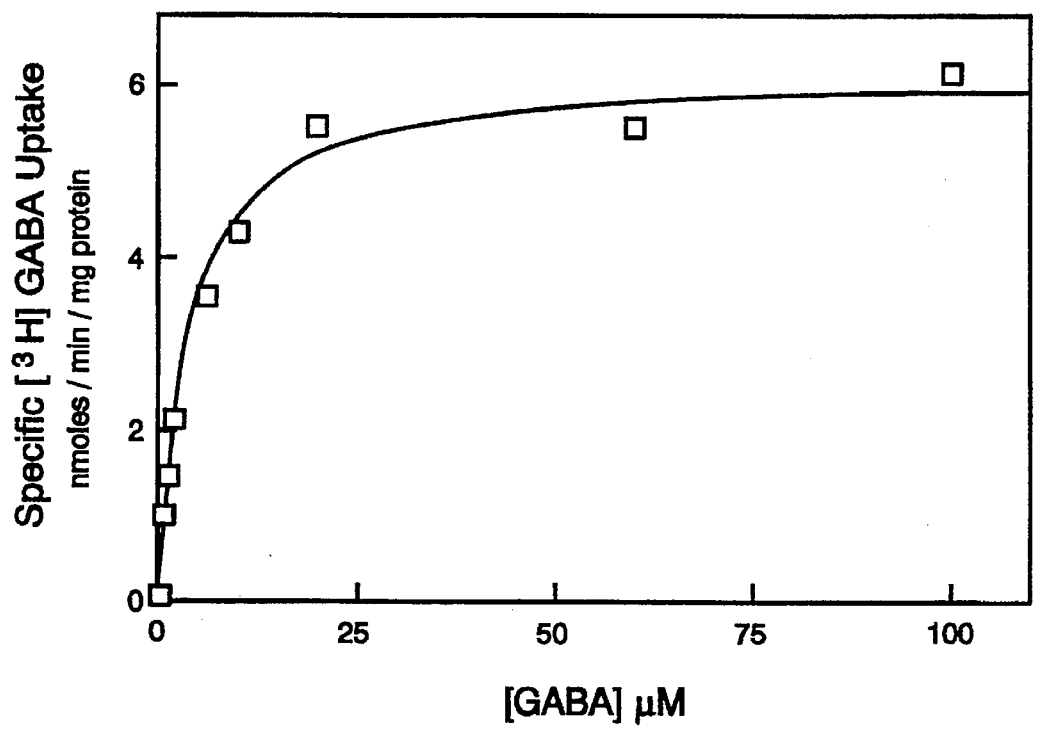
FIGS. 4A–4B Concentration dependence of GABA transport. COS cells transfected with GAT-2 (A) or GAT-3 (B)
Figure 4B:
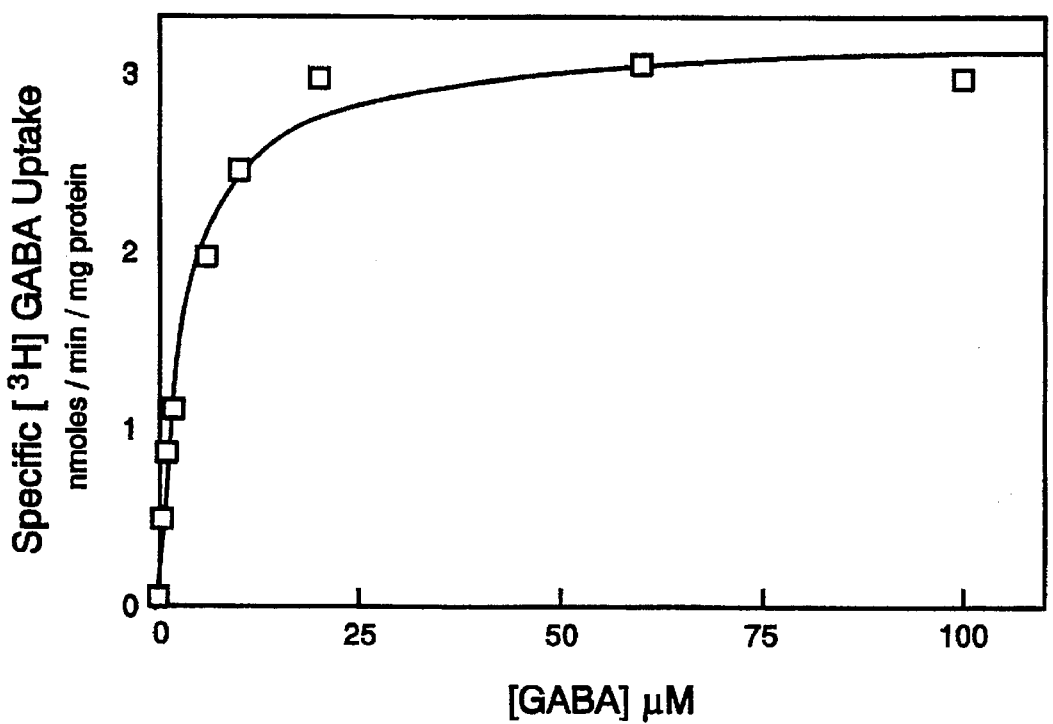

FIGS. 10A-1 to 10B-4 Nucleotide Sequence and Deduced Amino Acid of Human Transporters. FIGS. 10A-1 and 10A-2 Sequence Of the Human GAT-2 GABA Transporter (SEQ ID NOS: 7 and 8). Nucleotides are presented in the 5' to 3' orientation and the coding region is numbered starting from the first nucleotide in a partial cDNA clone. Deduced amino acid sequence by translation of a long open reading frame is shown. FIGS. 10B-1 to 10B-4 Sequence of the Human GAT-3 GABA Transporter (SEQ ID NOS: 9 and 10). Nucleotides are presented in the 5' to 3' orientation and the coding region is numbered starting from the putative initiating methionine and ending in the terminating codon. Deduced amino acid sequence by translation of a long open reading frame is shown.

DETAILED DESCRIPTION OF THE INVENTION

This invention provides an isolated nucleic acid molecule encoding a mammalian GABA transporter. This invention also provides an isolated nucleic acid molecule encoding a mammalian taurine transporter. This invention further provides an isolated nucleic acid molecule encoding a human GABA transporter. As used herein, the term "isolated nucleic acid molecule" means a non-naturally occurring nucleic acid molecule that is, a molecule in a form which does not occur in nature. Examples of such an isolated nucleic acid molecule are an RNA, cDNA, or isolated genomic DNA molecule encoding a mammalian GABA, or mammalian taurine transporter. As used herein, "GABA transporter" means a molecule which, under physiologic conditions, is substantially specific for the neurotransmitter GABA, is saturable, of high affinity for GABA (Km=4 µM), and exhibits pharmacological properties distinct from the neuronal GABA transporter. As used herein, "taurine transporter" means a molecule which, under physiologic conditions, is substantially specific for the neurotransmitter taurine, is saturable, and of high affinity for taurine. One embodiment of this invention is an isolated murine nucleic acid molecule encoding a GABA or taurine transporter. Such a molecule may have coding sequences substantially the same as the coding sequences shown in FIGS. 1A-1 to 1A-4, 1B-1 to 1B-2 or 1C-1 to 1C-4. The DNA molecules of FIGS. 1A-1 to 1A-4 (Sequence I.D. No. 1) and 1B-1 to 1B-2 (Seq I.D. No.3) encode the sequence of the mammalian GABA transporter genes. The DNA molecule of FIGS. 1C-1 to 1C-4 (Sequence I.D. No. 5) encodes the sequence of a mammalian taurine transporter gene. Another preferred embodiment of this invention is an isolated human nucleic acid molecule encoding a human GABA transporter. Such a molecule may have coding sequences substantially the same as the coding sequences shown in FIGS. 10A-1 to 10A-2 and 10B-1 to 10-B-4. The DNA molecules of FIGS. 10A-1 to 10A-2 (Sequence I.D. No.7) and 10B-1 to 10B-4 (Sequence I.D. No.9) encode the sequences of human GABA transporter genes. Another preferred embodiment of this invention is an isolated nucleic acid molecule encoding a human taurine transporter. Such a molecule may have coding sequences substantially similar to the sequence shown in FIGS. 1C-1 to 1C-4. One means of isolating a mammalian GABA or a mammalian taurine transporter is to probe a mammalian genomic library with a natural or artificially designed DNA probe, using methods well known in the art. In the preferred embodiment of this invention, the mammalian GABA and mammalian taurine transporter are human proteins and the nucleic acid molecules encoding them are isolated from a human cDNA library or a human genomic DNA library. DNA probes derived from the rat GABA transporter genes rB14b and rB8b, and DNA probes derived from the rat taurine transporter gene rB16a are useful probes for this purpose. DNA and cDNA molecules which encode mammalian GABA or mammalian taurine transporters are used to obtain complementary genomic DNA, cDNA or RNA from human, mammalian or other animal sources, or to isolate related cDNA or genomic clones by the screening of cDNA or genomic DNA libraries, by methods described in more detail below. Transcriptional regulatory elements from the 5' untranslated region of the isolated clone, and other stability, processing, transcription, translation, and tissue specificity determining regions from the 3' and 5' untranslated regions of the isolated gene are thereby obtained.

This invention provides a method for obtaining an isolated nucleic acid molecule encoding a human taurine transporter which comprises using oligonucleotide primers based on the nucleic acid sequence coding for a mammalian taurine receptor and the polymerase chain reaction (PCR) to detect the presence of the nucleic acid molecule coding for the taurine transporter in a human cDNA library. PCR is carried out at reduced annealing temperatures to allow for mismatches between the nucleic acid sequences encoding the rat taurine transporter and nucleic acid sequences encoding the human taurine transporter. Amplified DNA sequences encoding a human taurine transporter are detected by hybridization at reduced hybridization stringency with radiolabelled cDNA encoding the mammalian taurine receptor. A human cDNA library identified by the above method to contain a nucleic acid molecule encoding the human taurine transporter is then screened at low hybridization stringency with the same cDNA probe encoding the mammalian taurine receptor to isolate a cDNA clone encoding a human taurine transporter. A cDNA sequence from the resulting clone can then be used to screen additionally screen a human cDNA or human genomic DNA library to obtain the entire sequence of the human homologue of the mammalian taurine transporter. Primers used in the polymerase chain reaction to initially screen human cDNA libraries to identify human cDNA libraries containing clones encoding a human taurine receptor may be composed of a plurality of degenerate primers based on the sequence of the mammalian taurine transporter. The methods of synthesizing primers, of screening cDNA libraries by PCR to identify libraries containing a cDNA clone encoding the protein of interest are well known by one of skill in the art and examples of this method for obtaining a cDNA clone encoding the human homoloque of mammalian transporter are further given below. These same methods can be used to isolate cDNA and genomic DNAs encoding additional mammalian or human GABA transporter subtypes or taurine transporter subtypes encoded by different genes or encoded by the same gene and generated by alternative splicing of the RNA or rearrangement of the genomic DNA.

This invention provides an isolated nucleic acid molecule which has been so mutated as to be incapable of encoding a molecule having normal transporter activity, and not expressing native transporter. An example of a mutated nucleic acid molecule provided by this invention is an isolated nucleic acid molecule which has an in-frame stop codon inserted into the coding sequence such that the transcribed RNA is not translated into a protein having normal transporter activity.

This invention further provides a cDNA molecule encoding a mammalian GABA transporter, wherein the cDNA molecule has a coding sequence substantially the same as the coding sequence shown in FIGS. 1A-1 to 1A-4 or 1B-1 to 1B-2. (Sequence I.D. Nos. 1 or 3). This invention also provides a cDNA molecule encoding a mammalian taurine transporter, wherein the cDNA molecule has a coding sequence substantially the same as the coding sequence shown in FIGS. 1C-1 to 1C-4. (Sequence I.D. No. 5). This invention also provides a cDNA molecule encoding a human GABA transporter, wherein the cDNA molecule has a coding sequence substantially the same as the coding sequence shown in FIGS. 10A-1 to 10A-2 (Sequence I.D. No. 7) and 10B-1 to 10B-4 (Sequence I.D. No. 9). These molecules and their equivalents were obtained by the means described above.

This invention also provides an isolated protein which is a mammalian GABA transporter. This invention further provides an isolated protein which is a mammalian taurine transporter. In one embodiment of this invention, the protein is a murine GABA transporter protein having an amino acid sequence substantially similar to the amino acid sequence shown in FIGS. 1A-1 to 1A-4 (Seq. I.D. Nos. 1 and 2) or 1B-1 to 1B-2 (Seq. I.D. Nos. 3 and 4). In another embodiment of this invention, the protein is a murine taurine transporter protein having an amino acid sequence substantially similar to the amino acid sequence shown in FIGS. 1C-1 to 1C-4 (Seq. I.D. Nos. 5 and 6). In a preferred embodiment of this invention, the protein is a human GABA transporter protein having an amino acid sequence substantially the same as the sequence shown in FIGS. 10A-1 to 10A-2 (Sequence I.D. Nos. 7 and 8) and FIGS. 10B-1 to 10B-4 (Sequence I.D. Nos. 9 and 10). Another preferred embodiment of this invention, the protein is a human taurine transporter protein having an amino acid sequence substantially similar to the amino acid sequence shown in FIGS. 1C-1 to 1C-4 (Seq. I.D. Nos. 5 and 6). As used herein, the term "isolated protein" is intended to encompass a protein molecule free of other cellular components. One means for obtaining an isolated GABA or taurine transporter is to express DNA encoding the transporter in a suitable host, such as a bacterial, yeast, or mammalian cell, using methods well known to those skilled in the art, and recovering the transporter protein after it has been expressed in such a host, again using methods well known in the art. The transporter may also be isolated from cells which express it, in particular from cells which have been transfected with the expression vectors described below in more detail.

This invention also provides a vector comprising an isolated nucleic acid molecule such as DNA, RNA, or cDNA, encoding a mammalian GABA transporter. This invention also provides a vector comprising an isolated nucleic acid molecule such as DNA, RNA, or cDNA, encoding a mammalian taurine transporter. This invention also provides a vector comprising an isolated nucleic acid molecule such as DNA, RNA, or cDNA, encoding a human GABA transporter. This invention also provides a vector comprising an isolated nucleic acid molecule such as DNA, RNA, or cDNA, encoding a human taurine transporter. Examples of vectors are viruses such as bacteriophages (such as phage lambda), cosmids, plasmids (such as pUC18, available from Pharmacia, Piscataway, N.J.), and other recombination vectors. Nucleic acid molecules are inserted into vector genomes by methods well known to those skilled in the art. Examples of such plasmids are plasmids comprising cDNA having a coding sequence substantially the same as: the coding sequence shown in FIGS. 1A-1 to 1A-4 (Seq. I.D. No. 1) and designated clone pEVJB-rB14b deposited on Feb. 7, 1992 under ATCC Accession No. 75203, the coding sequence shown in FIGS. 1B-1 to 1B-2 (Seq. I.D. No. 3) and designated clone pEVJB-rBSb deposited on Feb. 7, 1992 under ATCC Accession No. 75201, the coding sequence shown in FIG. 1C (Seq. I.D. No. 5) and designated pEVJB-rB16a deposited on Feb. 7, 1992 under ATCC Accession No. 75202, the coding sequence shown in FIGS. 10A-1 to 10A-2, (Sequence I.D. No. 7) designated pBluescript-hHE7a and pBluescript-hS3a and deposited under ATCC Accession Nos. 75322 and 75323, both deposited on Oct. 8, 1992, respectively, or the coding sequence shown in FIGS. 10B-1 to 10B-4 (SEQ. I.D. No. 9) and designated pcEXV-hGAT-3 and deposited Oct. 8, 1992 under ATCC Accession No. 75324, deposited Oct. 8, 1992. Alternatively, to obtain these vectors, insert and vector DNA can both be exposed to a restriction enzyme to create complementary ends on both molecules which base pair with each other and are then ligated together with a ligase. Alternatively, linkers can be ligated to the insert DNA which correspond to a restriction site in the vector DNA, which is then digested with the restriction enzyme which cuts at that site. Other means are also available.

This invention also provides vectors comprising a DNA molecule encoding a mammalian GABA transporter and vectors comprising a DNA molecule encoding a mammalian taurine transporter, adapted for expression in a bacterial cell, a yeast cell, or a mammalian cell which additionally comprise the regulatory elements necessary for expression of the DNA in the bacterial, yeast, or mammalian cells so located relative to the DNA encoding a mammalian GABA transporter or to the DNA encoding a mammalian taurine transporter as to permit expression thereof. DNA having coding sequences substantially the same as the coding sequence shown in FIGS. 1A-1 to 1A-4 or FIGS. 1B-1 to 1B-2 may usefully be inserted into the vectors to express mammalian GABA transporters. DNA having coding sequences substantially the same as the coding sequence shown in FIG. 1C may usefully be inserted into the vectors to express mammalian taurine transporters. This invention also provides vectors comprising a DNA molecule encoding a human GABA transporter adapted for expression in a bacterial cell, a yeast cell, or a mammalian cell which additionally comprise the regulatory elements necessary for expression of the DNA in the bacterial, yeast, or mammalian cells so located relative to the DNA encoding a human GABA transporter as to permit expression thereof. DNA having coding sequences substantially the same as the coding sequence shown in FIGS. 10A and 10B may usefully be inserted into the vectors to express human GABA transporters. This invention also provides vectors comprising a DNA molecule encoding a human taurine transporter adapted for expression in a bacterial cell, a yeast cell, or a mammalian cell which additionally comprise the regulatory elements necessary for expression of the DNA in the bacterial, yeast, or mammalian cells so located relative to the DNA encoding a human taurine transporter as to permit expression thereof. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (Maniatis, et al., Molecular Cloning, Cold Spring Harbor Laboratory, 1982). Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well known in the art, for example the methods described above for constructing vectors in general. Expression vectors are useful to produce cells that express the transporter. Certain uses for such cells are described in more detail below.

In one embodiment of this invention a plasmid fs adapted for expression in a bacterial, yeast, or, in particular, a mammalian cell wherein the plasmid comprises a DNA molecule encoding a mammalian GABA transporter or a DNA molecule encoding a mammalian taurine transporter and the regulatory elements necessary for expression of the DNA in the bacterial, yeast, or mammalian cell so located relative to the DNA encoding a mammalian GABA transporter or to the DNA encoding a mammalian taurine transporter as to permit expression thereof. In another embodiment of this invention a plasmid is adapted for expression in a bacterial, yeast, or, in particular, a mammalian cell wherein the plasmid comprises a DNA molecule encoding a human GABA transporter or human taurine transporter and the regulatory elements necessary for expression of the DNA in the bacterial, yeast, or mammalian cell so located relative to the DNA encoding a human GABA transporter or human taurine transporter as to permit expression thereof. Suitable plasmids may include, but are not limited to plasmids adapted for expression in a mammalian cell, e.g., EVJB or EXV. Examples of such plasmids adapted for expression in a mammalian cell are plasmids comprising cDNA having coding sequences substantially the same as the coding sequence shown in FIGS. 1A-1 to 1A-4, 1B-1 to 1B-2, 1C-1 to 1C-4, 10A-1 to 10A-2 and 10B-1 to 10B-4 and the regulatory elements necessary for expression of the DNA in the mammalian cell. These plasmids have been designated pEVJB-rB14b deposited under ATCC Accession No.75203, pEVJB-rBSb deposited under ATCC Accession No.75201, pEVJB-rB16a deposited under ATCC Accession No.75202, pBluescript-hHE7a and pBluescript-hS3a deposited under ATCC Accession Nos. 75322 and 75323, respectively and pcEXV-hGAT-3 deposited under ATCC accession No. 75324, respectively. Those skilled in the art will readily appreciate that numerous plasmids adapted for expression in a mammalian cell which comprise DNA encoding a mammalian GABA transporter, a mammalian taurine transporter, a human GABA transporter or human taurine transporter and the regulatory elements necessary to express such DNA in the mammalian cell may be constructed utilizing existing plasmids and adapted as appropriate to contain the regulatory elements necessary to express the DNA in the mammalian cell. The plasmids may be constructed by the methods described above for expression vectors and vectors in general, and by other methods well known in the art.

The deposits discussed supra were made pursuant to, and in satisfaction of, the provisions of the Budapest Treaty on the International Recognition of the Deposit of Microorganisms for the Purpose of Patent Procedure with the American Type Culture Collection (ATCC), 12301 Parklawn Drive, Rockville, Md. 20852.

This invention provides a mammalian cell comprising a DNA molecule encoding a mammalian GABA transporter or a DNA molecule encoding a mammalian taurine transporter, such as a mammalian cell comprising a plasmid adapted for expression in a mammalian cell, which comprises a DNA molecule encoding a mammalian GABA transporter or a DNA encoding a mammalian taurine transporter and the regulatory elements necessary for expression of the DNA in the mammalian cell so located relative to the DNA encoding a mammalian transporter as to permit expression thereof. This invention also provides a mammalian cell comprising a DNA molecule encoding a human GABA transporter or a human taurine transporter, such as a mammalian cell comprising a plasmid adapted for expression in a mammalian cell, which comprises a DNA molecule encoding a human GABA transporter or DNA encoding a human taurine transporter and the regulatory elements necessary for expression of the DNA in the mammalian cell so located relative to the DNA encoding a human transporter as to permit expression thereof. Numerous mammalian cells may be used as hosts, including, but not limited to, the mouse fibroblast cell NIH3T3, CHO cells, HeLa cells, Ltk⁻ cells, Cos cells, etc. Expression plasmids such as that described supra may be used to transfect mammalian cells by methods well known in the art such as calcium phosphate precipitation, or DNA encoding these transporters may be otherwise introduced into mammalian cells, e.g., by microinjection, to obtain mammalian cells which comprise DNA, e.g., cDNA or a plasmid, encoding a mammalian GABA transporter, encoding a mammalian taurine transporter or encoding a human GABA transporter.

This invention provides a nucleic acid probe comprising a nucleic acid molecule of at least 15 nucleotides capable of specifically hybridizing with a sequence included within the sequence of a nucleic acid molecule encoding a mammalian GABA transporter, for example with a coding sequence included within the sequences shown in FIGS. 1A-1 to 1A-4 and 1B-1 to 1B-2. This invention also provides a nucleic acid probe comprising a nucleic acid molecule of at least 15 nucleotides capable of specifically hybridizing with a sequence included within the sequence of a nucleic acid molecule encoding a taurine transporter, for example with a coding sequence included within the sequence shown in FIG. 1C. This invention also provides a nucleic acid probe comprising a nucleic acid molecule of at least 15 nucleotides capable of specifically hybridizing with a sequence included within the sequence of a nucleic acid molecule encoding a human GABA transporter, for example with a coding sequence included within the sequence shown in FIGS. 10A-1 to 10A-2 and 10B-1 to 10B-4. This invention also provides a nucleic acid probe comprising a nucleic acid molecule of at least 15 nucleotides capable of specifically hybridizing with a sequence included within the sequence of a nucleic acid molecule encoding a human taurine transporter, for example with a coding sequence substantially similar to the coding sequence included within the sequence shown in FIGS. 1C-1 to 1C-4. As used herein, the phrase "specifically hybridizing" means the ability of a nucleic acid molecule to recognize a nucleic acid sequence complementary to its own and to form double-helical segments through hydrogen bonding between complementary base pairs. Nucleic acid probe technology is well known to those skilled in the art who will readily appreciate that such probes may vary greatly in length and may be labeled with a detectable label, such as a radioisotope or fluorescent dye, to facilitate detection of the probe. Detection of nucleic acid encoding a mammalian GABA transporter, mammalian taurine transporter, human GABA transporter or human taurine transporter is useful as a diagnostic test for any disease process in which levels of expression of the corresponding GABA or taurine transporter are altered. DNA probe molecules are produced by insertion of a DNA molecule which encodes the mammalian GABA transporter, the mammalian taurine transporter, the human GABA transporter or the human taurine transporter or fragments thereof into suitable vectors, such as plasmids or bacteriophages, followed by insertion into suitable bacterial host cells and replication and harvesting of the DNA probes, all using methods well known in the art. For example, the DNA may be extracted from a cell lysate using phenol and ethanol, digested with restriction enzymes corresponding to the insertion sites of the DNA into the vector (discussed above), electrophoresed, and cut out of the resulting gel. Examples of such DNA molecules are shown in FIGS. 1A-1 to 1A-4, 1B-1 to 1B-2, 1C-1 to 1C-4, 10A-1 to 10A-2 and 10B-1 to 10B-4. The probes are useful for 'in situ' hybridization or in order to locate tissues which express this gene family, or for other hybridization assays for the presence of these genes or their mRNA in various biological tissues. In addition, synthesized oligonucleotides (produced by a DNA synthesizer) complementary to the sequence of a DNA molecule which encodes a mammalian GABA transporter or a mammalian taurine transporter or complementary to the sequence of a DNA molecule which encodes a human GABA transporter or human taurine transporter, are useful as probes for these genes, for their associated mRNA, or for the isolation of related genes by homology screening of genomic or cDNA libraries, or by the use of amplification techniques such as the Polymerase Chain Reaction.

This invention also provides a method of detecting expression of a GABA transporter on the surface of a cell by detecting the presence of mRNA coding for a GABA transporter. This invention also provides a method of detecting expression of a taurine transporter on the surface of the cell by detecting the presence of mRNA coding for a taurine transporter. This invention further provides a method of detecting the expression of a human GABA or human taurine transporter on the surface of the cell by detecting the presence of mRNA coding for the corresponding GABA or taurine transporter. These methods comprise obtaining total mRNA from the cell using methods well known in the art and contacting the mRNA so obtained with a nucleic acid probe as described hereinabove, under hybridizing conditions, detecting the presence, of mRNA hybridized to the probe, and thereby detecting the expression of the transporter by the cell. Hybridization of probes to target nucleic acid molecules such as mRNA molecules employs techniques well known in the art. However, in one embodiment of this invention, nucleic acids are extracted by precipitation from lysed cells and the mRNA is isolated from the extract using a column which binds the poly-A tails of the mRNA molecules (48). The mRNA is then exposed to radioactively labelled probe on a nitrocellulose membrane, and the probe hybridizes to and thereby labels complementary mRNA sequences. Binding may be detected by autoradiography or scintillation counting. However, other methods for performing these steps are well known to those skilled in the art, and the discussion above is merely an example.

This invention provides an antisense oligonucleotide having a sequence capable of binding specifically with any sequences of an mRNA molecule which encodes a mammalian GABA transporter so as to prevent translation of the mammalian GABA transporter. This invention also provides an antisense oligonucleotide having a sequence capable of binding specifically with any sequences of an mRNA molecule which encodes a mammalian taurine transporter so as to prevent translation of the mammalian taurine transporter. This invention provides an antisense oligonucleotide having a sequence capable of binding specifically with any sequences of an mRNA molecule which encodes a human GABA transporter so as to prevent translation of the human GABA transporter. This invention also provides an antisense oligonucleotide having a sequence capable of binding specifically with any sequences of an mRNA molecule which encodes a human taurine transporter so as to prevent translation of the human taurine transporter. As used herein, the phrase "binding specifically" means the ability of an antisense oligonucleotide to recognize a nucleic acid sequence complementary to its own and to form double-helical segments through hydrogen bonding between complementary base pairs. The antisense oligonucleotide may have a sequence capable of binding specifically with any sequences of the cDNA molecules whose sequences are shown in FIGS. 1A-1 to 1A-4, 1B-1 to 1B-2, 1C-1 to 1C-4, 10A-1 to 10A-2 and 10B-1 to 10B-4. A particular example of an antisense oligonucleotide is an antisense oligonucleotide comprising chemical analogues of nucleotides.

This invention also provides a pharmaceutical composition comprising an effective amount of the oligonucleotide described above effective to reduce expression of a mammalian GABA transporter by passing through a cell membrane and binding specifically with mRNA encoding a mammalian GABA transporter in the cell so as to prevent its translation and a pharmaceutically acceptable hydrophobic carrier capable of passing through a cell membrane. This invention provides a pharmaceutical composition comprising an effective amount of the oligonucleotide described above effective to reduce expression of a mammalian taurine transporter by passing through a cell membrane and binding specifically with mRNA encoding a mammalian taurine transporter in the cell so as to prevent its translation and a pharmaceutically acceptable hydrophobic carrier Capable of passing through a cell membrane. This invention also provides a pharmaceutical composition comprising an effective amount of the oligonucleotide described above effective to reduce expression of a human GABA transporter by passing through a cell membrane and binding specifically with mRNA encoding a human GABA transporter in the cell so as to prevent its translation and a pharmaceutically acceptable hydrophobic carrier capable of passing through a cell membrane. This invention also provides a pharmaceutical composition comprising an effective amount of the oligonucleotide described above effective to reduce expression of a human taurine transporter by passing through a cell membrane and binding specifically with mRNA encoding a human taurine transporter in the cell so as to prevent its translation and a pharmaceutically acceptable hydrophobic carrier capable of passing through a cell membrane. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The oligonucleotide may be coupled to a substance which inactivates mRNA, such as a ribozyme. The pharmaceutically acceptable hydrophobic carrier capable of passing through cell membranes may also comprise a structure which binds to a transporter specific for a selected cell type and is thereby taken up by cells of the selected cell type. The structure may be part of a protein known to bind a cell-type specific transporter, for example an insulin molecule, which would target pancreatic cells. DNA molecules having coding sequences Substantially the same as the coding sequence shown in FIGS. 1A-1 to 1A-4, 1B-1 to 1B-2, 1C-1 to 1C-4, 10A-1 to 10A-2 and 10B-1 to 10B-4 may be used as the oligonucleotides of the pharmaceutical composition.

This invention also provides a method of treating abnormalities which are alleviated by reduction of expression of a GABA transporter. This method comprises administering to a subject an effective amount of the pharmaceutical composition described above effective to reduce expression of the GABA transporter by the subject. This invention further provides a method of treating an abnormal condition related to GABA transporter activity which comprises administering to a subject an amount of the pharmaceutical composition described above effective to reduce expression of the GABA transporter by the subject. Examples of such abnormal conditions are epilepsy and generalized anxiety. This invention also provides a method of treating abnormalities which are alleviated by reduction of expression of a taurine transporter. This method comprises administering to a subject an effective amount of the pharmaceutical composition described above effective to reduce expression of the taurine transporter by the subject. This invention further provides a method of treating an abnormal condition related to taurine transporter activity which comprises administering to a subject an amount of the pharmaceutical composition described above effective to reduce expression of the taurine transporter by the subject. Examples of such abnormal conditions are epilepsy, migraine, and ischemia.

Antisense oligonucleotide drugs inhibit translation of mRNA encoding these transporters. Synthetic antisense oligonucleotides, or other antisense chemical structures are designed to bind to mRNA encoding a GABA transporter or to mRNA encoding a taurine transporter and inhibit translation of mRNA and are useful as drugs to inhibit expression of GABA transporter genes or taurine transporter genes in patients.. This invention provides a means to therapeutically alter levels of expression of mammalian GABA or taurine transporters by the use of a synthetic antisense oligonucleotide drug (SAOD) which inhibits translation of mRNA encoding these transporters. Synthetic antisense oligonucleotides, or other antisense chemical structures designed to recognize and selectively bind to mRNA, are constructed to be Complementary to portions of the nucleotide sequences shown in FIGS. 1A-1 to 1A-4, 1B-1 to 1B-2, 1C-1 to 1C-4, 10A-1 to 10A-2 or 10B-1 to 10B-4 of DNA, RNA or of chemically modified, artificial nucleic acids. The SAOD is designed to be stable in the blood stream for administration to patients by injection, or in laboratory cell culture conditions, for administration to cells removed from the patient. The SAOD is designed to be capable of passing through cell membranes in order to enter the cytoplasm of the cell by virtue of physical and chemical properties of the SAOD which render it capable of passing through cell membranes (e.g., by designing small, hydrophobic SAOD chemical structures) or by virtue of specific transport systems in the cell which recognize and transport the SAOD into the cell. In addition, the SAOD can be designed for administration only to certain selected cell populations by targeting the SAOD to be recognized by specific cellular uptake mechanisms which bind and take up the SAOD only within certain selected cell populations. For example, the SAOD may be designed to bind to a transporter found only in a certain cell type, as discussed above. The SAOD is also designed to recognize and selectively bind to the target mRNA sequence, which may correspond to a sequence contained within the sequences shown in FIGS. 1A-1 to 1A-4, 1B-1 to 1B-2, 1C-1 to 1C-4, 10A-1 to 10A-2 or 10B-1 to 10B-4 by virtue of complementary base pairing to the mRNA. Finally, the SAOD is designed to inactivate the target mRNA sequence by any of three mechanisms: 1) by binding to the target mRNA and thus inducing degradation of the mRNA by intrinsic cellular mechanisms such as RNAse I digestion, 2) by inhibiting translation of the mRNA target by interfering with the binding of translation-regulating factors or of ribosomes, or 3) by inclusion of other chemical structures, such as ribozyme sequences or reactive chemical groups, which either degrade or chemically modify the target mRNA. Synthetic antisense oligonucleotide drugs have been shown to be capable of the properties described above when directed against mRNA targets (11,76). In addition, coupling of ribozymes to antisense oligonucleotides is a promising strategy for inactivating target mRNA (60). An SAOD serves as an effective therapeutic agent if it is designed to be administered to a patient by injection, or if the patient's target cells are removed, treated with the SAOD in the laboratory, and replaced in the patient. In this manner, an SAOD serves as a therapy to reduce transporter expression in particular target cells of a patient, in any clinical condition which may benefit from reduced expression of GABA or taurine transporters.

This invention provides an antibody directed to the mammalian GABA transporter. This antibody may comprise, for example, a monoclonal antibody directed to an epitope of a mammalian GABA transporter present on the surface of a cell, the epitope having an amino acid sequence substantially the same as an amino acid sequence for a cell surface epitope of the mammalian GABA transporter included in the amino acid sequence shown in FIGS. 1A-1 to 1A-4 or 1B-1 to 1B-2. This invention provides an antibody directed to the mammalian taurine transporter. This antibody may comprise, for example, a monoclonal antibody directed to an epitope of a mammalian taurine transporter present on the surface of a cell, the epitope having an amino acid sequence substantially the same as an amino acid sequence for a cell surface epitope of the mammalian taurine transporter included in the amino acid sequence shown in FIGS. 1C-1 to 1C-4. This invention provides an antibody directed to a human GABA transporter. This antibody may comprise, for example, a monoclonal antibody directed to an epitope of a human GABA transporter present on the surface of a cell, the epitope having an amino acid sequence substantially the same as an amino acid sequence for a cell surface epitope of the human GABA transporter, included in the amino acid sequence shown in FIGS. 10A-1 to 10A-2 and 10B-1 to 10B-4. This invention provides an antibody directed to a human taurine transporter. This antibody may comprise, for example, a monoclonal antibody directed to an epitope of a human taurine transporter present on the surface of a cell, the epitope having an amino acid sequence substantially similar to the amino acid sequence for a cell surface epitope of the mammalian taurine transporter shown in FIGS. 1C-1 to 1C-4. Amino acid sequences may be analyzed by methods well known to those skilled in the art to determine whether they produce hydrophobic or hydrophilic regions in the proteins which they build. In the case of cell membrane proteins, hydrophobic regions are well known to form the part of the protein that is inserted into the lipid bilayer which forms the cell membrane, while hydrophilic regions are located on the cell surface, in an aqueous environment. Therefore antibodies to the hydrophilic amino acid sequences shown in FIGS. 1A-1 to 1A-4 or 1B-1 to 1B-2 will bind to a surface epitope of a mammalian GABA transporter, and antibodies to the hydrophilic amino acid sequences shown in FIG. 1C will bind to a surface epitope of a mammalian taurine transporter, as described. Antibodies to the hydrophilic amino acid sequences shown in FIGS. 10A-1 to 10A-2 or 10B-1 to 10B-4 will bind to a surface epitope of a human GABA transporter. Antibodies directed to conserved hydrophilic amino acid sequences specific to a mammalian taurine transporter will bind to a surface epitope of a human taurine transporter. Antibodies directed to mammalian or human transporters may be serum-derived or monoclonal and are prepared using methods well known in the art. For example, monoclonal antibodies are prepared using hybridoma technology by fusing antibody producing B cells from immunized animals with myeloma cells and selecting the resulting hybridoma cell line producing the desired antibody. Cells such as NIH3T3 cells or Ltk⁻ cells may be used as immunogens to raise such an antibody. Alternatively, synthetic peptides may be prepared using commercially available machines and the amino acid sequences shown in FIGS. 1A-1 to 1A-4, 1B-1 to 1B-2, 1C-1 to 1C-4, 10A-1 to 10A-2 and 10B-1 to 10B-4. As a still further alternative, DNA, such as a cDNA or a fragment thereof, may be cloned and expressed and the resulting polypeptide recovered and used as an immunogen. These antibodies are useful to detect the presence of mammalian transporters encoded by the isolated DNA, or to inhibit the function of the transporters in living animals, in humans, or in biological tissues or fluids isolated from animals or humans.

This invention also provides a pharmaceutical composition which comprises an effective amount of an antibody directed to an epitope of the mammalian transporter, effective to block binding of naturally occurring substrates to the transporter, and a pharmaceutically acceptable carrier. A monoclonal antibody directed to an epitope of a mammalian GABA transporter present on the surface of a cell which has an amino acid sequence substantially the same as an amino acid sequence for a cell surface epitope of the mammalian GABA transporter included in the amino acid sequences shown in FIGS. 1A-1 to 1A-4 and 1B-1 to 1B-2 useful for this purpose. A monoclonal antibody directed to an epitope of a mammalian taurine transporter present on the surface of a cell which has an amino acid sequence substantially the same as an amino acid sequence for a cell surface epitope of the mammalian taurine transporter included in the amino acid sequence shown in FIGS. 1C-1 to 1C-4 is also useful for this purpose.

This invention also provides a pharmaceutical composition which comprises an effective amount of an antibody directed to an epitope of the human transporter, effective to block binding of naturally occurring substrates to the transporter, and a pharmaceutically acceptable carrier. A monoclonal antibody directed to an epitope of a human GABA transporter present on the surface of a cell which has an amino acid sequence substantially the same as an amino acid sequence for a cell surface epitope of the human GABA transporter included in the amino acid sequences shown in FIGS. 10A or 10B is useful for this purpose.

This invention also provides a pharmaceutical composition which comprises an effective amount of an antibody directed to an epitope of a human taurine transporter, effective to block binding of naturally occurring substrates to the human taurine transporter, and a pharmaceutically acceptable carrier. A monoclonal antibody directed to a conserved epitope specific to a mammalian taurine transporter present on the surface of a cell which has an amino acid sequence substantially the same as an amino acid sequence for a cell surface epitope of the mammalian taurine transporter included in the amino acid sequence shown in FIGS. 1C-1 to 1C-4 is useful for this purpose.

This invention also provides a method of treating abnormalities in a subject which are alleviated by reduction of expression of a mammalian transporter which comprises administering to the subject an effective amount of the pharmaceutical composition described above effective to block binding of naturally occurring substrates to the transporter and thereby alleviate abnormalities resulting from overexpression of a mammalian transporter. Binding of the antibody to the transporter prevents the transporter from functioning, thereby neutralizing the effects of overexpression. The monoclonal antibodies described above are both useful for this purpose. This invention additionally provides a method of treating an abnormal condition related to an excess of transporter activity which comprises administering to a subject an amount of the pharmaceutical composition described above effective to block binding of naturally occurring substrates to the transporter and thereby alleviate the abnormal condition. Some examples of abnormal conditions associated with excess GABA transporter activity are epilepsy and generalized anxiety. Excess taurine transporter activity associated disorders are epilepsy, migraine, and ischemia.

This invention provides methods of detecting the presence of a GABA or a taurine transporter on the surface of a cell which comprises contacting the cell with an antibody directed to the mammalian GABA transporter or an antibody directed to the mammalian taurine transporter, under conditions permitting binding of the antibody to the transporter, detecting the presence of the antibody bound to the cell, and thereby the presence of the mammalian GABA transporter or the presence of the taurine transporter on the surface of the cell. Such methods are useful for determining whether a given cell is defective in expression of GABA transporters or is defective in expression of taurine transporters on the surface of the cell. Bound antibodies are detected by methods well known in the art, for example by binding fluorescent markers to the antibodies and examining the cell sample under a fluorescence microscope to detect fluorescence on a cell indicative of antibody binding. The monoclonal antibodies described above are useful for this purpose.

This invention provides a transgenic nonhuman mammal expressing DNA encoding a mammalian GABA transporter and a transgenic nonhuman mammal expressing DNA encoding a mammalian taurine transporter. This invention further provides a transgenic nonhuman mammal expressing DNA encoding a human GABA transporter and a transgenic nonhuman mammal expressing DNA encoding a human taurine transporter. This invention also provides a transgenic nonhuman mammal expressing DNA encoding a mammalian GABA transporter so mutated as to be incapable of normal transporter activity, and not expressing native GABA transporter and a transgenic nonhuman mammal expressing DNA encoding a mammalian taurine transporter so mutated as to be incapable of normal transporter activity, and not expressing native taurine transported. This invention further provides a transgenic nonhuman mammal expressing DNA encoding a human GABA transporter so mutated as to be incapable of normal transporter activity, and not expressing native GABA transporter and a transgenic nonhuman mammal expressing DNA encoding a human taurine transporter so mutated as to be incapable of normal transporter activity, and not expressing native taurine transporter.

This invention provides a transgenic nonhuman mammal whose genome comprises DNA encoding a mammalian GABA transporter so placed as to be transcribed into antisense mRNA which is complementary to mRNA encoding a GABA transporter and which hybridizes to mRNA encoding a GABA transporter thereby reducing its translation and a transgenic nonhuman mammal whose genome comprises DNA encoding a mammalian taurine transporter so placed as to be transcribed into antisense mRNA which is complementary to mRNA encoding a taurine transporter and which hybridizes to mRNA encoding a taurine transporter thereby reducing its translation. This invention further provides a transgenic nonhuman mammal whose genome comprises DNA encoding a human GABA transporter so placed as to be transcribed into antisense mRNA which is complementary to mRNA encoding a GABA transporter and which hybridizes to mRNA encoding a GABA transporter thereby reducing its translation and a transgenic nonhuman mammal whose genome comprises DNA encoding a human taurine transporter so placed as to be transcribed into antisense mRNA which is complementary to mRNA encoding a taurine transporter and which hybridizes to mRNA encoding a taurine transporter thereby reducing its translation. The DNA may additionally comprise an inducible promoter or additionally comprise tissue specific regulatory elements, so that expression can be induced, or restricted to specific cell types. Examples of DNA are DNA or cDNA molecules having a coding sequence substantially the same as the coding sequences shown in FIGS. 1A-1 to 1A-4, 1B-1 to 1B-2, 1C-1 to 1C-4, 10A-1 to 10A-2 and 10B-1 to 10B-4. An example of a transgenic animal is a transgenic mouse. Examples of tissue specificity-determining regions are the metallothionein promotor (46,83) and the L7 promotor (84).

Animal model systems which elucidate the physiological and behavioral roles of mammalian transporters are produced by creating transgenic animals in which the expression of a transporter is either increased or decreased, or the amino acid sequence of the expressed transporter protein is altered, by a variety of techniques. Examples of these techniques include, but are not limited to: 1) Insertion of normal or mutant versions of DNA encoding a mammalian transporter or homologous animal versions of these genes, by microinjection, retroviral infection or other means well known to those skilled in the art, into appropriate fertilized embryos in order to produce a transgenic animal (24) or 2) Homologous recombination (7,82) of mutant or normal, human or animal versions of these genes with the native gene locus in transgenic animals to alter the regulation of expression or the structure of these transporters. The technique of homologous recombination is well known in the art. It replaces the native gene with the inserted gene and so is useful for producing an animal that cannot express native transporter but does express, for example, an inserted mutant transporter, which has replaced the native transporter in the animal's genome by recombination, resulting in underexpression of the transporter. Microinjection adds genes to the genome, but does not remove them, and so is useful for producing an animal which expresses its own and added transporters, resulting in overexpression of the transporter.

One means available for producing a transgenic animal, with a mouse as an example, is as follows: Female mice are mated, and the resulting fertilized eggs are dissected out of their oviducts. The eggs are stored in an appropriate medium such as M2 medium (24). DNA or cDNA encoding a mammalian transporter is purified from a vector (such as plasmids EVJB-rB14b, EVJB-rB8b, or EVJB-rB16a described above) by methods well known in the art. Inducible promoters may be fused with the coding region of the DNA to provide an experimental means to regulate expression of the trans-gene. Alternatively or in addition, tissue specific regulatory elements may be fused with the coding region to permit tissue-specific expression of the trans-gene2. The DNA, in an appropriately buffered solution, is put into a microinjection needle (which may be made from capillary tubing using a piper puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only for exemplary purposes.

Since the normal action of transporter-specific drugs is to activate or to inhibit the transporter, the transgenic animal model systems described above are useful for testing the biological activity of drugs directed against these transporters even before such drugs become available. These animal model systems are useful for predicting or evaluating possible therapeutic applications of drugs which activate or inhibit these transporters by inducing or inhibiting expression of the native or trans-gene and thus increasing or decreasing expression of normal or mutant transporters in the living animal. Thus, a model system is produced in which the biological activity of drugs directed against these transporters are evaluated before such drugs become available. The transgenic animals which over or under produce the transporter indicate by their physiological state whether over or under production of the transporter is therapeutically useful. It is therefore useful to evaluate drug action based on the transgenic model system. One use is based on the fact that it is well known in the art that a drug such as an antidepressant acts by blocking neurotransmitter uptake, and thereby increases the amount of neurotransmitter in the synaptic cleft. The physiological result of this action is to stimulate the production of less transporter by the affected cells, leading eventually to underexpression. Therefore, an animal which underexpresses transporter is useful as a test system to investigate whether the actions of such drugs which result in under expression are in fact therapeutic. Another use is that if overexpression is found to lead to abnormalities, then a drug which down-regulates or acts as an antagonist to the transporter is indicated as worth developing, and if a promising therapeutic application is uncovered by these animal model systems, activation or inhibition of the GABA transporter is achieved therapeutically either by producing agonist or antagonist drugs directed against these GABA transporters or by any method which increases or decreases the expression of these transporters in man.

Further provided by this invention is a method of determining the physiological effects of expressing varying levels of mammalian transporters which comprises producing a transgenic nonhuman animal whose levels of mammalian transporter expression are varied by use of an inducible promoter which regulates mammalian transporter expression. This invention also provides a method of determining the physiological effects of expressing varying levels of mammalian transporters which comprises producing a panel of transgenic nonhuman animals each expressing a different amount of mammalian transporter. Such animals may be produced by introducing different amounts of DNA encoding a mammalian transporter into the oocytes from which the transgenic animals are developed.

This invention provides a method of determining the physiological effects of expressing varying levels of human transporters which comprises producing a transgenic non-human animal whose levels of human transporter expression are varied by use of an inducible promoter which regulates transporter expression. This invention also provides a method of determining the physiological effects of expressing varying levels of human transporters which comprises producing a panel of transgenic nonhuman animals each expressing a different amount of the human transporter. Such animals may be produced by introducing different amounts of DNA encoding a human transporter into the oocytes from which the transgenic animals are developed.

This invention also provides a method for identifying a substance capable of alleviating abnormalities resulting from overexpression of a mammalian transporter comprising administering the substance to a transgenic nonhuman mammal expressing at least one artificially introduced DNA molecule encoding a mammalian transporter and determining whether the substance alleviates the physical and behavioral abnormalities displayed by the transgenic nonhuman mammal as a result of overexpression of a mammalian transporter. This invention also provides a method for identifying a substance capable of alleviating abnormalities resulting from overexpression of a human transporter comprising administering the substance to a transgenic nonhuman mammal expressing at least one artificially introduced DNA molecule encoding a human transporter and determining whether the substance alleviates the physical and behavioral abnormalities displayed by the transgenic nonhuman mammal as a result of overexpression of a human transporter. As used herein, the term "substance" means a compound or composition which may be natural, synthetic, or a product derived from screening. Examples of DNA molecules are DNA or cDNA molecules having a coding sequence substantially the same as the coding sequences shown in FIGS. 1A-1 to 1A-4, 1B-1 to 1B-2, 1C-1 to 1C-4, 10A-1 to 10A-2 or 10B-1 to 10B-4.

This invention provides a pharmaceutical composition comprising an amount of the substance described supra effective to alleviate the abnormalities resulting from overexpression of GABA transporter and a pharmaceutically acceptable carrier. This invention also provides a pharmaceutical composition comprising an amount of the substance described supra effective to alleviate the abnormalities resulting from overexpression of taurine transporter and a pharmaceutically acceptable carrier. This invention further provides a pharmaceutical composition comprising an amount of the substance described supra effective to alleviate the abnormalities resulting from overexpression of a human GABA or human taurine transporter and a pharmaceutically acceptable carrier.

This invention also provides a method for treating the abnormalities resulting from overexpression of a mammalian transporter which comprises administering to a subject an amount of the pharmaceutical composition described above effective to alleviate the abnormalities resulting from overexpression of a mammalian transporter. This invention further provides a method for treating the abnormalities resulting from overexpression of a human GABA or human taurine transporter which comprises administering to a subject an amount of the pharmaceutical composition described above effective to alleviate the abnormalities resulting from overexpression of a human GABA or taurine transporter.

This invention provides a method for identifying a substance capable of alleviating the abnormalities resulting from underexpression of a mammalian transporter comprising administering the substance to the transgenic nonhuman mammal described above which expresses only nonfunctional mammalian transporter and determining whether the substance alleviates the physical and behavioral abnormalities displayed by the transgenic nonhuman mammal as a result of underexpression of a mammalian transporter. This invention further provides a method for identifying a substance capable of alleviating the abnormalities resulting from underexpression of a human GABA or human taurine transporter comprising administering the substance to the transgenic nonhuman mammal described above which expresses only nonfunctional human GABA or human taurine transporter and determining whether the substance alleviates the physical and behavioral abnormalities displayed by the transgenic nonhuman mammal as a result of underexpression of a human GABA or human taurine transporter.

This invention also provides a pharmaceutical composition comprising an amount of a substance effective to alleviate abnormalities resulting from underexpression of transporter and a pharmaceutically acceptable carrier. This invention also provides a pharmaceutical composition comprising an amount of a substance effective to alleviate abnormalities resulting from underexpression of a human GABA or human taurine transporter and a pharmaceutically acceptable carrier.

This invention provides a method for treating the abnormalities resulting from underexpression of a mammalian transporter which comprises administering to a subject an amount of the pharmaceutical composition described above effective to alleviate the abnormalities resulting from underexpression of a mammalian transporter. This invention further provides a method for treating the abnormalities resulting from underexpression of a human GABA or human taurine transporter which comprises administering to a subject an amount of the pharmaceutical composition described above effective to alleviate the abnormalities resulting from underexpression of a human GABA or human taurine transporter.

This invention provides a method for diagnosing a predisposition to a disorder associated with the expression of a specific mammalian transporter allele which comprises: a) obtaining DNA of subjects suffering from the disorder; b) performing a restriction digest of the DNA with a panel of restriction enzymes; c) electrophoretically separating the resulting DNA fragments on a sizing gel; d) contacting the resulting gel with a nucleic acid probe capable of specifically hybridizing to DNA encoding a mammalian transporter and labelled with a detectable marker; e) detecting labelled bands which have hybridized to the DNA encoding a mammalian transporter labelled with a detectable marker to create a unique band pattern specific to the DNA of subjects suffering from the disorder; f) preparing DNA obtained for diagnosis by steps a–e; and g) comparing the unique band pattern specific to the DNA of subjects suffering from the disorder from step e and the DNA obtained for diagnosis from step f to determine whether the patterns are the same or different and thereby to diagnose predisposition to the disorder if the patterns are the same. This method may also be used to diagnose a disorder associated with the expression of a specific mammalian transporter allele.

This invention provides a method for diagnosing a predisposition to a disorder associated with the expression of a specific human GABA or human taurine transporter allele which comprises: a) obtaining DNA of subjects suffering from the disorder; b) performing a restriction digest of the DNA with a panel of restriction enzymes; c) electrophoretically separating the resulting DNA fragments on a sizing gel; d) contacting the resulting gel with a nucleic acid probe capable of specifically hybridizing to DNA encoding a human GABA or human taurine transporter and labelled with a detectable marker; e) detecting labelled bands which have hybridized to the DNA encoding a human GABA or human taurine transporter labelled with a detectable marker to create a unique band pattern specific to the DNA of subjects suffering from the disorder; f) preparing DNA obtained for diagnosis by steps a–e; and g) comparing the unique band pattern specific to the DNA of subjects suffering from the disorder from step e and the DNA obtained for diagnosis from step f to determine whether the patterns are the same or different and thereby to diagnose predisposition to the disorder if the patterns are the same. This method may also be used to diagnose a disorder associated with the expression of a specific human GABA or human taurine transporter allele.

This invention provides a method of preparing the isolated transporter which comprises inducing cells to express transporter, recovering the transporter from the resulting cells, and purifying the transporter so recovered. An example of an isolated GABA transporter is an isolated protein having substantially the same amino acid Sequence as the amino acid sequence shown in FIGS. 1A-1 to 1A-4 or 1B-1 to 1B-2. An example of an isolated taurine transporter is an isolated protein having substantially the same amino acid sequence shown in FIGS. 1C-1 to 1C-4. This invention further provides a method for preparing an isolated human GABA transporter which comprises inducing cells to express the human GABA transporter, recovering the human GABA transporter from the resulting cells, and purifying the human GABA transporter so recovered. An example of an isolated human GABA transporter is an isolated protein having substantially the same amino acid sequence as the amino acid sequence shown in FIGS. 10A-1 to 10A-2 or 10B-1 to 10B-4. This invention further provides a method for preparing an isolated human taurine transporter which comprises inducing cells to express the human taurine transporter, recovering the human taurine transporter from the resulting cells, and purifying the human taurine transporter so recovered. An example of an isolated human taurine transporter is an isolated protein having an amino acid sequence substantially similar to the amino acid sequence of a mammalian taurine transporter shown in FIGS. 1C-1 to 1C-4. For example, cells can be induced to express transporters by exposure to substances such as hormones. The cells can then be homogenized and the transporter isolated from the homogenate using an affinity column comprising, for example, GABA, taurine, or another substance which is known to bind to the transporter. The resulting fractions can then be purified by contacting them with an ion exchange column, and determining which fraction contains transporter activity or binds anti-transporter antibodies.

This invention provides a method of preparing the isolated mammalian GABA transporter which comprises inserting nucleic acid encoding the mammalian GABA transporter in a suitable vector, inserting the resulting vector in a suitable host cell, recovering the transporter produced by the resulting cell, and purifying the transporter so recovered. An example of an isolated GABA transporter is an isolated protein having substantially the same amino acid sequence as the amino acid sequence shown in FIGS. 1A-1 to 1A-4 or 1B-1 to 1B-2. This invention also provides a method of preparing the isolated mammalian taurine transporter which comprises inserting nucleic acid encoding a mammalian taurine transporter in a suitable vector, inserting the resulting vector in a suitable host cell, recovering the transporter produced by the resulting cell, and purifying the transporter so recovered. This invention also provides a method of preparing the isolated human GABA transporter which comprises inserting nucleic acid encoding the human GABA transporter in a suitable vector, inserting the resulting vector in a suitable host cell, recovering the human GABA transporter produced by the resulting cell, and purifying the human GABA transporter so recovered. These methods for preparing GABA or taurine transporters uses recombinant DNA technology methods well known in the art. For example, isolated nucleic acid encoding GABA or taurine transporter is inserted in a suitable vector, such as an expression vector. A suitable host cell, such as a bacterial cell, or a eukaryotic cell such as a yeast cell, is transfected with the vector. GABA or taurine transporter is isolated from the culture medium by affinity purification or by chromatography or by other methods well known in the art.

This invention provides a method for determining whether a substrate not known to be capable of binding to a mammalian GABA transporter can bind to the mammalian GABA transporter which comprises contacting a mammalian cell comprising a DNA molecule encoding a mammalian GABA transporter with the substrate under conditions permitting binding of substrates known to bind to the transporter, detecting the presence of any of the substrate bound to the transporter, and thereby determining whether the substrate binds to the transporter. The DNA in the cell may have a coding sequence substantially the same as the coding sequences shown in FIGS. 1A-1 to 1A-4 or 1B-1 to 1B-2. This invention provides a method for determining whether a substrate not known to be capable of binding to a mammalian taurine transporter can bind to the mammalian GABA transporter which comprises contacting a mammalian cell comprising a DNA molecule encoding a mammalian taurine transporter with the substrate under conditions permitting binding of substrates known to bind to the transporter, detecting the presence of any of the substrate bound to the transporter, and thereby determining whether the substrate binds to the transporter. The DNA in the cell may have a coding sequence substantially the same as the coding sequences shown in FIGS. 1C-1 to 1C-4.

This invention also provides a method for determining whether a substrate not known to be capable of binding to a human GABA transporter can bind to a human GABA transporter which comprises contacting a mammalian cell comprising a DNA molecule encoding a human GABA transporter with the substrate under conditions permitting binding of substrates known to bind to the transporter, detecting the presence of any of the substrate bound to the transporter, and thereby determining whether the substrate binds to the transporter. The DNA in the cell may have a coding sequence substantially the same as the coding sequences shown in FIGS. 10A-1 to 10A-2 or 10B-1 to 10B-4. This invention also provides a method for determining whether a substrate not known to be capable of binding to a human taurine transporter can bind to a human taurine transporter which comprises contacting a mammalian cell comprising a DNA molecule encoding a human taurine transporter with the substrate under conditions permitting binding of substrates known to bind to the transporter, detecting the presence of any of the substrate bound to the transporter, and thereby determining whether the substrate binds to the transporter. Preferably, the mammalian cell is nonneuronal in origin. An example of a nonneuronal mammalian cell is a Cos7 cell. The preferred method for determining whether a substrate is capable of binding to the mammalian transporter comprises contacting a transfected nonneuronal mammalian cell (i.e. a cell that does not naturally express any type of transporter, thus will only express such a transporter if it is transfected into the cell) expressing a transporter on its surface, or contacting a membrane preparation derived from such a transfected cell, with the substrate under conditions which are known to prevail, and thus to be associated with, in vivo binding of the substrates to a transporter, detecting the presence of any of the substrate being tested bound to the transporter on the surface of the cell, and thereby determining whether the substrate binds to the transporter. This response system is obtained by transfection of isolated DNA into a suitable host cell. Such a host system might be isolated from pre-existing cell lines, or can be generated by inserting appropriate components into existing cell lines. Such a transfection system provides a complete response system for investigation or assay of the functional activity of mammalian transporters with substrates as described above. Transfection systems are useful as living cell cultures for competitive binding assays between known or candidate drugs and substrates which bind to the transporter and which are labeled by radioactive, spectroscopic or other reagents. Membrane preparations containing the transporter isolated from transfected cells are also useful for these competitive binding assays. A transfection system constitutes a "drug discovery system" useful for the identification of natural or synthetic compounds with potential for drug development that can be further modified or used directly as therapeutic compounds to activate or inhibit the natural functions of the mammalian transporter and/or the human transporter. The transfection system is also useful for determining the affinity and efficacy of known drugs at the mammalian transporter sites and human transporter sites.

This invention provides a method for isolating membranes which comprise GABA or taurine transporters. In a preferred embodiment of the invention, membranes comprising a GABA or taurine transporter are isolated from transfected cells comprising a plasmid vector which further comprises the regulatory elements necessary for the expression of the DNA encoding a GABA or taurine transporter so located relative to the DNA encoding the GABA or taurine transporter as to permit expression thereof. The DNA may have the coding sequence substantially the same as the sequence shown in FIGS. 1A-1 to 1A-4, 1B-1 to 1B-2, 1C-1 to 1C-4, 10A-1 to 10A-2 or 10B-1 to 10B-4. The host cell may be a bacterial, yeast, or a mammalian cell. Examples of such cells include the mouse fibroblast cell line NIH3T3, CHO cells, HELA cells, Ltk- cells and Y1 cells. A method for isolating membranes which contain a GABA or taurine transporter comprises preparing a cell lysate from cells expressing the GABA or taurine transporter and isolating membranes from the cell lysate. Methods for the isolation of membranes are well known by one of skill in the art. A method for the isolation of membranes from transfected cells is further described by Branchek et al. (1990). Membranes isolated from transfected cells expressing a GABA or taurine transporter are useful for identifying compounds which may include substrates, drugs or other molecules that specifically bind to a GABA or taurine transporter using radioligand binding methods (Branchek et al. 1990) or other methods described herein. The specificity of the binding of the compound to the transporter may be identified by its high affinity for a particular transporter.

This invention further provides a method for the isolation of vesicles from cells expressing a GABA or taurine transporter. In a preferred embodiment of the invention, vesicles comprising a GABA or taurine transporter are isolated from transfected cells comprising a plasmid vector which further comprises the regulatory elements necessary for the expression of the DNA encoding a GABA or taurine transporter so located relative to the DNA encoding the GABA or taurine transporter as to permit expression thereof. The DNA may have the coding sequence substantially the same as the sequence shown in FIGS. 1A-1 to 1A-4, 1B-1 to 1B-2, 1C-1 to 1C-4, 10A-1 to 10A-2 or 10B-1 to 10B-4. A method for the isolation of vesicles is described by Barber and Jamieson (1970) and by Mabjeesh et al. (1992). Vesicles comprising a GABA or taurine transporter are useful for assaying and identifying compounds, which may include substrates, drugs or other molecules that enhance or decrease GABA or taurine transporter activity. The compounds may modulate transporter activity by interacting directly with the transporter or by interacting with other cellular components that modulate transporter activity. Vesicles provide an advantage over whole cells in that the vesicles permit one to choose the ionic compositions on both sides of the membrane such that transporter activity and its modulation by can be studied under a variety of controlled physiological or nonphysiological conditions. Methods for the assay of transporter activity are well known by one of skill in the art and are described herein below and by Kannner (1978) and Rudnick (1977).

This invention also provides a method of screening drugs to identify drugs which specifically interact with, and bind to, the mammalian GABA transporter on the surface of a cell which comprises contacting a mammalian cell comprising a DNA molecule encoding a mammalian GABA transporter on the surface of a cell with a plurality of drugs, detecting those drugs which bind to the mammalian cell, and thereby identifying drugs which specifically interact with, and bind to, the mammalian GABA transporter. The DNA in the cell may have a coding sequence substantially the same as the coding sequences shown in FIGS. 1A-1 to 1A-4 or 1B-1 to 1B-2. This invention also provides a method of screening drugs to identify drugs which specifically interact with, and bind to, the mammalian taurine transporter on the surface of a cell which comprises contacting a mammalian cell comprising a DNA molecule encoding a mammalian taurine transporter on the surface of a cell with a plurality of drugs, detecting those drugs which bind to the mammalian cell, and thereby identifying drugs which specifically interact with, and bind to, the mammalian taurine transporter. The DNA in the cell may have a coding sequence substantially the same as the coding sequences shown in FIGS. 1C-1 to 1C-4. This invention also provides a method of screening drugs to identify drugs which specifically interact with, and bind to, a human GABA transporter on the surface of a cell which comprises contacting a mammalian cell comprising a DNA molecule encoding a human GABA transporter on the surface of a cell with a plurality of drugs, detecting those drugs which bind to the mammalian cell, and thereby identifying drugs which specifically interact with, and bind to, the human GABA transporter. The DNA in the cell may have a coding sequence substantially the same as the coding sequences shown in FIGS. 10A-1 to 10A-2 or 10B-1 to 10-4. This invention also provides a method of screening drugs to identify drugs which specifically interact with, and bind to, a human taurine transporter on the surface of a cell which comprises contacting a mammalian cell comprising a DNA molecule encoding a human taurine transporter on the surface of a cell with a plurality of drugs, detecting those drugs which bind to the mammalian cell, and thereby identifying drugs which specifically interact with, and bind to, the human taurine transporter. Various methods of detection may be employed. The drugs may be "labeled" by association with a detectable marker substance (e.g., radiolabel or a non-isotopic label such as biotin). Preferably, the mammalian cell is nonneuronal in origin. An example of a nonneuronal mammalian cell is a Cos7 cell. Drug candidates are identified by choosing chemical compounds which bind with high affinity to the expressed transporter protein in transfected cells, using radioligand binding methods well known in the art, examples of which are shown in the binding assays described herein. Drug candidates are also screened for selectivity by identifying compounds which bind with high affinity to one particular transporter subtype but do not bind with high affinity to any other transporter subtype or to any other known transporter site. Because selective, high affinity compounds interact primarily with the target transporter site after administration to the patient, the chances of producing a drug with unwanted side effects are minimized by this approach. This invention provides a pharmaceutical composition comprising a drug identified by the method described above and a pharmaceutically acceptable carrier. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. Once the candidate drug has been shown to be adequately bio-available following a particular route of administration, for example orally or by injection (adequate therapeutic concentrations must be maintained at the site of action for an adequate period to gain the desired therapeutic benefit), and has been shown to be non-toxic and therapeutically effective in appropriate disease models, the drug may be administered to patients by that route of administration determined to make the drug bio-available, in an appropriate solid or solution formulation, to gain the desired therapeutic benefit.

Applicants have identified individual transporter subtype proteins and have described methods for the identification of pharmacological compounds for therapeutic treatments. Pharmacological compounds which are directed against specific transporter subtypes provide effective new therapies with minimal side effects.

Elucidation of the molecular structures of the neuronal GABA and taurine transporters is an important step in the understanding of GABAergic neurotransmission. This disclosure reports the isolation, amino acid sequence, and functional expression of a cDNA clones from rat brain which encode a GABA transporters and a cDNA clone from rat brain which encodes a taurine transporter. This disclosure reports the isolation, amino acid sequence, and functional expression of cDNA clones which encode human GABA transporters. The identification of these transporters will play a pivotal role in elucidating the molecular mechanisms underlying GABAergic transmission, and should also aid in the development of novel therapeutic agents.

Complementary DNA clones (designated rB14b, rBSb, and rB16a) encoding two GABA transporters and a taurine transporter, respectively, have been isolated from rat brain, and their functional properties have been examined in mammalian cells. The nucleotide sequence of rB14b predicts a protein of 602 amino acids, rBSb predicts a protein of 627 amino acids, and rB16a predicts a protein of 621 amino acids, with 12 highly hydrophobic regions compatible with membrane-spanning domains. When incubated with 50 nM [$^3$H]GABA, COS cells transiently transfected with rB14b or rB8b accumulated greater than 50-fold as much radioactivity as non-transfected control cells. The transporters encoded by rB14b and rBSb display high-affinity for GABA(Km=4 μM) and are dependent on external sodium and chloride. Similarly, when incubated with 50 nM [$^3$H]taurine, Cos cells transiently transfected with rB21a accumulated approximately 7-fold as much radioactivity as non-transfected control cells. The pattern of expression of mRNA encoding two GABA transporters has been examined in the rat brain. Additionally, complementary DNA clones (designated hGAT-3, hHE7a, hS3a) and a genomic DNA clone encoding human GABA transporters have been isolated and their functional properties examined in mammalian cells.

Analysis of the GABA and taurine transporter structure and function provides a model for the development of drugs useful for the treatment of epilepsy, generalized anxiety, migraine, ischemia and other neurological disorders.

This invention identifies for the first time three new mammalian transporter proteins, their amino acid sequences, and their mammalian genes. The invention further identifies the human homologues of two mammalian GABA transporter proteins, their amino acid sequence and their human genes. The information and experimental tools provided by this discovery are useful to generate new therapeutic agents, and new therapeutic or diagnostic assays for these new transporter proteins, their associated mRNA molecules or their associated genomic DNAs. The information and experimental tools provided by this discovery will be useful to generate new therapeutic agents, and new therapeutic or diagnostic assays for these new transporter proteins, their associated mRNA molecules, or their associated genomic DNAs.

Specifically, this invention relates to the first isolation of three mammalian cDNAs and genomic clones encoding GABA and taurine transporters and the first isolation of cDNAs and a genomic clone encoding the human homologues of two mammalian GABA transporters. The new mammalian genes for these transporters identified herein as rB14b, rBSb, and rB16a have been identified and characterized, and a series of related cDNA and genomic clones have been isolated. In addition, the mammalian GABA and mammalian taurine transporters have been expressed in Cos7 cells by transfecting the cells with the plasmids EVJB-rB14b, EVJB-rB8b, and EVJB-rB16a. The pharmacological binding properties of the proteins encoded have been determined,- and these binding properties classify these proteins as GABA transporters and a taurine transporter. Mammalian cell lines expressing the mammalian and human GABA transporters and the mammalian taurine transporter on the cell surface have been constructed, thus establishing the first well-defined, cultured cell lines with which to study the GABA and taurine transporters.

This invention will be better understood by reference to the Experimental Details which follow, but those skilled in the art will readily appreciate that the specific experiments detailed are only illustrative, and are not meant to limit the invention as described herein, which is defined by the claims which follow thereafter.

MATERIALS and METHODS

Materials for Mammalian GABA Transporter Studies

[$^3$H]GABA$^3$ (98.9 Ci/mmole) was obtained from New England Nuclear (Boston, Mass.). β-alanine, betaine and L-DABA (L-(2,4) diaminobutyric acid) were from Sigma Chemical Company (St. Louis, Mo.); guvacine, nipecotic acid, OH-nipecotic (hydroxynipecotic acid), and THPO (4,5,6,7-tetrahydroisoxazolo (4,5-c]pyridin-3-ol) were from RBI (Natick, Mass.). ACHC (cis-3-aminocyclohexanecarboxylic acid) was kindly provided by Drs. Richard Milius and William White of the NIgH Chemical Synthesis Program.

Materials for Mammalian Taurine Transporter Studies

[$^3$H]taurine (25.6 Ci/mmole) was from New England Nuclear (Boston, Mass.); taurine, GABA$^2$, hypotaurine, AEPA, AMSA, APSA, CSA, MEA, and β-alanine were from Sigma Chemical Corporation (St. Louis, Mo.); GES was a kind gift of Dr. J. Barry Lombardini (Department of Pharmacology, Texas Tech University).

Cloning and Sequencing of Mammalian GABA Transporters

A rat brain cDNA library in the Lambda ZAP II vector (Stratagene, La Jolla, Calif.) was screened at reduced stringency using probes representing the complete coding region of the rat GABA transporter cDNA (GAT-1 (21)). Exact primers derived from the nucleotide sequence of GAT-1 were used to generate GAT-1 PCR products from randomly-primed rat brain cDNA; the GAT-1 probes were then labeled and used to screen the library under reduced stringency as previously described (68). Lambda phage hybridizing with the probes at low stringency were plaque purified and rescreened at high stringency to eliminate clones which were identical to GAT-1. One of the clones hybridizing at high stringency was subsequently confirmed by sequence analysis to encode GAT-1 (21). Clones hybridizing only at low stringency were converted to phagemids by in vivo excision with fl helper phage. Nucleotide sequences of double-stranded cDNAs in pBluescript were analyzed by the Sanger dideoxy nucleotide chain-termination method (59) using Sequence (U.S. Biochemical Corp., Cleveland, Ohio).

Expression of Mammalian GABA Transporters cDNA clones (designated rB14b and rBSb) representing the complete coding regions of two putative transporters were cloned into the eukaryotic expression vector pEVJB (modified from pcEXV-3; (51)). Utilizing restriction enzyme sites present in pBluescript, rB14b was subcloned as a 2.0 kb HindIII/XbaI fragment which contained 126 base pairs of 5'-untranslated sequence and 94 base pairs of 3'-untranslated sequence. Similarly, rBSb was subcloned as a 2.1 kb XbaI/SalI fragment containing 0.3 kb of 3'-untranslated sequence. Transient transfections of COS cells were carried out using DEAE-dextran with DMSO according to the method of Lopata etal. (44) with minor modifications. COS cells were grown (37° C., 5% CO$_2$) in high glucose Dulbecco's modified Eagle medium supplemented with 10% bovine calf serum, 100 U/ml penicillin G, and 100 μg/ml streptomycin sulfate. Cells were routinely used two days after transfection for transport studies.

Transport Studies of Mammalian GABA Transporters

To measure transport, COS cells grown in 6-well (well diameter=35mm) or 24-well (well diameter=18mm) plates were washed 3× with HEPES-buffered saline (HBS, in mM: NaCl, 150; HEPES, 20; CaCl$_2$, 1; glucose, 10; KCl, 5; MgCl$_2$, 1; pH 7.4) and allowed to equilibrate in a 37° C. water bath. After 10 minutes the medium was removed and a solution containing [³H]GABA (New England Nuclear, sp. activity=89.8 Ci/mmole) and required drugs in HBS was added (1.5 ml/35 mm well; 0.5 ml/18 mm well). Nonspecific uptake was defined in parallel wells with 1 mM unlabeled substrate, and was subtracted from total uptake (no competitor) to yield specific uptake; all data represent specific uptake. Plates were incubated at 37° C. for 10 minutes unless indicated otherwise, then washed rapidly 3× with ice-cold HBS. Cells were solubilized with 0.05% sodium deoxycholate/0.1N NaOH, an aliquot neutralized with 1N HCl, and radioactivity was determined by scintillation counting. Protein was quantified in an aliquot of the solubilized cells using a BIO-RAD protein assay kit, according to the manufacturers directions.

Northern Blot Analysis of RNA Encoding Mammalian Transporters

Total cellular RNA was isolated from rat brain and liver using RNazol (Cinna/Biotecx Laboratories Inc.; Houston, Tex.) as outlined by the manufacturer. Denatured RNA samples (25 µg) were separated in a 1.0% agarose gel containing 3.3% formaldehyde. RNAs were transferred to nylon membranes (Genescreen Plus; New England Nuclear, Boston, Mass.) by overnight capillary blotting in 10× SSC. Northern blots were rinsed and then baked for 2 hours at 80° C. under vacuum. Prehybridization was for 2 hours at 65° C. in a solution containing 50% formamide, 1M NaCl, 10% dextran sulfate, and 1% sodium dodecyl sulfate. Blots were hybridized overnight at 65° C. with $^{32}$P-labeled DNA probes (randomly primed GAT-2 or GAT-3 full-length cDNA clones) in prehybridization mixture containing 100 µg/ml sonicated salmon sperm DNA. The blots were washed successively in 2× SSC/2% SDS, 1× SSC/2% SDS, and 0.2× SSC/2% SDS at 65° C., then exposed to Kodak XAR-5 film with one intensifying screen at –90° C. for four days.

Tissue Localization Studies

To identify tissues expressing mRNAs for the novel GABA transporters and the previously cloned GABA transporter GAT-1 (21), specific PCR primers (25 mers) were designed such that ≈700 base pair fragments encoding TMs 1 through 5 of each transporter could be amplified and detected by hybridization with $^{32}$P-labeled oligonucleotides. For rB14b, the sequences of the sense and anti-sense oligonucleotides were derived from amino acids 36 to 43 (5'-GACCAACAAGATGGAGTTCGTACTG) (SEQ ID NO: 14) and 247 to 254 TGTTACTCCTCGGATCAACAGGACC) (SEQ ID NO: 15); for rBSb, the oligonucleotides were derived from amino acids 52 to 60 (5'-GGAGTTCGTGTTGAGCGTAGGAGAG) (SEQ ID NO: 16) and 271 to 279 (5'-GAACTTGATGCCTTCCGAGGCACCC) (SEQ ID NO: 17); and for GAT-1 (21), the oligonucleotide sequences were derived from amino acids 50 to 57 (5'-ACGCTTCGACTTCCTCATGTCCTGT) (SEQ ID NO: 18) and 274 to 282 (5'-GAATCAGACAGCTTTCGGAAGTTGG) (SEQ ID NO: 19). Primers were also designed to amplify the cDNA encoding cyclophilin, a constitutively expressed gene, as a control (5'-GTCTGCTTCGAGCTGTTTGCAGACA (SEQ ID NO: 20), sense; 5'-TTAGAGTTGTCCACAGTCGGAGATG (SEQ ID NO: 21), anti-sense) (12). To detect amplified sequences, oligonucleotide probes were synthesized for GAT-1, rB14b, and rBSb which corresponded to amino acids 196 to 219, 161 to 183, and 207 to 229, respectively. Each probe was shown to hybridize with its respective transporter cDNA and not with any other transporter cDNA under study.

Poly A+ RNA (1 µg, Clonetech, Palo Alto, Calif.) from each of seven rat tissues was converted to single-stranded cDNA by random priming using Superscript reverse transcriptase (BRL, Gaithersburg, Md.). PCR reactions were carried out in a buffer containing 20 mM Tris (pH 8.3), 50 mM KCl, 1.5 mM MgCl$_2$, 0.001% gelatin, 2 mM dNTP's, 1 µM each primer, and Taq polymerase with either cDNA, RNA, water, or a control plasmid for 30 cycles of 94° c./2 min., 68° C./2 min., 72° C./3 min. PCR products were separated by electrophoresis in 1.2% agarose gels, blotted to nylon membranes (Genescreen Plus; New England Nuclear, Boston, Mass.), and hybridized at 40° C. overnight with $^{32}$P-labeled oligonucleotide probes in a solution containing 50% formamide, 10% dextran sulfate, 5× SSC, 1× Denhardt's, and 100 µg/ml sonicated salmon sperm DNA. Blots were washed successively in 2× SSC at room temperature and 0.1× SSC at 50° C., and exposed to Kodak XAR film for 0.5 to 4 hours with an intensifying screen at –70° C.

Cloning and Sequencing of Mammalian Taurine Receptor

A rat brain cDNA library in the Lambda ZAP II vector (Stratagene, La Jolla, Calif.) was screened at low stringency with the complete coding region of the rat GABA transporter cDNA (GAT-1; (21)). Exact primers were used to generate PCR products from randomly-primed rat brain cDNA; the products were labeled and used to screen the library under reduced stringency (25% formamide, 40° C. hybridization; 0.1× SSC, 40° C. wash) as previously described (68). Lambda phage hybridizing at low stringency with the GAT-1 sequence were plaque purified and rescreened with the same probes at high stringency (50% formamide, 40° C. hybridization; 0.1× SSC, 50° C. wash) to eliminate clones identical to GAT-1. Clones hybridizing only at low stringency were converted to phagemids by in vivo excision with fl helper phage. Nucleotide sequences of double-stranded cDNAs in pBluescript were analyzed by the Sanger dideoxy nucleotide chain-termination method (59) using Sequenase (U.S. Biochemical Corp., Cleveland, Ohio).

Expression of Mammalian Taurine Transporter

A complementary DNA (designated rB16a) containing the complete coding region of a putative transporter was cloned into the eukaryotic expression vector pEVJB (modified from pcEXV-3; (51)) as a 2.5 kb XbaISalI fragment using restriction enzyme sites within the vector. In addition to the coding region, 0.1 kb of 5'-untranslated sequence and 0.5 kb of 3'-untranslated sequence were included in the construct. Transient transfections of COS cells with the plasmid pEVJB-rB16a were carried out using DEAE-dextran with DMSO according to the method of Lopata et al. (44) with minor modifications. COS cells were grown (37° C.,5% CO$_2$) in high glucose Dulbecco's modified Eagle medium supplemented with 10% bovine calf serum, 100 U/ml penicillin G, and 100 µg/ml streptomycin sulfate. Cells were routinely used two days after transfection for transport studies.

Transport Studies of Mammalian Taurine Transporter

To measure transport, COS cells grown in 6-well (well diameter=35mm) or 24-well (well diameter=18mm) plates were washed 3× with HEPES-buffered saline (HBS, in mM: NaCl, 150; HEPES, 20; CaCl$_2$, 1; glucose, 10; KCl, 5; MgCl$_2$, 1; pH 7.4) and allowed to equilibrate in a 37° C. water bath. After 10 minutes the medium was removed and a solution containing [$^3$H]taurine (New England Nuclear, sp. activity=25.6 Ci/mmole) and required drugs in HBS was added (1.5 ml/35 mm well; 0.5 ml/18 mm well). Non-specific uptake was defined in parallel wells with 1 mM unlabeled taurine and was subtracted from total uptake (no competitor) to yield specific uptake; all data represent specific uptake. Plates were incubated at 37° C. for 10 minutes unless indicated otherwise, then washed rapidly 3× with ice-cold HBS. Cells were solubilized with 0.05% sodium deoxycholate/0.1N NaOH), an aliquot was neutralized with 1N HCl, and radioactivity was determined by scintillation counting. Protein was quantified in an aliquot of the solubilized cells using a BIO-RAD protein assay kit, according to the manufacturer's directions.

PCR Tissue Localization Studies of Mammalian Taurine Transporter

To identify tissues expressing mRNA for the taurine transporter, exact primers (25 mers) were designed such that a 707 base pair fragment of rB16a could be amplified from cDNA and detected by Southern blot analysis. The sequences of the sense and anti-sense primers were derived from amino acids 40 to 47 (5'-TCAGAGGGAGAAGTGGTCCAGCAAG (SEQ ID NO: 22)) and 268 to 275 (5'-ATTTCATGCCTTCACCAGCACCTGG (SEQ ID NO: 23)), respectively. Primers were also designed to amplify the cDNA encoding cyclophilin (12), a constitutively expressed gene, as control (5'-ACGCTTCGACTTCCTCATGTCCTGT (SEQ ID NO: 24), sense; 5'-TTAGAGTTGTCCACAGTCGGAGATG (SEQ ID NO: 25), antisense). To detect amplified sequences, an oligonucleotide probe was synthesized (corresponding to amino acids 249 to 271) which was specific for rB16a. Poly A+ RNA (1 μg, Clontech, Palo Alto, Calif.) from each of seven rat tissues was converted to single-stranded cDNA by random priming using Superscript reverse transcriptase (BRL, Gaithersburg, Md.). PCR reactions were carried out in a buffer containing 20 mM Tris (pH 8.3), 50 mM KCl, 1.5 mM MgCl$_2$, 0.001% gelatin, 2 mM dNTP's, 1 μM each primer, Taq polymerase, and either cDNA, RNA, water, or a control plasmid containing rB16a for 30 cycles of 94° C./2 min., 68° C./2 min., 72° C./3 min. PCR products were separated by electrophoresis in 1.2% agarose gels, blotted to nylon membranes (Genescreen Plus; New England Nuclear, Boston, Mass.), and hybridized at 40° C. overnight with specific $^{32}$p-labeled oligonucleotides in a solution containing 50% formamide, 10% dextran sulfate, 5× SSC, 1× Denhardt's, and 100 μg/ml of sonicated salmon sperm DNA. Blots were washed at high-stringency (0.1× SSC, 50° C.) and exposed to Kodak XAR film for 0.5 to 4 hours with one intensifying screen at −70° C.

Northern Blot Analysis of mRNA encoding Mammalian Taurine Transporter

Samples of poly A$^+$ RNA isolated from each of eight rat tissues (5 μg, Clontech; Palo Alto, Calif.) were separated in a 1.0% agarose gel containing 3.3% formaldehyde and transferred to a nylon membrane (Genescreen Plus; New England Nuclear, Boston, Mass.) by overnight capillary blotting in 10× SSC. Prior to hybridization, the Northern blot was incubated for 2 hours at 42° C. in a solution containing 50% formamide, 1M NaCl, 10% dextran sulfate, and 1% sodium dodecyl sulfate (SDS). The blot was hybridized overnight at 42° C. with $^{32}$P-labeled DNA probe (randomly-primed HindIII/KpnI fragment of rB16a representing amino acids 6–336) in the prehybridization solution containing 100 μg/ml sonicated salmon sperm DNA. The blot was washed successively in 2× SSC/2% SDS, 1× SSC/2% SDS, and 0.2× SSC/2% SDS at 65° C. and exposed to Kodak XAR-5 film with one intensifying screen at −70° C. for 1–4 days. To confirm that equal amounts of RNA were present in each lane, the same blot was rehybridized with a probe encoding cyclophilin (12).

Use of PCR to Identify human cDNA Libraries for Screening

For hGAT-2, the sequences of the rat PCR primers were 5'-GACCAACAAGATGGAGTT (SEQ ID NO: 26) (senae) and 5'-TGTTACTCCTCGGATCAA (SEQ ID NO: 27) (antisense). PCR reactions were carried out in a buffer containing 20 mM Tris (pH 8.3), 50 mM KCl, 1.5mM MgCl$_2$, 0.001% gelatin, 2 mM dNTP's, 1 μM each primer, Taq polymerase, and an aliquot of a lambda phage library, water, or a control plasmid for 40 cycles of 94° C. for 2 min., 50° C. for 2 min., and 72° C. for 3 min. For hGAT-3, the sequences of the degenerate primers were 5'-TGGAATTCG(G/C)CAA(C/T)GTITGG(C/A)GITT(C/T)CCITA (SEQ ID NO: 28) (sense) and 5'-TCGCGGCCGCAA(A/G)AAGATCTGIGTIGCIGC(A/G)TC (SEQ ID NO: 29) (antisense). PCR reactions were carried out as described above for 40 cycles of 94° C. for 2 min., 40° C. for 2 min., and 72° C. for 3 min. PCR products were separated by electrophoresis in 1.2% agarose gels, blotted to nylon membranes (Genescreen Plus; New England Nuclear, Boston, Mass.), and hybridized at 40° C. overnight with $^{32}$P-labeled probes in a solution containing 25% formamide, 10% dextran sulfate, 5× SSC, 1× Denhardt's, and 100 μg/ml of sonicated salmon sperm DNA. Blots were washed at low stringency (0.1× SSC, 40° C.) and exposed to Kodak XAR film for up to three days with one intensifying screen at −70° C.

Isolation and Sequencing of Human Clones

Human cDNA libraries in the Lambda ZAP II vector (Stratagene, La Jolla, Calif.) that were identified as containing hGAT-2 or hGAT-3 were screened under either reduced stringency (25% formamide, 40° C. hybridization; 0.1× SSC, 40° C. wash) or high stringency (50% formamide, 40° C. hybridization; 0.1× SSC, 50° C. wash). Hybridizing lambda phage were plaque purified and converted to phagemids by in vivo excision with fl helper phage. Nucleotide sequences of double-stranded cDNAs in pBluescript were analyzed by the Sanger dideoxy nucleotide chain-termination method (59) using Sequenase (U.S. Biochemical Corp., Cleveland, Ohio). Fragments of genomic clones in the lambda FIX II vector were subcloned into pUC18 prior to double-stranded sequencing.

Preparation of Primary Brain Cell Cultures

Astrocytes, neurons and meningeal fibroblasts were prepared from the brains of E19 embryonic rats. Briefly, the brains were removed, dissected free of meninges, and trypsinized. Cells were dissociated mechanically by passage through a Pasteur pipet, and resuspended in DMEM containing 10% fetal bovine serum and antibiotics. The cells were added to tissue culture dishes that had been previously coated with 10 μM poly-D-lysine.

For astrocytes, the cells were plated at a density of approximately 3×10⁶ cells per 100 mm dish. The astrocytes were allowed to reach confluence, then passaged 1 or 2 times prior to harvesting. For neurons, a plating density of 15×10⁶ cells per 100 mm dish was employed; the medium was supplemented with insulin. Cytosine arabinoside (ara-C) was added to a final concentration of 10 µM on day 2 or 3 to inhibit the proliferation of non-neuronal cells. The neurons were harvested 1 week after plating. To obtain meningeal fibroblasts the meninges were trypsinized, then mechanically dissociated as described above. The cells recovered from a single embryo were plated into a 100 mm dish, grown to confluence, and passaged 1–2 times prior to harvesting.

Isolation of RNA from Cell Cultures

Plates were placed on ice and quickly rinsed twice with ice-cold phosphate-buffered saline (PBS). Cells were then dissolved in 10 mls lysis solution (7M urea, 350 mM NaCl, 2% sodium dodecyl sulfate (SDS), 1 mM EDTA, and 10 mM Tris-HCl, pH 8.0) and transferred to a sterile tube. Lysates were homogenized (Virtis, lowest speed, 5 seconds) and then digested with proteinase K (0.1 mg/ml) at 37° C. for 30 minutes. Samples were extracted twice with phenol/chloroform and once with chloroform before ethanol precipitation. Total RNA was collected by centrifugation, resuspended in diethylpyrocarbonate (DEPC)-treated water, and stored at −20° C. until use.

Detection of Transporter mRNAs using PCR

To identify cell types expressing mRNAs for the GABA transporters GAT-1, GAT-2, and GAT-3, specific PCR primers (25 mers) were designed such that≈700 base pair fragments encoding transmembrane domains 1 through 5 of each transporter could be amplified and detected by hybridization with $^{32}$p-labeled oligonucleotides. For rB14b (GAT-2), the sequences of the sense and anti-sense oligonucleotides were derived from amino acids 36 to 43 (5'-GACCAACAAGATGGAGTTCGTACTG (SEQ ID NO: 30)) and 247 to 254 (5'-TGTTACTCCTCGGATCAACAGGACC (SEQ ID NO: 31)); for rBSb (GAT-3), the oligonucleotides were derived from amino acids 52 to 60 (5'-GGAGTTCGTGTTGAGCGTAGGAGAG (SEQ ID NO: 32)) and 271 to 279 (5'-GAACTTGATGCCTTCCGAGGCACCC (SEQ ID NO: 33)); and for GAT-1 (21), the oligonucleotide sequences were derived from amino acids 50 to 57 (5'-ACGCTTCGACTTCCTCATGTCCTGT (SEQ ID NO: 34)) and 274 to 282 (5'-GAATCAGACAGCTTTCGGAAGTTGG (SEQ ID NO: 35)). To detect amplified sequences, oligonucleotide probes were synthesized for GAT-1, GAT-2, and GAT-3 which corresponded to amino acids 196 to 219, 161 to 183, and 207 to 229, respectively. Each probe was shown to hybridize with its respective transporter cDNA and not with the other transporter cDNAs.

Total RNA (0.5 µg) isolated from cultured neurons, astrocytes, and fibroblasts was converted to single-stranded cDNA by random priming using Superscript reverse transcriptase (BRL, Gaithersburg, Md.). PCR reactions were carried out in a buffer containing 20 mM Tris (pH 8.3), 50 mM KCl, 1.5 mM MgCl$_2$, 0.001% gelatin, 2 mM dNTP's, 1 µM each primer, and Taq polymerase with either cDNA, RNA, water, or a control plasmid for 30 cycles of 94° c./2 min., 68° C./2 min., 72° C./3 min. PCR products were separated by electrophoresis in 1.2% agarose gels, blotted to nylon membranes (Genescreen Plus; New England Nuclear, Boston, Mass.), and hybridized at 40° C. overnight with $^{32}$P-labeled oligonucleotide probes in a solution containing 50% formamide, 10% dextran sulfate, 5× SSC, 1× Denhardt's, and 100 µg/ml sonicated salmon sperm DNA. Blots were washed successively in 2× SSC, 0.1% SDS at room temperature and 0.1× SSC, 0.1% SDS at 50° C., and exposed to Kodak XAR film for 0.5 to 4 hours with an intensifying screen at −70° C.

In Situ Hybriaization

Male Sprague-Dawley rats (Charles River) were decapitated and the brains rapidly frozen in isopentane. Sections were cut on a cryostat, thaw-mounted onto poly-L-lysine coated coverslips, and stored at −80° C. until use. Tissue was fixed in 4% paraformaldehyde, treated with 5 mM dithiothreitol (DTT), acetylated (0.25% acetic anhydride in 0.1M triethanolamine), and dehydrated. Tissue was prehybridized (1 hour, 40° C.) in a solution containing 50% formamide, 4× SSC (0.6M NaCl/0.06M sodium citrate), 1× Denhardt's solution (0.2% polyvinylpyrrolidine, 0.2% Ficoll, 0.2% bovine serum albumin), 50 mM DTT, 500 µg/ml salmon sperm DNA, 500 µg/ml yeast tRNA, 10% dextran sulfate, then hybridized overnight with $^{35}$S-labeled anti-sense oligonucleotides (45mers) in the same solution. After washing and dehydration, sections were apposed to Kodak X-OMAT AR film for 4 days at −20° C. To verify the specificity of the hybridization signal, parallel tissues were pretreated with 100 µg/ml RNase A (37°, 30 minutes) prior to hybridization. Two different oligonucleotides designed to separate regions of the GABA transporters (loop region between transmembrane domains III and IV, 3'untranslated region) showed identical patterns of hybridization.

1. GABA TRANSPORTERS

Results

Cloning of New Mammalian GABA Transporter Sequences

We screened a rat brain cDNA library at low stringency with probes encoding the rat neuronal GABA transporter (GAT-1; (21)) in order to identify additional inhibitory amino acid transporter genes. Two clones were identified which hybridized at low but not at high stringency with the GABA transporter probes. DNA sequence analysis revealed that the clones encoded putative transporters which were structurally related to GAT-1. The first clone, rB14b, contained a 2.0 kb sequence with an open reading frame of 1806 base pairs which could encode a protein of 602 amino acids (FIGS. 1A-1 to 1A-4). The second clone, rBSb, contained a 2.1 kb sequence which had an open reading frame of 1881 base pairs encoding a protein of 627 amino acids (FIGS. 1B-1 to 1B-2). rB14b and rB8b exhibited 59% nucleotide identity throughout the coding region with the neuronal rat GABA transporter (GAT-1) and 70% nucleotide identity with each other. Comparison to sequences in Genbank and EMBL data bases demonstrated that both nucleotide sequences were novel and that the most homologous sequence was the rat GABA transporter GAT-1 (21). Subsequent comparisons which included recently cloned transporters revealed that the most closely related sequence is the canine betaine transporter (79) which exhibits 69% nucleotide identity with both rB14b and rBSb. The taurine transporter (66) and the glycine transporter (68) are also significantly related, exhibiting ⁻64% and ⁻56% nucleotide identity, respectively, to both rB14b and rBSb.

The amino acid sequence deduced from the nucleotide sequence of rB14b is shown in FIGS. 1D-1 to 1D-2 modeled after the proposed membrane topology of GAT-1 (21). Residues identical to those in rBSb are shaded and represent 67% amino acid identity between the two clones. The translation products of both rB14b and rB8b are predicted to have relative molecular masses of ≈68,000 Daltons. Hydropathy analyses indicate the presence of 12 hydrophobic domains in both proteins which may represent membrane spanning segments. For each transporter, several potential sites for Asn-linked glycosylation are found in the extracellular loop between the third and fourth transmembrane domains. Comparison and alignment of the deduced amino acid sequences of rB14b (GAT-2) and rBSb (GAT-3) with the neuronal GABA transporter (GAT-1) (FIGS. 2A–2D) revealed 52.5% and 52% amino acid identities, respectively. The betaine transporter (FIGS. 2A–2D), which can also transport GABA (79) exhibited a significantly higher degree of homology—68% and 65% amino acid identities to rB14b and rBSb, respectively. Similarly, the transporter for taurine (66), an inhibitory amino acid, is 61% homologous to both. In contrast, comparison of the new transporters with the rat glycine transporter (FIGS. 2A–2D and Ref.(68)) or the human norepinephrine transporter (55) showed a lower degree of amino acid identity (43–45%), similar to that between the neuronal GABA and norepinephrine transporters (46%). These data suggested that the new sequences might encode additional amino acid transporters expressed in the brain. To explore this possibility, the sequences were each placed in a mammalian expression vector, transfected into COS cells, and screened for transport of a variety of radiolabeled neurotransmitters and amino acids. These studies revealed (see below) that rB14b and rBSb encode novel GABA transporters with pharmacological properties distinct from the neuronal GABA transporter.

Pharmacological Characterization of Mammalian GABA Transporters

Figure 3A:
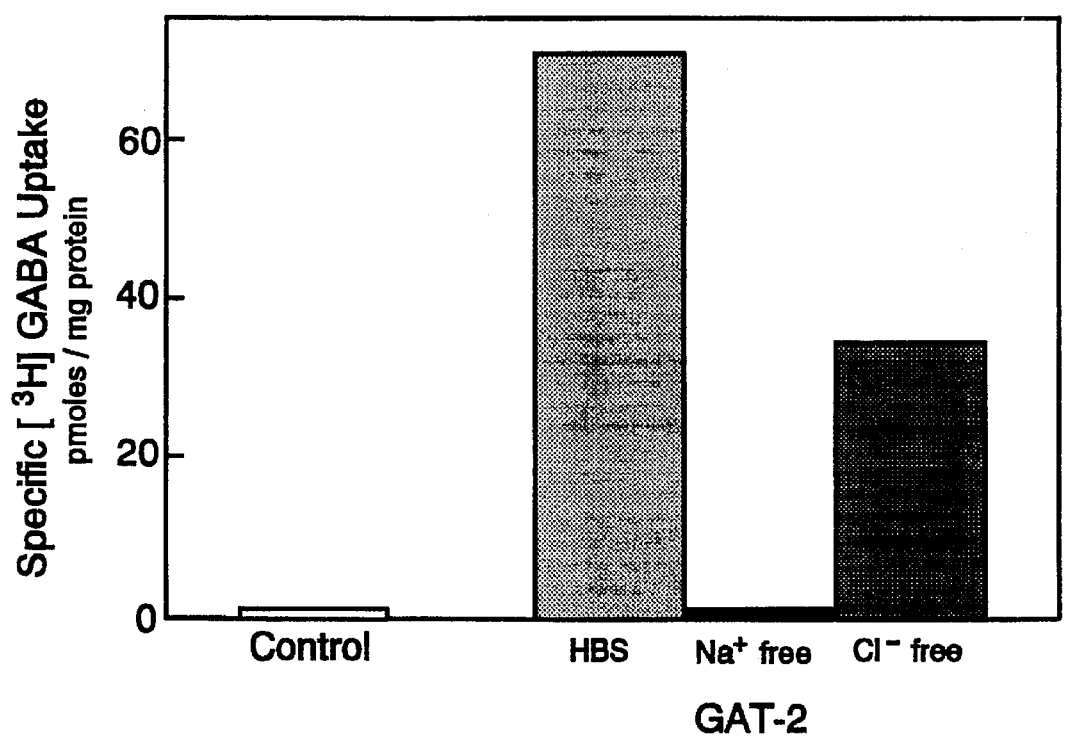
FIGS. 3A–3B GABA transport by COS cells transfected with clone rB14b and rBSb. Non-transfected COS cells (control) or COS cells transfected with GAT-2 (A) or GAT-3 (B) were incubated for 10 minutes (37° C.) with 50 nM [$^3$H]GABA in either HBS (150 mM NaCl) or in a similar solution in which $Na^+$ was replaced by equimolar $Li^+$ ($Na^+$-free), or $Cl^-$ was replaced by acetate, (in some experiments, calcium gluconate was used instead of calcium acetate; $Cl^-$-free). Data show the specific uptake of GABA, expressed as pmoles/mg protein cellular protein. Data are from a single experiment that was repeated with similar results.
Figure 3B:
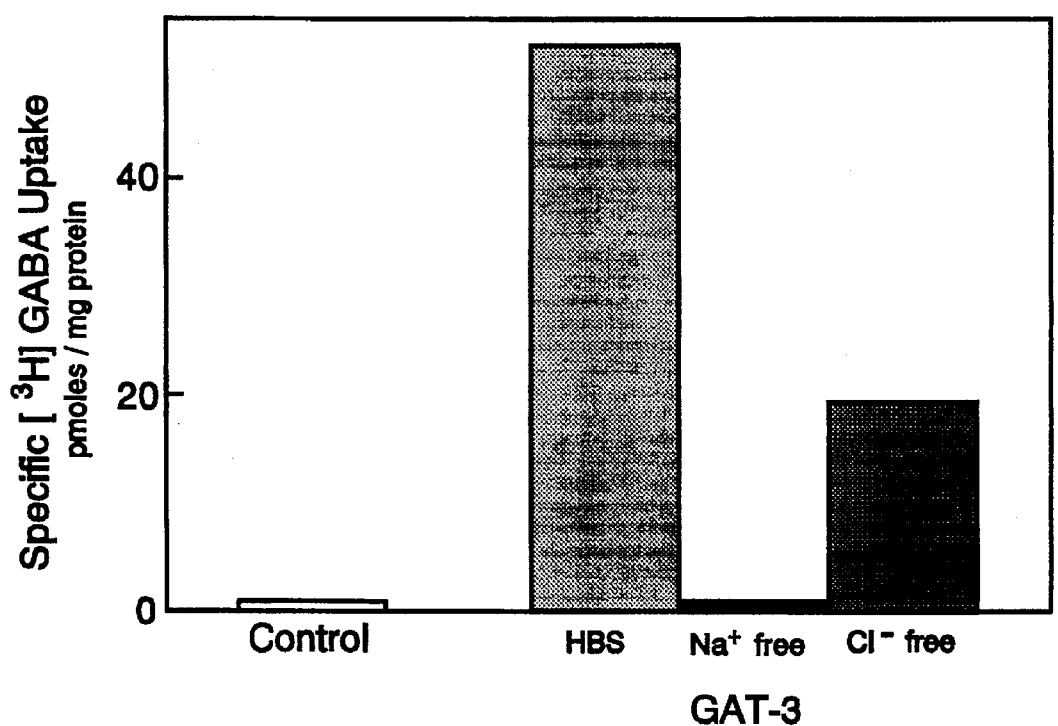

COS cells transiently transfected with rB14b or rBSb (COS/rB14b and COS/rBSB, respectively) accumulated more [$^3$H]GABA than non-transfected control cells; representative experiments are shown in FIG. 3. During a 10 minute incubation (37° C.) with a low concentration of [$^3$H]GABA, specific uptake was increased 52±11-fold (mean±SEM, n=6) and 64±12-fold (n=5) over control for rB14b and rBSb, respectively. In contrast, the uptake of [$^3$H]glutamate, [$^3$H]glycine, [$^3$H]5-HT, [$^3$H]dopamine, and [$^3$H]taurine was unaltered. Specific uptake represented greater than 95% of total uptake in transfected cells. Uptake of [$^3$H]GABA was not observed following mock transfection or transfection with an irrelevant insert, indicating that the enhanced uptake was not the result of non-specific perturbation of the membrane. The transport of [$^3$H]GABA by both COS/rB14b and COS/rBSb was decreased >95% when Na$^+$ was replaced by Li$^+$ (Table 1); similar results were obtained with COS cells expressing GAT-1 (COS/GAT-I), which we re-cloned (see Materials and Methods). When Cl$^-$ was replaced by acetate, [$^3$H]GABA transport by COS/GAT-1 was nearly completely eliminated (Table 1), consistent with previous results obtained with this transporter (21,29). In contrast, transport by COS/rB14b and COS/rBSb was decreased to 43 and 20% of control, respectively (Table 1). The difference in sensitivity to removal of chloride exhibited by the three transporters was statistically significant (GAT-1 vs. COS/rB14b, p<0.001; GAT-1 rs. rBSb, p<0.05; rB14b rs. rBSb, p<0.05).

To determine the affinity of GABA for the cloned transporters, COS/rB14b and COS/rBSb were incubated with various concentrations of [$^3$H]GABA and the specific accumulation of radioactivity was determined. Accumulation of [$^3$H]GABA was dose-dependent and reached saturation at higher concentrations (FIG. 4). Non-linear regression analysis of the data yielded the following values: $K_M$=8±3 μM and 12±6 μM, and $V_{MAX}$=2.5±1.2 and 3.0±0.9 nmoles/mg protein for COS/rB14b and COS/rBSb, respectively (mean±SEM, n=4 experiments). Taken together, these data indicate that both rB14b and rBSb encode saturable, high-affinity, sodium- and chloride-dependent GABA transporters. Accordingly, we propose the terms GAT-2 and GAT-3 for the transporters encoded by rB14b and rBSb, respectively, according to the nomenclature proposed by Guastella et al. (21).

To determine the pharmacological properties of the cloned GABA transporters, we examined the ability of various drugs to inhibit the accumulation of [$^3$H]GABA by GAT-2 and GAT-3; for comparison, we also examined the pharmacology of GAT-1. As shown in Table 2, the pharmacological properties of GAT-2 and GAT-3 are similar to one another, but differ considerably from GAT-1. For example, β-alanine, a ligand reported to be selective for glial GABA transport (36), is more potent at the new cloned transporters than at GAT-1. In contrast, ACHC, guvacine, nipecotic acid, and hydroxynipecotic acid are more potent at GAT-1 than at GAT-2 and GAT-3. Interestingly, the two newly cloned tranporters can be distinguished by L-DABA which displays high affinity for GAT-2 as well as GAT-1, but is less potent at GAT-3.

To further chararacterize the pharmacological properties of GAT-2 and GAT-3, we examined the ability of (R)-Tiagabine and CI-966 to inhibit the uptake of [$^3$H]GABA; for comparison, we also examined these compounds at GAT-1. These compounds are lipophilic derivatives of nipecotic acid and guvacine, respectively. As shown in Table 2, (R)-Tiagabine at a concentration of 100 μM completely inhibits uptake at GAT-1 but has no effect at GAT-2 and GAT-3. Tiagabine is reported to have high potency at both neuronal and glial GABA transporters (6), and has demonstrated efficacy as an anticonvulsant in early clinical trials (8). The finding that Tiagabine has very low affinity for GAT-2 and GAT-3 underscores the potential of these transporters as unique drug targets. Similar to Tiagabine, the GABA uptake blocker CI-966 (72) displays far greater potency at GAT-1 than at GAT-2 and GAT-3 (Table 2). CI-966 was developed as an anticonvulsant but was withdrawn due to severe side effects observed in Phase 1 clinical trials (63).

TABLE 1

Ion Dependence of [$^3$H]GABA Uptake

| Condition[a] | Uptake[a] | | |
|---|---|---|---|
| | GAT-1 | GAT-2 | GAT-3 |
| Na$^+$-free | 0.5 ± 0.3 (3) | 0.1 ± 0.06 (3) | 0.3 ± 0.03 (3) |
| Cl$^-$-free | 5 ± 2 (3) | 43.2 ± 4.0 (5) | 20.2 ± 5.8 (5) |

[a]COS-7 cells transfected with rB46a, rB14b, or rB8b were incubated for 10 minutes (37° C.) with 50 nM [$^3$H]GABA in either HBS, or in HBS in which Li$^+$ was substituted for Na$^+$ (Na$^+$-free), or in which acetate was substituted for Cl$^-$ (Cl$^-$-free). Non-specific uptake was determined with 1 mM GABA. Data represent specific uptake, expressed as percent of uptake in HBS (mean ± SEM; values in parentheses indicate number of experiments).

TABLE 2

Pharmacological Specificity of [³H]GABA Uptake

| Inhibitor[a] | concentration | % Inhibition[a] | | |
|---|---|---|---|---|
| | | GAT-1 | GAT-2 | GAT-3 |
| ACHC[b] | 100 μM | 49 ± 10 (3) | 3 ± 3 (3) | 0 ± 0 (3) |
| β-alanine | 100 μM | 11 ± 1 (8) | 86 ± 1 (8) | 70 ± 1 (7) |
| betaine | 500 μM | 0 (2) | 9 (2) | 1 (2) |
| L-DABA | 100 μM | 49 ± 8 (7) | 43 ± 8 (7) | 4 ± 1 (5) |
| guvacine | 10 μM | 41 ± 3 (4) | 13 ± 1 (3) | 8 ± 5 (3) |
| OH-nipecotic | 10 μM | 34 ± 5 (3) | 9 ± 7 (3) | 5 ± 2 (3) |
| nipecotic | 10 μM | 51 ± 5 (3) | 5 ± 5 (3) | 12 ± 6 (3) |
| THPO | 100 μM | 10 (2) | 9 (2) | 4 (2) |
| (R)-Tiagabine | 100 μM | 100 ± 1 (3) | 0 ± 1 (3) | 0 ± 1 (3) |
| CI-966 | 100 μM | 91 ± 2 (3) | 9 ± 6 (3) | 10 ± 6 (3) |

[a]COS-7 cells transfected with rB46a, rB14b, or rB8b were incubated for 10 minutes (37° C.) with 50 nM [³H]GABA and the indicated compounds. Non-specific uptake was determined with 1 mM GABA. Data show percent displacement of specific [³H]GABA uptake, mean ± SEM (values in parentheses indicate number of experiments).
[b]L-DABA = L-(2,4)diaminobutyric acid
THPO = 4,5,6,7-tetrahydroisoxazolo[4,5-c]pyridin-3-ol
ACHC = cis-3-aminocyclohexanecarboxylic acid
CI-966 = [1-[2-[bis 4-(trifluoromethyl)phenyl]methoxy]ethyl]-1,2,5,6-tetrahydro-3-pyridinecarboxylic acid
Tiagabine = (R)-N-[4,4-bis(3-methyl-2-thienyl)but-3-en-1-yl]nipecotic acid

Tissue Localization Studies of Mammalian GABA Transporters

To define the tissue distribution patterns of the novel GABA transporters, polymerase chain reaction (PCR) was used to detect each sequence in cDNA from seven different rat tissues. For comparison, the distribution of GAT-1 was also studied. Radiolabeled probes were used to detect individual PCR products by hybridization; each of the probes was highly specific for the transporter under study (data not shown). As shown in FIG. 5B, GAT-1 was detectable in brain and retina but not liver, kidney, heart, spleen, or pancreas after 30 cycles of PCR. GAT-2 was present not only in brain and retina, but also in liver, kidney, and heart. Levels of GAT-2 mRNA were also detectable in spleen with overexposure of the autoradiogram (data not shown). Similar to GAT-1, the distribution of GAT-3 was limited to brain and retina. Cyclophilin was amplified to a similar extent from all the tissues (data not shown), indicating that adequate cDNA was present in each sample. Samples of poly A+ RNA not treated with reverse transcriptase and subjected to identical PCR conditions showed no hybridization with the transporter probes (not shown), indicating that the signals obtained with cDNA could not be accounted for by genomic DNA contamination. Thus, among the tissues examined, the distribution of GAT-3 is limited to the CNS, while GAT-2 has a wide peripheral distribution as well. These results are supported by Northern blot analyses of total RNA isolated from rat brain and liver; a single ≈2.4 kb transcript hybridizing with GAT-2 is present in both liver and brain, while a ≈4.7 kb transcript hybridizing with GAT-3 is detectable only in brain (FIG. 5A).

Cellular Localization of GABA Transporter mRNAs

Prior to the recent cloning of GABA transporters (4,21), pharmacological evidence suggested that multiple transporters contributed to the high-affinity GABA uptake observed in rat brain (30). Both neuronal and glial elements transport GABA, and preparations enriched in each cell type display differential sensitivities to inhibitors of GABA transport (5, 53, 61), suggesting the presence of distinct neuronal and glial GABA transporters. The ability to design neuronal- or glial- selective GABA uptake inhibitors would be a major advantage in the design of effective therapeutic agents. The GABA transporter cloned from rat brain, designated GAT-1 (21), displays a pharmacological profile consistent with a "neuronal"-type carrier. Our cloning of two additional GABA transporters from rat brain, GAT-2 and GAT-3 (previously termed Ggabal and Ggaba2, respectively), confirms the principle of heterogeneity in high-affinity GABA transporters. Further, the sensitivity of GAT-2 and GAT-3 to inhibition by β-alanine distinguishes them from GAT-1, and raises the possibility that one or both represent "glial"-type transporters. The availability of three cloned high-affinity GABA transporters now provides the opportunity to begin to examine the relationship between the pharmacologically defined neuronal and glial subtypes, and the transporters encoded by the cloned genes.

The presence of mRNAs representing each of the three GABA transporters was investigated in primary cultures of embryonic rat brain neurons, astrocytes, and meningeal fibroblasts. Polymerass chain reaction (PCR) was used to amplify each sequence for detection with specific probes. As shown in Table 3, the messenger RNAs encoding each GABA transporter had a unique pattern of distribution. GAT-1 mRNA was present in all three culture types, whereas GAT-3 mRNA was restricted to neuronal cultures. GAT-2 mRNA was present in both astrocyte and fibroblast cultures, but not in neuronal cultures. Thus, GAT-2 and GAT-3, which exhibit extremely similar pharmacological profiles, display non-overlapping cellular distribution patterns. GAT-1, which displays a "neuronal"-type pharmacology, is apparently not restricted to a neuronal distribution.

TABLE 3

Cellular Localization of GABA Transporters by PCR.

| | Neuronal Cultures | Astrocyte Cultures | Fibroblast Cultures |
|---|---|---|---|
| GAT-1 | + | + | + |
| GAT-2 | − | + | + |
| GAT-3 | + | − | − |

Total RNA isolated from cultured embryonic rat neurons, astrocytes, or fibroblasts was converted to cDNA and subjected to PCR for detection of mRNAs encoding GAT-1, GAT-2, and GAT-3 as described in Experimental Procedures. Amplified products were separated on agarose gels, blotted to nylon membranes, and hybridized with radiolabeled oligonucleotides specific for each transporter cDNA. The blot was exposed to film and the autoradiogram developed after several hours. A (+) sign signifies that a positive signal was detected on the autoradiogram; a (−) signifies that no signal was detectable. The same results were observed in two independent experiments.

It is important to note that primary cultures, while enriched for a specific population of cells, may contain a small proportion of additional cell types. The sensitivity of PCR is sufficient to amplify a sequence contributed by a small number of cells; therefore, an unequivocal assignment of neuronal vs. glial localization would require combined in situ hybridization/immunocytochemistry. However, the presence of GAT-3 mRNA only in neuronal cultures suggests that detection of GAT-1 mRNA in astrocyte cultures is not due to the presence of contaminating neurons, and that GAT-1 is probably present in astrocytes in addition to neurons. The presence of GAT-1 and GAT-2 in fibroblast as well as astrocyte cultures may be explained by our recent finding that meningeal fibroblast cultures contain a large proportion of astrocytes as defined by staining with antibodies to glial fibrillary acidic protein (GFAP) (data not shown); thus, GAT-1 and GAT-2 signals in meningeal fibroblasts probably result from contaminating astrocytes.

These studies suggest that multiple high-affinity GABA transporter subtypes are present in different functional compartments, with at least two subtypes present in neurons (GAT-1 and GAT-3) and in glia (GAT-1 and GAT-2). Further, they indicate that pharmacologic agents selective for each subtype may have different therapeutic applications.

Localization of GAT-1 and GAT-3 mRNA by in situ Hybridization

In situ hybridization of GAT-1 and GAT-3 was carried out using antisense probes to the 3' untranslated region and the 3,4 extracellular loop of each clone. Hybridization of sense probes (control) to the same regions were also studied.

GAT-1 mRNA was observed in all rat brain areas examined (Table 4). In the telencephalon, the highest levels were observed in the glomerular layer of the olfactory bulb, the orbital cortex, the lateral septal nucleus, the ventral pallidum, the globus pallidus, amygdaloid area, and layer 4 of the cerebral cortex. Moderate levels were observed in the islands of Calleja, the internal and external plexiform layers, and the piriform, retrospenial, and cingulate cortices, as well as in all regions of the hippocampal formation.

In the diencephalon, the highest levels were found in the paraventricular and reticular thalamic nuclei, and in the dorsal lateral geniculate. Lower levels were seen in the reuniens and rhomboid thalamic nuclei. In the hypothalamus, moderate levels were seen in the suprachiasmatic and paraventricular nuclei, and in the medial preoptic area. Lower levels were seen in the supraoptic and anterior hypothalamic nuclei.

In the midbrain, high levels were seen in the substantia nigra (pars compacta and pars reticulata), median raphe, and the olivary pretectal nucleus. Lower levels were observed in the superior colliculus.

No label was seen in the pontine nuclei, nor in the cerebellar Purkinje cells.

GAT-3 mRNA was observed throughout the neuraxis (Table 5). Within the telencephalon, the highest levels were detected in the medial septal nucleus, the nucleus of the diagonal band, and the ventral pallidum. Lower levels were found in the amygdala and the shell of the nucleus accumbens. Low levels were observed in the hippocampus. No labeling above background was observed in the neocortex.

In the thalamus, many nuclear groups were labeled. The areas with the highest labeling were the xiphoid, paraventricular, and rhomboid nuclei, and the zona incerta. Lower levels were observed in the following nuclei: reuniens, reticular, medial and lateral ventral posterior, and the medial geniculate. In the hypothalamus, moderate labeling was found in the lateral and ventromedial regions. Lower levels were observed in the arcuate nucleus and median eminence.

In the midbrain, the highest levels were observed in the dorsal tegmentum.

In the metencephalon, the highest levels were found in the medial vestibular and deep cerebellar nuclei, and lower levels in the lateral superior olivary nucleus. No label was observed in the cerebellar cortex.

A comparison of the localization of GAT-1 and GAT-3 mRNAs indicates that both are widely distributed in the brain, and while GAT-1 is more abundant on a per cell basis, the two tend to have overlapping distributions. Notable exceptions are cortex and hippocampus which contain large numbers of neurons containing GAT-1 mRNA but few cells with GAT-3 mRNA. On the other hand, GAT-3 mRNA levels appear to be higher than GAT-1 in the superficial layers of the superior colliculus and in the deep cerebellar nuclei.

TABLE 4

In situ localization of GAT-1 in the Rat CNS

| Area[1] | Labeling[2] | |
|---|---|---|
| | Probe 191 AS 3'UT | Probe 179 AS 3,4 loop |
| BREGMA 6.20 mm | | |
| mitral cells | – | – |
| glomerular layer | ++ | ++ |
| ext. plexiform layer | +½ | + |
| ant. olf nerve | +/– | +/– |
| BREGMA 5.20 mm | | |
| ext.plexiform layer | + | + |
| int.plexiform layer | + | + |
| ant.comm.intrabulb | +/– | +/– |
| AOM,D,V | + | + |
| orbital cortex m,v,l | +½ | +½ |
| frontal. cortex | + | +½ |
| BREGMA 1.60 mm | | |
| tenia tecta | + | + |
| lat.septal nucleus | +/– | +/– |
| lat.septal interm. | ++ | ½+ |
| ICjM | +½ | +½ |
| caudate-putamen | +/– | – |
| AcbSh | + | ½+ |
| AcbC | ½+ | – |
| vent.pallidum | +++ | +++ |
| olf.tubercle | – | – |
| ICj | + | + |
| piriform ctx. | + | + |
| cingulate ctx | + | + |
| indusium griseum | ++ | +½ |
| BREGMA-1.40 mm | | |
| retrosplen.ctx | + | ½+ |
| cortex | | |
| I | + | + |
| IV | ++ | ++ |
| V | + | + |
| reticular thal.nu. | +½ | +½ |
| globus pallidus | +++ | ++½ |
| caudate-putamen | + | + |
| ant.dor thal.nu. | – | – |
| paraventr. thal. nu | +½ | +½ |
| supraoptic nu. | ½+ | ½+ |
| suprachiasmatic nu. | + | + |
| med.preoptic area | +½ | +½ |
| perivent. hypoth. nu. | + | + |
| anter. hypoth. nu. | + | + |
| paravent. hypoth. nu. | +½ | +½ |
| nu. horizontal. limb diag. band | + | + |
| ant. amygd. area | ++½ | ++½ |
| BREGMA-1.80 mm | | |
| reuniens thal.nu. | ½+ | ½+ |
| rhomboid thal.nu. | ½+ | ½+ |
| retrochiasmatic area | + | + |
| BREGMA-4.52 mm | | |
| choroid plexus | – | – |
| PMCo | + | + |

TABLE 4-continued

In situ localization of GAT-1 in the Rat CNS

| | Labeling[2] | |
|---|---|---|
| Area[1] | Probe 191 AS 3'UT | Probe 179 AS 3,4 loop |
| AHiA | + | + |
| Basolateral Amygdaloid nu. | ++ | ++ |
| dorsal endopiriform nu. | + | + |
| hippocampus (all levels) | + | + |
| polymorphic dendate gyrus | ++ | ++ |
| olivary pretectal nu. | ++ | ++ |
| dorsal lateral genicul. nu. | ++ | ++ |
| BREGMA-5.30 mm | | |
| substantia nigra | | |
| pars reticulata | ++ | ++½ |
| pars compacta | ++ | ++ |
| red nucleus parvocellular | − | − |
| retrospenial cortex | + | + |
| occipital cortex | + | + |
| nucleus Darkschewitsch | +½ | + |
| nucleus posterior commis., magnocellular | + | +½ |
| BREGMA-7.64 mm | | |
| superior colliculus | + | + |
| central grey | − | − |
| dorsal grey | +/− | +/− |
| median Raphe | +½ | +½ |
| pontine nuclei | − | − |
| Purkinje cells | +/− | +/− |

[1]abbreviations as in Paxinos, G. and Watson, C. (1986) The Rat Brain in Stereotactic Coordinates, second edition. Academic Press.
[2]Antisense probes 191 and 179 were to 3' untranslated region and to the 3,4 extracellular loop, respectively. Control data using sense probes to the sam regions showed no labeling.
Labeling scale: −, no labeling; ½+, very weak, +, weak; ++, moderate; +++, heavy. Note that the scale is based on maximal labeling obtained with GAT-1 probes and should not be compared to results for GAT-3.

TABLE 5

In situ Localization of GAT-3 in the Rat CNS

| Area[1] | Labeling |
|---|---|
| telencephalon: | |
| cortex | − |
| piriform ctx | ½+ |
| nu. accumbens | |
| core | − |
| shell | + |
| olf. tubercle | ½+ |
| med. septal nu. | ++ |
| nu. horiz.limb diag. band | ++ |
| ventral pallidum | ++ |
| ant. cortical amygdaloid nu. | + |
| medial amygdaloid nu. | +½ |
| Diencephalon: | |
| paraventricular thalamic nu. | ++½ |
| reticular thalamic nu. | +½ |
| VPM | +½ |
| VPL | + |
| zona incerta | ++½ |
| rhomboid thalamic nu. | ++½ |
| reuniens thalamic nu. | ++ |
| xiphoid thalamic nu. | +++ |
| medial geniculate nu. | + |
| arcuate hypoth. nu. | ½+ |
| ventromedial hypoth.nu. | + |
| lateral hypoth. nu. | +½ |
| median eminence | ½+ |
| hippocampus | ½+ |
| Mesencephalon: | |
| superior colliculus | ++½ |
| central gray, dorsal | ++ |
| central gray | ++ |
| substantia nigra | not examined |
| interpeduncular nu. | + |
| caudal | |
| dorsal raphe | + |
| cuneiform nu. | + |
| lateral dorsal tegmen. nu. | +++ |
| dorsal tegmental nu., pericentral | +++ |
| Metencephalon: | |
| medial vestibular nu. | +++ |
| lateral superior olive | ++ |
| inferior olive | not examined |
| cerebral cortex | − |
| deep cerebellar nuclei | +++ |

[1]abbreviations as in Paxinos, G. and Watson, C. (1986) The Rat Brain in Stereotactic Coordinates, second edition. Academic Press.
[2]Data are pooled from antisense probes to the 3' untranslated region and to the 3,4 extracellular loop. Control data using sense probes to the same regions showed no labeling.
Labeling scale: −, no labeling; ½+, very weak, +, weak; ++, moderate; +++, heavy. Note that the scale is based on maximal labeling obtained with GAT-3 probes and should not be compared to results for GAT-1.

Discussion

The recent cloning of transporters for GABA (21), norepinephrine (55), dopamine (33,65), serotonin (3,23), glycine (68), and taurine (66) has helped to define the structural properties of this class of membrane proteins. In contrast with neurotransmitter receptors, however, it has not been determined for neurotransmitter transporters whether multiple subtypes exist and/or play a role in synaptic transmission. Our identification of two cDNA clones from rat brain encoding novel GABA transporters (designated GAT-2 and GAT-3) provides the first molecular evidence for heterogeneity within the neurotransmitter transporter gene family, and raises the possibility that multiple GABA transporters participate in the regulation of GABAergic neurotransmission.

Both proteins have 12 putative transmembrane domains and can be modeled with a similar topology to the neuronal GABA transporter (GAT-1; (21)), including a large glycosylated extracellular loop between TMs 3 and 4. Analysis of amino acid homologies of the various transporters reveals some unexpected relationships. For example, GAT-2 and GAT-3 exhibit greater amino acid sequence identity to each other (67%) than to GAT-1 (~53%), despite all three transporters displaying nearly identical affinities for GABA. Surprisingly, the sequence closest to GAT-2 and GAT-3 is the dog betaine transporter (79) which, in fact, is as homologous to GAT-2 and GAT-3 as they are to one another. Significantly, the cloned betaine transporter has also been reported to transport GABA (79), although the affinity of GABA at the betaine transporter is nearly 10-fold lower than at GAT-2 and GAT-3. Conversely, the betaine transporter displays at least 10-fold higher affinity for betaine than do GAT-2 and GAT-3 (see Table 2). Thus, transporters with as little as 53% amino acid homology can display high affinity for the same substrate (e.g. GAT-1 vs. GAT-2 and GAT-3), whereas transporters only slightly more divergent can demonstrate markedly different substrate specificities (e.g., GAT-1 vs. glycine, 45% homology; (68)).

Pharmacologically distinct GABA transporters have previously been identified in neuronal and glial cell cultures (15, 36 and 62). Thus, it was of interest to examine the sensitivity of GAT-2 and GAT-3 to a variety of inhibitors and to compare this to published values for endogenous transporters in primary cell cultures, as well as to GAT-1. It is noteworthy that GAT-2 and GAT-3 display greater sensitivity to the glial-selective drug β-alanine than does the previously cloned GAT-1, suggesting similarity to the tranporter (s) characterized in glial cell cultures. However, a lack of identity with the pharmacologically defined glial-type transporter is demonstrated by the finding that guvacine, nipecotic acid, Tiagabine, and hydroxynipecotic acid are much less potent inhibitors of GABA uptake at GAT-2 and GAT-3 than at the transporter present in glial cultures (6, 15, 36, 62). Additionally, these compounds are more potent in neuronal cultures (and at the previously cloned GAT-1) than at GAT-2 and GAT-3, which also distinguishes the newly cloned transporters from the neuronal GABA transporter (6, 15, 21, 36 and 62). Lastly, although GAT-2 and GAT-3 display similar sensitivity to a number of the inhibitors examined and show similar affinity for GABA itself, they can be distinguished by L-DABA, which displays higher potency at GAT-2 than at GAT-3. Interestingly, the potency of L-DABA at GAT-2 is similar to that of GAT-1 (Table 2), blurring the distinction between the newly cloned tranporters and the neuronal-type transporter. This finding may indicate that a spectrum of GABA transport activities underlie the neuronal and glial profiles observed in tissue preparations. Lastly, the three cloned GABA transporters can also be distinguished by their differential dependence on external chloride: GAT-1 is the most chloride dependent, GAT-2 the least, and GAT-3 is intermediate in its sensitivity. The finding that GABA transport by GAT-2 and GAT-3 is not completely eliminated in chloride-free medium suggests that their mechanism of transport is fundamentally different from that of GAT-1.

It is somewhat surprising that the pharmacological profiles of GAT-2 and GAT-3 differ from those of previously characterized transporters in neuronal and glial cultures. One possible explanation is that the unique pharmacology of GAT-2 and GAT-3 reflects species differences, as the cloned transporters were obtained from a rat cDNA library, while mouse tissue was employed in many of the earlier studies (15, 36 and 62). This hypothesis gains validity from the finding that certain GABA uptake blockers are potent anticonvulsants in rats, but are ineffective in mice (82), although differences in drug metabolism or distribution have not been ruled out. A second possibility is that since neuronal and glial cultures are prepared from fetal or newborn animals, the discrepant results may reflect developmental changes in GABA transporters or peculiarities of glia and neurons when maintained in cell culture. Alternatively, the two newly cloned transporters may in fact represent members of a novel class of transporters that have not been previously identified, perhaps due to their low abundance in cultured cells. This would suggest that further GABA transporters with pharmacological profiles consistent with those seen in neuronal and glial cultures remain to be cloned. Lastly, it should be pointed out that the pharmacological profiles of cloned transporters for serotonin (3,23), dopamine (33,65), and norepinephrine (55), as well as GAT-1 are similar to those observed in brain homogenates, thus arguing that the unique properties of GAT-2 and GAT-3 are not the result of the heterologous expression system.

Despite the generally similar pharmacology of GAT-2 and GAT-3, their patterns of distribution are distinct. All three high-affinity GABA transporters are present in brain and retina, while only GAT-2 was detected in peripheral tissues. This finding is consistent with recent studies suggesting a role for GABA in liver (52), kidney (1,19) and other peripheral tissues (for review, ref. 14). Further distribution studies of GAT-2 and GAT-3 by in situ localization of transporter mRNAs in conjunction with immunocytochemistry will help to define the roles of these transporters in GABAergic transmission.

In conclusion, we now report the identification in mammalian brain of two novel high-affinity GABA transporters with unique pharmacological properties. These studies indicate previously unsuspected complexity in the regulation of GABAergic transmission, and provide the opportunity for the development of selective therapeutic agents to treat neurological and psychiatric disorders.

Cloning of Human High-Affinity GABA Transporters

The use of human gene products in the process of drug development offers significant advantages over those of other species, which may not exhibit the same pharmacologic profiles. To facilitate this human-target based approach to drug design in the area of inhibitory amino acid transporters, we used the nucleotide sequences of the rat GAT-2 and GAT-3 cDNAs to clone the human homologues of each gene.

To obtain a cDNA clone encoding the human GAT-2 GABA transporter (hGAT-2) we used PeR primers based on the rat GAT-2 sequence to detect the presence of hGAT-2 in human cDNA libraries. PCR was carried out at a reduced annealing temperature to allow mismatches between rat and human sequences (see Experimental Procedures); amplified hGAT-2 sequences were detected by hybridization at low stringency with radiolabeled (randomly primed) rat GAT-2 cDNA. A human heart cDNA library (Stratagene) was identified and screened at low stringency with the same probe, resulting in isolation of-a partial cDNA clone (hHE7a) containing the C-terminal portion of the coding region of hGAT-2. Using human sequence derived from this clone, a partial cDNA clone (hS3a) was isolated from a human striatum cDNA library (Stratagene) that provided additional sequence in the coding region. The hGAT-2 nucleotide sequence from these two clones and the deduced amino acid sequence based on translation of a long open reading frame is shown in FIG. 10A. The sequence includes 738 base pairs of coding region (246 amino acids) and 313 base pairs of 3' untranslated region. Comparison with the rat GAT-2 amino acid sequence reveals 90% identity over the region encoded by the clones, which includes predicted transmembrane domains 8–12 and the carboxy terminus of hGAT-2.

To obtain the nucleotide sequence of the human GAT-3 GABA transporter (hGAT-3), degenerate PCR primers were used to amplify transporter sequences from human cDNA libraries.

Amplified hGAT-3 sequences were detected in the library by hybridization at low stringency with radiolabeled oligonucleotides representing the region of the rat GAT-3 cDNA that encodes a portion of the second extracellular loop. The human fetal brain library (Stratagene) identified by this approach was screened at high-stringency with the same probes; positive plaques were purified by successive screening at low stringency. Two cDNA clones were isolated (hFB16a, hFB20a) which together comprise nearly the entire coding region of hGAT-3; the sequence of the remaining 7 base pairs was supplied by a genomic clone (hp28a) isolated from a human placental library. A vector comprising the complete coding sequence of hGAT-3 was constructed using appropriate fragments of these three clones, and is designated pcEXV-hGAT-3. The complete nucleotide sequence and predicted amino acid sequence of hGAT-3 are shown in FIG. 10B. In addition to 1896 base pairs of coding region, the sequence includes 5' and 3' untranslated sequence (34 and 61 base pairs, respectively). Translation of a long open reading frame predicts a protein of 632 amino acids that is 95% identical to the rat GAT-3 and contains 12 putative transmembrane domains. Methods similar to methods used to clone the human homologues of the mammalian GABA transporters can similarly be used to clone the human homologues of the mammalian taurine transporter.

The cloning and expression of the human GAT-2 and GAT-3 will allow comparison of pharmacological profiles with those of rat GABA transporters, and also provide a means for understanding and predicting the mechanism of action of GABA uptake inhibitors as human therapeutics. Recently, several additional transporters have been cloned which exhibit significant sequence homology with previously cloned neurotransmitter transporters. cDNA and genomic clones representing the mouse homologues of GAT-1 were recently reported (39). In addition, a glycine transporter cDNA that is similar but not identical to that cloned by Smith et al. (68) was cloned from both rat (22) and mouse (39). A high-affinity L-proline transporter was reported by Fremeau et al.(18), supporting a role for L-proline in excitatory neurotransmission. A rat cDNA identified as a choline transporter was reported by Mayser et al. (50). A taurine transporter cDNA was recently cloned from dog kidney cells (74) which is 90% identical to the rat taurine transporter amino acid sequence reported by Smith et al. (66). A cDNA encoding a mouse GABA transporter was recently cloned by Lopez-Corcuera et al. (45); the transporter encoded by this cDNA is 88% identical to the dog betaine transporter (79), and may represent the mouse homologue of that gene. Finally, a β-alanine-sensitive GABA transporter from rat brain has been cloned (10) that exhibits 100% amino acid identity with the rat GAT-3 sequence reported by Borden et al. (4).

2. TAURINE

Results and Discussion

Cloning of Mammalian Taurine Transporter

We screened a rat brain cDNA library at low stringency with probes encoding the rat brain GABA transporter GAT-1 (21) in order to identify additional inhibitory amino acid transporter genes. Several clones were isolated which hybridized at low but not at high stringency with the GABA transporter probes. Characterization of the clones by DNA sequence analysis revealed that they represented a novel transporter sequence related to GAT-1. None of the clones contained the complete coding region of the putative transporter, and thus the library was rescreened at high stringency using oligonucleotides designed from the new sequence. A 2.5 kb cDNA clone (designated rB16a) was isolated which contained an open reading frame of 1863 base pairs encoding a protein of 621 amino acids (FIG. 1C). Comparison of this sequence with the rat GABA transporter cDNA revealed 58% nucleotide identity within the coding region. Comparison with sequences in Genbank and EMBL data bases demonstrated that the sequence was novel and that the most closely related sequence was the rat GABA transporter (21) followed by the human norepinephrine transporter (55). Subsequent comparisons to recently cloned transporters indicate that the most homologous sequences are two novel GABA transporters designated GAT-2 and GAT-3 (4) and the betaine transporter (79), which exhibit 62–64% nucleotide identity with rB16a.

Figures 1, 1E:
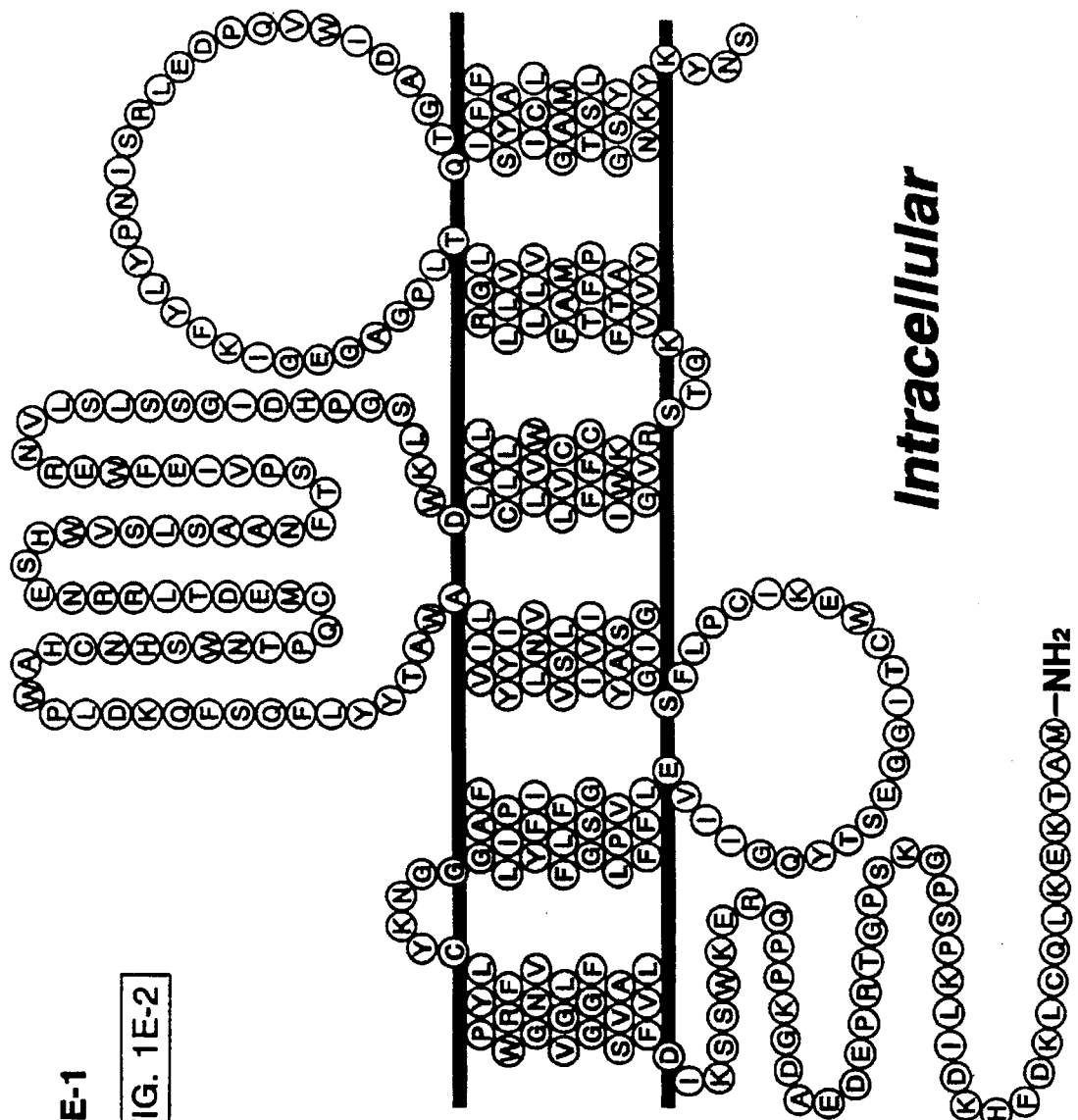
Figures 1, 1E, 2:
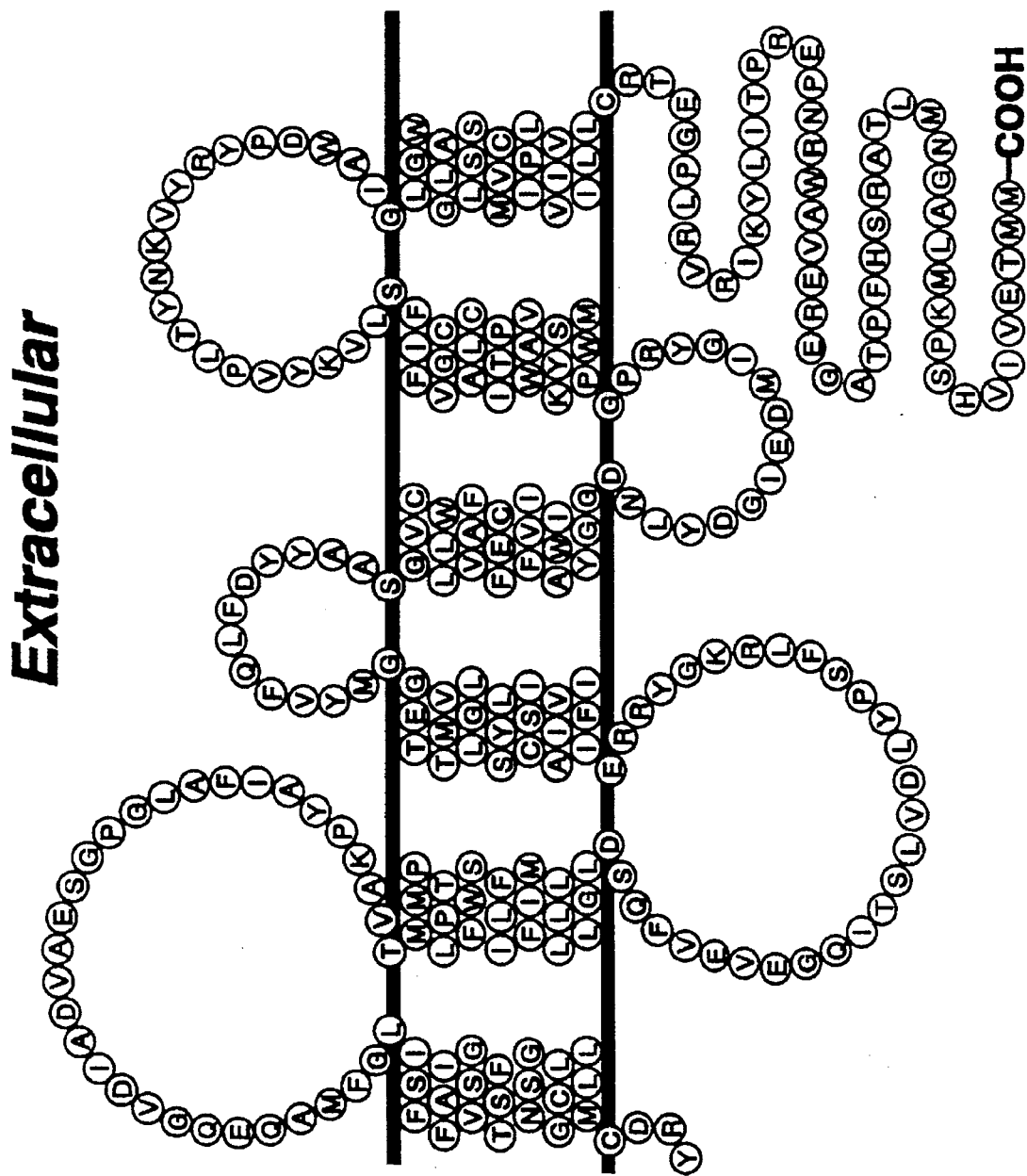

The amino acid sequence deduced from the nucleotide sequence of rB16a is shown in FIG. 1E with a membrane topology similar to that proposed for the rat GABA transporter (21) and other cloned neurotransmitter transporters (3, 23, 33, 55 and 65). The translation product of rB16a is predicted to have a relative molecular mass of ~70,000 Daltons. Hydropathy analysis indicates the presence of 12 hydrophobic domains which may represent membrane spanning segments. Three potential sites for Asn-linked glycosylation are found in the extracellular loop between the third and fourth transmembrane domains. Alignment of the deduced amino acid sequence of rB16a with the rat GABA transporter (GAT-1; (21)) and the dog betaine transporter (79) revealed 50% and 58% amino acid identities, respectively (FIG. 6). Comparison of rB16a with the glycine transporter (FIG. 6; (68)) and the human norepinephrine transporter (55) also showed significant amino acid homology (41–45%), similar to that between GAT-1 and the norepinephrine transporter (46%). As predicted from nucleotide comparisons, the strongest amino acid homology (~61%) is with the GABA transporters GAT-2 and GAT-3 recently cloned from rat brain (4). In contrast, the sodium/glucose cotransporter (22), which shows a low degree of homology with cloned neurotransmitter transporters, displays only 21% amino acid identity with rB16a. These data suggested that the new sequence might encode an inhibitory amino acid transporter expressed in the brain. To explore this possibility, rB16a was placed in a mammalian expression vector, transfected into COS cells, and screened for transport of a variety of radiolabeled neurotransmitters and amino acids.

Pharmacological Characterization of Mammalian Taurine Transporter

COS cells transiently transfected with rB16a (COS/rB16a) accumulated approximately 6-fold more [$^3$H]taurine than control, non-transfected cells (FIG. 7). Specific uptake represented greater than 95% of total uptake in transfected cells. In contrast, the uptake of [$^3$H]glutamate, [$^3$H]glycine, [$^3$H]5-HT, [$^3$H]dopamine, and [$^3$H]GABA was unaltered. Uptake of [$^3$H]taurine was not observed following mock transfection, indicating that the enhanced uptake was not the result of non-specific perturbation of the membrane. The transport of [$^3$H]taurine by COS/rB16a was decreased>95% when Na$^+$ was replaced by Li$^+$, or when Cl$^-$ was replace by acetate (FIG. 7). In the absence of sodium or chloride, taurine transport in COS/rB21a decreased to levels below that of non-transfected controls, demonstrating that endogenous taurine transporter activity present in COS cells is also dependent on these ions. A similar ion dependence has been observed for taurine transport in vivo (27), as well as for the activity of other cloned neurotransmitter transporters such as those for GABA (21), glycine (68), and norepinephrine (55).

To determine the affinity of taurine for the cloned transporter, COS/rB16a was incubated with various concentrations of [$^3$H]taurine and the specific accumulation of radioactivity was determined. Accumulation of [$^3$H]taurine was dose-dependent and reached saturation at higher concentrations (FIG. 8). Non-linear regression analysis of the data yielded the following values: $K_M$=43±6 μM, and $V_{MAX}$=0.96±0.27 nmoles/mg protein (mean±SEM, n=4 experiments). The affinity of the cloned transporter for taurine is similar to that of high-affinity taurine transporters in both the central nervous system (42,80) and peripheral tissues (37) which exhibit $K_M$ values from 10 to 60 μM. Taken together, these data indicate that rB16a encodes a saturable, high-affinity, sodium- and chloride-dependent taurine transporter.

To determine the pharmacological specificity of the cloned transporter, various agents were examined for their ability to inhibit the transport of [$^3$H]taurine by COS/rB16a (Table 6). As the endogenous taurine transporter in COS cells accounted for, on average, 16% of the total transport activity observed in transfected cells, we were concerned that this could influence results. Accordingly, we also examined the sensitivity of the endogenous taurine transporter present in non-transfected cells. As shown in Table 6, the pharmacologic properties of the cloned taurine transporter closely matched those of the endogenous transporter and thus did not lead to erroneous results.

The most potent inhibitors were taurine and hypotaurine, each of which inhibited specific [$^3$H]taurine uptake approximately 30–40% at 10 μM, 90% at 100 μM, and 100% at 1 mM. β-alanine was slightly less potent, inhibiting specific uptake 15%, 51%, and 96% at 10 μM, 100 μM, and 1 mM, respectively; the high potency of β-alanine as an inhibitor of taurine uptake is consistent with the finding that COS/rB16a showed a 6-fold increase in the specific uptake of [$^3$H]β-alanine (data not shown), essentially identical to the fold-increase observed with [$^3$H]taurine. The taurine analogue GES was also quite potent, inhibiting specific uptake of [$^3$]taurine 11%, 45% and 92% at 10 μM, 100 μM and 1 mM, respectively. APSA and GABA both inhibited uptake approximately 10% and 40% at 100 μM and 1 mM, respectively. The observations that GABA is a poor inhibitor of taurine uptake, and that transfection with rB16a did not result in enhanced uptake of [$^3$H]GABA (see above), are consistent with the previous report (38) that GABA is a weak non-competitive inhibitor of taurine uptake. Less than 10% inhibition of [$^3$H]taurine uptake was observed for the following compounds (each tested at 1 mM): the structural analogues AEPA and MEAas well as the sulfur-containing amino acids cysteine and methionine (Table 6), and (data not shown) norepinephrine, dopamine, glutamate, glycine, serine, betaine, L-methionine, and α-methylaminoisobutyric acid (a substrate for amino acid transporter designated system A; (21)). Taken together, these results indicate that the taurine transporter encoded by rB16a is similar to the endogenous taurine transporter in COS cells (Table 6), as well as the endogenous taurine transporter(s) present in neural tissue (25),(see also ref. 27 and references therein).

It is of interest that sensitivity to β-alanine is shared by the two high-affinity GABA transporters recently cloned from rat brain (GAT-2 and GAT-3 (4)), which are even more closely related to the taurine transporter (62% amino acid identity) than to the neuronal-type GABA transporter GAT-1 (51%). β-alanine has been shown to activate an inward chloride current in spinal neurons (9,49) and is released in a calcium-dependent manner from several brain areas (31, 58), suggesting a role as an inhibitory neurotransmitter in the CNS. The similar sensitivities of the newly cloned GABA transporters[4] and the taurine transporter to β-alanine, combined with their sequence homologies, suggest that they represent a subfamily of inhibitory neurotransmitter transporters. Despite these similarities, these transporters unexpectedly exhibit widely divergent affinities for GABA: GAT-2 and GAT-3 show the highest affinity (Km=10 μM (4)), while the affinity of the taurine transporter is extremely low (–1 mM, Table 6). Interestingly, the dog betaine transporter (79), which displays a similar degree of homology to the members of this subfamily (ca. 60%), exhibits an intermediate affinity for GABA (–100 μM). The finding that four structurally related transporters display overlapping substrate specificities for the neuroactive amino acids GABA and β-alanine suggests that multiple transporters may regulate the synaptic levels of these substances. This crossreactivity underscores the importance of understanding the action of therapeutic agents at both GABA and taurine transporters.

TABLE 6

Pharmacological Specificity of [$^3$H]taurine Uptake.

| Inhibitor[a] | Concentration | % Inhibition control | % Inhibition rB16a |
|---|---|---|---|
| AEPA | 1 mM | 0 ± 0 (4) | 3 ± 3 (5) |
| AMSA | 1 mM | 1 ± 1 (4) | 7 ± 3 (4) |
| APSA | 100 μM | 7 ± 3 (4) | 8 ± 4 (4) |
|  | 1 mM | 45 ± 3 (5) | 36 ± 4 (5) |
| β-alanine | 10 μM | 9 ± 2 (6) | 15 ± 6 (6) |
|  | 100 μM | 63 ± 3 (6) | 51 ± 4 (10) |
|  | 1 mM | 97 ± 1 (4) | 96 ± 1 (8) |
| CSA | 1 mM | 2 ± 1 (4) | 7 ± 5 (3) |
| cysteine | 1 mM | 4 ± 3 (3) | 2 ± 2 (3) |
| GABA | 10 μM | 1 ± 1 (4) | 9 ± 6 (4) |
|  | 100 μM | 9 ± 4 (6) | 10 ± 4 (10) |
|  | 1 mM | 49 ± 2 (5) | 44 ± 6 (8) |
| GES | 10 μM | 6 ± 3 (4) | 11 ± 4 (4) |
|  | 100 μM | 47 ± 3 (5) | 45 ± 5 (5) |
|  | 1 mM | 89 ± 1 (5) | 92 ± 1 (6) |
| hypotaurine | 10 μM | 41 ± 3 (7) | 26 ± 7 (7) |
|  | 100 μM | 91 ± 1 (4) | 84 ± 3 (4) |
|  | 1 mM | 99 ± 1 (4) | 100 ± 1 (4) |
| MEA | 1 mM | 1 ± 0 (3) | 3 ± 3 (4) |
| methionine | 1 mM | 1 ± 1 (3) | 1 ± 1 (3) |
| taurine | 10 μM | 38 ± 5 (7) | 29 ± 8 (5) |
|  | 100 μM | 89 ± 2 (4) | 83 ± 2 (5) |
|  | 1 mM | 100[b] | 100[b] |

[a]Non-transfected COS-7 cells (control), or COS-7 cells transfected with rB16a were incubated for 10 minutes (37° C.) with 50 nM [$^3$H]taurine and the indicated compounds. Data show percent displacement of specific [$^3$H]taurine uptake (mean ± SEM; values in parentheses indicate number of experiments).
[b]Non-specific uptake defined with 1 mM taurine.
Abbreviations: AEPA, 2-aminoethylphosphonic acid; AMSA, aminomethanesulfonic acid; APSA, 3-amino-1-propanesulfonic acid; CSA, cysteinesulfinic acid; GABA, gamma-aminobutyric acid; GES, guanidinoethanesulfonic acid; MEA, 2-mercaptoethylamine.

Tissue Localization Studies of Mammalian Taurine Transporter

To define the tissue distribution patterns of the taurine transporter, polymerase chain reaction (PCR) was used to detect the rB16a sequence in cDNA representing mRNA from seven different rat tissues. As a control, the distribution of the constitutively expressed protein cyclophilin was also examined. Radiolabeled oligonucleotides specific for rB16a were used to detect PCR products by hybridization. As shown in FIG. 9A, the taurine transporter was detectable in all tissues examined, including brain, retina, liver, kidney, heart, spleen, and pancreas, after 30 cycles of PCR. Cyclophilin was amplified to a similar extent from all the tissues (data not shown), demonstrating that adequate cDNA was present in each sample.

To evaluate both the abundance and the size of the mRNA encoding the taurine transporter, Northern blot analysis was carried out on poly A+ RNA isolated from the same rat tissues used for PCR analysis, with the addition of lung. As shown in FIG. 9B, a single~6.2 kb transcript which hybridized with the taurine transporter cDNA probe was detected in brain, kidney, heart, spleen, and lung after an overnight exposure of the autoradiogram. After a 3-day exposure, bands of the same size were also visible in liver and pancreas (data not shown). Rehybridization of the blot with the cDNA encoding cyclophilin (12) confirmed that roughly equal amounts of RNA were present in each sample except that of retina, which was significantly degraded (data not shown). Thus, taurine transporter mRNA levels were highest in brain and lung, intermediate in kidney, heart, and spleen, and lowest in liver and pancreas. The abundance and pattern of distribution of the taurine transporter mRNA by Northern blot are consistent with data obtained using PCR (FIG. 9); further, the same size transcript is present in all tissues evaluated. These findings suggest that a single taurine transporter functions in both the brain and peripheral tissues; however, we can not exclude the existence of additional taurine transporters.

Taurine is abundant in the central nervous system and is involved in a variety of neural activities. Unlike classical neurotransmitters, the effects of taurine are mediated both intra- and extracellularly. A major regulator of taurine levels, both within cells and in the synaptic cleft, is the transport of taurine across the plasma membrane. Our cloning of a high-affinity taurine transporter represents a critical step in defining the role of taurine in both neural and non-neural tissues, and in the development of therapeutic agents that alter taurine and GABA neurotransmission. In addition, the identification of a new member of the set of inhibitory amino acid transporters will aid in elucidating the molecular structure-function relationships within the transporter family.

REFERENCES

1. Amenta, F., Cavallotti, C., Iacopono, L., and Erdo, S. L. 36, 390–395.
2. Andrade, R., Malenka, R. C., and Nicoll, R. A. (1988) Science 234, 1261–1265.
3. Blakely, R. D., Berson, H. E., Fremeau, Jr., R. T., Caron, M. G., Peek, M. M., Prince, H. K., and Bradley, C. C. (1991). Nature 354, 66–70.
4. Borden, L. A., K. E. Smith, P. R. Hartig, T. A. Branchek, and R. L. Weinshank (1992) J. Biol. Chem. In press.
5. Bowery, N. G., G. P. Jones, and M. J. Neal (1976) Nature (London) 264, 281–284.
6. Braestrup, C., Nielsen, E. B., Sonnewald, U., Knutsen, L. J. S., Andersen, K. E., Jansen, J. A., Frederiksen, K., Andersen, P. H., Mortensen, A., and Suzdak, P. D. (1990) J. Neurochemistry 54, 639–647.
7. Capecchi M. R., Science 244, 1288–1292 (1989)
8. Chadwick, D., Richens, A., Duncan, J., Dam, M., Gram, L., Morrow, J., Mengel, H., Shu, V., McKelvy, J. F., and Pierce, M. W. (1991) Epilepsia 32 (supplement 3), 20.
9. Choquet, D. and Korn, H. Does β-alanine activate more than chloride channel associated receptor? Neurosci. Letters 84:329–340 (1988).
10. Clark, J. A., A. Y. Deutch, P. Z. Gallipoli, and S. G. Amara (1992) Neuron 9,337–348.
11. Cohen, J. S., Trends in Pharm. Sci. 10, 435 (1989).
12. Danielson, P. E., Forss-Petter, S., Brow, M. A., Calavetta, L., Douglass, J.., Milner, R. J., and Sutcliffe, J. G. (1988). DNA 7, 261–267.
13. Dichter, M. A. (1980) Brain Res. 190, 111–121.
14. Erdo, S. L. and Wolff, J. R. (1990) J. Neurochem. 54, 363–372.
15. Falch, E., Larsson, O. M., Schousboe, and Krogsgaard-Larsen, P. (1990). Drug Devel. Res. 21, 169–188.
17. Feinberg, A. P., and Bogelstein, B. (1988). A technique for radiolabeling DNA restriction endonuclease fragments to high specific activity. Anal. Biochem. 132, 6–13.
18. Fremeau, R. T., Jr., M. G. Caron, and R. D. Blakely (1992) Neuron 8,915–926.
19. Goodyer, P. R., Rozen, R., and Scriver, C. R. (1985) Biochem. Biophys. Acta 818, 45–54.
20. Guastella, J., N. Brecha, C. Wiegmann, H. A. Lester, and N. Davidson (1992) Proc. Natl. Acad. Sci. USA 89, 7189–7193.
21. Guastella, J., N. Nelson, H. Nelson, L. Czyzyk, S. Keynan, M. C. Miedel, N. Davidson, H. A. Lester, and B. I. Kanner (1990) Science 249:1303–6.
22. Hediger, M. A., Turk, E., and Wright, E. M. Homology of the human intestinal $Na^+$/glucose and *Escherichia coli* $Na^+$/proline cotransporters. Proc. Natl. Acad. Sci. USA 86:5748–5752.
23. Hoffman, B. J., Mezey, E., and Brownstein, M. J. Cloning of a serotonin transporter affected by antidepressants. Science 254:579–580 (1991).
24. Hogan B. et al., Manipulating the Mouse Embryo, A Laboratory Manual, Cold Spring Harbor Laboratory (1986).
25. Hruska, R. E., Huxtable, R. J., and Yamumbra, H. I. High-affinity, temperature-sensitive, and sodium-dependent transport of taurine in rat brain in Taurine and Neurological Disorders, ed. A. Barbeau and R. J. Huxtable. (Raven Press, NY, 1978).
26. Huxtable, R. J. Review: Taurine interactions with ionic conductances in excitable membranes. Prog. Clin. Biol. Res. 351:157–161 (1990).
27. Huxtable, R. J. Taurine in the central nervous system and the mammalian actions of taurine. Prog. Neurobiol. 32:471–533 (1989).
28. Iversen, L. L. amd Bloom, F. E. (1972) Brain Res. 41, 131–143.
29. Kanner, B. I. and Schuldiner, S. (1987) CRC Crit, rev. Biochem. 22, 1–38.
30. Kanner, B. I. and A. Bendahan (1990) Proc. Natl. Acad. Sci. USA 87, 2550–2554.
31. Kihara, M., Misu, Y., and Kubo, T. Release by electrical stimulation of endogenous glutamate, γ-aminobutyric acid, and other amino acids from slices of the rat medulla oblongata. J. Neurochem. 52:261–267 (1989).
32. Kilberg, M. S. Amino acid transport in isolated rat hepatocytes. J. Memb. Biol. 69:1–12 (1982).
33. Kilty, J. E., Lorang D., and Amara, S. G. (1991). Science 254, 578–579.
34. Kontro, P., Korpi, E. R., and Oja, S. S. Taurine interacts with $GABA_A$ and $GABA_B$ receptors in the brain. Prog. Clin. Biol. Res. 351:83–94 (1990).
35. Krnjevic, K. (1991) in GABA Mechanisms in Epilepsy, ed. G. Tunnicliff and B. U. Raess, pp 47–87, Wiley-Liss, NY.
36. Krogsgaard-Larsen, P., Falch, E., Larsson, O. M., and Schousboe, A. (1987) Epilepsy Res. 1, 77–93.
37. Lambert, I. H. and Hoffman, E. K. Taurine transport and cell volume regulation in a mammalian cell. Prog. Clin. Biol. Res. 351:267–276 (1990).
38. Larsson, O. M, Griffiths, R., Allen, I. C., and Schousboe, A. Mutual inhibition kinetic analysis of γ-aminobutyric acid, taurine, and β-alanine high-affinity transport into neurons and astrocytes: Evidence for similarity between the taurine and β-alanine carriers in both cell types. J. Neurochem. 47:426–432 (1986).

39. Liu, Q.-R., H. Nelson, S. Mandiyan, B. Lopez-Corcuera, and N. Nelson (1992a) FEBS Letters 305,110–114.
40. Liu, Q.-R., S. Mandiyan, H. Nelson, and N. Nelson (1992) Proc. Natl. Acad. Sci. USA 89,6639–6643.
41. Lombardini, J. B. (1988) Effects of taurine and mitochondrial metabolic inhibitors on ATP-dependent $Ca^{2+}$ uptake in synaptosomal and mitochondrial subcellular fractions of rat retina, J. Neurochemistry 51, 200–205.
42. Lombardini, J. B. High-affinity transport of taurine in the mammalian central nervous system, in Taurine and Neurological Disorders, (A. Barbeau and R. J. Huxtable, eds.). Raven Press, New York, 119–135 (1978).
43. Lombardini, J. B. and Kiebowitz, S. M. (1990) Inhibitory and stimulatory effects of structural and conformational analogues of taurine on ATP-dependent calcium ion uptake in the rat retina: Deductions concerning the conformation of taurine. In Progress in Clinical and Biological Research 351, 197–206.
44. Lopata, M. A., Cleveland, D. W., and Sollner-Webb, B. (1984). Nucl. Acids Res. 12, 5707–5717.
45. Lopez-Corcuera, B., Q.-R. Liu, S. Mandiyan, Nelson, and N. Nelson (1992) J. Biol. Chem. 267,17491–17493.
46. Low, M. J., Lechan, R. M., and Hammer, R. E. (1986) Science 231, 1002–1004.
47. Maniatis, T., Fritsch, E. F. Fritsch and Sambrook, J., Molecular Cloning, Cold Spring Harbor Laboratory, 1982.
48. Maniatis, T., Fritsch, E. F. and Sambrook, J., Molecular Cloning, Cold Spring Harbor Laboratory, pp 197–198, 1982.
49. Mathers, D. A., Grewal, A., and Wang, Y. β-alanine induced ion channels in the membrane of cultured spinal cord neurons. Neurosbi. Letters 108:127–131 (1990).
50. Mayser, W., P. Schloss, and H. Betz (1992) FEBS Letters 305, 31–36.
51. Miller, J., and Germain, R. N. (1986). J. Exp. Med. 164, 1478–1489.
52. Minuk, G. Y., Vergalla, J., Ferenci, P., and Jones, E. A. (1984) Hepatology 4, 180–185.
53. Neal, M. J. and N. G. Bowery (1977) Brain Res. 86, 243–257.
54. Oberdick, J., Smeyne, R. J., Mann, J. R., Jackson, S. and Morgan, J. I. (1990) Science 248, 223–226.
55. Pacholczyk, T., Blakely, R. D., and Amara, S. G. Expression cloning of a cocaine- and antidepressant-sensitive human noradrenaline transporter. Nature 350:350–354 (1991).
56. Quinn, M. R. Taurine allosterically modulates binding sites of the $GABA_A$ receptor. Prog. Clin. Biol. Res. 351:121–127 (1990).
57. Rogawski, M. A. and Porter, R. J. (1990) Pharmacological Reviews 42,224–286.
58. Sandberg, M. and Jacobson, I. β-alanine, a possible neurotransmitter in the visual system? J. Neurochem. 37:1353–1356 (19817.
59. Sanger, S. (1977). Proc. Natl. Acad. Sci. USA 74, 5463–5467.
60. Sarver, N. et al., Science 247, 1222 (1990)).
61. Schon, F. and J. S. Kelly (1975) Brain Res. 41, 131–143.
62. Schousboe, A., Larsson, O. M., and Krogsgaard-Larsen, P. (1991) in GABA Mechanisms in Epilepsy, ed. G. Tunnicliff and B. U. Raess, pp 165–187, Wiley-Liss, NY.
63. Sedman, A. J., Gilmet, G. P., Sayed, A. J., and Posvar, E. L. (1990) Drug Development Research 21, 235–242.
64. Shain, W., and Martin, D. L. Review: Uptake and release of taurine: an overview. Prog. Clin. Biol. Res. 351:243–252 (1990).
65. Shimada, S., Kitayama, S., Lin, C.-L., Patel, A., Nanthakumaar, E., Gregor, P. Kuhar, M. and Uhl, G. (1991). Science 254, 576–578.
66. Smith, K. E., L. A. Borden, C.-H. D. Wang, P. R. Hartig, T. A. Branchek, and R. L. Weinshank (1992a) Mol. Pharm. 42, 563–569.
67. Smith, K. E., Borden, L. A., Branchek, T., Hartig, P. R., and Weinshank, R. L. DNA encoding a glycine transporter and uses thereof. Pat. Pending.
68. Smith, K. E., L. A. Borden, P. R. Hartig, T. A. Branchek, and R. L. Weinshank (1992) Neuron 8, 927–935.
69. Smullin, D. H., Schamber, C. D., Skilling, S. R., and Larson, A. A. (1990) A possible role for taurine in analgesia. In Progress in Clinical and Biological Research 351, 129–132.
70. Sturman, J. A. Review: Taurine deficiency. Prog. Clin. Biol. Res. 351:385–395 (1990).
71. Tallman, J. F. and Hutchison, A. (1990) Molecular biological insights into GABA and benzodiazepine receptor structure in Progress in Clinical and Biological Research 361, 131–144.
72. Taylor, C. P., Vartanian, M. G., Schwarz, R. D., Rock, D. M., Callahan, M. J., and Davis, M. D. (1990) Drug Development Research 21, 195–215.
73. Twyman, R. E. and Macdonald, R. L. (1991) in GABA Mechanisms in Epilepsy, editors G. Tunnicliff and B. U. Raess, pp 89–104, Wiley-Liss, NY.
74. Uchida, S., H. M. Kwon, A. Yamauchi, A. S. Preston, F. Marumo, and J. Handler (1992) Proc. Natl. Acad. Sci. USA 89, 8230–8234.
75. Van Gelder, N. M. Neuronal discharge hypersynchrony and the intracranial water balance in relation to glutamic acid and taurine redistribution: Migraine and epilepsy. Prog. Clin. Biol. Res. 351:1–20 (1990).
76. Weintraub, H. M., Scientific American, January (1990) p. 40.
77. Williams, M. (1990) in Progress in Clinical and Biological Research 361, ed. B. S. Meldrum and M. Williams, pp 131–144, Wiley-Liss, MY.
78. Wu, J.-Y., Liao, C., Lin, C. J., Lee, Y. H., Ho, J. Y., and Tsai, W. H. (1990) Taurine receptor in mammalian brain in Progress in Clinical and Biological Research 351, 147–156.
79. Yamauchi, A., S. Uchida, H. M. Kwon, A. S. Preston, R. B. Robey, A. Garcia-Perez, M. B. Burg, and J. S. Handler (1992) J. Biol. Chem. 267,649–652.
80. Yorek, M. A. and Spector, A. A. Taurine transport and metabolism in human retinoblastoma cells, in Taurine: Biological actions and clinical perspectives. Alan R. Liss, Inc. 361–370 (1985).
81. Yunger, L. M., Fowler, P. J., Zarevics, P., and Setler, P. E. (1984) J. Pharmacol. Experimental Therapeutics 228, 109–115.
82. Zimmer, and Gruss, P-, Nature 338, 150–153 (1989).
83. Hammer, R. E. et al., Science 231:1002–1004 (1986).
84. Morgan, J. I., Science 248:223–226 (1986).
85. Branchek, T., Adham, A., Macchi, M., Kao, H. T. and Hartig, P. R., Molecular Pharmacology 36: 604–609 (1990).
86. Kanner, B. I., Biochemistry 17:1207–1211 (1978).
87. Mabjeesh, N. J., Frese, M., Rauen, T., Jeserich, G. and Kanner B. I., Federation of European Biochemical Societies 299:99–102 (1992).
88. Rudnick, G., Journal of Biological Sciences 252: 2170–2174 (1977).

What is claimed is:

1. An isolated nucleic acid molecule encoding a rat taurine transporter having the amino acid sequence shown in FIG. 1C (Seq. I.D. No. 6).

2. An isolated nucleic acid molecule of claim 1, wherein the nucleic acid molecule is a DNA molecule.

3. A DNA molecule of claim 2, wherein the DNA molecule is a cDNA molecule.

4. A vector comprising the DNA molecule of claim 2.

5. A plasmid comprising the vector of claim 4.

6. A vector of claim 4 adapted for expression in a bacteria cell which comprises the regulatory elements necessary for expression of the DNA in the bacterial cell so located relative to the DNA encoding the transporter as to permit expression thereof.

7. A vector of claim 4 adapted for expression in a yeast cell which comprises the regulatory elements necessary for expression of the DNA in the yeast cell so located relative to the DNA encoding the transporter as to permit expression thereof.

8. A vector of claim 4 adapted for expression in a mammalian cell which comprises the regulatory elements necessary for expression of the DNA in the mammalian cell so located relative to the DNA encoding the transporter as to permit expression thereof.

9. A plasmid of claim 5 adapted for expression in a mammalian cell which comprises the regulatory elements necessary for expression of the DNA in the mammalian cell so located relative to the DNA encoding the taurine transporter as to permit expression thereof.

10. The plasmid pEVJB-rB16a (ATCC Accession No. 75202).

11. A mammalian cell comprising the plasmid of claim 5.

12. The mammalian cell of claim 11, wherein the mammalian cell is a Cos7 cell.

13. A Cos7 cell comprising the plasmid of claim 9.

* * * * *

UNITED STATES PATENT AND TRADEMARK OFFICE
CERTIFICATE OF CORRECTION

PATENT NO. : 5,658,786
DATED : August 19, 1997
INVENTOR(S) : Kelli E. Smith, Richard L. Weinshank, Laurence A. Borden, Paul R. Hartig It is certified that error appears in the above-identified patent and that said Letters Patent is hereby corrected as shown below:

column 2, line 47: "rBSb" should read --rB8b--
column 3, line 12: "pEVJB-rBSb" should read --pEVJB-rB8b--
column 6, line 64: "electrol phoretically" should read --electrophoretically--
column 8, line 21: "rBSb" should read --rB8b--
        line 37: "rBSb" should read --rB8b--
        line 50: "rBSb" should read --rB8b--
        line 52: "betains" should read --betaine--
        line 55: "rBSb" should read --rB8b--
column 9, line 10: "rBSb" should read --rB8b--
        line 14: "rBSb" should read --rB8b--
        line 26: "rBSb" should read --rB8b--
        line 34: "betdine" should read -- betaine--
column 11, line 63: "homoloque" should read --homologue--
column 13, line 15: "pEVJB-rBSb" should read --pEVJB-rB8b--
column 14, line 19: "fs" should read --is--
        line 47: "pEVJB-rBSb" should read --pEVJB-rB8b--
column 17, line 41: "Capable" should read --capable--
column 18, line 47: "Complementary" should read --complementary--
column 23, line 5: "transgene2" should read --trans-gene--
column 30, line 57: "rBSb" should read --rB8b--
        line 62: "rBSb" should read --rB8b--
column 31, line 2: "rBSb" should read --rB8b--
        line 38: "rBSb" should read --rB8b--

UNITED STATES PATENT AND TRADEMARK OFFICE
CERTIFICATE OF CORRECTION

PATENT NO. : 5,658,786
DATED : August 19, 1997
INVENTOR(S) : Kelli E. Smith, Richard L. Weinshank, Laurence A. Borden, Paul R. Hartig It is certified that error appears in the above-identified patent and that said Letters Patent is hereby corrected as shown below:

column 32, line 5: "NIgH Chemical" should read --NIMH Chemical--
line 35: "fl" should read --f1--
line 42: "rBSb" should read --rB8b--
line 49: "rBSb" should read --rB8b--
column 33, line 50: "rBSb" should read --rB8b--
line 67: "rBSb" should read --rB8b--
column 34, line 40: "fl" should read --f1--
line 50: "XbaISalI" should read --XbaI/SalI--
column 35, line 51: "$^{32}$p-labeled" should read --$^{32}$P-labeled--
column 36, line 17: "senae" should read --sense--
line 51: "fl" should read --f1--
column 37, line 37: "$^{32}$p-labeled" should read --$^{32}$P-labeled--
line 43: "rBSb" should read --rB8b--
line 64, "$_{0.001}$% gelatin" should read --0.001% gelatin--
column 38, line 51: "rBSb" should read --rB8b--
line 64: "rBSb" should read --rB8b--
line 66: "`64%" should read -- ~64%--
line 66: "`56%" should read -- ~56%--
line 67: "rBSb" should read --rB8b--

UNITED STATES PATENT AND TRADEMARK OFFICE
CERTIFICATE OF CORRECTION

PATENT NO. : 5,658,786   Page 3 of 4
DATED : August 19, 1997
INVENTOR(S) : Kelli E. Smith, Richard L. Weinshank, Laurence A. Borden, Paul R. Hartig It is certified that error appears in the above-identified patent and that said Letters Patent is hereby corrected as shown below:

column 39, line 4: "rBSb" should read --rB8b--
line 14: "rBSb" should read --rB8b--
line 20: "rBSb" should read --rB8b--
line 32: "rBSb" should read --rB8b--
line 38: "rBSb" should read --rB8b--
line 39: "COS/rBSb" should read --COS/rB8b--
line 45: "rBSb" should read --rB8b--
line 53: "COS/rBSb" should read --COS/rB8b--
line 60: "COS/rBSb" should read --COS/rB8b--
line 64: "rs." should read --vs.--
line 64: "rBSb" should read --rB8b--
line 65: "rs." should read --vs.--
line 65: "rBSb" should read --rB8b--
line 67: "COS/rBSb" should read --COS/rB8b--
column 40, line 7: "COS/rBSb" should read --COS/rB8b--
line 9: "rBSb" should read --rB8b--
line 14: "rBSb" should read --rB8b--

UNITED STATES PATENT AND TRADEMARK OFFICE
CERTIFICATE OF CORRECTION

PATENT NO. : 5,657,786
DATED : August 19, 1997
INVENTOR(S) : Kelli E. Smith, Richard L. Weinshank, Laurence A. Borden, Paul R. Hartig It is certified that error appears in the above-identified patent and that said Letters Patent is hereby corrected as shown below:

column 41, line 44: "A" should read --a--
column 42, line 22: "Polymerass" should read --Polymerase--
column 45, line 33: "sam" should read --same--
column 46, line 55: "-53%" should read --~53%--
column 48, line 31: "PeR" should read --PCR--
          line 40: "of-a" should read --of a--
column 50, line 14: "-70,000" should read --~70,000--
          line 29: "61%" should read -- ~ 61%--
column 51, line 33: "[³]taurine" should read --[³H]taurine--
column 52, line 3: "-1 mM" should read --~ 1 mM--
          line 6: "-100mM' should read --~ 100mM--

Signed and Sealed this

Twenty-third Day of February, 1999

Attest:

Q. TODD DICKINSON

*Attesting Officer*      *Acting Commissioner of Patents and Trademarks*

SEQUENCE LISTING ( 1 ) GENERAL INFORMATION:

( i i i ) NUMBER OF SEQUENCES: 35

( 2 ) INFORMATION FOR SEQ ID NO:1:

( i ) SEQUENCE CHARACTERISTICS:
        ( A ) LENGTH: 2028 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: N ( i v ) ANTI-SENSE: N ( v ) FRAGMENT TYPE: N-terminal ( v i i ) IMMEDIATE SOURCE:
        ( A ) LIBRARY: rat brain
        ( B ) CLONE: rB14b ( i x ) FEATURE:
        ( A ) NAME/KEY: CDS
        ( B ) LOCATION: 126..1932
        ( D ) OTHER INFORMATION:

( x i ) SEQUENCE DESCRIPTION: SEQ ID NO:1:

```
GGCAGCGAAC ACAAGCGCAT CCGGTAGAAC GGAAAGAACA GGAATTGCAG AGTGACTTCA      60

AGTCTCCATA CGATTTACTA CCCGGGTGAC GGCAGTGACT CGACAGAGTA GCGGCTGCAG     120

GTGGG ATG GAT AAC AGG GTC TCG GGA ACG ACC AGT AAT GGA GAG ACA         167
      Met Asp Asn Arg Val Ser Gly Thr Thr Ser Asn Gly Glu Thr
        1               5                  10

AAG CCA GTG TGT CCA GTC ATG GAG AAG GTG GAG GAA GAC GGT ACC TTG       215
Lys Pro Val Cys Pro Val Met Glu Lys Val Glu Glu Asp Gly Thr Leu
 15              20                  25                  30

GAA CGG GAG CAA TGG ACC AAC AAG ATG GAG TTC GTA CTG TCA GTG GCG       263
Glu Arg Glu Gln Trp Thr Asn Lys Met Glu Phe Val Leu Ser Val Ala
                 35                  40                  45

GGA GAG ATC ATT GGC TTA GGC AAC GTC TGG AGG TTT CCC TAT CTC TGC       311
Gly Glu Ile Ile Gly Leu Gly Asn Val Trp Arg Phe Pro Tyr Leu Cys
             50                  55                  60

TAC AAG AAC GGG GGA GGT GCC TTC TTT ATT CCC TAC CTC ATC TTC CTA       359
Tyr Lys Asn Gly Gly Gly Ala Phe Phe Ile Pro Tyr Leu Ile Phe Leu
         65                  70                  75

TTT ACC TGT GGC ATT CCT GTC TTC TTC CTG GAG ACA GCG CTT GGC CAG       407
Phe Thr Cys Gly Ile Pro Val Phe Phe Leu Glu Thr Ala Leu Gly Gln
     80                  85                  90

TAC ACC AAC CAG GGA GGC ATC ACA GCC TGG AGG AAA ATC TGT CCC ATC       455
Tyr Thr Asn Gln Gly Gly Ile Thr Ala Trp Arg Lys Ile Cys Pro Ile
 95                 100                 105                 110

TTC GAG GGC ATC GGC TAT GCC TCA CAG ATG ATC GTC AGC CTT CTC AAT       503
Phe Glu Gly Ile Gly Tyr Ala Ser Gln Met Ile Val Ser Leu Leu Asn
115                 120                 125

GTC TAC TAC ATC GTT GTC CTG GCC TGG GCC CTC TTC TAC CTC TTC AGC       551
Val Tyr Tyr Ile Val Val Leu Ala Trp Ala Leu Phe Tyr Leu Phe Ser
                130                 135                 140

AGC TTC ACC ACT GAC CTC CCC TGG GGT AGC TGC AGC CAC GAG TGG AAT       599
Ser Phe Thr Thr Asp Leu Pro Trp Gly Ser Cys Ser His Glu Trp Asn
            145                 150                 155

ACA GAA AAC TGT GTG GAG TTC CAG AAA ACC AAC AAT TCC CTG AAT GTG       647
```

|     |     |     |     |     |     |     |     |     |     |     |     |     |     |     |      |
| --- | --- | --- | --- | --- | --- | --- | --- | --- | --- | --- | --- | --- | --- | --- | ---- |
| Thr | Glu | Asn | Cys | Val | Glu | Phe | Gln | Lys | Thr | Asn | Asn | Ser | Leu | Asn | Val  |
|     | 160 |     |     |     | 165 |     |     |     |     | 170 |     |     |     |     |      |
| ACT | TCT | GAG | AAT | GCC | ACA | TCC | CCT | GTC | ATC | GAG | TTC | TGG | GAG | AGG | CGA  | 695 |
| Thr | Ser | Glu | Asn | Ala | Thr | Ser | Pro | Val | Ile | Glu | Phe | Trp | Glu | Arg | Arg  |
| 175 |     |     |     |     | 180 |     |     |     |     | 185 |     |     |     |     | 190  |
| GTC | CTG | AAG | ATC | TCA | GAT | GGC | ATC | CAG | CAC | CTG | GGG | TCC | CTG | CGC | TGG  | 743 |
| Val | Leu | Lys | Ile | Ser | Asp | Gly | Ile | Gln | His | Leu | Gly | Ser | Leu | Arg | Trp  |
|     |     |     |     | 195 |     |     |     |     | 200 |     |     |     |     | 205 |      |
| GAG | CTG | GTC | CTG | TGC | CTC | CTG | CTT | GCC | TGG | ATC | ATC | TGC | TAT | TTC | TGC  | 791 |
| Glu | Leu | Val | Leu | Cys | Leu | Leu | Leu | Ala | Trp | Ile | Ile | Cys | Tyr | Phe | Cys  |
|     |     |     | 210 |     |     |     |     | 215 |     |     |     |     | 220 |     |      |
| ATC | TGG | AAA | GGG | GTC | AAG | TCC | ACA | GGC | AAG | GTG | GTG | TAC | TTC | ACA | GCT  | 839 |
| Ile | Trp | Lys | Gly | Val | Lys | Ser | Thr | Gly | Lys | Val | Val | Tyr | Phe | Thr | Ala  |
|     |     | 225 |     |     |     |     | 230 |     |     |     |     | 235 |     |     |      |
| ACT | TTC | CCT | TAC | CTC | ATG | CTG | GTG | GTC | CTG | TTG | ATC | CGA | GGA | GTA | ACA  | 887 |
| Thr | Phe | Pro | Tyr | Leu | Met | Leu | Val | Val | Leu | Leu | Ile | Arg | Gly | Val | Thr  |
|     | 240 |     |     |     | 245 |     |     |     |     | 250 |     |     |     |     |      |
| CTG | CCT | GGA | GCA | GCC | CAG | GGA | ATT | CAG | TTT | TAC | CTG | TAC | CCC | AAC | ATC  | 935 |
| Leu | Pro | Gly | Ala | Ala | Gln | Gly | Ile | Gln | Phe | Tyr | Leu | Tyr | Pro | Asn | Ile  |
| 255 |     |     |     |     | 260 |     |     |     |     | 265 |     |     |     |     | 270  |
| ACA | CGT | CTG | TGG | GAT | CCC | CAG | GTG | TGG | ATG | GAT | GCG | GGC | ACC | CAG | ATC  | 983 |
| Thr | Arg | Leu | Trp | Asp | Pro | Gln | Val | Trp | Met | Asp | Ala | Gly | Thr | Gln | Ile  |
|     |     |     |     | 275 |     |     |     |     | 280 |     |     |     |     | 285 |      |
| TTC | TTC | TCC | TTT | GCC | ATC | TGC | CTG | GGG | TGC | CTC | ACG | GCC | CTG | GGC | AGC  | 1031 |
| Phe | Phe | Ser | Phe | Ala | Ile | Cys | Leu | Gly | Cys | Leu | Thr | Ala | Leu | Gly | Ser  |
|     |     |     | 290 |     |     |     |     | 295 |     |     |     |     | 300 |     |      |
| TAC | AAC | AAG | TAC | CAC | AAC | AAC | TGC | TAC | AGG | GAC | TGC | GTC | GCC | CTT | TGC  | 1079 |
| Tyr | Asn | Lys | Tyr | His | Asn | Asn | Cys | Tyr | Arg | Asp | Cys | Val | Ala | Leu | Cys  |
|     |     | 305 |     |     |     |     | 310 |     |     |     |     | 315 |     |     |      |
| ATT | CTC | AAC | AGC | AGC | ACC | AGC | TTC | GTG | GCC | GGG | TTT | GCC | ATC | TTC | TCC  | 1127 |
| Ile | Leu | Asn | Ser | Ser | Thr | Ser | Phe | Val | Ala | Gly | Phe | Ala | Ile | Phe | Ser  |
|     | 320 |     |     |     |     | 325 |     |     |     |     | 330 |     |     |     |      |
| ATC | CTG | GGC | TTC | ATG | TCT | CAG | GAG | CAG | GGC | GTA | CCC | ATA | TCT | GAG | GTT  | 1175 |
| Ile | Leu | Gly | Phe | Met | Ser | Gln | Glu | Gln | Gly | Val | Pro | Ile | Ser | Glu | Val  |
| 335 |     |     |     |     | 340 |     |     |     |     | 345 |     |     |     |     | 350  |
| GCT | GAA | TCA | GGC | CCT | GGC | CTG | GCA | TTC | ATC | GCC | TAC | CCT | CGA | GCT | GTG  | 1223 |
| Ala | Glu | Ser | Gly | Pro | Gly | Leu | Ala | Phe | Ile | Ala | Tyr | Pro | Arg | Ala | Val  |
|     |     |     |     | 355 |     |     |     |     | 360 |     |     |     |     | 365 |      |
| GTG | ATG | TTA | CCT | TTC | TCG | CCT | TTG | TGG | GCC | TGC | TGT | TTC | TTC | TTC | ATG  | 1271 |
| Val | Met | Leu | Pro | Phe | Ser | Pro | Leu | Trp | Ala | Cys | Cys | Phe | Phe | Phe | Met  |
|     |     |     | 370 |     |     |     |     | 375 |     |     |     |     | 380 |     |      |
| GTG | GTT | CTC | CTG | GGA | CTA | GAC | AGC | CAG | TTT | GTG | TGT | GTA | GAA | AGC | CTC  | 1319 |
| Val | Val | Leu | Leu | Gly | Leu | Asp | Ser | Gln | Phe | Val | Cys | Val | Glu | Ser | Leu  |
|     |     | 385 |     |     |     |     | 390 |     |     |     |     | 395 |     |     |      |
| GTG | ACA | GCG | CTG | GTG | GAC | ATG | TAT | CCC | CGG | GTG | TTC | CGT | AAG | AAG | AAC  | 1367 |
| Val | Thr | Ala | Leu | Val | Asp | Met | Tyr | Pro | Arg | Val | Phe | Arg | Lys | Lys | Asn  |
|     | 400 |     |     |     |     | 405 |     |     |     |     | 410 |     |     |     |      |
| CGG | AGG | GAG | ATT | CTC | ATC | CTC | ATC | GTG | TCT | GTC | GTC | TCT | TTC | TTC | ATC  | 1415 |
| Arg | Arg | Glu | Ile | Leu | Ile | Leu | Ile | Val | Ser | Val | Val | Ser | Phe | Phe | Ile  |
| 415 |     |     |     |     | 420 |     |     |     |     | 425 |     |     |     |     | 430  |
| GGG | CTC | ATT | ATG | CTC | ACA | GAG | GGC | GGC | ATG | TAC | GTG | TTC | CAG | CTC | TTC  | 1463 |
| Gly | Leu | Ile | Met | Leu | Thr | Glu | Gly | Gly | Met | Tyr | Val | Phe | Gln | Leu | Phe  |
|     |     |     |     | 435 |     |     |     |     | 440 |     |     |     |     | 445 |      |
| GAC | TAC | TAT | GCG | GCC | AGT | GGC | ATG | TGT | CTT | CTC | TTT | GTG | GCC | ATC | TTT  | 1511 |
| Asp | Tyr | Tyr | Ala | Ala | Ser | Gly | Met | Cys | Leu | Leu | Phe | Val | Ala | Ile | Phe  |
|     |     |     |     | 450 |     |     |     |     | 455 |     |     |     |     | 460 |      |
| GAG | TCC | CTC | TGT | GTG | GCT | TGG | GTT | TAC | GGA | GCC | AGC | CGC | TTC | TAT | GAC  | 1559 |
| Glu | Ser | Leu | Cys | Val | Ala | Trp | Val | Tyr | Gly | Ala | Ser | Arg | Phe | Tyr | Asp  |
|     |     | 465 |     |     |     |     | 470 |     |     |     |     | 475 |     |     |      |
| AAC | ATT | GAA | GAT | ATG | ATT | GGG | TAC | AAG | CCG | TGG | CCT | CTT | ATC | AAA | TAC  | 1607 |

```
Asn Ile Glu Asp Met Ile Gly Tyr Lys Pro Trp Pro Leu Ile Lys Tyr
    480             485                 490

TGT TGG CTC TTT TTC ACG CCA GCT GTG TGC CTG GCA ACC TTC CTG TTC    1655
Cys Trp Leu Phe Phe Thr Pro Ala Val Cys Leu Ala Thr Phe Leu Phe
495                 500                 505                 510

TCC CTG ATC AAA TAC ACG CCA CTG ACC TAC AAC AAG AAG TAC ACA TAT    1703
Ser Leu Ile Lys Tyr Thr Pro Leu Thr Tyr Asn Lys Lys Tyr Thr Tyr
                515                 520                 525

CCA TGG TGG GGG GAT GCC CTG GGG TGG CTC CTA GCT CTG TCC TCC ATG    1751
Pro Trp Trp Gly Asp Ala Leu Gly Trp Leu Leu Ala Leu Ser Ser Met
            530                 535                 540

GTC TGC ATT CCT GCC TGG AGC ATC TAC AAG CTC AGG ACT CTC AAG GGC    1799
Val Cys Ile Pro Ala Trp Ser Ile Tyr Lys Leu Arg Thr Leu Lys Gly
        545                 550                 555

CCA CTC AGA GAG AGA CTT CGC CAG CTC GTG TGC CCG GCT GAA GAC CTT    1847
Pro Leu Arg Glu Arg Leu Arg Gln Leu Val Cys Pro Ala Glu Asp Leu
    560                 565                 570

CCC CAG AAG AGC CAA CCA GAG CTG ACT TCT CCA GCG ACA CCG ATG ACG    1895
Pro Gln Lys Ser Gln Pro Glu Leu Thr Ser Pro Ala Thr Pro Met Thr
575                 580                 585                 590

TCC CTC CTC AGG CTC ACA GAA CTG GAG TCT AAC TGC T AGGGACGAGG       1942
Ser Leu Leu Arg Leu Thr Glu Leu Glu Ser Asn Cys
                595                 600

CCTTTGACAC ACCTGCGAGT CTGTCTGTGG GGACAGCTAC AGACACAGAG GGCAGAACCA  2002

CCCCTCCGTG CTGGGGCAGA GAGACA                                      2028
```

(2) INFORMATION FOR SEQ ID NO:2:

(i) SEQUENCE CHARACTERISTICS:
        (A) LENGTH: 602 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asp Asn Arg Val Ser Gly Thr Thr Ser Asn Gly Glu Thr Lys Pro
1               5                   10                  15

Val Cys Pro Val Met Glu Lys Val Glu Glu Asp Gly Thr Leu Glu Arg
                20                  25                  30

Glu Gln Trp Thr Asn Lys Met Glu Phe Val Leu Ser Val Ala Gly Glu
            35                  40                  45

Ile Ile Gly Leu Gly Asn Val Trp Arg Phe Pro Tyr Leu Cys Tyr Lys
        50                  55                  60

Asn Gly Gly Gly Ala Phe Phe Ile Pro Tyr Leu Ile Phe Leu Phe Thr
65                  70                  75                  80

Cys Gly Ile Pro Val Phe Phe Leu Glu Thr Ala Leu Gly Gln Tyr Thr
                85                  90                  95

Asn Gln Gly Gly Ile Thr Ala Trp Arg Lys Ile Cys Pro Ile Phe Glu
                100                 105                 110

Gly Ile Gly Tyr Ala Ser Gln Met Ile Val Ser Leu Leu Asn Val Tyr
        115                 120                 125

Tyr Ile Val Val Leu Ala Trp Ala Leu Phe Tyr Leu Phe Ser Ser Phe
    130                 135                 140

Thr Thr Asp Leu Pro Trp Gly Ser Cys Ser His Glu Trp Asn Thr Glu
145                 150                 155                 160

Asn Cys Val Glu Phe Gln Lys Thr Asn Asn Ser Leu Asn Val Thr Ser
                165                 170                 175
```

| | | | | | | | | | | | | | | |
|---|---|---|---|---|---|---|---|---|---|---|---|---|---|---|
| Glu | Asn | Ala | Thr | Ser | Pro | Val | Ile | Glu | Phe | Trp | Glu | Arg | Arg | Val | Leu |
| | | | 180 | | | | 185 | | | | | 190 | | |
| Lys | Ile | Ser | Asp | Gly | Ile | Gln | His | Leu | Gly | Ser | Leu | Arg | Trp | Glu | Leu |
| 195 | | | | | | | 200 | | | | | 205 | | | |
| Val | Leu | Cys | Leu | Leu | Leu | Ala | Trp | Ile | Ile | Cys | Tyr | Phe | Cys | Ile | Trp |
| 210 | | | | | | | 215 | | | | | 220 | | | |
| Lys | Gly | Val | Lys | Ser | Thr | Gly | Lys | Val | Val | Tyr | Phe | Thr | Ala | Thr | Phe |
| 225 | | | | | 230 | | | | | 235 | | | | | 240 |
| Pro | Tyr | Leu | Met | Leu | Val | Val | Leu | Leu | Ile | Arg | Gly | Val | Thr | Leu | Pro |
| | | | | 245 | | | | | 250 | | | | | 255 | |
| Gly | Ala | Ala | Gln | Gly | Ile | Gln | Phe | Tyr | Leu | Tyr | Pro | Asn | Ile | Thr | Arg |
| | | | 260 | | | | | 265 | | | | | 270 | | |
| Leu | Trp | Asp | Pro | Gln | Val | Trp | Met | Asp | Ala | Gly | Thr | Gln | Ile | Phe | Phe |
| | | 275 | | | | | 280 | | | | | 285 | | | |
| Ser | Phe | Ala | Ile | Cys | Leu | Gly | Cys | Leu | Thr | Ala | Leu | Gly | Ser | Tyr | Asn |
| | 290 | | | | | 295 | | | | | 300 | | | | |
| Lys | Tyr | His | Asn | Asn | Cys | Tyr | Arg | Asp | Cys | Val | Ala | Leu | Cys | Ile | Leu |
| 305 | | | | | 310 | | | | | 315 | | | | | 320 |
| Asn | Ser | Ser | Thr | Ser | Phe | Val | Ala | Gly | Phe | Ala | Ile | Phe | Ser | Ile | Leu |
| | | | | 325 | | | | | 330 | | | | | 335 | |
| Gly | Phe | Met | Ser | Gln | Glu | Gln | Gly | Val | Pro | Ile | Ser | Glu | Val | Ala | Glu |
| | | | 340 | | | | | 345 | | | | | 350 | | |
| Ser | Gly | Pro | Gly | Leu | Ala | Phe | Ile | Ala | Tyr | Pro | Arg | Ala | Val | Val | Met |
| | | 355 | | | | | 360 | | | | | 365 | | | |
| Leu | Pro | Phe | Ser | Pro | Leu | Trp | Ala | Cys | Cys | Phe | Phe | Met | Val | Val |
| | 370 | | | | | 375 | | | | | 380 | | | | |
| Leu | Leu | Gly | Leu | Asp | Ser | Gln | Phe | Val | Cys | Val | Glu | Ser | Leu | Val | Thr |
| 385 | | | | | 390 | | | | | 395 | | | | | 400 |
| Ala | Leu | Val | Asp | Met | Tyr | Pro | Arg | Val | Phe | Arg | Lys | Lys | Asn | Arg | Arg |
| | | | | 405 | | | | | 410 | | | | | 415 | |
| Glu | Ile | Leu | Ile | Leu | Ile | Val | Ser | Val | Ser | Phe | Phe | Ile | Gly | Leu |
| | | | 420 | | | | | 425 | | | | | 430 | | |
| Ile | Met | Leu | Thr | Glu | Gly | Gly | Met | Tyr | Val | Phe | Gln | Leu | Phe | Asp | Tyr |
| | | 435 | | | | | 440 | | | | | 445 | | | |
| Tyr | Ala | Ala | Ser | Gly | Met | Cys | Leu | Leu | Phe | Val | Ala | Ile | Phe | Glu | Ser |
| | 450 | | | | | 455 | | | | | 460 | | | | |
| Leu | Cys | Val | Ala | Trp | Val | Tyr | Gly | Ala | Ser | Arg | Phe | Tyr | Asp | Asn | Ile |
| 465 | | | | | 470 | | | | | 475 | | | | | 480 |
| Glu | Asp | Met | Ile | Gly | Tyr | Lys | Pro | Trp | Pro | Leu | Ile | Lys | Tyr | Cys | Trp |
| | | | | 485 | | | | | 490 | | | | | 495 | |
| Leu | Phe | Phe | Thr | Pro | Ala | Val | Cys | Leu | Ala | Thr | Phe | Leu | Phe | Ser | Leu |
| | | | 500 | | | | | 505 | | | | | 510 | | |
| Ile | Lys | Tyr | Thr | Pro | Leu | Thr | Tyr | Asn | Lys | Lys | Tyr | Thr | Tyr | Pro | Trp |
| | | 515 | | | | | 520 | | | | | 525 | | | |
| Trp | Gly | Asp | Ala | Leu | Gly | Trp | Leu | Leu | Ala | Leu | Ser | Ser | Met | Val | Cys |
| | 530 | | | | | 535 | | | | | 540 | | | | |
| Ile | Pro | Ala | Trp | Ser | Ile | Tyr | Lys | Leu | Arg | Thr | Leu | Lys | Gly | Pro | Leu |
| 545 | | | | | 550 | | | | | 555 | | | | | 560 |
| Arg | Glu | Arg | Leu | Arg | Gln | Leu | Val | Cys | Pro | Ala | Glu | Asp | Leu | Pro | Gln |
| | | | | 565 | | | | | 570 | | | | | 575 | |
| Lys | Ser | Gln | Pro | Glu | Leu | Thr | Ser | Pro | Ala | Thr | Pro | Met | Thr | Ser | Leu |
| | | | 580 | | | | | 585 | | | | | 590 | | |
| Leu | Arg | Leu | Thr | Glu | Leu | Glu | Ser | Asn | Cys |
| | | 595 | | | | | 600 | | |

( 2 ) INFORMATION FOR SEQ ID NO:3:

( i ) SEQUENCE CHARACTERISTICS:
        ( A ) LENGTH: 1938 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: N ( i v ) ANTI-SENSE: N ( v ) FRAGMENT TYPE: N-terminal ( v i i ) IMMEDIATE SOURCE:
        ( A ) LIBRARY: rat brain
        ( B ) CLONE: rB8b ( i x ) FEATURE:
        ( A ) NAME/KEY: CDS
        ( B ) LOCATION: 16..1897
        ( D ) OTHER INFORMATION:

( x i ) SEQUENCE DESCRIPTION: SEQ ID NO:3:

```
GGCGGCAGGG CGGCC ATG ACT GCG GAG CAA GCG CTG CCC CTG GGC AAC GGG        51
              Met Thr Ala Glu Gln Ala Leu Pro Leu Gly Asn Gly
                1           5                      10

AAG GCG GCC GAG GAG GCG CGA GGG TCC GAG GCG CTG GGC GGC GGC GGC        99
Lys Ala Ala Glu Glu Ala Arg Gly Ser Glu Ala Leu Gly Gly Gly Gly
         15                  20                  25

GGG GGC GCG GCG GGG ACG CGC GAG GCG CGC GAC AAG GCG GTC CAC GAG       147
Gly Gly Ala Ala Gly Thr Arg Glu Ala Arg Asp Lys Ala Val His Glu
         30                  35                  40

CGC GGT CAC TGG AAC AAC AAG GTG GAG TTC GTG TTG AGC GTA GCG GGA       195
Arg Gly His Trp Asn Asn Lys Val Glu Phe Val Leu Ser Val Ala Gly
 45                  50                  55                  60

GAG ATC ATC GGT CTG GGC AAC GTG TGG CGC TTC CCC TAC CTG TGC TAC       243
Glu Ile Ile Gly Leu Gly Asn Val Trp Arg Phe Pro Tyr Leu Cys Tyr
                 65                  70                  75

AAG AAC GGC GGA GGG GCA TTC CTG ATT CCT TAC GTG GTG TTT TTC ATC       291
Lys Asn Gly Gly Gly Ala Phe Leu Ile Pro Tyr Val Val Phe Phe Ile
             80                  85                  90

TGC TGT GGA ATC CCC GTC TTC TTC CTG GAA ACG GCT CTG GGG CAG TTC       339
Cys Cys Gly Ile Pro Val Phe Phe Leu Glu Thr Ala Leu Gly Gln Phe
         95                 100                 105

ACG AGC GAG GGC GGC ATC ACG TGC TGG AGG AGA GTC TGT CCT TTA TTT       387
Thr Ser Glu Gly Gly Ile Thr Cys Trp Arg Arg Val Cys Pro Leu Phe
     110                 115                 120

GAA GGC ATC GGC TAT GCA ACA CAG GTG ATC GAG GCG CAT CTC AAT GTC       435
Glu Gly Ile Gly Tyr Ala Thr Gln Val Ile Glu Ala His Leu Asn Val
125                 130                 135                 140

TAC TAC ATC ATC ATC CTG GCG TGG GCC ATC TTC TAC TTA AGC AAC TGC       483
Tyr Tyr Ile Ile Ile Leu Ala Trp Ala Ile Phe Tyr Leu Ser Asn Cys
                145                 150                 155

TTC ACC ACC GAG CTC CCC TGG GCC ACC TGT GGG CAT GAG TGG AAC ACA       531
Phe Thr Thr Glu Leu Pro Trp Ala Thr Cys Gly His Glu Trp Asn Thr
            160                 165                 170

GAG AAA TGT GTG GAG TTC CAG AAG CTG AAC TTC AGC AAC TAC AGT CAT       579
Glu Lys Cys Val Glu Phe Gln Lys Leu Asn Phe Ser Asn Tyr Ser His
        175                 180                 185

GTG TCC CTG CAG AAC GCA ACC TCC CCG GTC ATG GAG TTC TGG GAA CGC       627
Val Ser Leu Gln Asn Ala Thr Ser Pro Val Met Glu Phe Trp Glu Arg
    190                 195                 200
```

```
CGG GTC TTG GCT ATA TCT GAT GGC ATT GAA CAC ATC GGG AAC CTC CGA       675
Arg Val Leu Ala Ile Ser Asp Gly Ile Glu His Ile Gly Asn Leu Arg
205                 210                 215                 220

TGG GAG CTG GCA CTG TGT CTC CTG GCG GCT TGG ACC ATC TGC TAC TTC       723
Trp Glu Leu Ala Leu Cys Leu Leu Ala Ala Trp Thr Ile Cys Tyr Phe
                    225                 230                 235

TGC ATC TGG AAG GGT ACG AAG TCA ACT GGA AAG GTC GTG TAT GTC ACT       771
Cys Ile Trp Lys Gly Thr Lys Ser Thr Gly Lys Val Val Tyr Val Thr
                240                 245                 250

GCA ACC TTC CCC TAC ATC ATG CTG CTG ATC CTC CTG ATC CGA GGG GTC       819
Ala Thr Phe Pro Tyr Ile Met Leu Leu Ile Leu Leu Ile Arg Gly Val
                255                 260                 265

ACG TTG CCG GGT GCC TCG GAA GGC ATC AAG TTC TAC CTG TAC CCT GAC       867
Thr Leu Pro Gly Ala Ser Glu Gly Ile Lys Phe Tyr Leu Tyr Pro Asp
            270                 275                 280

CTC TCC CGG CTC TCT GAT CCA CAG GTG TGG GTG GAT GCT GGG ACG CAG       915
Leu Ser Arg Leu Ser Asp Pro Gln Val Trp Val Asp Ala Gly Thr Gln
285                 290                 295                 300

ATC TTT TTC TCC TAT GCC ATC TGC CTG GGC TGC CTG ACC GCT CTG GGG       963
Ile Phe Phe Ser Tyr Ala Ile Cys Leu Gly Cys Leu Thr Ala Leu Gly
                    305                 310                 315

AGT TAC AAC AAC TAT AAC AAC AAC TGC TAC AGG GAC TGT ATT ATG CTC       1011
Ser Tyr Asn Asn Tyr Asn Asn Asn Cys Tyr Arg Asp Cys Ile Met Leu
                320                 325                 330

TGC TGT CTG AAC AGT GGC ACC AGC TTC GTG GCT GGG TTT GCT ATC TTC       1059
Cys Cys Leu Asn Ser Gly Thr Ser Phe Val Ala Gly Phe Ala Ile Phe
            335                 340                 345

TCA GTC CTG GGC TTC ATG GCG TAC GAG CAG GGC GTG CCT ATT GCT GAG       1107
Ser Val Leu Gly Phe Met Ala Tyr Glu Gln Gly Val Pro Ile Ala Glu
350                 355                 360

GTG GCA GAA TCA GGT CCT GGA CTG GCT TTC ATC GCC TAC CCC AAG GCT       1155
Val Ala Glu Ser Gly Pro Gly Leu Ala Phe Ile Ala Tyr Pro Lys Ala
365                 370                 375                 380

GTC ACT ATG ATG CCC CTG TCC CCA TTG TGG GCC ACC CTG TTC TTC ATG       1203
Val Thr Met Met Pro Leu Ser Pro Leu Trp Ala Thr Leu Phe Phe Met
                385                 390                 395

ATG CTC ATC TTC CTG GGC CTG GAC AGT CAG TTT GTG TGT GTG GAG AGC       1251
Met Leu Ile Phe Leu Gly Leu Asp Ser Gln Phe Val Cys Val Glu Ser
                400                 405                 410

CTT GTG ACA GCC GTG GTT GAC ATG TAC CCC AAG GTC TTC CGG CGG GGC       1299
Leu Val Thr Ala Val Val Asp Met Tyr Pro Lys Val Phe Arg Arg Gly
            415                 420                 425

TAC CGG CGA GAA CTG CTC ATC CTG GCC CTG TCC ATT GTC TCT TAT TTC       1347
Tyr Arg Arg Glu Leu Leu Ile Leu Ala Leu Ser Ile Val Ser Tyr Phe
        430                 435                 440

CTA GGC CTG GTG ATG CTG ACA GAG GGA GGC ATG TAC ATT TTC CAG CTT       1395
Leu Gly Leu Val Met Leu Thr Glu Gly Gly Met Tyr Ile Phe Gln Leu
445                 450                 455                 460

TTT GAC TCA TAC GCC GCC AGT GGC ATG TGC TTG CTC TTC GTG GCC ATC       1443
Phe Asp Ser Tyr Ala Ala Ser Gly Met Cys Leu Leu Phe Val Ala Ile
                465                 470                 475

TTT GAG TGT GTC TGC ATC GGC TGG GTG TAT GGA AGT AAC AGG TTC TAT       1491
Phe Glu Cys Val Cys Ile Gly Trp Val Tyr Gly Ser Asn Arg Phe Tyr
            480                 485                 490

GAC AAT ATT GAG GAC ATG ATT GGA TAC CGG CCA CTG TCA CTC ATC AAG       1539
Asp Asn Ile Glu Asp Met Ile Gly Tyr Arg Pro Leu Ser Leu Ile Lys
        495                 500                 505

TGG TGC TGG AAA GTT GTG ACC CCT GGG ATC TGT GCG GGC ATC TTC ATC       1587
Trp Cys Trp Lys Val Val Thr Pro Gly Ile Cys Ala Gly Ile Phe Ile
510                 515                 520
```

```
TTC TTT CTG GTC AAG TAC AAG CCG CTC AAG TAC AAC AAT GTG TAC ACA      1635
Phe Phe Leu Val Lys Tyr Lys Pro Leu Lys Tyr Asn Asn Val Tyr Thr
525                 530                 535                 540

TAT CCT GCT TGG GGC TAC GGC ATT GGC TGG CTC ATG GCT CTG TCC TCC      1683
Tyr Pro Ala Trp Gly Tyr Gly Ile Gly Trp Leu Met Ala Leu Ser Ser
                545                 550                 555

ATG CTG TGC ATC CCG CTC TGG ATC TTC ATC AAG CTG TGG AAG ACA GAG      1731
Met Leu Cys Ile Pro Leu Trp Ile Phe Ile Lys Leu Trp Lys Thr Glu
            560                 565                 570

GGC ACC CTG CCC GAG AAA TTA CAG AAG TTG ACA GTC CCC AGC GCT GAT      1779
Gly Thr Leu Pro Glu Lys Leu Gln Lys Leu Thr Val Pro Ser Ala Asp
        575                 580                 585

CTG AAA ATG AGG GGC AAG CTT GGG GCC AGC CCA CGG ATG GTG ACC GTT      1827
Leu Lys Met Arg Gly Lys Leu Gly Ala Ser Pro Arg Met Val Thr Val
    590                 595                 600

AAT GAC TGT GAG GCC AAG GTC AAA GGC GAC GGT ACC ATC TCT GCC ATC      1875
Asn Asp Cys Glu Ala Lys Val Lys Gly Asp Gly Thr Ile Ser Ala Ile
605                 610                 615                 620

ACA GAG AAG GAG ACG CAC TTC T GATCCCCGCC AGCCACTTGG ATGTGTCTCC       1927
Thr Glu Lys Glu Thr His Phe
                625

AGCCTTCCTT C                                                          1938
```

( 2 ) INFORMATION FOR SEQ ID NO:4:

( i ) SEQUENCE CHARACTERISTICS:
        ( A ) LENGTH: 627 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Thr Ala Glu Gln Ala Leu Pro Leu Gly Asn Gly Lys Ala Ala Glu
1               5                   10                  15

Glu Ala Arg Gly Ser Glu Ala Leu Gly Gly Gly Gly Gly Ala Ala
            20                  25                  30

Gly Thr Arg Glu Ala Arg Asp Lys Ala Val His Glu Arg Gly His Trp
        35                  40                  45

Asn Asn Lys Val Glu Phe Val Leu Ser Val Ala Gly Glu Ile Ile Gly
    50                  55                  60

Leu Gly Asn Val Trp Arg Phe Pro Tyr Leu Cys Tyr Lys Asn Gly Gly
65                  70                  75                  80

Gly Ala Phe Leu Ile Pro Tyr Val Val Phe Phe Ile Cys Cys Gly Ile
                85                  90                  95

Pro Val Phe Phe Leu Glu Thr Ala Leu Gly Gln Phe Thr Ser Glu Gly
                100                 105                 110

Gly Ile Thr Cys Trp Arg Arg Val Cys Pro Leu Phe Glu Gly Ile Gly
        115                 120                 125

Tyr Ala Thr Gln Val Ile Glu Ala His Leu Asn Val Tyr Tyr Ile Ile
    130                 135                 140

Ile Leu Ala Trp Ala Ile Phe Tyr Leu Ser Asn Cys Phe Thr Thr Glu
145                 150                 155                 160

Leu Pro Trp Ala Thr Cys Gly His Glu Trp Asn Thr Glu Lys Cys Val
                165                 170                 175

Glu Phe Gln Lys Leu Asn Phe Ser Asn Tyr Ser His Val Ser Leu Gln
                180                 185                 190

Asn Ala Thr Ser Pro Val Met Glu Phe Trp Glu Arg Arg Val Leu Ala
```

-continued

```
                195                        200                        205
Ile Ser Asp Gly Ile Glu His Ile Gly Asn Leu Arg Trp Glu Leu Ala
    210                 215                 220
Leu Cys Leu Leu Ala Ala Trp Thr Ile Cys Tyr Phe Cys Ile Trp Lys
225                 230                 235                 240
Gly Thr Lys Ser Thr Gly Lys Val Val Tyr Val Thr Ala Thr Phe Pro
                245                 250                 255
Tyr Ile Met Leu Leu Ile Leu Leu Ile Arg Gly Val Thr Leu Pro Gly
                260                 265                 270
Ala Ser Glu Gly Ile Lys Phe Tyr Leu Tyr Pro Asp Leu Ser Arg Leu
            275                 280                 285
Ser Asp Pro Gln Val Trp Val Asp Ala Gly Thr Gln Ile Phe Phe Ser
    290                 295                 300
Tyr Ala Ile Cys Leu Gly Cys Leu Thr Ala Leu Gly Ser Tyr Asn Asn
305                 310                 315                 320
Tyr Asn Asn Asn Cys Tyr Arg Asp Cys Ile Met Leu Cys Cys Leu Asn
                325                 330                 335
Ser Gly Thr Ser Phe Val Ala Gly Phe Ala Ile Phe Ser Val Leu Gly
                340                 345                 350
Phe Met Ala Tyr Glu Gln Gly Val Pro Ile Ala Glu Val Ala Glu Ser
            355                 360                 365
Gly Pro Gly Leu Ala Phe Ile Ala Tyr Pro Lys Ala Val Thr Met Met
    370                 375                 380
Pro Leu Ser Pro Leu Trp Ala Thr Leu Phe Phe Met Met Leu Ile Phe
385                 390                 395                 400
Leu Gly Leu Asp Ser Gln Phe Val Cys Val Glu Ser Leu Val Thr Ala
                405                 410                 415
Val Val Asp Met Tyr Pro Lys Val Phe Arg Arg Gly Tyr Arg Arg Glu
                420                 425                 430
Leu Leu Ile Leu Ala Leu Ser Ile Val Ser Tyr Phe Leu Gly Leu Val
            435                 440                 445
Met Leu Thr Glu Gly Gly Met Tyr Ile Phe Gln Leu Phe Asp Ser Tyr
    450                 455                 460
Ala Ala Ser Gly Met Cys Leu Leu Phe Val Ala Ile Phe Glu Cys Val
465                 470                 475                 480
Cys Ile Gly Trp Val Tyr Gly Ser Asn Arg Phe Tyr Asp Asn Ile Glu
                485                 490                 495
Asp Met Ile Gly Tyr Arg Pro Leu Ser Leu Ile Lys Trp Cys Trp Lys
                500                 505                 510
Val Val Thr Pro Gly Ile Cys Ala Gly Ile Phe Ile Phe Phe Leu Val
            515                 520                 525
Lys Tyr Lys Pro Leu Lys Tyr Asn Asn Val Tyr Thr Tyr Pro Ala Trp
    530                 535                 540
Gly Tyr Gly Ile Gly Trp Leu Met Ala Leu Ser Ser Met Leu Cys Ile
545                 550                 555                 560
Pro Leu Trp Ile Phe Ile Lys Leu Trp Lys Thr Glu Gly Thr Leu Pro
                565                 570                 575
Glu Lys Leu Gln Lys Leu Thr Val Pro Ser Ala Asp Leu Lys Met Arg
                580                 585                 590
Gly Lys Leu Gly Gly Ala Ser Pro Arg Met Val Thr Val Asn Asp Cys Glu
            595                 600                 605
Ala Lys Val Lys Gly Asp Gly Thr Ile Ser Ala Ile Thr Glu Lys Glu
    610                 615                 620
```

Thr His Phe
625

( 2 ) INFORMATION FOR SEQ ID NO:5:

( i ) SEQUENCE CHARACTERISTICS:
        ( A ) LENGTH: 2093 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: N ( i v ) ANTI-SENSE: N ( v ) FRAGMENT TYPE: N-terminal ( v i ) ORIGINAL SOURCE:
        ( A ) ORGANISM: Taurine ( v i i ) IMMEDIATE SOURCE:
        ( A ) LIBRARY: rat brain
        ( B ) CLONE: rB16a ( i x ) FEATURE:
        ( A ) NAME/KEY: CDS
        ( B ) LOCATION: 127..1989
        ( D ) OTHER INFORMATION:

( x i ) SEQUENCE DESCRIPTION: SEQ ID NO:5:

```
GCCAACGCCG CGATCGCCGC CAATCCCGCC AGCCTCGGGC CGGGCCATCC GCTGTGGGCT      60

TAGCCACCCA GATGCAGAGC CAGTGCCACA GCCTCTTCAG AGGAGCCTCT CAAGCAAAAC     120

GAGGAG ATG GCC ACC AAG GAG AAG CTT CAA TGT CTG AAA GAC TTC CAC        168
       Met Ala Thr Lys Glu Lys Leu Gln Cys Leu Lys Asp Phe His
         1               5                  10

AAA GAC ATC CTG AAG CCT TCT CCA GGG AAG AGC CCA GGC ACG CGG CCT       216
Lys Asp Ile Leu Lys Pro Ser Pro Gly Lys Ser Pro Gly Thr Arg Pro
 15              20                  25                  30

GAG GAT GAG GCT GAT GGG AAG CCC CCT CAG AGG GAG AAG TGG TCC AGC       264
Glu Asp Glu Ala Asp Gly Lys Pro Pro Gln Arg Glu Lys Trp Ser Ser
                 35                  40                  45

AAG ATC GAC TTT GTG CTG TCT GTG GCC GGA GGC TTC GTG GGT TTG GGC       312
Lys Ile Asp Phe Val Leu Ser Val Ala Gly Gly Phe Val Gly Leu Gly
             50                  55                  60

AAT GTC TGG CGT TTC CCG TAC CTC TGC TAC AAA AAT GGT GGA GGT GCA       360
Asn Val Trp Arg Phe Pro Tyr Leu Cys Tyr Lys Asn Gly Gly Gly Ala
         65                  70                  75

TTC CTC ATA CCG TAT TTT ATT TTC CTG TTT GGG AGC GGC CTG CCT GTG       408
Phe Leu Ile Pro Tyr Phe Ile Phe Leu Phe Gly Ser Gly Leu Pro Val
     80                  85                  90

TTT TTC CTG GAG GTC ATC ATA GGC CAG TAC ACC TCA GAA GGG GGC ATC       456
Phe Phe Leu Glu Val Ile Ile Gly Gln Tyr Thr Ser Glu Gly Gly Ile
 95                 100                 105                 110

ACC TGC TGG GAG AAG ATC TGC CCC TTG TTC TCT GGC ATT GGC TAC GCG       504
Thr Cys Trp Glu Lys Ile Cys Pro Leu Phe Ser Gly Ile Gly Tyr Ala
                115                 120                 125

TCC ATC GTC ATC GTG TCC CTC CTG AAT GTG TAC TAC ATC GTC ATC CTG       552
Ser Ile Val Ile Val Ser Leu Leu Asn Val Tyr Tyr Ile Val Ile Leu
            130                 135                 140

GCC TGG GCC ACA TAC TAC CTA TTC CAG TCT TTC CAG AAG GAT CTT CCC       600
Ala Trp Ala Thr Tyr Tyr Leu Phe Gln Ser Phe Gln Lys Asp Leu Pro
        145                 150                 155

TGG GCC CAC TGC AAC CAT AGC TGG AAC ACG CCA CAG TGC ATG GAG GAC       648
Trp Ala His Cys Asn His Ser Trp Asn Thr Pro Gln Cys Met Glu Asp
```

|       |       |       |       |       |       |       |       |       |       |       |       |       |       |       |       |      |
|-------|-------|-------|-------|-------|-------|-------|-------|-------|-------|-------|-------|-------|-------|-------|-------|------|
|       | 160   |       |       |       |       | 165   |       |       |       |       | 170   |       |       |       |       |      |
| ACC   | CTG   | CGT   | AGG   | AAC   | GAG   | AGT   | CAC   | TGG   | GTC   | TCC   | CTT   | AGC   | GCC   | GCC   | AAC   | 696  |
| Thr   | Leu   | Arg   | Arg   | Asn   | Glu   | Ser   | His   | Trp   | Val   | Ser   | Leu   | Ser   | Ala   | Ala   | Asn   |      |
| 175   |       |       |       |       | 180   |       |       |       |       | 185   |       |       |       |       | 190   |      |
| TTC   | ACT   | TCG   | CCT   | GTG   | ATC   | GAG   | TTC   | TGG   | GAG   | CGC   | AAC   | GTG   | CTC   | AGC   | CTG   | 744  |
| Phe   | Thr   | Ser   | Pro   | Val   | Ile   | Glu   | Phe   | Trp   | Glu   | Arg   | Asn   | Val   | Leu   | Ser   | Leu   |      |
|       |       |       |       | 195   |       |       |       |       | 200   |       |       |       |       | 205   |       |      |
| TCC   | TCC   | GGA   | ATC   | GAC   | CAC   | CCA   | GGC   | AGT   | CTG   | AAA   | TGG   | GAC   | CTC   | GCG   | CTC   | 792  |
| Ser   | Ser   | Gly   | Ile   | Asp   | His   | Pro   | Gly   | Ser   | Leu   | Lys   | Trp   | Asp   | Leu   | Ala   | Leu   |      |
|       |       |       | 210   |       |       |       |       | 215   |       |       |       |       | 220   |       |       |      |
| TGC   | CTC   | CTC   | TTA   | GTC   | TGG   | CTC   | GTC   | TGT   | TTT   | TTC   | TGC   | ATC   | TGG   | AAG   | GGT   | 840  |
| Cys   | Leu   | Leu   | Leu   | Val   | Trp   | Leu   | Val   | Cys   | Phe   | Phe   | Cys   | Ile   | Trp   | Lys   | Gly   |      |
|       |       | 225   |       |       |       |       | 230   |       |       |       |       | 235   |       |       |       |      |
| GTT   | CGG   | TCC   | ACA   | GGC   | AAG   | GTT   | GTC   | TAC   | TTC   | ACT   | GCT   | ACT   | TTC   | CCG   | TTT   | 888  |
| Val   | Arg   | Ser   | Thr   | Gly   | Lys   | Val   | Val   | Tyr   | Phe   | Thr   | Ala   | Thr   | Phe   | Pro   | Phe   |      |
|       | 240   |       |       |       |       | 245   |       |       |       |       | 250   |       |       |       |       |      |
| GCC   | ATG   | CTT   | CTG   | GTG   | CTG   | CTG   | GTC   | CGT   | GGA   | CTG   | ACC   | CTG   | CCA   | GGT   | GCT   | 936  |
| Ala   | Met   | Leu   | Leu   | Val   | Leu   | Leu   | Val   | Arg   | Gly   | Leu   | Thr   | Leu   | Pro   | Gly   | Ala   |      |
| 255   |       |       |       |       | 260   |       |       |       |       | 265   |       |       |       |       | 270   |      |
| GGT   | GAA   | GGC   | ATC   | AAA   | TTC   | TAC   | CTG   | TAC   | CCT   | AAC   | ATC   | AGC   | CGC   | CTT   | GAG   | 984  |
| Gly   | Glu   | Gly   | Ile   | Lys   | Phe   | Tyr   | Leu   | Tyr   | Pro   | Asn   | Ile   | Ser   | Arg   | Leu   | Glu   |      |
|       |       |       |       | 275   |       |       |       |       | 280   |       |       |       |       | 285   |       |      |
| GAC   | CCA   | CAG   | GTG   | TGG   | ATC   | GAC   | GCT   | GGA   | ACT   | CAG   | ATA   | TTC   | TTT   | TCC   | TAC   | 1032 |
| Asp   | Pro   | Gln   | Val   | Trp   | Ile   | Asp   | Ala   | Gly   | Thr   | Gln   | Ile   | Phe   | Phe   | Ser   | Tyr   |      |
|       |       |       | 290   |       |       |       |       | 295   |       |       |       |       | 300   |       |       |      |
| GCT   | ATC   | TGC   | CTG   | GGG   | GCC   | ATG   | ACC   | TCA   | CTG   | GGA   | AGC   | TAT   | AAC   | AAG   | TAC   | 1080 |
| Ala   | Ile   | Cys   | Leu   | Gly   | Ala   | Met   | Thr   | Ser   | Leu   | Gly   | Ser   | Tyr   | Asn   | Lys   | Tyr   |      |
|       |       | 305   |       |       |       |       | 310   |       |       |       |       | 315   |       |       |       |      |
| AAG   | TAT   | AAC   | TCG   | TAC   | AGG   | GAC   | TGT   | ATG   | CTG   | CTG   | GGA   | TGC   | CTG   | AAC   | AGT   | 1128 |
| Lys   | Tyr   | Asn   | Ser   | Tyr   | Arg   | Asp   | Cys   | Met   | Leu   | Leu   | Gly   | Cys   | Leu   | Asn   | Ser   |      |
|       | 320   |       |       |       |       | 325   |       |       |       |       | 330   |       |       |       |       |      |
| GGT   | ACC   | AGT   | TTT   | GTG   | TCT   | GGC   | TTC   | GCA   | ATT   | TTT   | TCC   | ATC   | CTG   | GGC   | TTC   | 1176 |
| Gly   | Thr   | Ser   | Phe   | Val   | Ser   | Gly   | Phe   | Ala   | Ile   | Phe   | Ser   | Ile   | Leu   | Gly   | Phe   |      |
| 335   |       |       |       |       | 340   |       |       |       |       | 345   |       |       |       |       | 350   |      |
| ATG   | GCA   | CAA   | GAG   | CAA   | GGG   | GTG   | GAC   | ATT   | GCT   | GAT   | GTG   | GCT   | GAG   | TCA   | GGT   | 1224 |
| Met   | Ala   | Gln   | Glu   | Gln   | Gly   | Val   | Asp   | Ile   | Ala   | Asp   | Val   | Ala   | Glu   | Ser   | Gly   |      |
|       |       |       |       | 355   |       |       |       |       | 360   |       |       |       |       | 365   |       |      |
| CCT   | GGC   | TTG   | GCC   | TTC   | ATT   | GCC   | TAC   | CCA   | AAA   | GCT   | GTG   | ACC   | ATG   | ATG   | CCG   | 1272 |
| Pro   | Gly   | Leu   | Ala   | Phe   | Ile   | Ala   | Tyr   | Pro   | Lys   | Ala   | Val   | Thr   | Met   | Met   | Pro   |      |
|       |       |       | 370   |       |       |       |       | 375   |       |       |       |       | 380   |       |       |      |
| CTG   | CCC   | ACC   | TTT   | TGG   | TCC   | ATT   | CTG   | TTT   | TTT   | ATT   | ATG   | CTC   | CTC   | TTG   | CTT   | 1320 |
| Leu   | Pro   | Thr   | Phe   | Trp   | Ser   | Ile   | Leu   | Phe   | Phe   | Ile   | Met   | Leu   | Leu   | Leu   | Leu   |      |
|       |       | 385   |       |       |       |       | 390   |       |       |       |       | 395   |       |       |       |      |
| GGA   | CTG   | GAC   | AGC   | CAG   | TTT   | GTT   | GAA   | GTC   | GAA   | GGA   | CAG   | ATC   | ACA   | TCC   | TTG   | 1368 |
| Gly   | Leu   | Asp   | Ser   | Gln   | Phe   | Val   | Glu   | Val   | Glu   | Gly   | Gln   | Ile   | Thr   | Ser   | Leu   |      |
|       | 400   |       |       |       |       | 405   |       |       |       |       | 410   |       |       |       |       |      |
| GTT   | GAT   | CTT   | TAC   | CCG   | TCC   | TTC   | CTA   | AGG   | AAG   | GGT   | TAT   | CGT   | CGG   | GAA   | ATC   | 1416 |
| Val   | Asp   | Leu   | Tyr   | Pro   | Ser   | Phe   | Leu   | Arg   | Lys   | Gly   | Tyr   | Arg   | Arg   | Glu   | Ile   |      |
| 415   |       |       |       |       | 420   |       |       |       |       | 425   |       |       |       |       | 430   |      |
| TTC   | ATT   | GCC   | ATC   | GTG   | TGC   | AGC   | ATC   | AGC   | TAC   | CTG   | CTG   | GGG   | CTG   | ACG   | ATG   | 1464 |
| Phe   | Ile   | Ala   | Ile   | Val   | Cys   | Ser   | Ile   | Ser   | Tyr   | Leu   | Leu   | Gly   | Leu   | Thr   | Met   |      |
|       |       |       |       | 435   |       |       |       |       | 440   |       |       |       |       | 445   |       |      |
| GTG   | ACG   | GAG   | GGT   | GGC   | ATG   | TAT   | GTG   | TTT   | CAA   | CTC   | TTT   | GAC   | TAC   | TAT   | GCA   | 1512 |
| Val   | Thr   | Glu   | Gly   | Gly   | Met   | Tyr   | Val   | Phe   | Gln   | Leu   | Phe   | Asp   | Tyr   | Tyr   | Ala   |      |
|       |       |       |       | 450   |       |       |       |       | 455   |       |       |       |       | 460   |       |      |
| GCT   | AGT   | GGT   | GTA   | TGC   | CTT   | TTG   | TGG   | GTC   | GCA   | TTC   | TTT   | GAA   | TGT   | TTT   | GTT   | 1560 |
| Ala   | Ser   | Gly   | Val   | Cys   | Leu   | Leu   | Trp   | Val   | Ala   | Phe   | Phe   | Glu   | Cys   | Phe   | Val   |      |
|       |       |       | 465   |       |       |       |       | 470   |       |       |       |       | 475   |       |       |      |
| ATT   | GCC   | TGG   | ATA   | TAT   | GGC   | GGT   | GAT   | AAC   | TTA   | TAT   | GAC   | GGT   | ATT   | GAG   | GAC   | 1608 |
| Ile   | Ala   | Trp   | Ile   | Tyr   | Gly   | Gly   | Asp   | Asn   | Leu   | Tyr   | Asp   | Gly   | Ile   | Glu   | Asp   |      |

```
            480                        485                         490
ATG ATC GGC TAT CGG CCT GGA CCC TGG ATG AAG TAC AGC TGG GCT GTC       1656
Met Ile Gly Tyr Arg Pro Gly Pro Trp Met Lys Tyr Ser Trp Ala Val
495                 500                 505                 510

ATC ACT CCA GCT CTC TGT GTT GGA TGT TTC ATC TTC TCT CTC GTC AAG       1704
Ile Thr Pro Ala Leu Cys Val Gly Cys Phe Ile Phe Ser Leu Val Lys
                    515                 520                 525

TAT GTA CCC CTG ACC TAC AAC AAA GTC TAC CGG TAC CCT GAT TGG GCA       1752
Tyr Val Pro Leu Thr Tyr Asn Lys Val Tyr Arg Tyr Pro Asp Trp Ala
                530                 535                 540

ATC GGG CTG GGC TGG GGC CTG GCC CTT TCC TCC ATG GTG TGT ATC CCC       1800
Ile Gly Leu Gly Trp Gly Leu Ala Leu Ser Ser Met Val Cys Ile Pro
            545                 550                 555

TTG GTC ATT GTC ATC CTC CTC TGC CGG ACG GAG GGA CCG CTC CGC GTG       1848
Leu Val Ile Val Ile Leu Leu Cys Arg Thr Glu Gly Pro Leu Arg Val
    560                 565                 570

AGA ATC AAA TAC CTG ATA ACC CCC AGG GAG CCC AAC CGC TGG GCT GTG       1896
Arg Ile Lys Tyr Leu Ile Thr Pro Arg Glu Pro Asn Arg Trp Ala Val
575                 580                 585                 590

GAG CGT GAA GGG GCT ACG CCC TTT CAC TCC AGA GCA ACC CTC ATG AAC       1944
Glu Arg Glu Gly Ala Thr Pro Phe His Ser Arg Ala Thr Leu Met Asn
                595                 600                 605

GGT GCA CTC ATG AAA CCC AGT CAC GTC ATT GTG GAG ACC ATG ATG           1989
Gly Ala Leu Met Lys Pro Ser His Val Ile Val Glu Thr Met Met
            610                 615                 620

TGAGGTCCGG GCTGTGTGAC CGGCGCCGCT TTCCTGCCGT TTACTAACCT TAGATTCTCC    2049

TAGGACCAGG TTTACAGAGC TTTATATTTG TACTAGGATT TTTT                     2093
```

( 2 ) INFORMATION FOR SEQ ID NO:6:

( i ) SEQUENCE CHARACTERISTICS:
        ( A ) LENGTH: 621 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met Ala Thr Lys Glu Lys Leu Gln Cys Leu Lys Asp Phe His Lys Asp
 1               5                  10                  15

Ile Leu Lys Pro Ser Pro Gly Lys Ser Pro Gly Thr Arg Pro Glu Asp
            20                  25                  30

Glu Ala Asp Gly Lys Pro Pro Gln Arg Glu Lys Trp Ser Ser Lys Ile
                35                  40                  45

Asp Phe Val Leu Ser Val Ala Gly Gly Phe Val Gly Leu Gly Asn Val
         50                  55                  60

Trp Arg Phe Pro Tyr Leu Cys Tyr Lys Asn Gly Gly Gly Ala Phe Leu
 65                  70                  75                  80

Ile Pro Tyr Phe Ile Phe Leu Phe Gly Ser Gly Leu Pro Val Phe Phe
                     85                  90                  95

Leu Glu Val Ile Ile Gly Gln Tyr Thr Ser Glu Gly Gly Ile Thr Cys
                100                 105                 110

Trp Glu Lys Ile Cys Pro Leu Phe Ser Gly Ile Gly Tyr Ala Ser Ile
             115                 120                 125

Val Ile Val Ser Leu Leu Asn Val Tyr Tyr Ile Val Ile Leu Ala Trp
         130                 135                 140

Ala Thr Tyr Tyr Leu Phe Gln Ser Phe Gln Lys Asp Leu Pro Trp Ala
145                 150                 155                 160
```

| | | | | | | | | | | | | | | |
|---|---|---|---|---|---|---|---|---|---|---|---|---|---|---|
| His | Cys | Asn | His | Ser<br>165 | Trp | Asn | Thr | Pro<br>170 | Gln | Cys | Met | Glu | Asp<br>175 | Leu |
| Arg | Arg | Asn | Glu<br>180 | Ser | His | Trp | Val<br>185 | Ser | Leu | Ser | Ala | Ala<br>190 | Asn | Phe | Thr |
| Ser | Pro | Val<br>195 | Ile | Glu | Phe | Trp | Glu<br>200 | Arg | Asn | Val | Leu | Ser<br>205 | Leu | Ser | Ser |
| Gly | Ile | Asp<br>210 | His | Pro | Gly | Ser<br>215 | Leu | Lys | Trp | Asp | Leu<br>220 | Ala | Leu | Cys | Leu |
| Leu<br>225 | Leu | Val | Trp | Leu | Val<br>230 | Cys | Phe | Phe | Cys | Ile<br>235 | Trp | Lys | Gly | Val | Arg<br>240 |
| Ser | Thr | Gly | Lys | Val<br>245 | Val | Tyr | Phe | Thr | Ala<br>250 | Thr | Phe | Pro | Phe | Ala<br>255 | Met |
| Leu | Leu | Val | Leu<br>260 | Leu | Val | Arg | Gly | Leu<br>265 | Thr | Leu | Pro | Gly | Ala<br>270 | Gly | Glu |
| Gly | Ile | Lys<br>275 | Phe | Tyr | Leu | Tyr | Pro<br>280 | Asn | Ile | Ser | Arg | Leu<br>285 | Glu | Asp | Pro |
| Gln | Val<br>290 | Trp | Ile | Asp | Ala | Gly<br>295 | Thr | Gln | Ile | Phe | Phe<br>300 | Ser | Tyr | Ala | Ile |
| Cys<br>305 | Leu | Gly | Ala | Met | Thr<br>310 | Ser | Leu | Gly | Ser | Tyr<br>315 | Asn | Lys | Tyr | Lys | Tyr<br>320 |
| Asn | Ser | Tyr | Arg | Asp<br>325 | Cys | Met | Leu | Leu | Gly<br>330 | Cys | Leu | Asn | Ser | Gly<br>335 | Thr |
| Ser | Phe | Val | Ser<br>340 | Gly | Phe | Ala | Ile | Phe<br>345 | Ser | Ile | Leu | Gly | Phe<br>350 | Met | Ala |
| Gln | Glu | Gln<br>355 | Gly | Val | Asp | Ile | Ala<br>360 | Asp | Val | Ala | Glu | Ser<br>365 | Gly | Pro | Gly |
| Leu | Ala<br>370 | Phe | Ile | Ala | Tyr | Pro<br>375 | Lys | Ala | Val | Thr | Met<br>380 | Met | Pro | Leu | Pro |
| Thr<br>385 | Phe | Trp | Ser | Ile | Leu<br>390 | Phe | Phe | Ile | Met | Leu<br>395 | Leu | Leu | Leu | Gly | Leu<br>400 |
| Asp | Ser | Gln | Phe | Val<br>405 | Glu | Val | Glu | Gly | Gln<br>410 | Ile | Thr | Ser | Leu | Val<br>415 | Asp |
| Leu | Tyr | Pro | Ser<br>420 | Phe | Leu | Arg | Lys | Gly<br>425 | Tyr | Arg | Arg | Glu | Ile<br>430 | Phe | Ile |
| Ala | Ile | Val<br>435 | Cys | Ser | Ile | Ser | Tyr<br>440 | Leu | Leu | Gly | Leu | Thr<br>445 | Met | Val | Thr |
| Glu | Gly<br>450 | Gly | Met | Tyr | Val | Phe<br>455 | Gln | Leu | Phe | Asp | Tyr<br>460 | Tyr | Ala | Ala | Ser |
| Gly<br>465 | Val | Cys | Leu | Leu | Trp<br>470 | Val | Ala | Phe | Phe | Glu<br>475 | Cys | Phe | Val | Ile | Ala<br>480 |
| Trp | Ile | Tyr | Gly | Gly<br>485 | Asp | Asn | Leu | Tyr | Asp<br>490 | Gly | Ile | Glu | Asp | Met<br>495 | Ile |
| Gly | Tyr | Arg | Pro<br>500 | Gly | Pro | Trp | Met | Lys<br>505 | Tyr | Ser | Trp | Ala | Val<br>510 | Ile | Thr |
| Pro | Ala | Leu<br>515 | Cys | Val | Gly | Cys | Phe<br>520 | Ile | Phe | Ser | Leu | Val<br>525 | Lys | Tyr | Val |
| Pro | Leu<br>530 | Thr | Tyr | Asn | Lys | Val<br>535 | Tyr | Arg | Tyr | Pro | Asp<br>540 | Trp | Ala | Ile | Gly |
| Leu<br>545 | Gly | Trp | Gly | Leu | Ala<br>550 | Leu | Ser | Ser | Met | Val<br>555 | Cys | Ile | Pro | Leu | Val<br>560 |
| Ile | Val | Ile | Leu | Leu<br>565 | Cys | Arg | Thr | Glu | Gly<br>570 | Pro | Leu | Arg | Val | Arg<br>575 | Ile |
| Lys | Tyr | Leu | Ile<br>580 | Thr | Pro | Arg | Glu | Pro<br>585 | Asn | Arg | Trp | Ala | Val<br>590 | Glu | Arg |

| Glu | Gly | Ala | Thr | Pro | Phe | His | Ser | Arg | Ala | Thr | Leu | Met | Asn | Gly | Ala |
|-----|-----|-----|-----|-----|-----|-----|-----|-----|-----|-----|-----|-----|-----|-----|-----|
|     |     | 595 |     |     |     |     | 600 |     |     |     |     | 605 |     |     |     |

| Leu | Met | Lys | Pro | Ser | His | Val | Ile | Val | Glu | Thr | Met | Met |
|-----|-----|-----|-----|-----|-----|-----|-----|-----|-----|-----|-----|-----|
|     | 610 |     |     |     |     | 615 |     |     |     |     | 620 |     |

( 2 ) INFORMATION FOR SEQ ID NO:7:

( i ) SEQUENCE CHARACTERISTICS:
        ( A ) LENGTH: 1051 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: N ( i v ) ANTI-SENSE: N ( v i i ) IMMEDIATE SOURCE:
        ( A ) LIBRARY: human heart, human brain
        ( B ) CLONE: hHE7a,hS3a ( i x ) FEATURE:
        ( A ) NAME/KEY: CDS
        ( B ) LOCATION: 1..739
        ( D ) OTHER INFORMATION:

( x i ) SEQUENCE DESCRIPTION: SEQ ID NO:7:

| CTG | GCT | TTC | ATC | GCT | TAC | CCG | CGG | GCT | GTG | GTG | ATG | CTG | CCC | TTC | TCT | 48 |
|-----|-----|-----|-----|-----|-----|-----|-----|-----|-----|-----|-----|-----|-----|-----|-----|----|
| Leu | Ala | Phe | Ile | Ala | Tyr | Pro | Arg | Ala | Val | Val | Met | Leu | Pro | Phe | Ser |    |
| 1   |     |     |     | 5   |     |     |     |     | 10  |     |     |     |     | 15  |     |    |

| CCT | CTC | TGG | GCC | TGC | TGT | TTC | TTC | TTC | ATG | GTC | GTT | CTC | CTG | GGA | CTG | 96 |
|-----|-----|-----|-----|-----|-----|-----|-----|-----|-----|-----|-----|-----|-----|-----|-----|----|
| Pro | Leu | Trp | Ala | Cys | Cys | Phe | Phe | Phe | Met | Val | Val | Leu | Leu | Gly | Leu |    |
|     |     |     | 20  |     |     |     |     | 25  |     |     |     |     | 30  |     |     |    |

| GAT | AGC | CAG | TTT | GTG | TGT | GTA | GAA | AGC | CTG | GTG | ACA | GCG | CTG | GTG | GAC | 144 |
|-----|-----|-----|-----|-----|-----|-----|-----|-----|-----|-----|-----|-----|-----|-----|-----|-----|
| Asp | Ser | Gln | Phe | Val | Cys | Val | Glu | Ser | Leu | Val | Thr | Ala | Leu | Val | Asp |     |
|     |     | 35  |     |     |     |     | 40  |     |     |     |     | 45  |     |     |     |     |

| ATG | TAC | CCT | CAC | GTG | TTC | CGC | AAG | AAG | AAC | CGG | AGG | GAA | GTC | CTC | ATC | 192 |
|-----|-----|-----|-----|-----|-----|-----|-----|-----|-----|-----|-----|-----|-----|-----|-----|-----|
| Met | Tyr | Pro | His | Val | Phe | Arg | Lys | Lys | Asn | Arg | Arg | Glu | Val | Leu | Ile |     |
|     | 50  |     |     |     |     | 55  |     |     |     |     | 60  |     |     |     |     |     |

| CTT | GGA | GTA | TCT | GTC | GTC | TCC | TTC | CTT | GTG | GGG | CTG | ATC | ATG | CTC | ACA | 240 |
|-----|-----|-----|-----|-----|-----|-----|-----|-----|-----|-----|-----|-----|-----|-----|-----|-----|
| Leu | Gly | Val | Ser | Val | Val | Ser | Phe | Leu | Val | Gly | Leu | Ile | Met | Leu | Thr |     |
| 65  |     |     |     |     | 70  |     |     |     |     | 75  |     |     |     |     | 80  |     |

| GAG | GGC | GGA | ATG | TAC | GTG | TTC | CAG | CTC | TTT | GAC | TAC | TAT | GCG | GCC | AGT | 288 |
|-----|-----|-----|-----|-----|-----|-----|-----|-----|-----|-----|-----|-----|-----|-----|-----|-----|
| Glu | Gly | Gly | Met | Tyr | Val | Phe | Gln | Leu | Phe | Asp | Tyr | Tyr | Ala | Ala | Ser |     |
|     |     |     |     | 85  |     |     |     |     | 90  |     |     |     |     | 95  |     |     |

| GGC | ATG | TGC | CTC | CTG | TTC | GTG | GCC | ATC | TTC | GAG | TCC | CTC | TGT | GTG | GCT | 336 |
|-----|-----|-----|-----|-----|-----|-----|-----|-----|-----|-----|-----|-----|-----|-----|-----|-----|
| Gly | Met | Cys | Leu | Leu | Phe | Val | Ala | Ile | Phe | Glu | Ser | Leu | Cys | Val | Ala |     |
|     |     |     |     | 100 |     |     |     |     | 105 |     |     |     |     | 110 |     |     |

| TGG | GTT | TAC | GGA | GCC | AAG | CGC | TTC | TAC | GAC | AAC | ATC | GAA | GAC | ATG | ATT | 384 |
|-----|-----|-----|-----|-----|-----|-----|-----|-----|-----|-----|-----|-----|-----|-----|-----|-----|
| Trp | Val | Tyr | Gly | Ala | Lys | Arg | Phe | Tyr | Asp | Asn | Ile | Glu | Asp | Met | Ile |     |
|     |     | 115 |     |     |     |     | 120 |     |     |     |     | 125 |     |     |     |     |

| GGG | TAC | AGG | CCA | TGG | CCT | CTT | ATC | AAA | TAC | TGT | TGG | CTC | TTC | CTC | ACA | 432 |
|-----|-----|-----|-----|-----|-----|-----|-----|-----|-----|-----|-----|-----|-----|-----|-----|-----|
| Gly | Tyr | Arg | Pro | Trp | Pro | Leu | Ile | Lys | Tyr | Cys | Trp | Leu | Phe | Leu | Thr |     |
|     | 130 |     |     |     |     | 135 |     |     |     |     | 140 |     |     |     |     |     |

| CCA | GCT | GTG | TGC | ACA | GCC | ACC | TTT | CTC | TTC | TCC | CTG | ATA | AAG | TAC | ACT | 480 |
|-----|-----|-----|-----|-----|-----|-----|-----|-----|-----|-----|-----|-----|-----|-----|-----|-----|
| Pro | Ala | Val | Cys | Thr | Ala | Thr | Phe | Leu | Phe | Ser | Leu | Ile | Lys | Tyr | Thr |     |
| 145 |     |     |     |     | 150 |     |     |     |     | 155 |     |     |     |     | 160 |     |

| CCG | CTG | ACC | TAC | AAC | AAG | AAG | TAC | ACG | TAC | CCG | TGG | TGG | GGC | GAT | GCC | 528 |
|-----|-----|-----|-----|-----|-----|-----|-----|-----|-----|-----|-----|-----|-----|-----|-----|-----|
| Pro | Leu | Thr | Tyr | Asn | Lys | Lys | Tyr | Thr | Tyr | Pro | Trp | Trp | Gly | Asp | Ala |     |
|     |     |     |     | 165 |     |     |     |     | 170 |     |     |     |     | 175 |     |     |

| CTG | GGC | TGG | CTC | CTG | GCT | CTG | TCC | TCC | ATG | GTC | TGC | ATT | CCT | GCC | TGG | 576 |
|-----|-----|-----|-----|-----|-----|-----|-----|-----|-----|-----|-----|-----|-----|-----|-----|-----|
| Leu | Gly | Trp | Leu | Leu | Ala | Leu | Ser | Ser | Met | Val | Cys | Ile | Pro | Ala | Trp |     |
|     |     |     | 180 |     |     |     |     | 185 |     |     |     |     | 190 |     |     |     |

```
AGC CTC TAC AGA CTC GGA ACC CTC AAG GGC CCC TTC AGA GAG AGA ATC      624
Ser Leu Tyr Arg Leu Gly Thr Leu Lys Gly Pro Phe Arg Glu Arg Ile
    195                 200             205

CGT CAG CTC ATG TGC CCA GCC GAG GAC CTG CCC CAG CGG AAC CCA GCA      672
Arg Gln Leu Met Cys Pro Ala Glu Asp Leu Pro Gln Arg Asn Pro Ala
210                 215                 220

GGA CCC TCG GCT CCC GCC ACC CCC AGG ACC TCA CTG CTC AGA CTC ACA      720
Gly Pro Ser Ala Pro Ala Thr Pro Arg Thr Ser Leu Leu Arg Leu Thr
225                 230                 235                 240

GAG CTA GAG TCT CAC TGC T AGGGGCAGG CCCTTGGATG GTGCCTGTGT            769
Glu Leu Glu Ser His Cys
                245

GCCTGGCCTT GGGGATGGCT GTGGAGGGAA CGTGGCAGAA GCAGCCCCAT GTGCTTCCCT    829

GCCCCCGACC TGGAGTGGAT AAGACAAGAG GGTATTTTG GAGTCCACCT GCTGAGCTGG     889

AGGCCTCCCA CTGCAACTTT TCAGCTCAGG GGTTGTTGAA CAGATGTGAA AGGCCAGTGC    949

CAAGAGTGTC CCTCTGAGAC CCTTGGGAAG CTGGGTGGGG GCTGGTAGGT GGGGCGAGAC   1009

TTGCTGGCTT CGGGCCCTCT CATCCTTCAT TCCATTAAAT CC                      1051
```

( 2 ) INFORMATION FOR SEQ ID NO:8:

( i ) SEQUENCE CHARACTERISTICS:
        ( A ) LENGTH: 246 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Leu Ala Phe Ile Ala Tyr Pro Arg Ala Val Val Met Leu Pro Phe Ser
1               5                   10                  15

Pro Leu Trp Ala Cys Cys Phe Phe Met Val Val Leu Leu Gly Leu
            20              25                  30

Asp Ser Gln Phe Val Cys Val Glu Ser Leu Val Thr Ala Leu Val Asp
        35              40                  45

Met Tyr Pro His Val Phe Arg Lys Lys Asn Arg Arg Glu Val Leu Ile
    50                  55                  60

Leu Gly Val Ser Val Val Ser Phe Leu Val Gly Leu Ile Met Leu Thr
65                  70                  75                  80

Glu Gly Gly Met Tyr Val Phe Gln Leu Phe Asp Tyr Tyr Ala Ala Ser
                85                  90                  95

Gly Met Cys Leu Leu Phe Val Ala Ile Phe Glu Ser Leu Cys Val Ala
            100                 105                 110

Trp Val Tyr Gly Ala Lys Arg Phe Tyr Asp Asn Ile Glu Asp Met Ile
        115                 120                 125

Gly Tyr Arg Pro Trp Pro Leu Ile Lys Tyr Cys Trp Leu Phe Leu Thr
    130                 135                 140

Pro Ala Val Cys Thr Ala Thr Phe Leu Phe Ser Leu Ile Lys Tyr Thr
145                 150                 155                 160

Pro Leu Thr Tyr Asn Lys Lys Tyr Thr Tyr Pro Trp Trp Gly Asp Ala
                165                 170                 175

Leu Gly Trp Leu Leu Ala Leu Ser Ser Met Val Cys Ile Pro Ala Trp
            180                 185                 190

Ser Leu Tyr Arg Leu Gly Thr Leu Lys Gly Pro Phe Arg Glu Arg Ile
        195                 200                 205

Arg Gln Leu Met Cys Pro Ala Glu Asp Leu Pro Gln Arg Asn Pro Ala
    210                 215                 220
```

```
Gly  Pro  Ser  Ala  Pro  Ala  Thr  Pro  Arg  Thr  Ser  Leu  Leu  Arg  Leu  Thr
225                 230                      235                           240

Glu  Leu  Glu  Ser  His  Cys
                    245
```

( 2 ) INFORMATION FOR SEQ ID NO:9:

( i ) SEQUENCE CHARACTERISTICS:
        ( A ) LENGTH: 1991 base pairs
        ( B ) TYPE: nucleic acid
        ( C ) STRANDEDNESS: both
        ( D ) TOPOLOGY: linear ( i i ) MOLECULE TYPE: cDNA ( i i i ) HYPOTHETICAL: N ( i v ) ANTI-SENSE: N ( v i i ) IMMEDIATE SOURCE:
        ( A ) LIBRARY: human brain
        ( B ) CLONE: hGAT-3

( i x ) FEATURE:
        ( A ) NAME/KEY: CDS
        ( B ) LOCATION: 35..1930
        ( D ) OTHER INFORMATION:

( x i ) SEQUENCE DESCRIPTION: SEQ ID NO:9:

```
AGCCGGGCCG  GCGCACGAGG  CAGCCAGCGC  GGCC ATG ACG GCG GAG AAG GCG            52
                                         Met Thr Ala Glu Lys Ala
                                         1                 5

CTG  CCC  CTG  GGC  AAT  GGG  AAG  GCT  GCT  GAG  GAG  GCG  CGG  GAG  TCC  GAG   100
Leu  Pro  Leu  Gly  Asn  Gly  Lys  Ala  Ala  Glu  Glu  Ala  Arg  Glu  Ser  Glu
               10                   15                      20

GCG  CCG  GGT  GGC  GGC  TGC  AGC  AGC  GGG  GGC  GCG  GCG  CCC  GCG  CGC  CAC   148
Ala  Pro  Gly  Gly  Gly  Cys  Ser  Ser  Gly  Gly  Ala  Ala  Pro  Ala  Arg  His
               25                   30                      35

CCG  CGC  GTC  AAG  CGC  GAC  AAG  GCG  GTC  CAC  GAG  CGC  GGC  CAC  TGG  AAC   196
Pro  Arg  Val  Lys  Arg  Asp  Lys  Ala  Val  His  Glu  Arg  Gly  His  Trp  Asn
          40                        45                      50

AAC  AAG  GTG  GAG  TTC  GTG  CTG  AGC  GTG  GCC  GGG  GAG  ATC  ATT  GGG  CTG   244
Asn  Lys  Val  Glu  Phe  Val  Leu  Ser  Val  Ala  Gly  Glu  Ile  Ile  Gly  Leu
55                       60                      65                         70

GGC  AAC  GTG  TGG  CGC  TTC  CCC  TAC  CTG  TGC  TAC  AAG  AAC  GGA  GGA  GGG   292
Gly  Asn  Val  Trp  Arg  Phe  Pro  Tyr  Leu  Cys  Tyr  Lys  Asn  Gly  Gly  Gly
               75                   80                           85

GCA  TTC  CTG  ATT  CCC  TAC  GTG  GTG  TTT  TTT  ATT  TGC  TGT  GGA  ATT  CCT   340
Ala  Phe  Leu  Ile  Pro  Tyr  Val  Val  Phe  Phe  Ile  Cys  Cys  Gly  Ile  Pro
               90                   95                          100

GTT  TTT  TTC  CTG  GAG  ACA  GCT  CTG  GGG  CAG  TTC  ACA  AGT  GAA  GGT  GGC   388
Val  Phe  Phe  Leu  Glu  Thr  Ala  Leu  Gly  Gln  Phe  Thr  Ser  Glu  Gly  Gly
          105                       110                     115

ATT  ACG  TGT  TGG  AGG  AAA  GTT  TGC  CCT  TTA  TTT  GAA  GGC  ATT  GGC  TAT   436
Ile  Thr  Cys  Trp  Arg  Lys  Val  Cys  Pro  Leu  Phe  Glu  Gly  Ile  Gly  Tyr
          120                       125                     130

GCA  ACA  CAG  GTG  ATT  GAG  GCC  CAT  CTG  AAT  GTG  TAC  TAC  ATC  ATC  ATC   484
Ala  Thr  Gln  Val  Ile  Glu  Ala  His  Leu  Asn  Val  Tyr  Tyr  Ile  Ile  Ile
135                      140                     145                        150

CTG  GCA  TGG  GCC  ATT  TTT  TAC  CTG  AGC  AAC  TGC  TTC  ACT  ACT  GAG  CTA   532
Leu  Ala  Trp  Ala  Ile  Phe  Tyr  Leu  Ser  Asn  Cys  Phe  Thr  Thr  Glu  Leu
               155                  160                     165

CCC  TGG  GCT  ACC  TGT  GGG  CAT  GAG  TGG  AAC  ACA  GAG  AAT  TGT  GTG  GAG   580
Pro  Trp  Ala  Thr  Cys  Gly  His  Glu  Trp  Asn  Thr  Glu  Asn  Cys  Val  Glu
               170                  175                     180
```

5,658,786

-continued

| | | | | | | | | | | | | | | | | |
|---|---|---|---|---|---|---|---|---|---|---|---|---|---|---|---|---|
| TTC | CAG | AAA | CTG | AAT | GTG | AGC | AAC | TAC | AGC | CAT | GTG | TCT | CTG | CAG | AAT | 628 |
| Phe | Gln | Lys | Leu | Asn | Val | Ser | Asn | Tyr | Ser | His | Val | Ser | Leu | Gln | Asn | |
| | | 185 | | | | | 190 | | | | | 195 | | | | |
| GCC | ACC | TCC | CCT | GTC | ATG | GAG | TTT | TGG | GAG | CAC | CGG | GTC | CTG | GCC | ATC | 676 |
| Ala | Thr | Ser | Pro | Val | Met | Glu | Phe | Trp | Glu | His | Arg | Val | Leu | Ala | Ile | |
| | | 200 | | | | 205 | | | | 210 | | | | | | |
| TCT | GAC | GGG | ATC | GAG | CAC | ATC | GGG | AAC | CTT | CGC | TGG | GAG | CTG | GCC | TTG | 724 |
| Ser | Asp | Gly | Ile | Glu | His | Ile | Gly | Asn | Leu | Arg | Trp | Glu | Leu | Ala | Leu | |
| 215 | | | | | 220 | | | | | 225 | | | | | 230 | |
| TGT | CTC | TTG | GCA | GCC | TGG | ACC | ATC | TGT | TAC | TTC | TGT | ATC | TGG | AAG | GGG | 772 |
| Cys | Leu | Leu | Ala | Ala | Trp | Thr | Ile | Cys | Tyr | Phe | Cys | Ile | Trp | Lys | Gly | |
| | | | | 235 | | | | | 240 | | | | | 245 | | |
| ACC | AAG | TCT | ACA | GGA | AAG | GTT | GTA | TAC | GTG | ACT | GCG | ACA | TTC | CCC | TAC | 820 |
| Thr | Lys | Ser | Thr | Gly | Lys | Val | Val | Tyr | Val | Thr | Ala | Thr | Phe | Pro | Tyr | |
| | | | 250 | | | | | 255 | | | | | 260 | | | |
| ATC | ATG | CTG | CTG | ATC | CTC | CTG | ATA | CGA | GGG | GTC | ACG | TTG | CCC | GGG | GCC | 868 |
| Ile | Met | Leu | Leu | Ile | Leu | Leu | Ile | Arg | Gly | Val | Thr | Leu | Pro | Gly | Ala | |
| | | | 265 | | | | | 270 | | | | | 275 | | | |
| TCA | GAG | GGC | ATC | AAG | TTC | TAC | TTG | TAC | CCT | GAC | CTC | TCC | CGG | CTC | TCC | 916 |
| Ser | Glu | Gly | Ile | Lys | Phe | Tyr | Leu | Tyr | Pro | Asp | Leu | Ser | Arg | Leu | Ser | |
| | 280 | | | | | 285 | | | | | 290 | | | | | |
| GAC | CCC | CAG | GTC | TGG | GTA | GAT | GCT | GGA | ACG | CAG | ATC | TTT | TTC | TCC | TAT | 964 |
| Asp | Pro | Gln | Val | Trp | Val | Asp | Ala | Gly | Thr | Gln | Ile | Phe | Phe | Ser | Tyr | |
| 295 | | | | | 300 | | | | | 305 | | | | | 310 | |
| GCC | ATT | TGC | CTG | GGC | TGT | CTG | ACC | GCT | CTG | GGA | AGT | TAT | AAC | AAT | TAT | 1012 |
| Ala | Ile | Cys | Leu | Gly | Cys | Leu | Thr | Ala | Leu | Gly | Ser | Tyr | Asn | Asn | Tyr | |
| | | | | 315 | | | | | 320 | | | | | 325 | | |
| AAC | AAC | AAC | TGC | TAC | AGG | GAC | TGC | ATC | ATG | CTC | TGT | TGC | CTG | AAC | AGC | 1060 |
| Asn | Asn | Asn | Cys | Tyr | Arg | Asp | Cys | Ile | Met | Leu | Cys | Cys | Leu | Asn | Ser | |
| | | | 330 | | | | | 335 | | | | | 340 | | | |
| GGC | ACC | AGC | TTC | GTG | GCT | GGG | TTT | GCC | ATC | TTC | TCA | GTC | CTG | GGT | TTT | 1108 |
| Gly | Thr | Ser | Phe | Val | Ala | Gly | Phe | Ala | Ile | Phe | Ser | Val | Leu | Gly | Phe | |
| | | 345 | | | | | 350 | | | | | 355 | | | | |
| ATG | GCG | TAC | GAG | CAG | GGG | GTA | CCC | ATT | GCT | GAG | GTG | GCA | GAG | TCA | GGC | 1156 |
| Met | Ala | Tyr | Glu | Gln | Gly | Val | Pro | Ile | Ala | Glu | Val | Ala | Glu | Ser | Gly | |
| | | 360 | | | | | 365 | | | | | 370 | | | | |
| CCC | GGC | CTG | GCC | TTT | ATT | GCG | TAC | CCC | AAG | GCG | GTC | ACC | ATG | ATG | CCT | 1204 |
| Pro | Gly | Leu | Ala | Phe | Ile | Ala | Tyr | Pro | Lys | Ala | Val | Thr | Met | Met | Pro | |
| 375 | | | | | 380 | | | | | 385 | | | | | 390 | |
| CTC | TCC | CCG | CTG | TGG | GCC | ACC | TTG | TTC | TTC | ATG | ATG | CTC | ATC | TTC | CTG | 1252 |
| Leu | Ser | Pro | Leu | Trp | Ala | Thr | Leu | Phe | Phe | Met | Met | Leu | Ile | Phe | Leu | |
| | | | | 395 | | | | | 400 | | | | | 405 | | |
| GGC | CTG | GAC | AGC | CAG | TTT | GTG | TGT | GTG | GAA | AGC | CTG | GTG | ACC | GCC | GTG | 1300 |
| Gly | Leu | Asp | Ser | Gln | Phe | Val | Cys | Val | Glu | Ser | Leu | Val | Thr | Ala | Val | |
| | | | 410 | | | | | 415 | | | | | 420 | | | |
| GTG | GAC | ATG | TAC | CCC | AAG | GTT | TTC | CGG | AGG | GGT | TAC | CGG | CGG | GAG | CTG | 1348 |
| Val | Asp | Met | Tyr | Pro | Lys | Val | Phe | Arg | Arg | Gly | Tyr | Arg | Arg | Glu | Leu | |
| | | 425 | | | | | 430 | | | | | 435 | | | | |
| CTC | ATC | CTA | GCC | TTG | TCT | GTT | ATC | TCC | TAT | TTT | CTG | GGC | CTC | GTG | ATG | 1396 |
| Leu | Ile | Leu | Ala | Leu | Ser | Val | Ile | Ser | Tyr | Phe | Leu | Gly | Leu | Val | Met | |
| | | 440 | | | | | 445 | | | | | 450 | | | | |
| TTA | ACA | GAG | GGT | GGC | ATG | TAC | ATC | TTC | CAG | CTC | TTT | GAC | TCC | TAT | GCC | 1444 |
| Leu | Thr | Glu | Gly | Gly | Met | Tyr | Ile | Phe | Gln | Leu | Phe | Asp | Ser | Tyr | Ala | |
| 455 | | | | | 460 | | | | | 465 | | | | | 470 | |
| GCC | AGT | GGG | ATG | TGC | CTT | CTC | TTC | GTG | GCC | ATC | TTT | GAG | TGC | ATC | TGC | 1492 |
| Ala | Ser | Gly | Met | Cys | Leu | Leu | Phe | Val | Ala | Ile | Phe | Glu | Cys | Ile | Cys | |
| | | | | 475 | | | | | 480 | | | | | 485 | | |
| ATC | GGC | TGG | GTG | TAT | GGA | AGC | AAC | CGG | TTC | TAT | GAT | AAC | ATT | GAA | GAC | 1540 |
| Ile | Gly | Trp | Val | Tyr | Gly | Ser | Asn | Arg | Phe | Tyr | Asp | Asn | Ile | Glu | Asp | |
| | | | 490 | | | | | 495 | | | | | 500 | | | |

```
ATG ATT GGC TAC CGG CCA CCG TCG CTC ATT AAG TGG TGC TGG ATG ATC                     1588
Met Ile Gly Tyr Arg Pro Pro Ser Leu Ile Lys Trp Cys Trp Met Ile
    505                 510                 515

ATG ACC CCT GGG ATC TGC GCG GGG ATC TTC ATC TTC TTC TTG ATC AAG                     1636
Met Thr Pro Gly Ile Cys Ala Gly Ile Phe Ile Phe Phe Leu Ile Lys
    520                 525                 530

TAC AAG CCA CTC AAG TAC AAC AAC ATC TAC ACC TAC CCA GCC TGG GGC                     1684
Tyr Lys Pro Leu Lys Tyr Asn Asn Ile Tyr Thr Tyr Pro Ala Trp Gly
535                     540                 545                 550

TAT GGC ATT GGC TGG CTC ATG GCC CTG TCC TCC ATG CTC TGC ATC CCG                     1732
Tyr Gly Ile Gly Trp Leu Met Ala Leu Ser Ser Met Leu Cys Ile Pro
                555                 560                 565

CTC TGG ATC TGC ATC ACA GTG TGG AAG ACG GAG GGG ACA CTG CCC GAG                     1780
Leu Trp Ile Cys Ile Thr Val Trp Lys Thr Glu Gly Thr Leu Pro Glu
                570                 575                 580

AAA CTC CAG AAG TTG ACG ACC CCC AGC ACA GAT CTG AAA ATG CGG GGC                     1828
Lys Leu Gln Lys Leu Thr Thr Pro Ser Thr Asp Leu Lys Met Arg Gly
            585                 590                 595

AAG CTT GGG GTG AGC CCA CGG ATG GTG ACA GTT AAT GAC TGT GAT GCC                     1876
Lys Leu Gly Val Ser Pro Arg Met Val Thr Val Asn Asp Cys Asp Ala
    600                 605                 610

AAA CTC AAG AGT GAC GGG ACC ATC GCA GCC ATC ACA GAG AAG GAG ACG                     1924
Lys Leu Lys Ser Asp Gly Thr Ile Ala Ala Ile Thr Glu Lys Glu Thr
615                 620                 625                     630

CAC TTC TGAGCGGCCA CCAGCCATCT GGGGCTCTTC TTCCTTTCTT CCCCCCGTGT                      1980
His Phe
ATGTAAATGA A                                                                        1991

( 2 ) INFORMATION FOR SEQ ID NO:10:

( i ) SEQUENCE CHARACTERISTICS:
                ( A ) LENGTH: 632 amino acids
                ( B ) TYPE: amino acid
                ( D ) TOPOLOGY: linear ( i i ) MOLECULE TYPE: protein ( x i ) SEQUENCE DESCRIPTION: SEQ ID NO:10:

Met Thr Ala Glu Lys Ala Leu Pro Leu Gly Asn Gly Lys Ala Ala Glu
 1               5                  10                  15

Glu Ala Arg Glu Ser Glu Ala Pro Gly Gly Cys Ser Ser Gly Gly
            20                  25                  30

Ala Ala Pro Ala Arg His Pro Arg Val Lys Arg Asp Lys Ala Val His
        35                  40                  45

Glu Arg Gly His Trp Asn Asn Lys Val Glu Phe Val Leu Ser Val Ala
    50                  55                  60

Gly Glu Ile Ile Gly Leu Gly Asn Val Trp Arg Phe Pro Tyr Leu Cys
65                  70                  75                  80

Tyr Lys Asn Gly Gly Gly Ala Phe Leu Ile Pro Tyr Val Val Phe Phe
                85                  90                  95

Ile Cys Cys Gly Ile Pro Val Phe Phe Leu Glu Thr Ala Leu Gly Gln
            100                 105                 110

Phe Thr Ser Glu Gly Gly Ile Thr Cys Trp Arg Lys Val Cys Pro Leu
        115                 120                 125

Phe Glu Gly Ile Gly Tyr Ala Thr Gln Val Ile Glu Ala His Leu Asn
    130                 135                 140

Val Tyr Tyr Ile Ile Ile Leu Ala Trp Ala Ile Phe Tyr Leu Ser Asn
145                 150                 155                 160

Cys Phe Thr Thr Glu Leu Pro Trp Ala Thr Cys Gly His Glu Trp Asn
```

|  |  |  | 165 |  |  |  | 170 |  |  |  | 175 |  |  |
|---|---|---|---|---|---|---|---|---|---|---|---|---|---|
| Thr | Glu | Asn | Cys<br>180 | Val | Glu | Phe | Gln<br>185 | Lys | Leu | Asn | Val | Ser<br>190 | Asn | Tyr | Ser |
| His | Val | Ser<br>195 | Leu | Gln | Asn | Ala | Thr<br>200 | Ser | Pro | Val | Met | Glu<br>205 | Phe | Trp | Glu |
| His | Arg<br>210 | Val | Leu | Ala | Ile | Ser<br>215 | Asp | Gly | Ile | Glu | His<br>220 | Ile | Gly | Asn | Leu |
| Arg<br>225 | Trp | Glu | Leu | Ala | Leu<br>230 | Cys | Leu | Leu | Ala | Ala<br>235 | Trp | Thr | Ile | Cys | Tyr<br>240 |
| Phe | Cys | Ile | Trp | Lys<br>245 | Gly | Thr | Lys | Ser | Thr<br>250 | Gly | Lys | Val | Val | Tyr<br>255 | Val |
| Thr | Ala | Thr | Phe<br>260 | Pro | Tyr | Ile | Met | Leu<br>265 | Leu | Ile | Leu | Leu | Ile<br>270 | Arg | Gly |
| Val | Thr | Leu<br>275 | Pro | Gly | Ala | Ser | Glu<br>280 | Gly | Ile | Lys | Phe | Tyr<br>285 | Leu | Tyr | Pro |
| Asp | Leu<br>290 | Ser | Arg | Leu | Ser | Asp<br>295 | Pro | Gln | Val | Trp | Val<br>300 | Asp | Ala | Gly | Thr |
| Gln<br>305 | Ile | Phe | Phe | Ser | Tyr<br>310 | Ala | Ile | Cys | Leu | Gly<br>315 | Cys | Leu | Thr | Ala | Leu<br>320 |
| Gly | Ser | Tyr | Asn | Asn<br>325 | Tyr | Asn | Asn | Cys<br>330 | Tyr | Arg | Asp | Cys | Ile<br>335 | Met |
| Leu | Cys | Cys | Leu<br>340 | Asn | Ser | Gly | Thr | Ser<br>345 | Phe | Val | Ala | Gly | Phe<br>350 | Ala | Ile |
| Phe | Ser | Val<br>355 | Leu | Gly | Phe | Met | Ala<br>360 | Tyr | Glu | Gln | Gly | Val<br>365 | Pro | Ile | Ala |
| Glu | Val<br>370 | Ala | Glu | Ser | Gly | Pro<br>375 | Gly | Leu | Ala | Phe | Ile<br>380 | Ala | Tyr | Pro | Lys |
| Ala<br>385 | Val | Thr | Met | Met | Pro<br>390 | Leu | Ser | Pro | Leu | Trp<br>395 | Ala | Thr | Leu | Phe | Phe<br>400 |
| Met | Met | Leu | Ile | Phe<br>405 | Leu | Gly | Leu | Asp | Ser<br>410 | Gln | Phe | Val | Cys | Val<br>415 | Glu |
| Ser | Leu | Val | Thr<br>420 | Ala | Val | Val | Asp | Met<br>425 | Tyr | Pro | Lys | Val | Phe<br>430 | Arg | Arg |
| Gly | Tyr | Arg<br>435 | Arg | Glu | Leu | Leu | Ile<br>440 | Leu | Ala | Leu | Ser | Val<br>445 | Ile | Ser | Tyr |
| Phe | Leu<br>450 | Gly | Leu | Val | Met | Leu<br>455 | Thr | Glu | Gly | Gly | Met<br>460 | Tyr | Ile | Phe | Gln |
| Leu<br>465 | Phe | Asp | Ser | Tyr | Ala<br>470 | Ala | Ser | Gly | Met | Cys<br>475 | Leu | Leu | Phe | Val | Ala<br>480 |
| Ile | Phe | Glu | Cys | Ile<br>485 | Cys | Ile | Gly | Trp | Val<br>490 | Tyr | Gly | Ser | Asn | Arg<br>495 | Phe |
| Tyr | Asp | Asn | Ile | Glu<br>500 | Asp | Met | Ile | Gly<br>505 | Tyr | Arg | Pro | Pro | Ser<br>510 | Leu | Ile |
| Lys | Trp | Cys<br>515 | Trp | Met | Ile | Met | Thr<br>520 | Pro | Gly | Ile | Cys | Ala<br>525 | Gly | Ile | Phe |
| Ile | Phe<br>530 | Phe | Leu | Ile | Lys | Tyr<br>535 | Lys | Pro | Leu | Lys | Tyr<br>540 | Asn | Asn | Ile | Tyr |
| Thr<br>545 | Tyr | Pro | Ala | Trp | Gly<br>550 | Tyr | Gly | Ile | Gly | Trp<br>555 | Leu | Met | Ala | Leu | Ser<br>560 |
| Ser | Met | Leu | Cys | Ile<br>565 | Pro | Leu | Trp | Ile | Cys<br>570 | Ile | Thr | Val | Trp | Lys<br>575 | Thr |
| Glu | Gly | Thr | Leu<br>580 | Pro | Glu | Lys | Leu | Gln<br>585 | Lys | Leu | Thr | Thr | Pro<br>590 | Ser | Thr |

Asp Leu Lys Met Arg Gly Lys Leu Gly Val Ser Pro Arg Met Val Thr
    595                     600                 605

Val Asn Asp Cys Asp Ala Lys Leu Lys Ser Asp Gly Thr Ile Ala Ala
    610             615                 620

Ile Thr Glu Lys Glu Thr His Phe
625             630

( 2 ) INFORMATION FOR SEQ ID NO:11:

( i ) SEQUENCE CHARACTERISTICS:
( A ) LENGTH: 599 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:11:

Met Ala Thr Asp Asn Ser Lys Val Ala Asp Gly Gln Ile Ser Thr Glu
1               5                   10                  15

Val Ser Glu Ala Pro Val Ala Ser Lys Pro Lys Thr Leu Val Val
            20                  25                  30

Lys Val Gln Lys Lys Ala Gly Asp Leu Pro Asp Arg Asp Thr Trp Lys
        35                  40                  45

Gly Arg Phe Asp Phe Leu Met Ser Cys Val Gly Tyr Ala Ile Gly Leu
    50                  55                  60

Gly Asn Val Trp Arg Phe Pro Tyr Leu Cys Gly Lys Asn Gly Gly Gly
65                  70                  75                  80

Ala Phe Leu Ile Pro Tyr Phe Leu Thr Leu Ile Phe Ala Gly Val Pro
                85                  90                  95

Leu Phe Leu Leu Glu Cys Ser Leu Gly Gln Tyr Thr Ser Ile Gly Gly
            100                 105                 110

Leu Gly Val Trp Lys Leu Ala Pro Met Phe Lys Gly Val Gly Leu Ala
        115                 120                 125

Ala Ala Val Leu Ser Phe Trp Leu Asn Ile Tyr Tyr Ile Val Ile Ile
    130                 135                 140

Ser Trp Ala Ile Tyr Tyr Leu Tyr Asn Ser Phe Thr Thr Thr Leu Pro
145                 150                 155                 160

Trp Lys Gln Cys Asp Asn Pro Trp Asn Thr Asp Arg Cys Phe Ser Asn
                165                 170                 175

Tyr Ser Leu Val Asn Thr Thr Asn Met Thr Ser Ala Val Val Glu Phe
            180                 185                 190

Trp Glu Arg Asn Met His Gln Met Thr Asp Gly Leu Asp Lys Pro Gly
        195                 200                 205

Gln Ile Arg Trp Pro Leu Ala Ile Thr Leu Ala Ile Ala Trp Val Leu
    210                 215                 220

Val Tyr Phe Cys Ile Trp Lys Gly Val Gly Trp Thr Gly Lys Val Val
225                 230                 235                 240

Tyr Phe Ser Ala Thr Tyr Pro Tyr Ile Met Leu Ile Ile Leu Phe Phe
                245                 250                 255

Arg Gly Val Thr Leu Pro Gly Ala Lys Glu Gly Ile Leu Phe Tyr Ile
            260                 265                 270

Thr Pro Asn Phe Arg Lys Leu Ser Asp Ser Glu Val Trp Leu Asp Ala
        275                 280                 285

Ala Thr Gln Ile Phe Phe Ser Tyr Gly Leu Gly Leu Gly Ser Leu Ile
    290                 295                 300

Ala Leu Gly Ser Tyr Asn Ser Phe His Asn Asn Val Tyr Arg Asp Ser

|     |     |     |     |     |     |     |     |     |     |     |     |     |     |     |
|-----|-----|-----|-----|-----|-----|-----|-----|-----|-----|-----|-----|-----|-----|-----|
| 305 |     |     |     |     | 310 |     |     |     |     | 315 |     |     |     | 320 |
| Ile | Ile | Val | Cys | Cys | Ile | Asn | Ser | Cys | Thr | Ser | Met | Phe | Ala | Phe |
|     |     |     |     | 325 |     |     |     |     | 330 |     |     |     | 335 |     |
| Val | Ile | Phe | Ser | Ile | Val | Gly | Phe | Met | Ala | His | Val | Thr | Lys | Arg | Ser |
|     |     |     | 340 |     |     |     |     | 345 |     |     |     | 350 |     |     |
| Ile | Ala | Asp | Val | Ala | Ala | Ser | Gly | Pro | Gly | Leu | Ala | Phe | Leu | Ala | Tyr |
|     |     | 355 |     |     |     | 360 |     |     |     |     | 365 |     |     |     |
| Pro | Glu | Ala | Val | Thr | Gln | Leu | Pro | Ile | Ser | Pro | Leu | Trp | Ala | Ile | Leu |
|     | 370 |     |     |     | 375 |     |     |     |     | 380 |     |     |     |     |
| Phe | Phe | Ser | Met | Leu | Leu | Met | Leu | Gly | Ile | Asp | Ser | Gln | Phe | Cys | Thr |
| 385 |     |     |     | 390 |     |     |     |     | 395 |     |     |     |     | 400 |
| Val | Glu | Gly | Phe | Ile | Thr | Ala | Leu | Val | Asp | Glu | Tyr | Pro | Arg | Leu | Leu |
|     |     |     | 405 |     |     |     |     | 410 |     |     |     |     | 415 |     |
| Arg | Asn | Arg | Arg | Glu | Leu | Phe | Ile | Ala | Ala | Val | Cys | Ile | Val | Ser | Tyr |
|     |     |     | 420 |     |     |     | 425 |     |     |     |     | 430 |     |     |
| Leu | Ile | Gly | Leu | Ser | Asn | Ile | Thr | Gln | Gly | Gly | Ile | Tyr | Val | Phe | Lys |
|     |     | 435 |     |     |     | 440 |     |     |     | 445 |     |     |     |     |
| Leu | Phe | Asp | Tyr | Tyr | Ser | Ala | Ser | Gly | Met | Ser | Leu | Leu | Phe | Leu | Val |
|     | 450 |     |     |     | 455 |     |     |     | 460 |     |     |     |     |     |
| Phe | Phe | Glu | Cys | Val | Ser | Ile | Ser | Trp | Phe | Tyr | Gly | Val | Asn | Arg | Phe |
| 465 |     |     |     | 470 |     |     |     | 475 |     |     |     |     | 480 |     |
| Tyr | Asp | Asn | Ile | Gln | Glu | Met | Val | Gly | Ser | Arg | Pro | Cys | Ile | Trp | Trp |
|     |     |     | 485 |     |     |     |     | 490 |     |     |     | 495 |     |     |
| Lys | Leu | Cys | Trp | Ser | Phe | Phe | Thr | Pro | Ile | Ile | Val | Ala | Gly | Val | Phe |
|     |     |     | 500 |     |     |     |     | 505 |     |     |     | 510 |     |     |
| Leu | Phe | Ser | Ala | Val | Gln | Met | Thr | Pro | Leu | Thr | Met | Gly | Ser | Tyr | Val |
|     |     | 515 |     |     |     |     | 520 |     |     |     | 525 |     |     |     |
| Phe | Pro | Lys | Trp | Gly | Gln | Gly | Val | Gly | Trp | Leu | Met | Ala | Leu | Ser | Ser |
|     | 530 |     |     |     | 535 |     |     |     | 540 |     |     |     |     |     |
| Met | Val | Leu | Ile | Pro | Gly | Tyr | Met | Ala | Tyr | Met | Phe | Leu | Thr | Leu | Lys |
| 545 |     |     |     |     | 550 |     |     |     | 555 |     |     |     |     | 560 |
| Gly | Ser | Leu | Lys | Gln | Arg | Leu | Gln | Val | Met | Ile | Gln | Pro | Ser | Glu | Asp |
|     |     |     | 565 |     |     |     | 570 |     |     |     | 575 |     |     |
| Ile | Val | Arg | Pro | Glu | Asn | Gly | Pro | Glu | Gln | Pro | Gln | Ala | Gly | Ser | Ser |
|     |     |     | 580 |     |     |     | 585 |     |     |     | 590 |     |     |     |
| Ala | Ser | Lys | Glu | Ala | Tyr | Ile |     |     |     |     |     |     |     |     |     |
|     |     | 595 |     |     |     |     |     |     |     |     |     |     |     |     |

(2) INFORMATION FOR SEQ ID NO:12:

(i) SEQUENCE CHARACTERISTICS:
        (A) LENGTH: 614 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

|     |     |     |     |     |     |     |     |     |     |     |     |     |     |     |
|-----|-----|-----|-----|-----|-----|-----|-----|-----|-----|-----|-----|-----|-----|-----|
| Met | Asp | Arg | Lys | Val | Ala | Val | Pro | Glu | Asp | Gly | Pro | Pro | Val | Val | Ser |
| 1   |     |     |     | 5   |     |     |     |     | 10  |     |     |     |     | 15  |     |
| Trp | Leu | Pro | Glu | Glu | Gly | Glu | Lys | Leu | Asp | Gln | Glu | Gly | Glu | Asp | Gln |
|     |     |     | 20  |     |     |     |     | 25  |     |     |     |     | 30  |     |     |
| Val | Lys | Asp | Arg | Gly | Gln | Trp | Thr | Asn | Lys | Met | Glu | Phe | Val | Leu | Ser |
|     |     | 35  |     |     |     |     | 40  |     |     |     |     | 45  |     |     |     |
| Val | Ala | Gly | Glu | Ile | Ile | Gly | Leu | Gly | Asn | Val | Trp | Arg | Phe | Pro | Tyr |
|     | 50  |     |     |     |     | 55  |     |     |     |     | 60  |     |     |     |     |

| | | | | | | | | | | | | | | |
|---|---|---|---|---|---|---|---|---|---|---|---|---|---|---|
| Leu | Cys | Tyr | Lys | Asn | Gly | Gly | Ala | Phe | Phe | Ile | Pro | Tyr | Phe | Ile |
| 65 | | | | 70 | | | | 75 | | | | | | 80 |
| Phe | Phe | Phe | Thr | Cys | Gly | Ile | Pro | Val | Phe | Leu | Glu | Val | Ala | Leu |
| | | | | 85 | | | | 90 | | | | | 95 | |
| Gly | Gln | Tyr | Thr | Ser | Gln | Gly | Ser | Val | Thr | Ala | Trp | Arg | Lys | Ile | Cys |
| | | | 100 | | | | | 105 | | | | | 110 | |
| Pro | Leu | Leu | Gln | Gly | Ile | Gly | Leu | Ala | Ser | Val | Val | Ile | Glu | Ser | Tyr |
| | | 115 | | | | | 120 | | | | | 125 | | |
| Leu | Asn | Ile | Tyr | Tyr | Ile | Ile | Ile | Leu | Ala | Trp | Ala | Leu | Phe | Tyr | Leu |
| | 130 | | | | | 135 | | | | | 140 | | | |
| Phe | Ser | Ser | Phe | Thr | Ser | Glu | Leu | Pro | Trp | Thr | Thr | Cys | Thr | Asn | Thr |
| 145 | | | | | 150 | | | | | 155 | | | | | 160 |
| Trp | Asn | Thr | Glu | His | Cys | Met | Asp | Phe | Leu | Asn | His | Ser | Gly | Ala | Arg |
| | | | | 165 | | | | | 170 | | | | | 175 | |
| Thr | Ala | Thr | Ser | Ser | Glu | Asn | Phe | Thr | Ser | Pro | Val | Met | Glu | Phe | Trp |
| | | | 180 | | | | | 185 | | | | | 190 | | |
| Glu | Arg | Arg | Val | Leu | Gly | Ile | Thr | Ser | Gly | Ile | His | Asp | Leu | Gly | Ala |
| | | 195 | | | | | 200 | | | | | 205 | | | |
| Leu | Arg | Trp | Glu | Leu | Ala | Leu | Cys | Leu | Leu | Leu | Ala | Trp | Leu | Ile | Cys |
| | 210 | | | | | 215 | | | | | 220 | | | | |
| Tyr | Phe | Cys | Ile | Trp | Lys | Gly | Val | Lys | Thr | Thr | Gly | Lys | Val | Val | Tyr |
| 225 | | | | | 230 | | | | | 235 | | | | | 240 |
| Phe | Thr | Ala | Thr | Phe | Pro | Tyr | Leu | Met | Leu | Val | Ile | Leu | Leu | Ile | Arg |
| | | | | 245 | | | | | 250 | | | | | 255 | |
| Gly | Ile | Thr | Leu | Pro | Gly | Ala | Tyr | Gln | Gly | Val | Ile | Tyr | Tyr | Leu | Lys |
| | | | 260 | | | | | 265 | | | | | 270 | | |
| Pro | Asp | Leu | Leu | Arg | Leu | Lys | Asp | Pro | Gln | Val | Trp | Met | Asp | Ala | Gly |
| | | 275 | | | | | 280 | | | | | 285 | | | |
| Thr | Gln | Ile | Phe | Phe | Ser | Phe | Ala | Ile | Cys | Gln | Gly | Cys | Leu | Thr | Ala |
| | 290 | | | | | 295 | | | | | 300 | | | | |
| Leu | Gly | Ser | Tyr | Asn | Lys | Tyr | His | Asn | Asn | Cys | Tyr | Arg | Asp | Ser | Ile |
| 305 | | | | | 310 | | | | | 315 | | | | | 320 |
| Ala | Leu | Cys | Phe | Leu | Asn | Ser | Ala | Thr | Ser | Phe | Ala | Ala | Gly | Phe | Val |
| | | | | 325 | | | | | 330 | | | | | 335 | |
| Val | Phe | Ser | Ile | Leu | Gly | Phe | Met | Ala | Gln | Glu | Gln | Gly | Leu | Pro | Ile |
| | | | 340 | | | | | 345 | | | | | 350 | | |
| Ser | Glu | Val | Ala | Glu | Ser | Gly | Pro | Gly | Leu | Ala | Phe | Ile | Ala | Phe | Pro |
| | | 355 | | | | | 360 | | | | | 365 | | | |
| Lys | Ala | Val | Thr | Met | Met | Pro | Leu | Ser | Gln | Leu | Trp | Ser | Cys | Leu | Phe |
| | 370 | | | | | 375 | | | | | 380 | | | | |
| Phe | Ile | Met | Leu | Ile | Phe | Leu | Gly | Leu | Asp | Ser | Gln | Phe | Val | Cys | Val |
| 385 | | | | | 390 | | | | | 395 | | | | | 400 |
| Glu | Cys | Leu | Val | Thr | Ala | Ser | Met | Asp | Met | Phe | Pro | Ser | Gln | Leu | Arg |
| | | | | 405 | | | | | 410 | | | | | 415 | |
| Lys | Ser | Gly | Arg | Arg | Glu | Leu | Leu | Ile | Leu | Ala | Ile | Ala | Val | Phe | Cys |
| | | | 420 | | | | | 425 | | | | | 430 | | |
| Tyr | Leu | Ala | Gly | Leu | Phe | Leu | Val | Thr | Glu | Gly | Gly | Met | Tyr | Ile | Phe |
| | | 435 | | | | | 440 | | | | | 445 | | | |
| Gln | Leu | Phe | Asp | Tyr | Tyr | Ala | Ser | Ser | Gly | Ile | Cys | Leu | Leu | Phe | Leu |
| | 450 | | | | | 455 | | | | | 460 | | | | |
| Ala | Met | Phe | Glu | Val | Ile | Cys | Ile | Ser | Trp | Val | Tyr | Gly | Ala | Asp | Arg |
| 465 | | | | | 470 | | | | | 475 | | | | | 480 |
| Phe | Tyr | Asp | Asn | Ile | Glu | Asp | Met | Ile | Gly | Tyr | Arg | Pro | Trp | Pro | Leu |

|  |  |  |  |  | 485 |  |  |  | 490 |  |  |  | 495 |  |
|---|---|---|---|---|---|---|---|---|---|---|---|---|---|---|
| Val | Lys | Ile | Ser<br>500 | Trp | Leu | Phe | Leu | Thr<br>505 | Pro | Gly | Leu | Cys | Leu<br>510 | Ala | Thr |
| Phe | Leu | Phe<br>515 | Ser | Leu | Ser | Gln | Tyr | Thr<br>520 | Pro | Leu | Lys | Tyr<br>525 | Asn | Asn | Ile |
| Tyr | Val<br>530 | Tyr | Pro | Pro | Trp | Gly<br>535 | Tyr | Ser | Ile | Gly | Trp<br>540 | Phe | Leu | Ala | Leu |
| Ser<br>545 | Ser | Met | Ile | Cys | Val<br>550 | Pro | Leu | Phe | Val | Ile<br>555 | Ile | Thr | Leu | Leu | Lys<br>560 |
| Thr | Arg | Gly | Ser | Phe<br>565 | Lys | Lys | Arg | Leu | Arg<br>570 | Gln | Leu | Thr | Thr | Pro<br>575 | Asp |
| Pro | Ser | Leu | Pro<br>580 | Gln | Pro | Lys | Gln | His<br>585 | Leu | Tyr | Leu | Asp | Gly<br>590 | Gly | Thr |
| Ser | Gln | Asp<br>595 | Cys | Gly | Pro | Ser | Pro<br>600 | Thr | Lys | Glu | Gly | Leu<br>605 | Ile | Val | Gly |
| Glu | Lys<br>610 | Glu | Thr | His | Leu |  |  |  |  |  |  |  |  |  |  |

( 2 ) INFORMATION FOR SEQ ID NO:13:

( i ) SEQUENCE CHARACTERISTICS:
        ( A ) LENGTH: 638 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

| Met<br>1 | Ala | Val | Ala | His<br>5 | Gly | Pro | Val | Ala | Thr<br>10 | Ser | Ser | Pro | Glu | Gln<br>15 | Asn |
|---|---|---|---|---|---|---|---|---|---|---|---|---|---|---|---|
| Gly | Ala | Val | Pro<br>20 | Ser | Glu | Ala | Thr | Lys<br>25 | Lys | Asp | Gln | Asn | Leu<br>30 | Thr | Arg |
| Gly | Asn | Trp<br>35 | Gly | Asn | Gln | Ile | Glu<br>40 | Phe | Val | Leu | Thr | Ser<br>45 | Val | Gly | Tyr |
| Ala | Val<br>50 | Gly | Leu | Gly | Asn | Val<br>55 | Trp | Arg | Phe | Pro | Tyr<br>60 | Leu | Cys | Tyr | Arg |
| Asn<br>65 | Gly | Gly | Gly | Ala | Phe<br>70 | Met | Phe | Pro | Tyr | Phe<br>75 | Ile | Met | Leu | Val | Phe<br>80 |
| Cys | Gly | Ile | Pro | Leu<br>85 | Phe | Phe | Met | Glu | Leu<br>90 | Ser | Phe | Gly | Gln | Phe<br>95 | Ala |
| Ser | Gln | Gly | Cys<br>100 | Leu | Gly | Val | Trp | Arg<br>105 | Ile | Ser | Pro | Met | Phe<br>110 | Lys | Gly |
| Val | Gly | Tyr<br>115 | Gly | Met | Met | Val | Val<br>120 | Ser | Thr | Tyr | Ile | Gly<br>125 | Ile | Tyr | Tyr |
| Asn | Val<br>130 | Val | Ile | Cys | Ile | Ala<br>135 | Phe | Tyr | Tyr | Phe | Phe<br>140 | Ser | Ser | Met | Thr |
| His<br>145 | Val | Leu | Pro | Trp | Ala<br>150 | Tyr | Cys | Asn | Asn | Pro<br>155 | Trp | Asn | Thr | Pro | Asp<br>160 |
| Cys | Ala | Gly | Val | Leu<br>165 | Asp | Ala | Ser | Asn | Leu<br>170 | Thr | Asn | Gly | Ser | Arg<br>175 | Pro |
| Thr | Ala | Leu | Ser<br>180 | Gly | Asn | Leu | Ser | His<br>185 | Leu | Phe | Asn | Tyr | Thr<br>190 | Leu | Gln |
| Arg | Thr | Ser<br>195 | Pro | Ser | Glu | Glu | Tyr<br>200 | Trp | Arg | Leu | Tyr | Val<br>205 | Leu | Lys | Leu |
| Ser | Asp<br>210 | Asp | Ile | Gly | Asp | Phe<br>215 | Gly | Glu | Val | Arg | Leu<br>220 | Pro | Leu | Leu | Gly |

```
Cys Leu Gly Val Ser Trp Val Val Phe Leu Cys Leu Ile Arg Gly
225             230             235             240

Val Lys Ser Ser Gly Lys Val Val Tyr Phe Thr Ala Thr Phe Pro Tyr
                245             250             255

Val Val Leu Thr Ile Leu Phe Val Arg Gly Val Thr Leu Glu Gly Ala
            260             265             270

Phe Thr Gly Ile Met Tyr Tyr Leu Thr Pro Lys Trp Asp Lys Ile Leu
        275             280             285

Glu Ala Lys Val Trp Gly Asp Ala Ala Ser Gln Ile Phe Tyr Ser Leu
    290             295             300

Gly Cys Ala Trp Gly Gly Leu Ile Thr Met Ala Ser Tyr Asn Lys Phe
305             310             315             320

His Asn Asn Cys Tyr Arg Asp Ser Val Ile Ile Ser Ile Thr Asn Cys
                325             330             335

Ala Thr Ser Val Tyr Ala Gly Phe Val Ile Phe Ser Ile Leu Gly Phe
            340             345             350

Met Ala Asn His Leu Gly Val Asp Val Ser Arg Val Ala Asp His Gly
        355             360             365

Pro Gly Leu Ala Phe Val Ala Tyr Pro Glu Ala Leu Thr Leu Leu Pro
    370             375             380

Ile Ser Pro Leu Trp Ser Leu Leu Phe Phe Met Leu Ile Leu Leu
385             390             395             400

Gly Leu Gly Thr Gln Phe Cys Leu Leu Glu Thr Leu Val Thr Ala Ile
            405             410             415

Val Asp Glu Val Gly Asn Glu Trp Ile Leu Gln Lys Lys Thr Tyr Val
            420             425             430

Thr Leu Gly Val Ala Val Ala Gly Phe Leu Leu Gly Ile Pro Leu Thr
            435             440             445

Ser Gln Ala Gly Ile Tyr Trp Leu Leu Leu Met Asp Asn Tyr Ala Ala
    450             455             460

Ser Phe Ser Leu Val Val Ile Ser Cys Ile Met Cys Val Ser Ile Met
465             470             475             480

Tyr Ile Tyr Gly His Arg Asn Tyr Phe Gln Asp Ile Gln Met Met Leu
            485             490             495

Gly Phe Pro Pro Pro Leu Phe Phe Gln Ile Cys Trp Arg Phe Val Ser
        500             505             510

Pro Thr Ile Ile Phe Phe Ile Leu Ile Phe Thr Val Ile Gln Tyr Arg
        515             520             525

Pro Ile Thr Tyr Asn His Tyr Gln Tyr Pro Gly Trp Ala Val Ala Ile
    530             535             540

Gly Phe Leu Met Ala Leu Ser Ser Val Ile Cys Ile Pro Leu Tyr Ala
545             550             555             560

Leu Phe Gln Leu Cys Arg Thr Asp Gly Asp Thr Leu Leu Gln Arg Leu
            565             570             575

Lys Asn Ala Thr Lys Pro Ser Arg Asp Trp Gly Pro Ala Leu Leu Glu
            580             585             590

His Arg Thr Gly Arg Tyr Ala Pro Thr Thr Thr Pro Ser Pro Glu Asp
    595             600             605

Gly Phe Glu Val Gln Pro Leu His Pro Asp Lys Ala Gln Ile Pro Ile
    610             615             620

Val Gly Ser Asn Gly Ser Ser Arg Leu Gln Asp Ser Arg Ile
625             630             635
```

( 2 ) INFORMATION FOR SEQ ID NO:14:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:14:

GACCAACAAG ATGGAGTTCG TACTG      25

( 2 ) INFORMATION FOR SEQ ID NO:15:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:15:

TGTTACTCCT CGGATCAACA GGACC      25

( 2 ) INFORMATION FOR SEQ ID NO:16:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:16:

GGAGTTCGTG TTGAGCGTAG GAGAG      25

( 2 ) INFORMATION FOR SEQ ID NO:17:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:17:

GAACTTGATG CCTTCCGAGG CACCC      25

( 2 ) INFORMATION FOR SEQ ID NO:18:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:18:

ACGCTTCGAC TTCCTCATGT CCTGT      25

( 2 ) INFORMATION FOR SEQ ID NO:19:

( i ) SEQUENCE CHARACTERISTICS:
        ( A ) LENGTH: 25 base pairs
        ( B ) TYPE: nucleic acid ( C ) STRANDEDNESS: single
( D ) TOPOLOGY: linear ( i i ) MOLECULE TYPE: DNA ( x i ) SEQUENCE DESCRIPTION: SEQ ID NO:19:

GAATCAGACA GCTTTCGGAA GTTGG                    25

( 2 ) INFORMATION FOR SEQ ID NO:20:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:20:

GTCTGCTTCG AGCTGTTTGC AGACA                    25

( 2 ) INFORMATION FOR SEQ ID NO:21:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:21:

TTAGAGTTGT CCACAGTCGG AGATG                    25

( 2 ) INFORMATION FOR SEQ ID NO:22:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:22:

TCAGAGGGAG AAGTGGTCCA GCAAG                    25

( 2 ) INFORMATION FOR SEQ ID NO:23:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:23:

ATTTCATGCC TTCACCAGCA CCTGG                    25

( 2 ) INFORMATION FOR SEQ ID NO:24:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:24:

ACGCTTCGAC TTCCTCATGT CCTGT             25

( 2 ) INFORMATION FOR SEQ ID NO:25:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:25:

TTAGAGTTGT CCACAGTCGG AGATG             25

( 2 ) INFORMATION FOR SEQ ID NO:26:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:26:

GACCAACAAG ATGGAGTT             18

( 2 ) INFORMATION FOR SEQ ID NO:27:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:27:

TGTTACTCCT CGGATCAA             18

( 2 ) INFORMATION FOR SEQ ID NO:28:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:28:

TGGAATTCGSC AA Y GTNTGGMGNTT CCNTA             30

( 2 ) INFORMATION FOR SEQ ID NO:29:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:29:

TCGCGGCCGC AARAAGATCTGN GTNGCNGCRTC             33

( 2 ) INFORMATION FOR SEQ ID NO:30:

( i ) SEQUENCE CHARACTERISTICS:
  ( A ) LENGTH: 25 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:30:

GACCAACAAG ATGGAGTTCG TACTG  25

( 2 ) INFORMATION FOR SEQ ID NO:31:

( i ) SEQUENCE CHARACTERISTICS:
  ( A ) LENGTH: 25 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:31:

TGTTACTCCT CGGATCAACA GGACC  25

( 2 ) INFORMATION FOR SEQ ID NO:32:

( i ) SEQUENCE CHARACTERISTICS:
  ( A ) LENGTH: 25 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:32:

GGAGTTCGTG TTGAGCGTAG GAGAG  25

( 2 ) INFORMATION FOR SEQ ID NO:33:

( i ) SEQUENCE CHARACTERISTICS:
  ( A ) LENGTH: 25 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:33:

GAACTTGATG CCTTCCGAGG CACCC  25

( 2 ) INFORMATION FOR SEQ ID NO:34:

( i ) SEQUENCE CHARACTERISTICS:
  ( A ) LENGTH: 25 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:34:

ACGCTTCGAC TTCCTCATGT CCTGT  25

( 2 ) INFORMATION FOR SEQ ID NO:35:

( i ) SEQUENCE CHARACTERISTICS:
  ( A ) LENGTH: 25 base pairs
  ( B ) TYPE: nucleic acid

```
        ( C ) STRANDEDNESS: single
        ( D ) TOPOLOGY: linear ( i i ) MOLECULE TYPE: DNA ( x i ) SEQUENCE DESCRIPTION: SEQ ID NO:35:

GAATCAGACA  GCTTTCGGAA  GTTGG                    2 5
```